United States Patent
Pasternak et al.

(10) Patent No.: US 9,062,070 B2
(45) Date of Patent: Jun. 23, 2015

(54) INHIBITORS OF THE RENAL OUTER MEDULLARY POTASSIUM CHANNEL

(75) Inventors: Alexander Pasternak, Princeton, NJ (US); Timothy Blizzard, Princeton, NJ (US); Harry Chobanian, Aberdeen, NJ (US); Reynalda de Jesus, East Brunswick, NJ (US); Fa-Xiang Ding, Staten Island, NY (US); Shuzhi Dong, Plainsboro, NJ (US); Candido Gude, Staten Island, NY (US); Dooseop Kim, Seoul (KR); Haifeng Tang, Metuchen, NJ (US); Shawn Walsh, Bridgewater, NJ (US); Barbara Pio, West Orange, NJ (US); Jinlong Jiang, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,649

(22) PCT Filed: Aug. 16, 2012

(86) PCT No.: PCT/US2012/051195
§ 371 (c)(1),
(2), (4) Date: Feb. 19, 2014

(87) PCT Pub. No.: WO2013/028474
PCT Pub. Date: Feb. 28, 2013

(65) Prior Publication Data
US 2014/0206618 A1    Jul. 24, 2014

Related U.S. Application Data

(60) Provisional application No. 61/525,261, filed on Aug. 19, 2011, provisional application No. 61/668,680, filed on Jul. 6, 2012.

(51) Int. Cl.
| | | |
|---|---|---|
| *C07D 498/04* | (2006.01) | |
| *A61K 31/4985* | (2006.01) | |
| *A61K 31/5383* | (2006.01) | |
| *A61K 31/542* | (2006.01) | |
| *A61K 31/553* | (2006.01) | |
| *A61K 45/06* | (2006.01) | |
| *C07D 487/04* | (2006.01) | |
| *C07D 513/04* | (2006.01) | |

(52) U.S. Cl.
CPC .......... *C07D 498/04* (2013.01); *A61K 31/4985* (2013.01); *A61K 31/5383* (2013.01); *A61K 31/542* (2013.01); *A61K 31/553* (2013.01); *A61K 45/06* (2013.01); *C07D 487/04* (2013.01); *C07D 513/04* (2013.01)

(58) Field of Classification Search
None
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2008/0003214 A1 | 1/2008 | Cezanne et al. |
| 2010/0286123 A1 | 11/2010 | Pasternak et al. |

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

ACCF/AHA Practice Guideline, 2009 Focused update incorporated into the ACC/AHA 2005 guidelines . . . , Circulation, 2009, e391-e436, 119.

(Continued)

*Primary Examiner* — Maury Audet
*Assistant Examiner* — Fred Reynolds
(74) *Attorney, Agent, or Firm* — Nicole M. Beeler; Catherine D. Fitch

(57) ABSTRACT

The present invention provides compounds of Formula Ia and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and conditions associated with excessive salt and water retention.

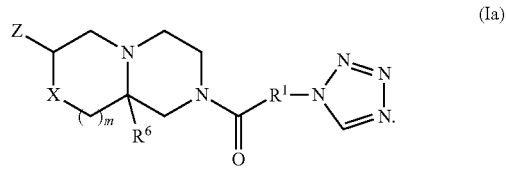

15 Claims, No Drawings

(56) References Cited

FOREIGN PATENT DOCUMENTS

| | | |
|---|---|---|
| EP | 1094063 A1 | 4/2001 |
| EP | 1939175 A1 | 7/2009 |
| FR | 2673182 | 8/1992 |
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0232874 | 4/2002 |
| WO | 0204314 A1 | 6/2002 |
| WO | 0250061 A1 | 6/2002 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2006129199 A1 | 12/2006 |
| WO | WO 2007056170 A2 * | 5/2007 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2013039802 A1 | 3/2013 |
| WO | 2013062892 A1 | 5/2013 |
| WO | 2013062900 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014018764 A1 | 1/2014 |

OTHER PUBLICATIONS

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave,G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-Isobenzofurandione 5-[[4-[(5-chloro-2-methoxyphenyl) sulfonyl]-1- . . . "

Cheymol et al., Increase in the effects of epinephrine and acetylcholine . . . , Comptes Rendus des seances de la Societe de Biologie, 1951, 496-499 (English trans.), 145.

Fallen, K., The Kir channel immunoglobuling domain is essential for Kir1.1 (ROMK) thermodynamic stability, trafficing and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report of PCT/US2012/51195 mailed on Oct. 23, 2012, 7 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US2012/051195 filed Aug. 16, 2012, which claims priority from U.S. Provisional Application Ser. No. 61/525,261, filed Aug. 19, 2011 and Provisional Application Ser. No. 61/668,680, filed Jul. 6, 2012.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

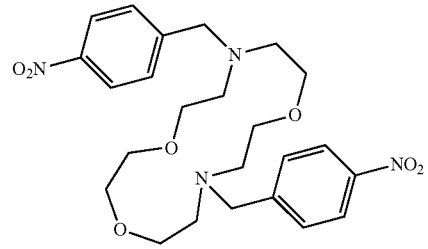

VU590

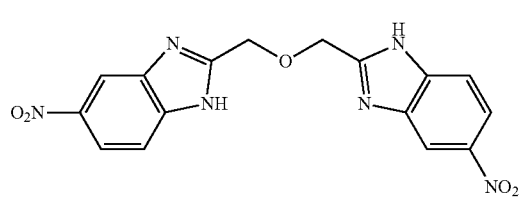

VU591

However, continuing discovery of selective small molecule inhibitors of ROMK is still needed for the development of new treatments for hypertension and related disorders. The compounds of Formula Ia of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula Ia

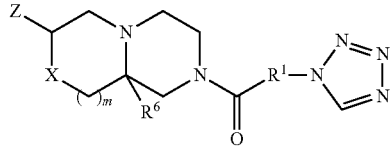

Ia and the pharmaceutically acceptable salts thereof. The compounds of Formula Ia are inhibitors of the ROMK (Kir1.1) channel. As a result, the compounds of Formula Ia could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula Ia to a patient in need of a diuretic and/or natriuretic agent. Therefore, the compounds of Formula Ia could be valuable pharmaceutically active compounds for the therapy, prophylaxis or both of medical conditions, including, but not limited to, cardiovascular diseases such as hypertension, heart failure and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula Ia, and pharmaceutical compositions which comprise compounds of Formula Ia. These and other aspects of the invention will be evident from the description contained herein.

DETAILED DESCRIPTION OF THE INVENTION

The present invention is directed to compounds having structural Formula Ia:

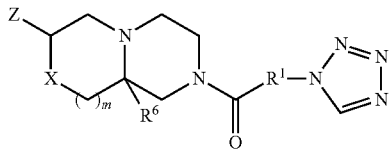

and the pharmaceutically acceptable salts thereof wherein:
Z is

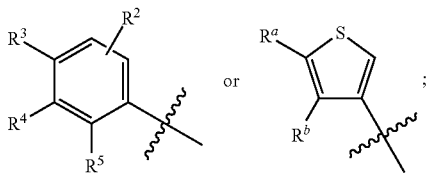

$R^1$ is

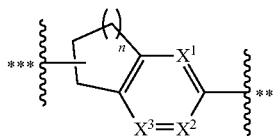

wherein *** indicates attachment to the carbonyl carbon and *-* indicates attachment to the tetrazolyl ring in Formula Ia;
X is O, NH or S;
m is an integer selected from 1 or 2;
n is an integer selected from 1 or 2;
$X^1$, $X^2$ and $X^3$ are each independently selected from $C(R^7)$ or N, provided that at least one of $X^1$, $X^2$ and $X^3$ must be N and at most two of $X^1$, $X^2$ and $X^3$ are N;
$R^a$ is —CN;
$R^b$ is —H or —$C_{1-6}$alkyl;
$R^2$ is —H, —F, —$C_{1-6}$alkyl, —$C_{3-6}$cycloalkyl or —$OC_{1-6}$alkyl;
$R^3$ is —H, —F, —Cl, —CN, —$C_{1-6}$alkyl, —$C_{3-6}$cycloalkyl or —$OC_{1-6}$alkyl;
$R^4$ is —F, —Cl, —CN, —$C_{1-6}$alkyl, —$C_{3-6}$cycloalkyl, —$OC_{1-4}$alkyl or N-tetrazolyl;
or $R^3$ and $R^4$ are joined together with the carbon atoms in the phenyl ring to which they are attached to form:

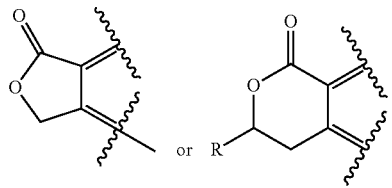

wherein R is —H or —$C_{1-4}$alkyl;
$R^5$ is —H, —Cl, —F, —CN, —$C_{1-4}$alkyl, —$C_{3-6}$cycloalkyl or —$OC_{1-4}$alkyl;
provided that when $R^3$ and $R^4$ are not joined together, then one and only one of $R^3$, $R^4$ or $R^5$ is —CN;
$R^6$ is —H or —$C_{1-4}$alkyl; and
$R^7$ is —H, —F, —Cl or —$C_{1-4}$alkyl.

In an embodiment of this invention are compounds of Formula Ia having structural Formula I:

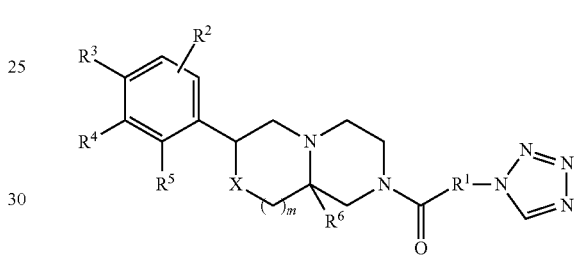

and the pharmaceutically acceptable salts thereof wherein each of the variables X, m, n, $R^1$, $R^2$, $R^3$, $R^4$, $R^5$, $R^6$, $R^7$, and all other variables therein are as defined in Formula Ia.

In Embodiment A are compounds of Formula Ia or I and the pharmaceutically acceptable salts thereof wherein:
X is O, NH or S;
$R^1$ is

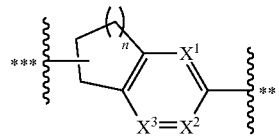

wherein * indicates attachment to the carbonyl carbon and  indicates attachment to the tetrazolyl ring in Formula Ia or I;
m is an integer selected from 1 or 2;
n is an integer selected from 1 or 2;
$X^1$, $X^2$ and $X^3$ are each independently selected from CH or N, provided that at least one of $X^1$, $X^2$ and $X^3$ must be N and at most two of $X^1$, $X^2$ and $X^3$ are N;
when Z is thienyl in Formula Ia, then $R^a$ is —CN, and $R^b$ is —H or —$C_{1-3}$alkyl, and more particularly $R^b$—$CH_3$;
$R^2$ is —H or —F;
$R^3$ is —H, —F, —CN or —$OCH_3$;
$R^4$ is —F, —CN or —$OCH_3$;
or $R^3$ and $R^4$ are joined together with the carbon atoms in the phenyl ring to which they are attached to form:

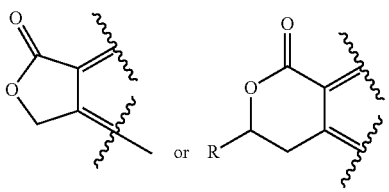

wherein R is —H or —CH₃;
R⁵ is —H, —Cl, —F, —CN, —CH₃, —CH₂CH₃, cyclopropyl or —OCH₃;
provided that when R³ and R⁴ are not joined together, then one and only one
of R³, R⁴ or R⁵ is —CN; and further provided that when R³ and R⁴ are joined together, then R⁵ is —H, —Cl, —F, —CH₃ or —CH₂CH₃;
R⁶ is —H or —C₁₋₄alkyl; and
R⁷ is —H, —F, —Cl or —C₁₋₄alkyl.

The present invention is further directed to compounds of Formulas Ia or I having structural Formula II:

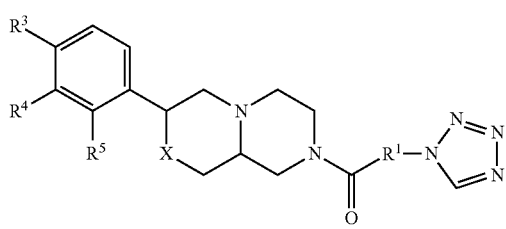

II and the pharmaceutically acceptable salts thereof wherein each of the variables X, R¹, R³, R⁴, R⁵ and all other variables therein are as defined in Formula Ia. Compounds and salts thereof within the scope of Formula II include those wherein:
X is O or NH;
R¹ is:

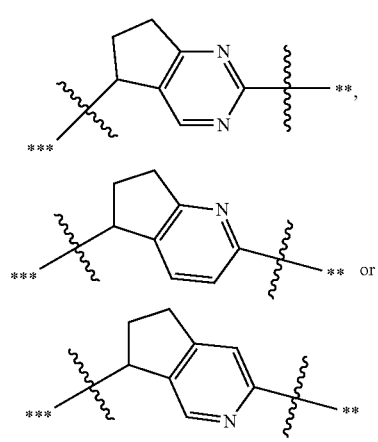

wherein * indicates attachment to the carbonyl carbon and  indicates attachment to the tetrazolyl ring in Formula II; and
R³ is —F, R⁴ is —CN and R⁵ is —CH₃; or
R³ and R⁴ are joined together with the carbon atoms in the phenyl ring to which they are attached to form:

wherein R is —H or —CH₃, and R⁵ is —H.

The present invention is further directed to compounds of Formulas Ia, I or II having structural Formula III:

III and the pharmaceutically acceptable salts thereof, wherein R², R³, R⁴, and R⁵ and all other variables therein are as defined in Formula Ia.

In an embodiment of this invention are compounds of Formula Ia, Formula I, Embodiment A or Formula II wherein X is O. In another embodiment are compounds of Formula Ia, Formula I, Embodiment A or Formula II wherein X is NH. In another embodiment are compounds of Formula Ia, Formula I, Embodiment A or Formula II wherein X is S.

In an embodiment are compounds of Formula Ia, Formula I, Embodiment A or Formula II wherein R¹ is:

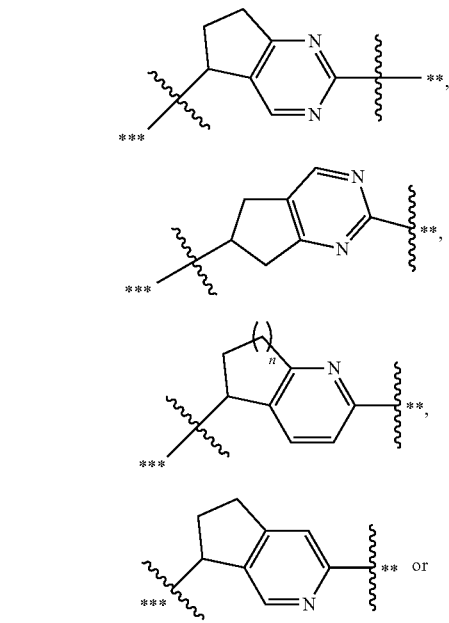

-continued

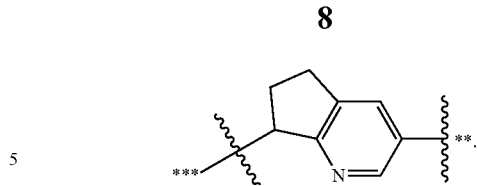

In another embodiment are compounds of Formula Ia, Formula I, Embodiment A, or Formula II

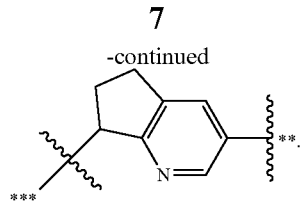

wherein $R^1$ is:

In another embodiment are compounds of Formula Ia, Formula I, Embodiment A, or Formula II

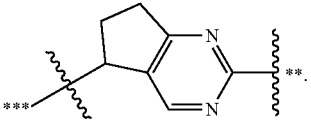

wherein $R^1$ is:

In another embodiment are compounds of Formula Ia, Formula I, Embodiment A or Formula II wherein $R^1$ is:

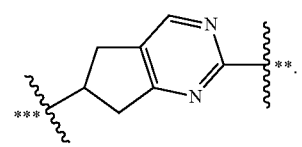

wherein n is 1 or 2, and more particularly is

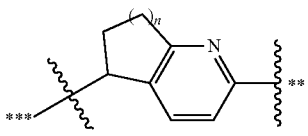

In another embodiment are compounds of Formula Ia, Formula I, Embodiment A or Formula II wherein $R^1$ is:

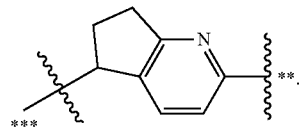

In another embodiment are compounds of Formula Ia, Formula I, Embodiment A, or Formula II wherein $R^1$ is:

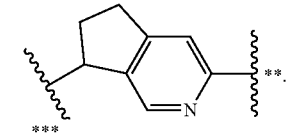

In an embodiment are compounds of Formula Ia, Formula I or Embodiment A wherein m is 1. In another embodiment are compounds of Formula Ia, Formula I or Embodiment A wherein m is 2.

In another embodiment are compounds of Formula Ia, Formula I, Embodiment A or Formula II wherein n is 1. In another embodiment are compounds of Formula I, Embodiment A or Formula II wherein n is 2. In a class thereof are compounds wherein m and n are both 1.

In another embodiment are compounds of Formula Ia, Formula I, Embodiment A, Formula II or Formula III wherein $R^2$ is —H or —F; $R^3$ is —H, —F, —CN or —OCH$_3$; $R^4$ is —F, —CN or —OCH$_3$; and $R^5$ is —H, —Cl, —F, —CN, —CH$_3$, —CH$_2$CH$_3$, cyclopropyl or —OCH$_3$; provided that one and only one of $R^3$, $R^4$ or $R^5$ is —CN. In a class thereof are compounds wherein one of $R^3$ or $R^4$ is —CN. In a sub-class thereof are compounds wherein $R^4$ is —CN. In a further sub-class thereof are compounds wherein $R^2$ is —H; $R^3$ is —F; $R^4$ is —CN; and $R^5$ is —CH$_3$.

In an embodiment are compounds of Formula Ia, Formula I, Embodiment A, Formula II or Formula III wherein $R^3$ and $R^4$ are joined together with the carbon atoms in the phenyl ring to which they are attached to form:

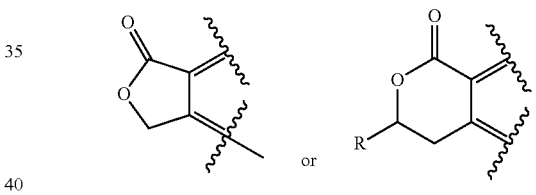

wherein R is —H or —CH$_3$; $R^2$ is —H; and $R^5$ is —H, —Cl, —F, —CN, —C$_{1-4}$alkyl, —C$_{3-6}$cycloalkyl or —OC$_{1-4}$alkyl. In a class of this embodiment are compounds wherein $R^3$ and $R^4$ are joined to form the 5-membered ring and $R^5$ is —H, —CH$_3$ or —CH$_2$CH$_3$. In another class of this embodiment are compounds wherein $R^3$ and $R^4$ are joined to form the 6-membered ring and $R^5$ is —H or —F.

In an embodiment are compounds of Formula Ia, Formula I or Embodiment A wherein $R^6$ is —H. In another embodiment are compounds of Formula Ia or Formula I wherein $R^6$ is methyl, ethyl, —C$_3$alkyl or —C$_4$alkyl.

In an embodiment are compounds of Formula Ia, Formula I, Embodiment A or Formula II wherein $R^7$ is —H. In another embodiment are compounds of Formula Ia, Formula I, Embodiment A or Formula II wherein $R^7$ is —F, —Cl, methyl or ethyl, —C$_3$alkyl or —C$_4$alkyl, and more particularly is —F, —Cl, methyl or ethyl.

In an embodiment are compounds of Formula Ia and Embodiment A wherein $R^b$ is —CH$_3$.

All structural Formulas, Embodiment A and other embodiments described above include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1-C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl.

Unless expressly depicted or described otherwise, variables depicted in a structural formula with a "floating" bond, such as $R^2$, are permitted on any available carbon atom in the ring to which the variable is attached.

The present invention encompasses all stereoisomeric forms of the compounds of Formula Ia. Centers of asymmetry that are present in the compounds of Formula Ia can all independently of one another have (R) or (S) configuration. When bonds to the chiral carbon are depicted as straight lines in the structural Formulas of the invention, or when a compound name is recited without a chiral designation for a chiral carbon, it is understood that both the (R) and (S) configurations of the chiral carbon and hence both enantiomers and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula Ia or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

The compounds of the instant invention have at least two chiral (i.e., asymmetric) centers from the central fused bicyclic ring of Formula Ia, as indicated by the asterisk at each chiral center in example A. Also, the carbon in the non-aromatic ring of $R^1$ (as defined in Formula Ia) which is alpha to the carbonyl carbon in Formula Ia is a chiral center and is referred to herein for brevity as an "aza-indane" chiral center or a similar-meaning variation thereof. An illustrative example of an aza-indane chiral center is indicated by the asterisk in example B:

A)

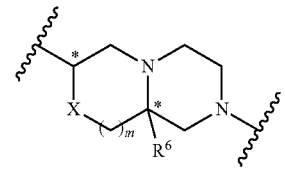

B)

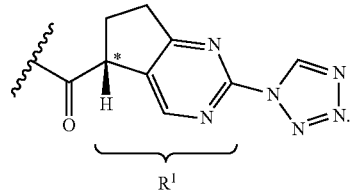

The term aza-indane as used herein may be any structure encompassed by the definition of $R^1$ in Formula Ia, including where the non-aromatic ring is 5 or -6-membered and where the fused aromatic ring contains one or two nitrogens. In some examples, such as Examples 2A and 2B, a stereochemical assignment was made that identifies each of the separated isomers as S or R at the aza-indane chiral center. In some examples, an assignment was not made but the isomers created by the aza-indane chiral center were nevertheless separated and are referred to as the aza-indane diastereomers(s) or similar language that conveys this particular chiral center in the compound.

Additional chiral centers may be present depending upon the nature of the various substituents on a molecule. In some of the chemical structures shown in the examples an asterisk is used to identify one or more chiral centers.

Reference to the compounds of Formula Ia herein encompasses the compounds of Formulas I, II and III and all embodiments thereof. Reference to the compounds of this invention as those of a specific formula or embodiment, e.g., Formula Ia, I, II or III or embodiments thereof, or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula Ia, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula Ia. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula Ia can be prepared without undue experimentation by conventional techniques well known to those skilled in the art or by processes analogous to those described in the Schemes and Examples herein using appropriate isotopically-enriched reagents and/or intermediates.

When the compounds of Formula Ia contain one or more acidic or basic groups the invention also includes the corresponding pharmaceutically acceptable salts. Thus, the compounds of Formula Ia which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula Ia which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula Ia simultaneously contain acidic and basic groups in the molecule the invention also includes, in addition to the salt forms mentioned, inner salts or betaines (zwitterions). Salts can be obtained from the compounds of Formula Ia by customary methods which are known to the person skilled in the art, for example by combination with an organic or inorganic acid or base in a solvent or dispersant, or by anion exchange or cation exchange from other salts. The present invention also includes all salts of the compounds of Formula Ia which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula Ia are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula Ia according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula Ia in a ROMK-inhibitory effective amount to a patient in need thereof. The inhibition of ROMK by the compounds of Formula Ia can be examined, for example, in the Thallium Flux Assay and/or Electrophysiology Assay described below. Moreover, this invention also relates to the use of the compounds of Formula Ia or salts thereof to validate in vitro assays, for example but not limited to the Thallium Flux and Electrophysiology Assays described herein.

The compounds of this invention could be used in a method for causing diuresis, natriuresis or both, comprising administering a compound of Formula Ia in a therapeutically effective amount to a patient in need thereof. Therefore, the compounds of Formula Ia of this invention could be used in methods for treatment of, prevention of or reduction of risk for developing medical conditions that benefit from increased excretion of water and sodium, such as but not limited to one or more of hypertension, heart failure (both acute and chronic, the latter also known as congestive heart failure) and/or other conditions associated with excessive salt and water retention. Furthermore, the compounds of Formula Ia could be used in methods for treatment of, prevention of or reduction of risk for developing one or more disorders such as pulmonary arterial hypertension (PAH), cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, nephrotic syndrome, acute and chronic kidney insufficiency (also referred to as chronic kidney disease, or more generally as renal impairment), hypercalcemia, Dent's disease, Meniere's disease, edematous states, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula Ia may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 μM or less, preferably 1 μM or less, and more preferably 0.25 µM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula Ia. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula Ia and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula Ia with a pharmaceutically acceptable carrier. Also encompassed is the pharmaceutical composition which is made by combining a compound of Formula Ia with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula Ia and/or its pharmaceutically acceptable salts in the pharmaceutical composition may be, for example but not limited to, from 0.1 to 200 mg, particularly from 0.1 to 100 mg, and more particularly from 0.1 to 50 mg, per dose on a free acid/free base weight basis, but depending on the type of the pharmaceutical composition, potency of the active ingredient and/or the medical condition being treated, it could also be lower or higher. Pharmaceutical compositions usually comprise 0.5 to 90 percent by weight of the active compound on a free acid/free base weight basis.

The compounds of Formula Ia inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula Ia can also be employed as intermediates for the preparation of other pharmaceutically active compounds.

One or more additional pharmacologically active agents may be administered in combination with a compound of Formula Ia. The additional active agent (or agents) is intended to mean a compound that is different from the compound of Formula Ia, and which is a pharmaceutically active agent (or agents) that is active in the body, including pro-drugs that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula Ia in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Several methods for preparing the compounds of this invention are described in the examples. Starting materials and intermediates are purchased, made from known procedures, or as otherwise illustrated. Some frequently applied routes to the compounds of Formula Ia are also described by the Schemes as follows. In some cases the order of carrying out the steps of reaction schemes may be varied to facilitate the reaction or to avoid unwanted reaction products.

Compounds of this invention may be prepared as shown in Scheme 1 by coupling of appropriately substituted piperazines 1 with carboxylic acids of the structure 2 to form amides. This can be accomplished in many ways well-known to the chemist, including by using EDC in the presence or absence of HOBt and a base such as triethylamine, or by using a variety of other amide coupling reagents such as HATU.

Scheme 1

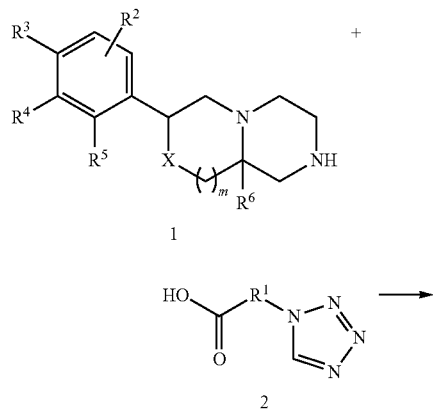

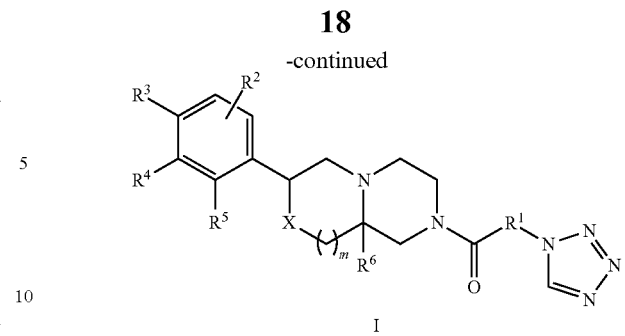

Piperazines 1 can be prepared according to Scheme 2. Epoxides 3 can be coupled with appropriately protected hydroxyalkylpiperazines 4 by heating in a solvent such as ethanol, DMSO, or toluene to afford the diols 5 (Nomura, Y. et al. Chemical & Pharmaceutical Bulletin, 1995, 43(2), 241-6). Heating can be by conventional thermal bath or by microwave irradiation. The diols 5 can be cyclized to afford 6 or 7-membered rings 6 by a variety of ways, including by heating with the reagent cyanomethylene tri-n-butylphosphorane in a suitable solvent such as benzene or toluene. Heating can be by conventional thermal bath or by microwave irradiation. The resulting compounds 6 are generally mixtures of cis and trans isomers. The protective group (Greene, T.; Wuts, P. G. M. *protective Groups in Organic Synthesis*, John Wiley and Sons, Inc., New York, N.Y. 1991) can then be removed. For example, when the protective group is Boc as shown in Scheme 2, removal can be achieved by treatment with an acid such as TFA or HCl to afford piperazines 1A. Alternatively, compounds 6 can be separated by means of silica chromatography or preparative high pressure liquid chromatography employing a chiral column to afford the separated cis 6 (cis) and trans 6 (trans) isomers. The protective group of the pure cis and trans isomers can be removed by treatment with an acid such as TFA or HCl, in the case of a Boc group, to afford piperazines 1A as pure cis and trans isomers 1A (cis) and 1A (trans). If a single enantiomer of the hydroxyalkylpiperazines 4 is employed, then single enantiomer cis and trans isomers 1A (cis), and 1A (trans) can be obtained.

Scheme 2

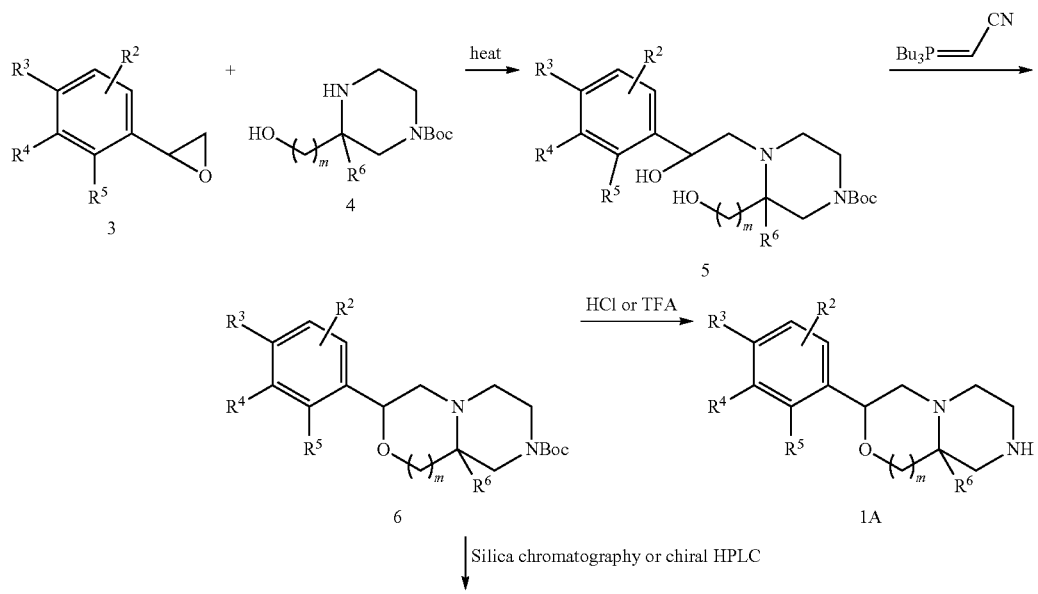

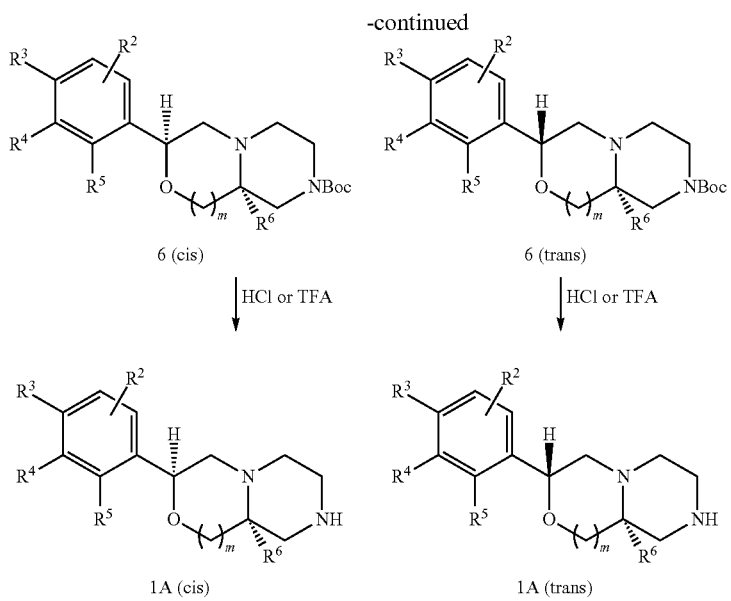

6 (cis)       6 (trans)

↓ HCl or TFA     ↓ HCl or TFA 1A (cis)       1A (trans)

Protected piperazines 6 can also be prepared according to Scheme 3 by initially coupling hydroxyalkylpiperazines 4 with bromomethylketones (or chloromethyl ketones) 7 to afford hemiketals 8. This is typically accomplished in the presence of a base such as triethylamine or diethylisopropylamine. The resulting hemiketals 8 can be converted directly to piperazines 1A by reduction using, for example, triethylsilane in the presence of an acid catalyst such as trifluoroacetic acid. If separation of the cis and trans isomers is desired, a protective group such as Boc may be installed using, for example, Boc$_2$O, to give intermediates 6 which can be separated into cis and trans isomers as described in Scheme 2. Alternatively, the hemiketals 8 may be reduced by a three step sequence involving formation of a mesylate with mesyl chloride and a base such as triethylamine, followed by elimination in the presence of base to give enol ethers 9. Enol ethers 9 can then be reduced by hydrogenation in the presence of a catalyst such as palladium on carbon to afford protected piperazines 6 which can be separated into cis and trans isomers as described in Scheme 2. These may then be converted to piperazine intermediates 1A (cis) and 1A (trans) as described in Scheme 2.

Scheme 3

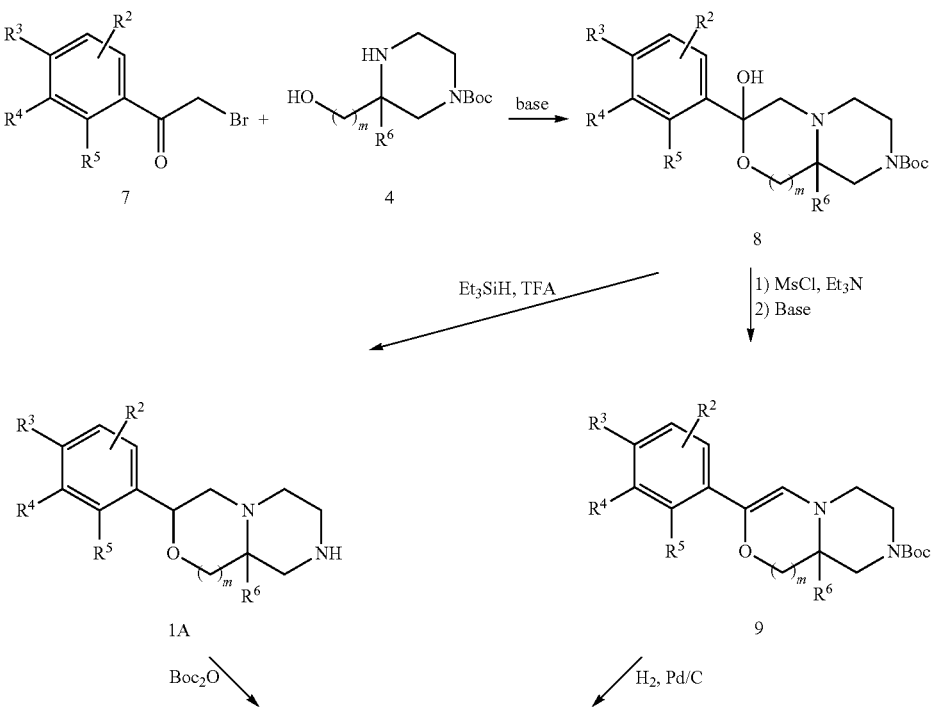

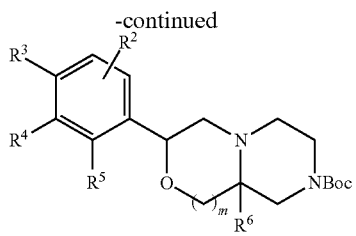

6

Alternatively, a subclass of intermediates 1, piperazines 1B, can be prepared as described in Scheme 4. The Boc protective group of intermediates 5 (prepared as described in Scheme 2) are switched to benzyl carbamate (Cbz) groups by initial treatment with an acid such as TFA or HCl, followed by coupling with benzyl chloroformate in the presence of a base such as triethylamine. The resulting Cbz-piperazine diols 5A are converted to the corresponding dichloro intermediates by heating with thionyl chloride; then, the dichlorides are heated with allylamine in the presence of sodium iodide to afford the allyl substituted fised piperazines 10. The allyl groups may be removed in several ways, including by warming with 1,3-dimethylpyrimidine-2,4,6(1H,3H,5H)-trione in the presence of a catalyst such as palladium tetrakis triphenylphosphine. The revealed amines are then re-protected with tert-butoxycarbamate groups by treatment with $Boc_2O$ in the presence of an amine such as triethylamine to provide intermediates 6B, generally as mixtures of cis and trans isomers. The cis and trans isomers can be separated as described in Scheme 2 by silica chromatography or by chiral preparative HPLC. If intermediates 5 are prepared from single enantiomers of 4 (as described in Scheme 2), then the resulting intermediates 6B (cis) and 6B (trans) are also single isomers. Alternatively, separation of the cis and trans isomers can be performed at an earlier stage by separation of the cis/trans isomers of intermediates 10. The Cbz protective groups of intermediates 6B (cis) and 6B (trans) can be removed, for example, by hydrogenolysis in the presence of a catalyst such as palladium on carbon to afford intermediates 1B (cis) and 1B (trans).

Scheme 4

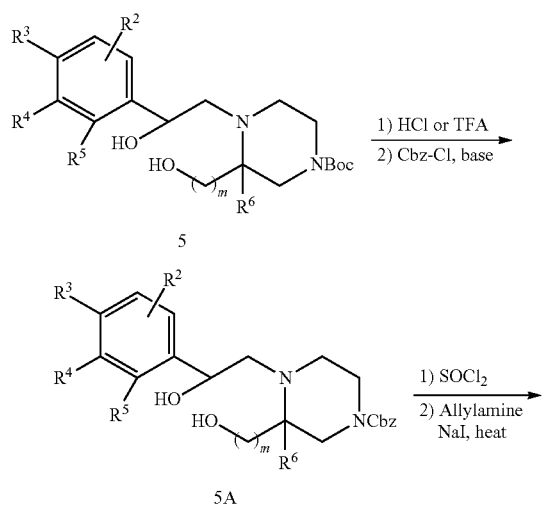

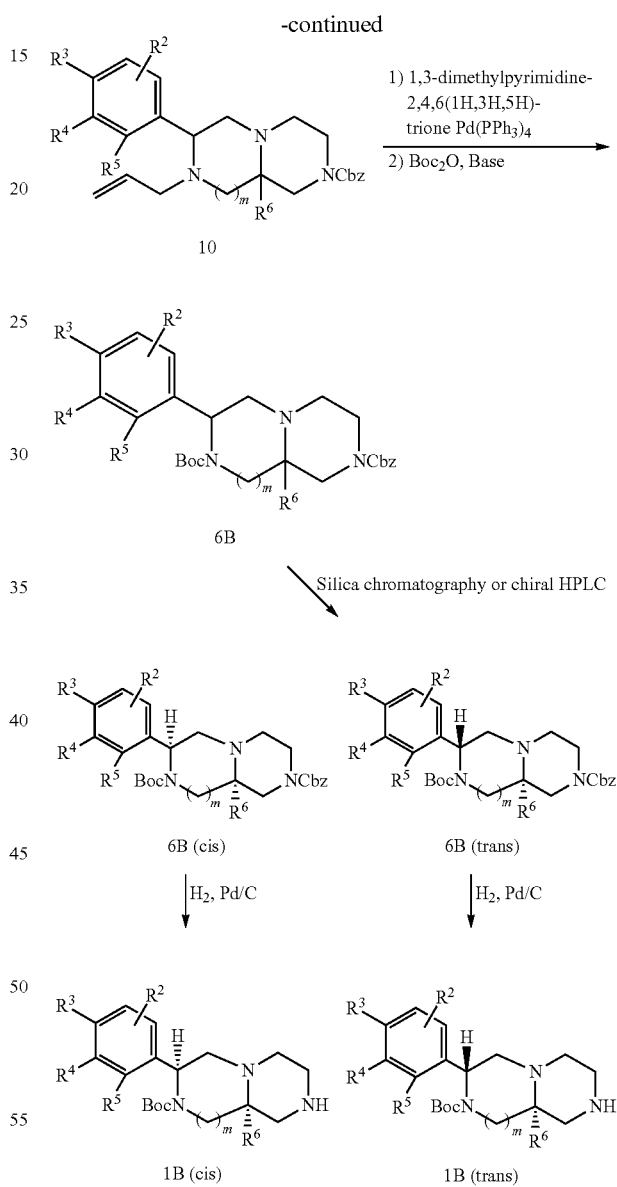

Alternatively, a sub-class of intermediates 1 (1C) may be prepared according to Scheme 5. Diols 5 are initially converted to their corresponding mono-mesylates by treatment with mathanesulfonyl chloride, a base such as triethyl amine, and a catalyst such as 4-dimethylaminopyridine. Subsequent reaction with potassium thiocetate in a solvent such as dimethyl sulfoxide (DMSO) provides intermediates 11. The remaining hydroxyl group of 11 is then converted to the corresponding chloro intermediate by treatment with, for example, thionyl chloride, followed by addition of a base such as pyridine. The resulting chloro intermediate is then treated with sodium methoxide to afford the cyclized sulfides 6C. When the starting diols 5 used are single isomers (starting from enantiomerically pure epoxides 3 and enantiomerically pure hydroxyalkylpiperazines 4 (Scheme 2), the resulting intermediates 6C may be obtained as single isomers. Alternatively, when racemic epoxides 3, and single enantiomer hydroxyalkylpiperazines 4 are employed, the resulting intermediates 6C are obtained as a mixture of two isomers (cis and trans), which can then be separated to single isomers 6C (cis) and 6C (trans) by silica chromatography or by chiral preparative HPLC. Removal of the tert-butyl carbamate protective group can then be achieved by treatment with an acid such as TFA or HCl to provide the piperazines 1C (cis) and 1C (trans).

Intermediates 2 (in Scheme 1) are be prepared in a variety of ways depending on the structure of 2; several methods are shown in the experimental section below.

Epoxides 3 may be prepared by a variety of methods. One approach is described by Scheme 6. Aryl or heterocycle halides (bromide 12 shown) may be coupled to form alkene products 13 in a number of ways, for example by Heck reaction or by reaction with vinyl tetrafluoroborate (Molander, G.; Luciana, A. Journal of Organic Chemistry, 2005, 70(10), 3950-3956) under palladium catalyzed coupling conditions with an appropriate phosphine ligand (Molander, G.; Brown, A. Journal of Organic Chemistry, 2006, 71(26), 9681-9686). The alkenes 13 can then be converted to the corresponding epoxides 3 by several ways, including treatment with meta-chloroperoxybenzoic acid (Fringuelli, F. et al. Organic Preparations and Procedures International, 1989, 21(6), 757-761).

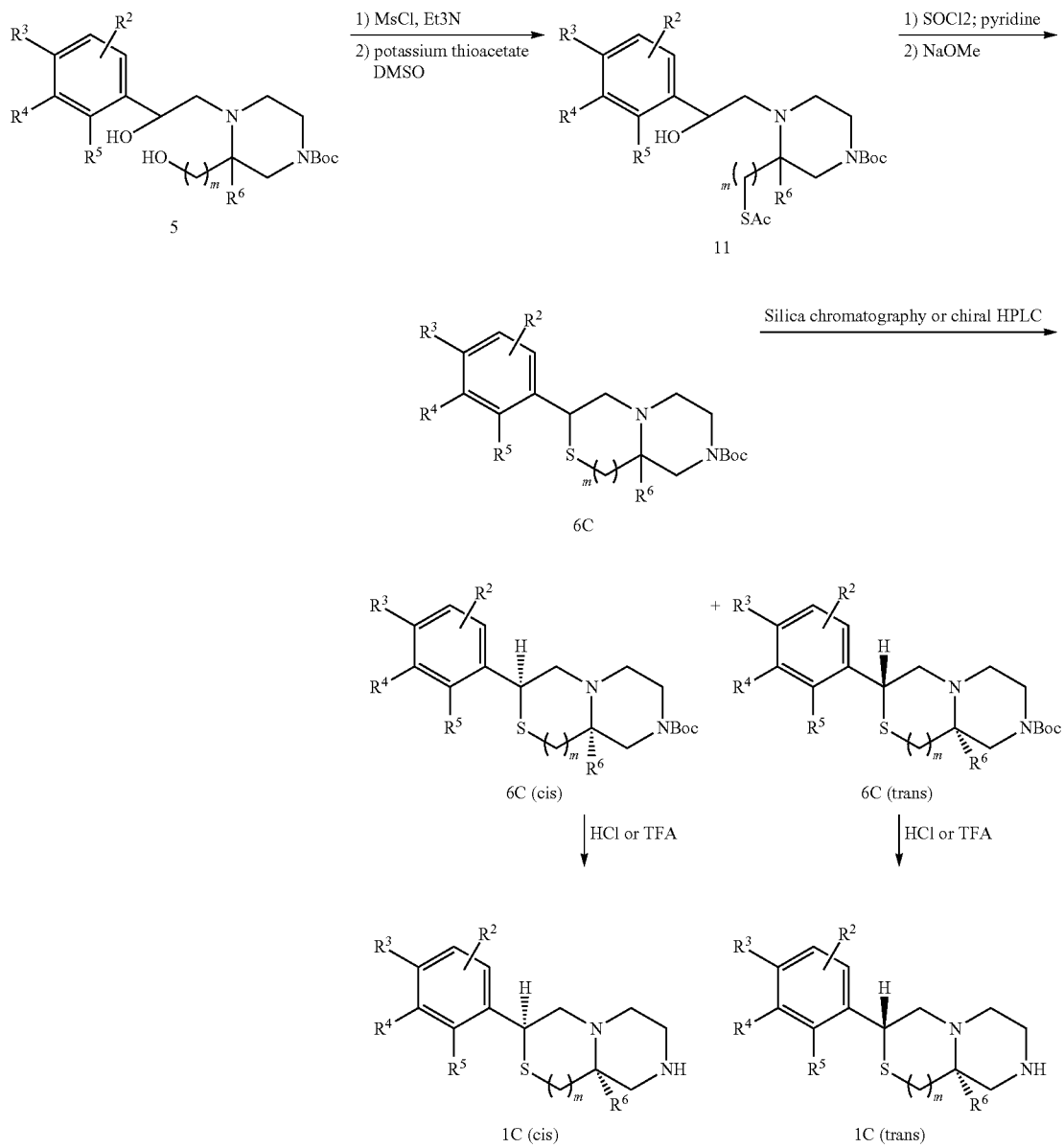

Scheme 5

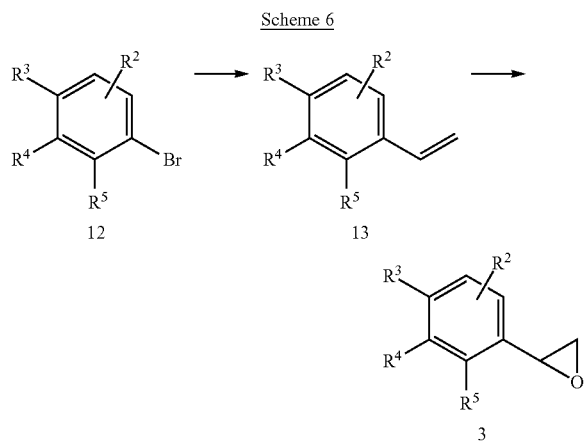

Bromomethylketones 7 may be prepared in a variety of ways; one route is depicted in Scheme 7. According to the Scheme, aryl or heterocyclic halides (bromide 12 shown) can be reacted with tributyl(1-ethoxyvinyl)tin in the presence of a metal catalyst such as PdCl$_2$(PPh$_3$)$_2$ to provide an intermediate ethylenolether. This is subsequently treated in the same reaction vessel with N-bromosuccinimide (NBS) with added tetrahydrofuran and water to provide bromomethylketones 7. Chloromethyl ketones can similarly be prepared by employing N-chlorosuccinimide in place of N-bromosuccinimide.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl₃ solution unless otherwise noted. Coupling constants (J) are in hertz (Hz). Abbreviations used herein: ethyl acetate (EtOAc), dichloromethane (DCM), starting material (SM), diethyl ether (ether), trifluoroacetic acid (TFA), triethylamine (TEA), N,N-diisopropylethylamine (DIEA, Hunig's base, DIPEA), 1-ethyl-3-(3-dimethylaminopropyl), carbodiimide (EDC, EDAC, or EDCI), 2-(7-Aza-1H-benzotriazole-1-yl)-1,1,3,3-tetramethyluronium hexafluorophosphate (HATU), 1-Hydroxybenzotriazole hydrate (HOBt), methyl tert-butyl ether (MTBE), Cyclopentyl methyl ether (CPME), 1,3-Bis(diphenylphosphino)propane (DPPP), 2-Dicyclohexylphosphino-2',4',6'-triisopropylbiphenyl (X-Phos), 1,2-dichloroethane (DCE), N-bromo succinimide (NBS), N-iodosuccinimide (NIS), lithium diisopropylamide (LDA), tetrahydrofuran (THF), dimethylsulfoxide (DMSO), isopropanol (IPA), t-butyloxycarbonyl (Boc or BOC), di-t-butyl dicarbonate (BOC₂O, Boc₂O), acetic acid (AcOH; HOAc), N;N-dimethylformamide (DMF), 4-dimethylaminopyridine (DMAP), mCPBA (3-chloroperoxybenzoic acid), nicotinamide adenine dinucleotide phosphate (NADP), petroleum ether (PE), lithium aluminum hydride (LAH), di-isopropylamine (DIPA), Carbonyldiimidazole (CDI), p-toluenesulfonic acid (TsOH), p-toluene-SO₂— (tosyl or Ts), methane sulfonyl chloride or mesyl chloride (Ms-Cl), methanesulfonic acid (MsOH), CH₃SO₂-(mesyl or Ms), dimethoxyethane (DME), Pd(dppf)Cl₂ or PdCl₂(dppf) is 1,1'-Bis(diphenylphosphino) ferrocene]dichloropalladium(II) which may be complexed with CH₂Cl₂, hexamethylphosphoramide (HMPA), isopropyl acetate (IPAc) round-bottom flask (RB or RBF), saturated aqueous (sat'd), medium pressure liquid chromatography (MPLC), high pressure liquid chromatography (HPLC), liquid chromatography (LC), thin layer chromatography (TLC), liquid chromatography-mass spectrometry (LC-MS or LC/MS), column volume (CV), room temperature (rt, r.t. or RT), hour(s) (h or hr), minute(s) (min). Celite is a trademark name for diatomaceous earth, and Solka Floc is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

Intermediates 1A and 1B

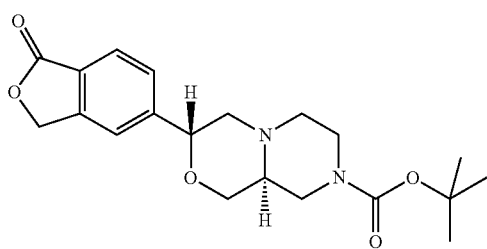

1A

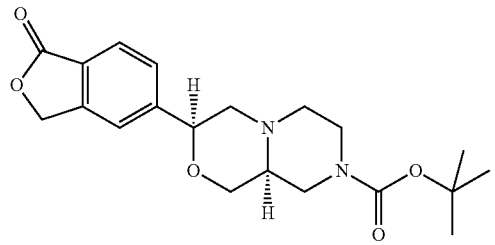

1B

1A: tert-butyl(3R,9aS)-3-(1-oxo-1,3-dihydro-2-benzofuran-5-yl)hexahydropyrazino[2,1-c][1,4]oxazine-8(1H)-carboxylate; 1B: tert-butyl(3S,9aS)-3-(1-oxo-1,3-dihydro-2-benzofuran-5-yl)hexahydropyrazino[2,1-c][1,4]oxazine-8(1H)-carboxylate Step A: 5-ethenyl-2-benzofuran-1(3H)-one 5-Bromophthalide (50 g, 235 mmol), potassium vinyl trifluoroborate (62.9 g, 469 mmol), and PdCl₂(dppf)-CH₂Cl₂ Adduct (9.58 g, 11.7 mmol) were added to ethanol (500 mL) then TEA (65.4 mL, 469 mmol) was added. The reaction mixture was degassed then heated at reflux for 8 h. The reaction was worked up by diluting with ethyl acetate and washing with brine twice. The organic layer was dried and evaporated to dryness. The crude product was purified by MPLC (silica, 600 g column) with 25% EtOAc/hexane (3 L) then with 30% EtOAc/Hexane (2 L) to yield the title compound.

Step B: 5-(oxiran-2-yl)-2-benzofuran-1(3H)-one

5-Ethenyl-2-benzofuran-1(3H)-one (28.4 g, 177 mmol) was dissolved in DCM (400 mL) then mCPBA (47.7 g, 213 mmol) was added. The mixture was stirred at room temperature overnight. Some starting olefin remained. Another 25 g of mCPBA was added and the mixture was stirred overnight. The mixture was poured into ice cold Na₂SO₃ solution (saturated). The layers were separated and the organic layer was washed with 5% NaOH solution, brine, then was dried (MgSO₄). The crude product was purified by MPLC (330 g column, eluting with 40% EtOAc/hexane, 2 L, then with 45% EtOAc/hexane, 2 L, to afford 5-(oxiran-2-yl)-2-benzofuran-1(3H)-one. LC-MS: M+1=177.

Step C: tert-butyl(3S)-3-(hydroxymethyl)-4-[2-hydroxy-2-(1-oxo-1,3-dihydro-2-benzofuran-5-yl)ethyl]piperazine-1-carboxylate 5-(Oxiran-2-yl)-2-benzofuran-1(3H)-one (1.5 g, 8.5 mmol) and commercially available (S)-4-N-BOC-2-hydroxymethyl piperazine (2.394 g, 11.07 mmol) were combined in ethanol (10 mL) in a microwave tube. The mixture was degassed then heated for 60 min at 150° C. LC-MS showed the product peak. The reaction was worked up by adding ethyl acetate and washing once with brine. The organic layer was separated, dried, and concentrated to dryness. The crude product was purified by MPLC using an 80 g Redi-sep column and eluted with 50%-100% EtOAc/hexane yielding the title compound.

Step D: tert-butyl(9aS)-3-(1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(1-oxo-1,3-dihydro-2-benzofuran-5-yl)ethyl]piperazine-1-carboxylate (3.3 g, 8.4 mmol) and cyanomethylene tri-n-butylphosphorane (3.65 g, 15.1 mmol) were dissolved in 30 mL of benzene, the solution was degassed, and then heated to 100° C. for 3 h. LC-MS showed the product peak (M+1=389). The reaction mixture was cooled and evaporated to dryness. The residue was purified by MPLC through a 330 g Redi-sep column and eluted with a 15% acetone/85% hexane mixture to yield a cis-trans mixture of the title compound.

Step E: tert-butyl(3R,9aS)-3-(1-oxo-1,3-dihydro-2-benzofuran-5-yl)hexahydropyrazino[2,1-c][1,4]oxazine-8(1H)-carboxylate and tert-butyl(3S,9aS)-3-(1-oxo-1,3-dihydro-2-benzofuran-5-yl)hexahydropyrazino[2,1-c][1,4]oxazine-8(1H)-carboxylate The cis-trans isomer mixture from the prior step was separated using a ChiralCEL OD 4.6×250 mm 10µ, column eluting with a 45% IPA/55% heptane solvent system. The trans-isomer 1A eluted first at 11.46 min and the cis-isomer 1B second at 17.43 min. 1A: $^1$H-NMR (500 MHz, CDCl$_3$): δ ppm 7.915 (d, J=8 Hz, 1H), 7.56 (s, 1H), 7.52 (d, J=8 Hz, 1H), 5.33 (s, 2H), 4.81 (dd, J=2 Hz, 10.5 Hz, 1H), 4.03-4.07 (m, 2H), 4.00 (dd, J=3, 11.25 Hz, 1H), 3.51 (t, J=10.5 Hz, 1H), 3.04 (b, 1H), 2.96 (dd J=2, 11.75 Hz, 1H), 2.76 (d, J=10.5 Hz, 1H), 2.57 (b, 1H), 2.21-2.32 (m, 3H), 1.5 (s, 9H). 1B: $^1$H-NMR (500 MHz, CDCl$_3$): δ ppm 7.95 (d, J=8 Hz, 1H), 7.72 (d, J=8 Hz, 1H), 7.70 (s, 1H), 5.37 (s, 2H), 4.91 (t, J=3.5 Hz, 1H), 3.65-4.07 (b, 2H), 3.64 (dd, J=3, 11.5 Hz, 1H), 3.40 (t, J=11.5 Hz, 1H), 3.29 (dd, J=3.5, 12 Hz, 1H), 3.02 (b, 1H), 2.82 (dd, J=3.5, 12 Hz, 2H), 2.66-2.67 (b, 1H), 2.50 (t, J=11 Hz, 2H), 1.5 (s, 9H).

Intermediate 2

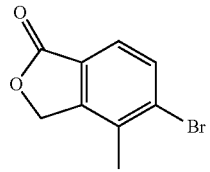

5-bromo-4-methyl-2-benzofuran-1(3H)-one

Step A: (3-bromo-2-methylphenyl)methanol

To a solution of 3-bromo-2-methyl benzoic acid (35.0 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-bromo-4-methyl-2-benzofuran-1(3H)-one

To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The solution was filtered through a Celite pad, washed with EtOAc, adsorbed onto silica and purified by silica gel chromatography to afford the title compound: $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 3

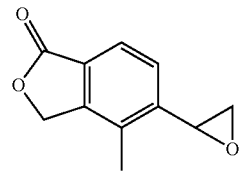

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. LC-MS: M+1=175.

Step B: 4-methyl-5-oxiran-2-yl-2-benzofuran-1(3H)-one

5-Ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC through a 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H); LC-MS: M+1=191.

Intermediates 3A and 3B (Method 1)

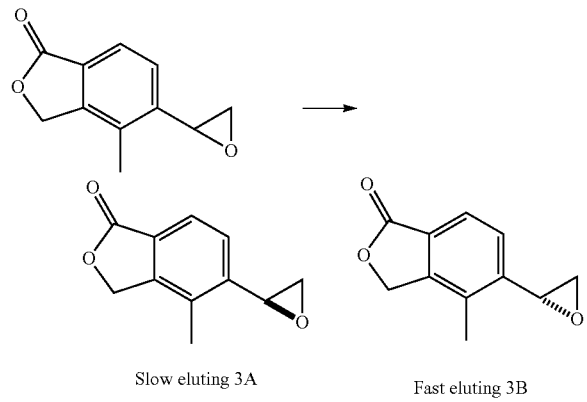

Slow eluting 3A                    Fast eluting 3B

3A: 4-methyl-5-[(2S)-oxiran-2-yl]-2-benzofuran-1 (3H)-one and 3B: 4-methyl-5-[(2R)-oxiran-2-yl]-2-benzofuran-1(3H)-one Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul Injections were spaced every 2.12 mins. The faster eluting epoxide 3B eluted at 5.2 min, and the slower eluting epoxide 3A eluted at 5.6 min.

Alternatively, the resolution could also be achieved using a mobile phase of 8% MeOH/98% CO$_2$ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer 3A and 3B was inferred based on the X-ray crystal structure determination of a final compound made with 3B, and by Mosher ester and Trost ester HNMR analysis of esters made starting from 3B (used tert-butyl-4-[(2R-2-hydroxy-2-(4-methyl-1-oxo-1,3-dihydro-2-benzofuran-5-yl)ethyl}piperazine-1-carboxylate).

Intermediate 3B (Method 2)

Step A: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9.735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5.358 mmol) diluted with water to a total of 1.0 L was added. Off-gassing was observed, and the temperature increased to 25° C. MTBE (1.5 L) was added, and the reaction mixture was transferred to a reparatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the solids were washed with 4:1 heptane:MTBE (500 mL), followed by heptane (500 mL). The solid was dried under vacuum, providing 4-bromo-3-hydroxymethyl-2-methyl phenol.

Step C: 5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then reaction mixture was cooled to 95° C. 41.5 mL water was added (sparged with N$_2$), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flok and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

Step D: Trifluoromethanesulfonic acid 4-methyl-1-oxo-1,3-dihydro-isobenzofuran-5-yl ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature<10° C. After stirring the reaction mixture for an additional 15 min, the reaction mixture was quenched with water (200 mL), then stirred with DARCO® KB (activated carbon, 25 g) for 15 min. The biphasic mixture was filtered over Solka Floc, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product precipitating during concentration. The suspension was filtered, the solid washed with heptane and dried under vacuum and nitrogen, providing the title compound.

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one.

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck RB flask equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

Intermediates 4A and 4B

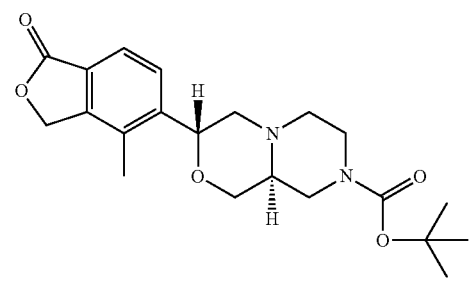

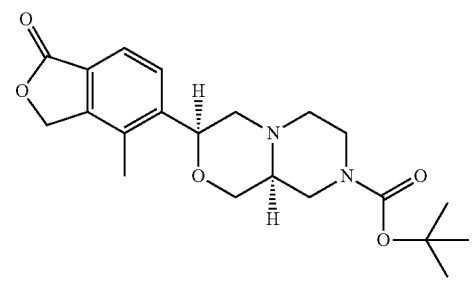

4A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate Step A: tert-butyl(3S)-3-(hydroxymethyl)-4-[2-hydroxy-2-(4-methyl-1-oxo-1,3-dihydro-2-benzofuran-5-yl)ethyl]piperazine-1-carboxylate 4-Methyl-5-oxiran-2-yl-2-benzofuran-1(3H)-one (3.00 g, 15.8 mmol) and (S)-4-N-BOC-2-hydroxymethylpiperazine (5.12 g. 23.7 mmol) were suspended in ethanol (10 mL) in a 20 mL microwave tube. The reaction mixture was degassed and heated in a microwave apparatus for 30 min at 150° C. The reaction mixture was evaporated to dryness, then chromatographed through a 330 g Redi-sep column and eluted with a solvent system of 1:1 EtOAc/hexane to 100% EtOAc to yield the title compound. LC-MS: M+1=407.

Step B: tert-butyl(9aS)-3-(4-methyl-1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(4-methyl-1-oxo-1,3-dihydro-2-benzofuran-5-yl)ethyl]piperazine-1-carboxylate (3.3 g, 8.2 mmol) and cyanomethylene tri-n-butylphosphorane (2 equivalents) were dissolved in 45 mL benzene in a sealed and degassed tube. The mixture was heated to 100° C. for 3 h. The reaction mixture was cooled and evaporated to dryness. The residue was purified by chromatography through a 330 g Redi-sep column and eluted with 30% acetone/70% hexane mixture to yield the title compound as a cis-trans mixture. LC-MS: M+1=389.

Step C: Intermediates 4A and 4B

The cis/trans mixture of the product of Step B was separated using a Chiralpak AD 4.6×250 mm 10μ column with a 30% IPA/70% heptane solvent system. The trans isomer 4A eluted first at 15.7 min and the cis-isomer 4B second at 24.9 min. 4A: ¹H-NMR (500 MHz, CDCl₃): δ ppm 7.82 (d, J=8 Hz, 1H) 7.73 (d, J=8 Hz, 1H), 5.28 (s, 2H), 4.97 ppm (dd, J=2.5, 10 Hz, 1H), 4.02 (dd, J=2.5, 11 Hz, 1H), 3.87-4.18 ppm (b, 2H) 3.53 ppm (t, J=11 Hz, 1H), 3.04 (b, 1H), 2.88 ppm (d, J=12 Hz, 1H), 2.76 (d, J=11.5 Hz, 1H), 2.54-2.59 (b, 1H), 2.36 (s, 3H), 2.22-2.34 (m, 3H), 1.50 (s, 9H): LC-MS: M+1=389.
4B: ¹H-NMR (500 MHz, CDCl₃): δ ppm 8.12 (d, J=8 Hz, 1H), 7.79 (d, J=8 Hz, 1H), 5.29 (s, 2H), 5.01 (t, J=4 Hz, 1H), 3.69-4.03 (b, 2H), 3.62 (t, J=8.5 Hz, 1H), J=7.5 Hz, 1H), 3.23 (dd, J=4, 12 Hz, 1H), 3.09-3.20 ppm (b, 1H), 2.81 (dd, J=4, 12 Hz, 1H), 2.69-2.90 ppm (b, 2H), 2.55-2.58 (b, 2H), 2.38 ppm (s, 3H), 1.50 ppm (s, 9H): LC-MS: M+1=389.

Intermediates 4C and 4D

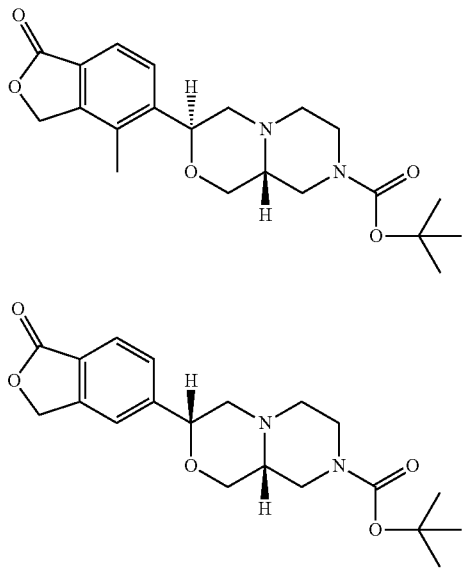

4C

4D

4C: tert-butyl(3S,9aR)-3-(4-methyl-1-oxo-1,3-dihydro-2-benzofuran-5-yl)hexahydropyrazino[2,1-c][1,4]oxazine-8(1H)-carboxylates 4D: tert-butyl(3R,9aR)-3-(4-methyl-1-oxo-1,3-dihydro-2-benzofuran-5-yl)hexahydropyrazino[2,1-c][1,4]oxazine-8(1H)-carboxylate Intermediates 4C and 4D were made in a similar fashion to that described above for 4A and 4B, except (R)-4-N-BOC-2-hydroxymethylpiperazine was used in place of (S)-4-N-BOC-2-hydroxymethylpiperazine. The cis-trans isomers 4C and 4D were separated using a ChiralCEL OD 4.6×250 mm 10μ column with the 20% IPA/80% heptane solvent system. The trans-isomer 4C eluted first at 22.8 min. and the cis-isomer 4D eluted at 37.8 min.: 4C: ¹H-NMR (500 MHz, CDCl₃): δ ppm 7.82 (d, J=8 Hz, 1H) 7.73 (d, J=8 Hz, 1H), 5.28 (s, 2H), 4.97 (dd, J=2.5, 10 Hz, 1H), 4.02 (dd, J=3, 11 Hz, 1H), 4.05-4.20 (b, 2H) 3.53 (t, J=4 Hz, 1H), 3.05 (b, 1H), 2.88 (dd, J=2, 11.7 Hz, 1H), 2.75 (d, J=10.5 Hz, 1H), 2.55 (b, 1H), 2.36 (s, 3H), 2.22-2.36 (m, 3H), 1.51 (s, 9H); LC-MS: M+1=389. 4D: ¹H-NMR (500 MHz, CDCl₃): δ ppm 8.12 (d, J=7.8 Hz, 1H), 7.79 (d, J=8 Hz, 1H), 5.30 (d, J=1.8, 2H), 5.02 (t, J=3.85 Hz, 1H), 3.70-4.05 (b, 2H), 3.62 (dd, J=3, 11.65 Hz, 1H), 3.37 (t, J=9 Hz, 1H), 3.23 (dd, J=4, 12 Hz, 1H), 3.10 (b, 1H), 2.80-2.86 (m, 3H), 2.57 (b, 2H), 2.38 ppm (s, 3H), 1.50 ppm (s, 9H); LC-MS: M+1=389.

Intermediate 5

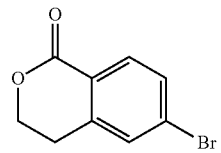 [SMILES: O=C1OCCc2cc(Br)ccc21]

6-bromo-3,4-dihydro-1H-isochromen-1-one

Method A:
A 250-mL, three-necked, round-bottomed flask equipped with a septum, nitrogen inlet needle, and thermocouple was charged with diisopropylamine (3.10 g, 30.6 mmol) and 30 mL of THF. The reaction mixture was cooled at −20° C. while n-BuLi (2.5 M, 12.2 mL, 30.6 mmol) was added dropwise via syringe keeping the internal temperature below 0° C. The resulting reaction mixture was stirred at 0° C. for 15 min. The reaction mixture was then cooled at −40° C. while 4-bromo-2-methylbenzonitrile (4.00 g, 20.4 mmol) in 10 mL of THF was added dropwise via syringe over 1 h. An internal temperature of ca. −40° C. was maintained during the addition. The resulting reaction mixture was stirred at −40° C. for 30 min and then charged with DMF (2.98 g, 40.8 mmol, ca. 50 ppm water) in one portion. The reaction mixture was stirred at −40° C. for 15 min. The reaction mixture was quenched with MeOH (5 vol., 20 mL) and then charged with NaBH₄ (0.770 g, 20.4 mmol) in one portion and allowed to warm to room temperature. After complete reduction of intermediate aldehyde (as judged by HPLC analysis), the reaction mixture was carefully quenched with 5 M HCl (with cooling) to adjust the pH to 2-3. The reaction mixture was extracted with EtOAc and then solvent-switched to EtOH (40 mL). H₂SO₄ (98%, 20.0 g, 204 mmol) was added in one portion and the resulting reaction mixture was stirred at reflux for 24 h. After complete cyclization (monitored by HPLC analysis), the reaction mixture was cooled to room temperature and then solvent-switched to EtOAc. The resulting organic layer was washed with water, brine, and solvent-switched to MTBE. Precipitation from 1:1 MTBE:heptane afforded 6-bromo-3,4-dihydro-1H-isochromen-1-one.

Method B:

A solution of DIPA (4 M, 270 mL, 1080 mmol) in THF (900 mL) was cooled to −65° C. and hexyl lithium (2.1 M, 505 mL, 1060 mmol) was added dropwise over 15 min maintaining the internal temp<−55° C. Upon completion of the addition, the reaction mixture was warmed up to −40° C. where it was stirred 30 min. To the resulting solution of LDA was added 4-bromo-2-methylbenzoic acid (90 g, 419 mmol) slowly (over 15 min) as a solution in THF (400 mL). The reaction mixture was stirred for 30 min at −40° C. and then warmed to 15° C. at which point paraformaldehyde (50.30 g, 1674 mmol) was added in 3 portions as a solid keeping the internal temperature (ice water bath) below <18° C. Stirring was then continued at room temperature for 1 hour. After a second hour of stirring, the vessel was immersed in an ice water bath and 3N HCl (650 mL) was added at such a rate to keep the internal temperature less than 30° C. The contents of the reaction vessel was subsequently transferred to a separatory funnel where it was extracted 3×400 mL EtOAc and the combined organic phases were then concentrated to ~800 mL total volume. To this was added Amberlyst 15 resin (12 g) and the resulting mixture stirred at 48° C. overnight (~14 h). HPLC analysis the following morning indicated that cyclization to the desired 6-bromo-3,4-dihydro-1H-isochromen-1-one was nearly complete. The resin was removed by filtration and the solution concentrated to ~200 mL total volume at which point the desired product began to precipitate and the solids were then collected by filtration. The cake was subsequently washed with MTBE (2×80 mL) to give the first crop of product. Additional material was salvaged by washing the collected supernatant 2× with 200 mL 10% $K_2CO_3$, aq followed by 200 mL 1M $H_3PO_4$. After concentration to ~100 mL the precipitated material was collected by filtration, washed with MTBE and then combined with the first crop of 6-bromo-3,4-dihydro-1H-isochromen-1-one and dried.

Intermediate 6A and 6B

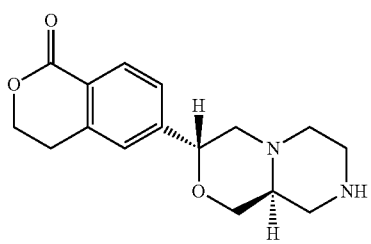

6A

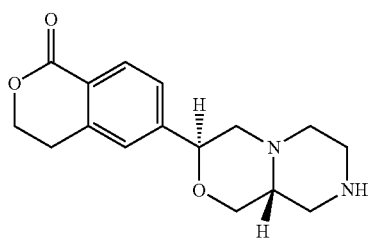

6B

6A: 6-[(3R,9aS)-octahydropyrazino[2,1-c][1,4]oxazin-3-yl]-3,4-dihydro-1H-isochromen-1-one Step A:
6-(bromoacetyl)-3,4-dihydro-1H-isochromen-1-one 6-Bromo-3,4-dihydro-1H-isochromen-1-one (6.90 g, 30.4 mmol), tributyl(1-ethoxyethenyl)stannane (10.8 mL, 31.9 mmol, 1.05 equiv), and $PdCl_2(PPh_3)_2$ (1.07 g, 1.52 mmol, 0.05 equiv) were weighed into a 250 mL round bottom flask. To this was added dioxane (70 mL) and the resulting mixture stirred at 80° C. for 4 h. The reaction was not complete by HPLC, therefore another 0.1 equiv of tin reagent was added. After 30 min 6-bromo-3,4-dihydro-1H-isochromen-1-one had been fully consumed as indicated by HPLC. The reaction mixture was cooled to 0° C. and 35 mL THF followed by 14 mL $H_2O$ were added. To this was introduced solid N-bromosuccinimide (5.68 g, 31.9 mmol, 1.05 equiv), added in portions over 5 min. After stirring for 30 min there was still evidence of remaining enol ether, therefore NBS was added in small portions (~300 additional mg added) until it was consumed as evidenced by HPLC. Water was then added and the mixture extracted with EtOAc. The aqueous layer was extracted 2 additional times with EtOAc, the combined organics dried with $MgSO_4$, filtered and concentrated in vacuo. This was transferred with EtOAc to a 100 mL round bottom flask, the resulting solution concentrated to ~25 mL total volume, at which point hexane (50 mL) was added dropwise. When complete the heterogeneous mixture was stirred for 30 min, then cooled to 0° C. and stirred for 10 min, then filtered and washed twice with hexanes. The desired product was dried under a nitrogen bag, then purified by flash chromatography (12 to 100% EtOAc/Hex) to provide the title compound.

Step B: tert-butyl(9aS)-3-hydroxy-3-(1-oxo-3,4-dihydro-1H-isochromen-6-yl)hexahydropyrazino[2,1-c][1,4]oxazine-8(1H)-carboxylate 6-(Bromoacetyl)-3,4-dihydro-1H-isochromen-1-one (~1.54 g, ~5.72 mmol, presence of α-chloroketone was noted, ~10%) and commercially available (S)-4-N-BOC-2-hydroxymethylpiperazine (1.24 g, 5.72 mmol) were added to a round bottom flask and diluted with THF (50 mL). Diisopropylethylamine (1.30 mL, 7.44 mmol) was then introduced and the mixture left stirring for 14 h at RT during which time a considerable amount of solid had formed (presumably HBr salt of DIPEA). The reaction mixture was diluted with EtOAc, then washed with saturated $NH_4Cl_{aq}$ followed by $H_2O$. Both aqueous layers were sequentially back extracted once with another portion of EtOAc, the organics were then combined, dried with $MgSO_4$, filtered, and concentrated in vacuo. The recovered crude product was subjected to purification by flash chromatography (Biotage, 50% EtOAc/Hex) to afford the title compound.

Step C: 6-[(3R,9aS)-octahydropyrazino[2,1-c][1,4]oxazin-3-yl]-3,4-dihydro-1H-isochromen-1-one tert-Butyl(9aS)-3-hydroxy-3-(1-oxo-3,4-dihydro-1H-isochromen-6-yl)hexahydropyrazino[2,1-c][1,4]oxazine-8(1H)-carboxylate (1.84 g, 4.55 mmol) was diluted with TFA (18 mL, 234 mmol) and cooled to 0° C. Some offgassing was apparent and after a few minutes a homogenous solution had been formed. Approximately 5 minutes post-TFA addition, $Et_3SiH$ (5.09 mL, 31.8 mmol) was added and the reaction mixture allowed to slowly warm to RT (allowed to warm naturally in the ice bath) where it was stirred for 18 h. The trans:cis diastereomeric ratio appeared to be ~95:5. The reaction vessel was transferred to a rotary evaporator and concentrated in vacuo to a two phase liquid. This crude material was diluted with CH$_2$Cl$_2$ washed with NaHCO$_{3,aq}$ then water. The separately kept aqueous layers were subsequently extracted once with the same portion of CH$_2$Cl$_2$, the combined organics dried with MgSO$_4$, filtered and concentrated in vacuo. The crude residue was dried under house vacuum then the mixture was further purified by flash chromatography (2% MeOH 2% Et$_3$N in CH$_2$Cl$_2$) to afford the title compound.

6B: 6-[(3S,9aR)-octahydropyrazino[2,1-c][1,4]oxazin-3-yl]-3,4-dihydro-1H-isochromen-1-one The same procedure described above to prepare 6-[(3R,9aS)-octahydropyrazino[2,1-c][1,4]oxazin-3-yl]-3,4-dihydro-1H-isochromen-1-one was used to prepare the title compound starting from 6-(bromoacetyl)-3,4-dihydro-1H-isochromen-1-one and commercially available (R)-4-N-BOC-2-hydroxymethylpiperazine; LC-MS (IE, m/z): 289.1 [M+1]$^+$.

Intermediate 7 and Isomers 7A and 7B

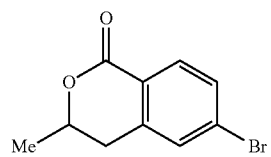

7

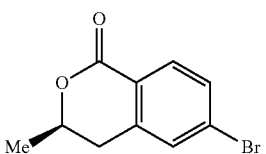

7A

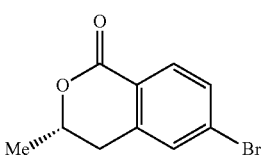

7B 6-bromo-3-methyl-3,4-dihydro-1H-isochromen-1-one and individual isomers (3R)-6-bromo-3-methyl-3,4-dihydro-1H-isochromen-1-one and (3S)-6-bromo-3-methyl-3,4-dihydro-1H-isochromen-1-one A −78° C. solution of diisopropylamine (13.3 mL, 93.0 mmol) in THF (155 mL) was treated with n-BuLi (1.6 M in Hexanes; 58 mL, 93 mmol) over a period of 15 minutes using a syringe pump. In a separate flask, a solution of 2-methyl-4-bromo benzoic acid (10.0 g, 46.5 mmol) and HMPA (8.33 mL, 46.5 mmol) in THF (155 mL) was cooled to −78° C. Methyl Lithium (29.1 mL, 46.5 mmol) was added slowly via syringe to the cooled solution. The resulting solution was stirred for 10 minutes and then transferred via cannula to the LDA solution at −78° C. The resulting solution was stirred at −78° C. for an additional 1 h before being quenched with anhydrous acetaldehyde (7.88 mL, 140 mmol) and the reaction was then taken out of the dry ice acetone bath and allowed to stir for an additional 1 h. The flask containing the reaction mixture was then resubmerged in the dry ice acetone bath before it was quenched with 4M HCl in dioxane (50 mL) followed by 25 mL of MeOH. The reaction was stirred at room temp for an additional 1 h. The crude reaction mixture was partitioned between 200 mL ethyl acetate and 200 mL water. The organic layer was washed with water, brine, dried with magnesium sulfate, filtered and concentrated. Purification via MPLC (30-70% DCM/Hexanes) afforded 7 as a racemic mixture which was separable by chiral SFC HPLC using, for example, a Chiralpak AS column to obtain 7A and 7B. $^1$H NMR (500 MHz; CDCl$_3$): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS (IE, m/z): 241 [M+1]$^+$.

Intermediate 7A (Method 2)

(3R)-6-bromo-3-methyl-3,4-dihydro-1H-isochromen-1-one

Step A: 4-bromo-N,N-diethyl-2-methylbenzamide

A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide: LC-MS: (M+H)$^+$ 270.

Step B: 4-bromo-N,N-diethyl-2-(2-oxopropyl)benzamide

A 2M solution of LDA (35.2 mL, 70.3 mmol) in THF (176 mL) cooled to −78° C. was treated with slow addition of 4-bromo-N,N-diethyl-2-methylbenzamide (19 g, 70.3 mmol) in dry THF (176 mL). The reaction was allowed to stir at −78° C. for 1 hour before it was quenched with N-methoxy-N-methylacetamide (22.43 mL, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an oil out of which the product precipitated. The oil was decanted off and the solid was washed with hexanes and dried using a buchner funnel to afford 4-bromo-N,N-diethyl-2-(2-oxopropyl)benzamide: LC-MS: (M+H)$^+$ 312.

Step C: 4-bromo-N,N-diethyl-2-[(2R)-2-hydroxypropyl]benzamide

A flask equipped with an overhead stirrer was charge with pH=8 Phosphate Buffer (156 mL, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg of keto-reductase enzyme KRED P1B2 (available from Codexis, Inc., 200 Penobscot Drive, Redwood City, Calif. 94063, www.codexis.com, tel. 1-650-421-8100) was added to the reaction vessel and stirred at 500 rpm at 30° C. until enzyme was wetted (about 40 min). Lastly, a solution of 4-bromo-N,N-diethyl-2-(2-oxopropyl)benzamide (1.5 g, 4.80 mmol) dissolved in DMSO (14.56 mL) (pre-warmed on stir plate to 30° C.) was added to the reaction over ~3 min and agitate at 30° C. (400 rpm) overnight.

After 48 hours the reaction was cooled to room temperature and then 75 g of potassium carbonate was added to the reaction in portions and stirred for 15 minutes until enzyme clumps together when stirring is stopped. Next, acetonitrile (50 mL) was poured into the reaction flask and the layers were thoroughly mixed. Stirring was stopped after 15-20 minutes, the layers allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 mL MTBE. The combined organic extracts were dried over magnesium sulfate, filtered and concentrated. Purification via MPLC (30-70% EtOAc/Hex) afforded 4-bromo-N,N-diethyl-2-[(2R)-2-hydroxypropyl]benzamide.

Step D: (3R)-6-bromo-3-methyl-3,4-dihydro-1H-isochromen-1-one

A solution of 4-bromo-N,N-diethyl-2-[(2R)-2-hydroxypropyl]benzamide (12.2 g, 38.8 mmol) dissolved in 4N HCl in dioxane (200 mL) was stirred at room temperature and monitored by TLC. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one: $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS: (M+1)$^+$ 241.

Intermediate 7B (Method 2)

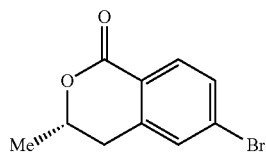 [SMILES: C[C@H]1Cc2cc(Br)ccc2C(=O)O1]

(3S)-6-bromo-3-methyl-3,4-dihydro-1H-isochromen-1-one (3S)-6-Bromo-3-methyl-3,4-dihydro-1H-isochromen-1-one was prepared in a similar manner as (3R)-6-Bromo-3-methyl-3,4-dihydro-1H-isochromen-1-one except using keto-reductase enzyme KRED P1H9 (available from Codexis, Inc., 200 Penobscot Drive, Redwood City, Calif. 94063, www.codexis.com, tel. 1-650-421-8100) in Step C, which gave the opposite enantiomer of the resulting alcohol.

Intermediates 8A and 8B

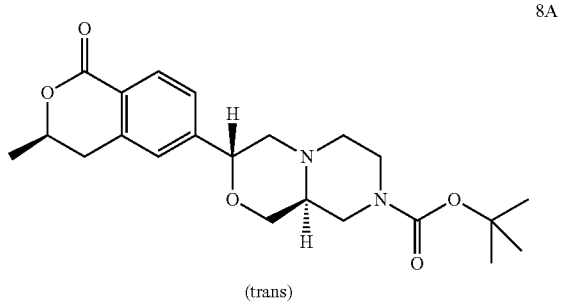

(trans)

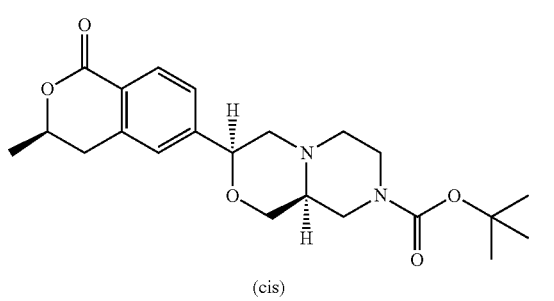

(cis)

8A: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate 8B: tert-Butyl (3S,9aS)-3-[(3R)-3-methyl-1-oxo-3,4-dihydro-1H-isochromen-6-yl]hexahydropyrazino[2,1-c][1,4]oxazine-8(1H)-carboxylate Step A: (3R)-6-ethenyl-3-methyl-3,4-dihydro-1H-isochromen-1-one A solution of (3R)-6-bromo-3-methyl-3,4-dihydro-1H-isochromen-1-one (2.4 g, 9.96 mmol) and triethylamine (2.78 mL, 19.91 mmol) in EtOH (39.8 mL) was added to a microwave vial containing PdCl$_2$(dppf)-CH$_2$Cl$_2$, (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave the title compound.

Step B: (3R)-3-methyl-6-(oxiran-2-yl)-3,4-dihydro-1H-isochromen-1-one

A solution of 6-ethenyl-3-methyl-3,4-dihydro-1H-isochromen-1-one (1.69 g, 8.98 mmol) in DCM (60 mL) was treated with mCPBA (3.100 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give the title compound.

Step C: tert-butyl (3S)-3-(hydroxymethyl)-4-{2-hy-droxy-2-[(3R)-3-methyl-1-oxo-3,4-dihydro-1H-iso-chromen-6-yl]ethyl}piperazine-1-carboxylate A solution of (3R)-3-methyl-6-(oxiran-2-yl)-3,4-dihydro-1H-isochromen-1-one (325 mg, 1.59 mmol) and tert-butyl (3S)-3-(hydroxymethyl)piperazine-1-carboxylate (345 mg, 1.59 mmol dissolved in EtOH (7 mL) was heated in a sealed tube to 155° C. for 3 hours in the microwave. The reaction was cooled and concentrated to give crude product which was purified via MPLC (40-100% EtOAc/Hexane) to give the title compound as a mixture of diastereomers.

Step D: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate and tert-Butyl (3S,9aS)-3-[(3R)-3-methyl-1-oxo-3,4-dihydro-1H-isochromen-6-yl]hexahydropyrazino[2,1-c][1,4]ox-azine-8(1R)-carboxylate A sealed tube containing tert-butyl (3S)-3-(hydroxymethyl)-4-{2-hydroxy-2-[(3R)-3-methyl-1-oxo-3,4-dihydro-1H-isochromen-6-yl]ethyl}piperazine-1-carboxylate as a mixture of diastereomers (530 mg, 1.26 mmol) and cyanomethylenetributylphosphorane (304 mg, 1.26 mmol) dissolved in anhydrous benzene (8 mL) was degassed twice with nitrogen and then heated using a microwave to 135° C. for 2.5 hours. The reaction was allowed to cool and the crude mixture was concentrated and purified on MPLC (20-65% EtOAc/Hex) to afford a mixture of diastereomers as well as recovered starting material. The cis/trans mixture was purified via chiral HPLC (10% EtOH/Heptane) using AS column to give the trans isomer as the faster eluting peak and the cis isomer as the slower eluting peak. Alternatively, the mixture can be separated by chiral SFC-HPLC (40% 2:1 MeOH:MeCN/CO$_2$) using an IC column.

8A: $^1$H NMR (500 MHz; CDCl$_3$): 8.08 (d, J=8.1 Hz, 1H), 7.35 (d, J=8.0 Hz, 1H), 7.28 (s, 1H), 4.70 (m, 2H), 4.00 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.53 (d, J=6.4 Hz, 3H), 1.49 (s, 9H);

LC-MS: (M+1)$^+$ 403; 8B: $^1$H NMR (500 MHz; CDCl$_3$): 8.10 (d, J=8.2 Hz, 1H), 7.54 (d, J=8.0 Hz, 1H), 7.40 (s, 1H), 4.81 (bt, 1H), 4.71 (m, 1H), 3.62 (dd, J=2.8, 11.5 Hz, 1H), 3.41 (m, 1H), 3.25 (dd, J=3.7, 12.1 Hz, 1H), 2.95 (m, 4H), 2.76 (m, 3H), 2.50 (m, 2H), 2.28 (m, 1H), 1.54 (d, J=6.2 Hz, 3H), 1.49 (s, 9H); LC-MS: (M+1)$^+$ 403.

Intermediates 8C and 8D

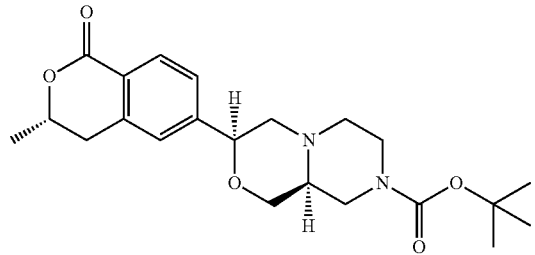

8C: tert-Butyl (3R,9aS)-3-[(3S)-3-methyl-1-oxo-3,4-dihydro-1H-isochromen-6-yl]hexahydropyrazino[2,1-c][1,4]oxazine-8(1H)-carboxylate 8D: tert-Butyl (3S,9aS)-3-[(3S)-3-methyl-1-oxo-3,4-dihydro-1H-isochromen-6-yl]hexahydropyrazino[2,1-c][1,4]oxazine-8(1H)-carboxylate 8C and 8D were prepared in a similar manner as Intermediates 8A and 8B except (3S)-6-Bromo-3-methyl-3,4-dihydro-1H-isochromen-1-one was used as the starting material. The cis/trans mixture was purified via chiral HPLC (30% 2:1 MeOH:MeCN/CO$_2$) on an AD column. The faster eluting diastereomer was the trans isomer. 8C: $^1$H NMR (500 MHz; CDCl$_3$): 8.07 (d, J=8.1 Hz, 1H), 7.35 (d, J=8.0 Hz, 1H), 7.28 (s, 1H), 4.72 (dd, J=1.8, 10.5 Hz, 1H), 4.68 (m, 1H), 4.1-3.8 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.54 (d, J=6.2 Hz, 3H), 1.49 (s, 9H); LC-MS: (M+1)$^+$ 403; 8D: $^1$H NMR (500 MHz; CDCl$_3$): 8.10 (d, J=8.2 Hz, 1H), 7.54 (d, J=8.0 Hz, 1H), 7.39 (s, 1H), 4.81 (bt, 1H), 4.71 (m, 1H), 3.62 (dd, J=2.8, 11.5 Hz, 1H), 3.41 (m, 1H), 3.25 (dd, J=3.7, 12.1 Hz, 1H), 2.95 (m, 4H), 2.76 (m, 3H), 2.50 (m, 2H), 2.28 (m, 1H), 1.54 (d, J=6.2 Hz, 3H), 1.48 (s, 9H); LC-MS: (M+1)$^+$ 403.

Intermediates 8E and 8F

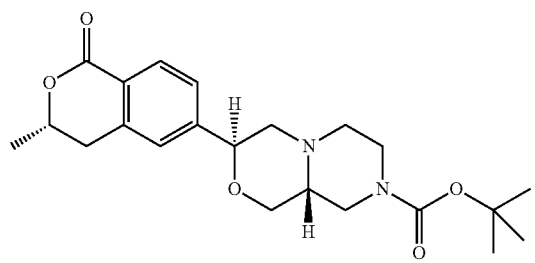

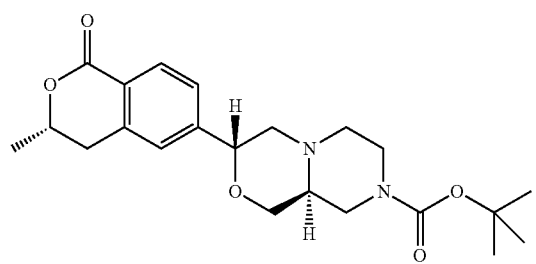

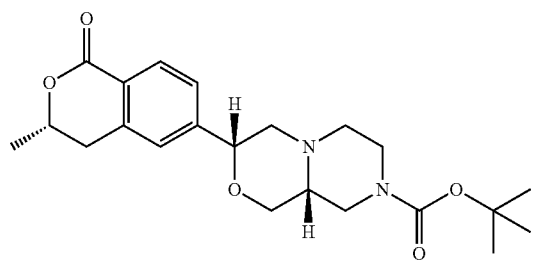

8E: tert-Butyl (3S,9aR)-3-[(3S)-3-methyl-1-oxo-3,4-dihydro-1H-isochromen-6-yl]hexahydropyrazino[2,1-c][1,4]oxazine-8(1H)-carboxylate 8F: tert-Butyl (3R,9aR)-3-[(3S)-3-methyl-1-oxo-3,4-dihydro-1H-isochromen-6-yl]hexahydropyrazino[2,1-c][1,4]oxazine-8(1H)-carboxylate Intermediates 8E and 8F were prepared in a similar manner as Intermediates 8A and 8B except (3S)-6-Bromo-3-methyl-3,4-dihydro-1H-isochromen-1-one and tert-butyl (3R)-3-(hydroxymethyl)piperazine-1-carboxylate were used as the starting materials. The cis/trans mixture was purified via MPLC (20-65% EtOAc/Hex). The faster eluting diastereomer was the trans isomer: 8E: $^1$H NMR (500 MHz; CDCl$_3$): 8.07 (d, J=8.2 Hz, 1H), 7.35 (d, J=8.0 Hz, 1H), 7.27 (s, 1H), 4.71 (dd, J=2.0, 10.7 Hz, 1H), 4.68 (m, 1H), 4.0 (bs, 2H), 3.97 (dd, J=2.0, 11.1 Hz, 2H), 3.48 (t, J=10.8 Hz, 1H), 2.99 (m, 4H), 2.74 (d, J=10.5 Hz, 1H), 2.2 (m, 3H), 1.53 (d, J=6.4 Hz, 3H), 1.49 (s, 9H). (M+1)$^+$ 403. 8F: $^1$H NMR (500 MHz; CDCl$_3$): 8.09 (d, J=8.9 Hz, 1H), 7.53 (d, J=8.3 Hz, 1H), 7.39 (s, 1H), 4.81 (t, J=3.6 Hz, 1H), 4.69 (m, 1H), 3.62 (dd, J=3.0, 11.5 Hz, 1H), 3.42 (m, 1H), 3.24 (dd, J=3.6, 12.1 Hz, 1H), 2.97 (m, 4H), 2.76 (m, 3H), 2.50 (m, 2H), 2.28 (m, 1H), 1.54 (d, J=6.2 Hz, 3H), 1.47 (s, 9H). (M+1)$^+$ 403.

Intermediates 8G and 8H

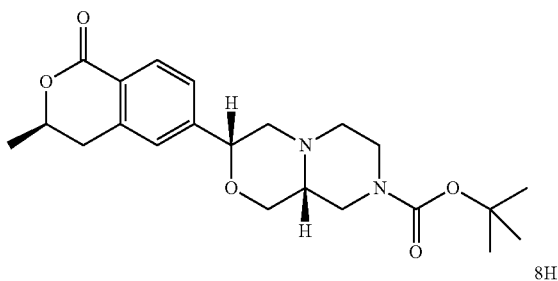

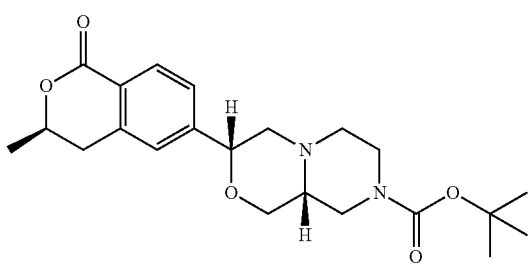

8G: tert-Butyl (3S,9aR)-3-[(3R)-3-methyl-1-oxo-3,4-dihydro-1H-isochromen-6-yl]hexahydropyrazino[2,1-c][1,4]oxazine-8(1H)-carboxylate 8H: tert-Butyl (3R,9aR)-3-[(3R)-3-methyl-1-oxo-3,4-dihydro-1H-isochromen-6-yl]hexahydropyrazino[2,1-c][1,4]oxazine-8(1H)-carboxylate 8G and 8H were prepared in a similar manner as 8A and 8B except (3R)-6-Bromo-3-methyl-3,4-dihydro-1H-isochromen-1-one and tert-butyl (3R)-3-(hydroxymethyl)piperazine-1-carboxylate were used as the starting materials. The cis/trans mixture was purified via chiral HPLC (20% 2:1 MeOH:MeCN/CO$_2$) on OJ column. The slower eluting diastereomer was the trans isomer: 8G LC-MS: (M+1)+ 403; 8H: LC-MS: (M+1)+ 403.

Intermediate 9

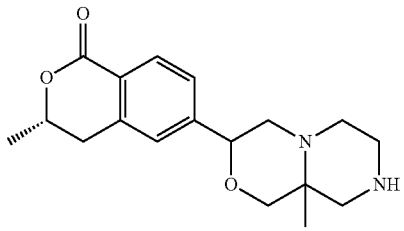 [SMILES: C[C@H]1Cc2cc(C3CN4CCNCC4(C)CO3)ccc2C(=O)O1]

(3S)-3-Methyl-6-(9a-methyloctahydropyrazino[2,1-c][1,4]oxazin-3-yl)isochroman-1-one Step A: Benzyl 4-(2-hydroxy-2-((S)-3-methyl-1-oxoisochroman-6-yl)ethyl)-3-(hydroxymethyl)-3-methylpiperazine-1-carboxylate To a solution of racemic benzyl 3-(hydroxymethyl)-3-methylpiperazine-1-carboxylate (1.0 g, 3.8 mmol) (prepared as described in US Patent Application Publication No. US2007/0088039A1, Example 10) in EtOH (13 mL) was added (3S)-3-methyl-6-(oxiran-2-yl)isochroman-1-one (773 mg, 3.80 mmol), the resulting mixture was heated at 80° C. for 16 h, the reaction mixture was concentrated to dryness and purified on silica gel to afford the title compound: LC/MS: m/e 469.2 (M+H)$^+$.

Step B: Benzyl 9a-methyl-3-((S)-3-methyl-1-oxoisochroman-6-yl)hexahydropyrazino[2,1-c][1,4]oxazine-8(1H)-carboxylate The mixture of benzyl 4-(2-hydroxy-2-((S)-3-methyl-1-oxoisochroman-6-yl)ethyl)-3-(hydroxymethyl)-3-methylpiperazine-1-carboxylate (762 mg, 1.60 mmol) and cyanomethylenetributylphosphorane (471 mg, 1.90 mmol) in dry benzene was degassed and heated to 135° C. in a microwave reactor for 3.5 h. After which point, the reaction mixture was cooled down to rt, concentrated to dryness and purified on silica gel to afford the title compound (cis or trans): MS: m/e 451.2 (M+H)$^+$.

Step C: (3S)-3-Methyl-6-(9a-methyloctahydropyrazino[2,1-c][1,4]oxazin-3-yl)isochroman-1-one The mixture of Benzyl 9a-methyl-3-((S)-3-methyl-1-oxoisochroman-6-yl)hexahydropyrazino[2,1-c][1,4]oxazine-8(1H)-carboxylate (215 mg, 0.500 mmol) and 10% Pd-C (56 mg, 0.05 mmol) in MeOH (10 mL) was stirred under a hydrogen balloon for 16 h. After which point, the solution was filtered through Celite and the resulting filtrate was concentrated to afford the title compound: LC/MS: m/e 317.2 (M+H)$^+$.

Intermediate 10

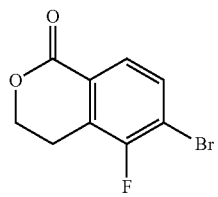 [SMILES: O=C1OCCc2c1ccc(Br)c2F]

6-Bromo-5-fluoro-3,4-dihydro-1H-isochromen-1-one

Step A: 4-Bromo-N-tert-butyl-3-fluoro-2-(2-hydroxyethyl)benzamide

A solution of diisopropylamine (6.2 mL, 44 mmol) in THF (200 mL) was treated with n-butyllithium (17.4 mL, 44.0 mmol) at 0° C. The solution was stirred for 30 min before being cooled to −78° C. Next, a solution of 4-bromo-N-tert-butyl-3-fluorobenzamide (4.8 g, 17 mmol) in THF (100 mL) was added. The solution was then warmed to −40° C. and maintained there for 1 h. Next, ethylene oxide (10 mL, 200 mmol) was added and the solution warmed to 0° C. After 1 h, the ice bath was removed and the solution was allowed to warm to rt. LC/MS indicated desired product present. The solution was quenched with MeOH, diluted with brine (200 mL), and extracted with EtOAc (300 mL). The organic layer was removed, dried over MgSO$_4$, filtered and concentrated. The crude product was purified using a 340 g Biotage SNAP (0-60% Hexanes: EtOAc) cartridge to yield the title compound: LC-MS: m/z 319.98 (M+H)$^+$.

Step B: 6-Bromo-5-fluoro-3,4-dihydro-1H-isochromen-1-one

A solution of 4-bromo-N-tert-butyl-3-fluoro-2-(2-hydroxyethyl)benzamide. (1.8 g, 5.7 mmol) and TsOH (1.3 g, 6.9 mmol) in toluene (100 mL)/THF (10 mL) was heated to reflux. After 1 h, TLC and LC/MS analysis indicated complete conversion. The solution was concentrated to dryness followed by dilution with Et$_2$O (150 mL). The organic layer was washed with brine, dried over MgSO$_4$, filtered and concentrated affording the title compound: LC-MS: m/z 246.92 (M+H)$^+$.

Intermediate 11A (trans)

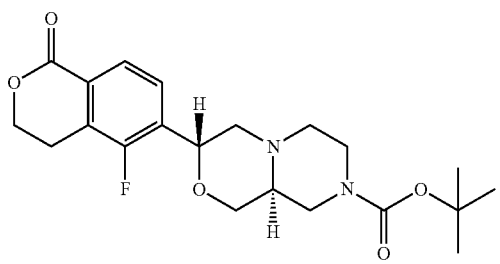 [SMILES: CC(C)(C)OC(=O)N1CCN2C[C@@H](c3ccc4c(c3F)CCOC4=O)OC[C@@H]2C1]

(3R,9aS)-tert-Butyl 3-(5-fluoro-1-oxoisochroman-6-yl)hexahydropyrazino[2,1-c][1,4]oxazine-8(1H)-carboxylate The title compound was made from 6-Bromo-5-fluoro-3,4-dihydro-1H-isochromen-1-one using a procedure analagous to that described for tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate above. The major trans isomer was isolated via MPLC (30-100% EtOAc/Hex) as the faster eluting isomer: $^1$H NMR (500 MHz, DMSO): δ 1.39 (s, 9H), 2.03-2.21 (m, 3H), 2.62-3.07 (m, 6H), 3.71-3.88 (m, 2H), 3.95 (dd, J=2.5, 11 Hz, 1H), 4.35 (m, 1H), 4.53 (t, J=6.0 Hz, 2H), 4.88 (d, J=10.0, 1H), 7.50 (t, J=7.0 Hz, 1H), 7.79 (d, J=8.0 Hz, 1H); LC/MS: m/e 317.2 (M+H)$^+$.

Intermediate 12A

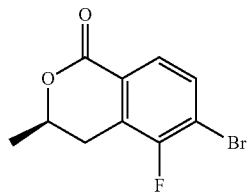

3-(R)-6-Bromo-5-fluoro-3-methyl-3,4-dihydro-1H-isochromen-1-one

Step A: 4-Bromo-N-tert-butyl-3-fluorobenzamide

To a suspension of 4-bromo-3-fluorobenzoic acid (19 g, 87 mmol) in DCM (200 mL) was added oxalyl chloride (9.10 mL, 104 mmol), followed by 1 drop of DMF. The mixture was allowed to stir at rt for 2 h. Upon clarification of the suspension, the solution was concentrated to dryness. The residue was redissolved in DCM (200 mL) and cooled to 0° C. Next the solution was treated with TEA (30.2 mL, 217 mmol) followed by tert-butyl amine (12.0 mL, 113 mmol). The solution was allowed to stir for 12 h. The reaction was diluted with 1N HCl (200 mL). The organic layer was then removed and washed with 1N NaOH. The organic layer was dried over MgSO$_4$, filtered and concentrated to afford the title compound.

Step B: 4-Bromo-N-tert-butyl-3-fluoro-2-[(2R)-2-hydroxypropyl]benzamide

A solution of diisopropylamine (11.7 mL, 82.0 mmol) in THF (200 mL) was treated with n-butyllithium (33 mL, 82 mmol) at 0° C. The solution was stirred for 30 min before being cooled to −78° C. Next, a solution of 4-bromo-N-tert-butyl-3-fluorobenzamide (9.0 g, 33 mmol) in THF (100 mL) was added. The solution was then warmed to −40° C. and maintained there for 1 h. Next, (R)-(+)-propylene oxide (6.9 mL, 98 mmol) was added and the solution warmed to 0° C. After 1 h, the ice bath was removed and the solution was allowed to warm to rt. LC/MS indicated desired product present. The solution was quenched with MeOH, diluted with brine (200 mL), and extracted with EtOAc (300 mL). The organic layer was removed, dried over MgSO$_4$, filtered and concentrated. The crude material was purified using a 340 g Biotage SNAP (0-60% Hexanes: EtOAc) cartridge to yield the title compound. LC-MS: m/z 332.08 (M+H)+.

Step C: 3-(R)-6-bromo-5-fluoro-3-methyl-3,4-dihydro-1H-isochromen-1-one

A solution of 4-bromo-N-tert-butyl-3-fluoro-2-[(2R)-2-hydroxypropyl]benzamide (4.60 g, 13.8 mmol) and TsOH (2.60 g, 13.8 mmol) in toluene (100 mL) was heated to reflux. After 1 h, TLC and LC/MS analysis indicated complete conversion. The solution was concentrated to dryness followed by dilution with Et$_2$O (150 mL). The organic layer was washed with brine, dried over MgSO$_4$, filtered and concentrated to yield the title compound: $^1$H-NMR (500 MHz, (CD$_3$)$_2$CO) δ ppm 7.76 (m, 2H), 4.80 (m, 1H), 3.25 (m, 1H), 2.91 (m, 1H), 1.52 (d, J=6.0 Hz, 3H); LCMS: m/z 257.95 (M+H)+.

Intermediate 12B

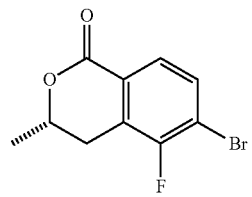

3-(S)-6-Bromo-5-fluoro-3-methyl-3,4-dihydro-1H-isochromen-1-one

The title compound was made according to the procedure described for 3-(R)-6-bromo-5-fluoro-3-methyl-3,4-dihydro-1H-isochromen-1-one, except using (S)-(+)-propylene oxide in Step B: $^1$H-NMR (500 MHz, (CD$_3$)$_2$CO) δ ppm 7.76 (m, 2H), 4.80 (m, 1H), 3.25 (m, 1H), 2.91 (m, 1H), 1.52 (d, J=6.0 Hz, 3H); LCMS: m/z 257.95 (M+H)+.

Intermediate 13A (trans)

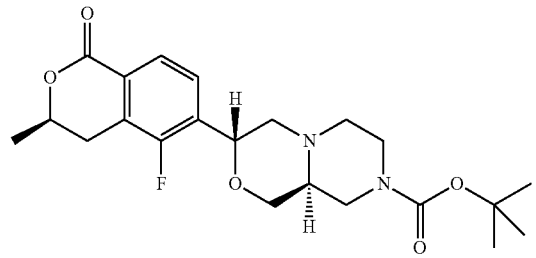 [SMILES: C[C@@H]1Cc2c(ccc([C@@H]3CN4CCN(C(=O)OC(C)(C)C)C[C@H]4CO3)c2F)C(=O)O1]

tert-butyl (3R,9aS)-3-[(3R)-5-fluoro-3-methyl-1-oxo-3,4-dihydro-1H-isochromen-6-yl]hexahydropyrazino[2,1-c][1,4]oxazine-8(1H)-carboxylate The title compound was made from 3-(R)-6-bromo-5-fluoro-3-methyl-3,4-dihydro-1H-isochromen-1-one using a procedure similar to that described for tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate (above). The cis/trans mixture was purified via chiral HPLC (30% 2:1 MeOH:MeCN/CO$_2$) on the AD column. The slower eluting diastereomer was the trans isomer. LC-MS: (M+1)+ 421.

Intermediate 13B (cis)

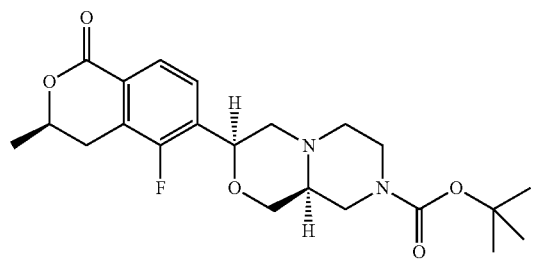 [SMILES: C[C@@H]1Cc2c(ccc([C@H]3CN4CCN(C(=O)OC(C)(C)C)C[C@H]4CO3)c2F)C(=O)O1]

tert-butyl (3S,9aS)-3-[(3R)-5-fluoro-3-methyl-1-oxo-3,4-dihydro-1H-isochromen-6-yl]hexahydropyrazino[2,1-c][1,4]oxazine-8(1H)-carboxylate The title compound was isolated as the faster eluting peak during chiral HPLC purification of tert-butyl (3R,9aS)-3-[(3R)-5-fluoro-3-methyl-1-oxo-3,4-dihydro-1H-isochromen-6-yl]hexahydropyrazino[2,1-c][1,4]oxazine-8(1H)-carboxylate: LC-MS: (M+1)+ 421.

Intermediate 13C (trans)

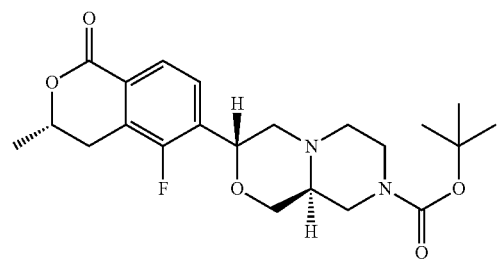 [SMILES: C[C@H]1Cc2c(ccc([C@@H]3CN4CCN(C(=O)OC(C)(C)C)C[C@H]4CO3)c2F)C(=O)O1]

tert-butyl (3R,9aS)-3-[(3S)-5-fluoro-3-methyl-1-oxo-3,4-dihydro-1H-isochromen-6-yl]hexahydropyrazino[2,1-c][1,4]oxazine-8(1H)-carboxylate The title compound was made from 3-(S)-6-Bromo-5-fluoro-3-methyl-3,4-dihydro-1H-isochromen-1-one using a procedure similar to that described for tert-butyl (3R,9aS)-3-[(3R)-5-fluoro-3-methyl-1-oxo-3,4-dihydro-1H-isochromen-6-yl]hexahydropyrazino[2,1-c][1,4]oxazine-8(1H)-carboxylate (above). The cis/trans mixture was purified via chiral SFC-HPLC (30% 2:1 MeOH:MeCN/CO$_2$) on OJ column. The faster eluting diastereomer was the trans isomer. LC-MS: (M+1)+ 421.

Intermediate 13D (cis)

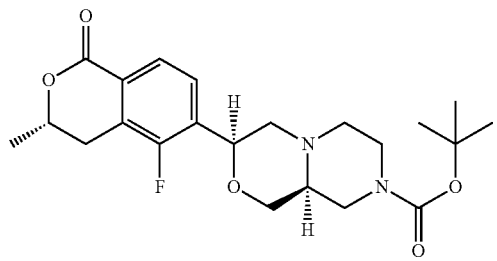 [SMILES: C[C@H]1Cc2c(ccc([C@H]3CN4CCN(C(=O)OC(C)(C)C)C[C@H]4CO3)c2F)C(=O)O1]

tert-butyl (3S,9aS)-3-[(3S)-5-fluoro-3-methyl-1-oxo-3,4-dihydro-1H-isochromen-6-yl]hexahydropyrazino[2,1-c][1,4]oxazine-8(1H)-carboxylate The title compound was isolated as slower eluting peak during chiral SFC-HPLC purification of tert-Butyl (3R,9aS)-3-[(3S)-5-fluoro-3-methyl-1-oxo-3,4-dihydro-1H-isochromen-6-yl]hexahydropyrazino[2,1-c][1,4]oxazine-8(1H)-carboxylate: LC-MS: (M+1)$^+$ 421.

Intermediate 13E (trans)

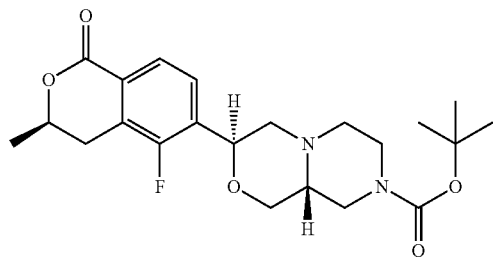 [SMILES: C[C@@H]1Cc2c(ccc([C@H]3CN4CCN(C(=O)OC(C)(C)C)C[C@@H]4CO3)c2F)C(=O)O1]

tert-butyl (3S,9aR)-3-[(3R)-5-fluoro-3-methyl-1-oxo-3,4-dihydro-1H-isochromen-6-yl]hexahydropyrazino[2,1-c][1,4]oxazine-8(1H)-carboxylate The title compound was made from 3-(R)-6-bromo-5-fluoro-3-methyl-3,4-dihydro-1H-isochromen-1-one using a procedure similar to that described for tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate (above), substituting tert-butyl (3R)-3-(hydroxymethyl)piperazine-1-carboxylate as the amino alcohol in Step C. The cis/trans mixture was purified via chiral HPLC (40% 2:1 MeOH:MeCN/CO$_2$) on AD column. The faster eluting diastereomer was the trans isomer. LC-MS: (M+1)$^+$ 421.

Intermediate 13F (cis)

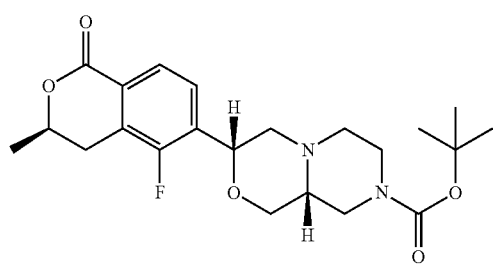 [SMILES: C[C@@H]1Cc2c(ccc([C@@H]3CN4CCN(C(=O)OC(C)(C)C)C[C@@H]4CO3)c2F)C(=O)O1]

tert-butyl (3R,9aR)-3-[(3R)-5-fluoro-3-methyl-1-oxo-3,4-dihydro-1H-isochromen-6-yl]hexahydropyrazino[2,1-c][1,4]oxazine-8(1H)-carboxylate The title compound was isolated as the slower eluting peak during chiral SFC-HPLC purification of tert-Butyl (3S,9aR)-3-[(3R)-5-fluoro-3-methyl-1-oxo-3,4-dihydro-1H-isochromen-6-yl]hexahydropyrazino[2,1-c][1,4]oxazine-8(1H)-carboxylate: LC-MS: (M+1)$^+$ 421.

Intermediate 13G (trans)

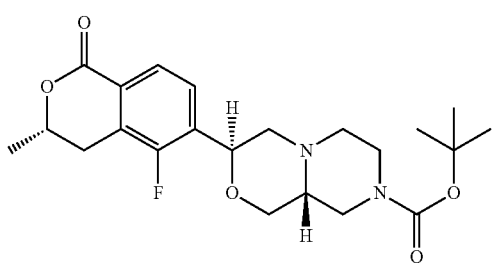 [SMILES: C[C@H]1Cc2c(ccc([C@H]3CN4CCN(C(=O)OC(C)(C)C)C[C@@H]4CO3)c2F)C(=O)O1]

tert-butyl (3S,9aR)-3-[(3S)-5-fluoro-3-methyl-1-oxo-3,4-dihydro-1H-isochromen-6-yl]hexahydropyrazino[2,1-c][1,4]oxazine-8(1H)-carboxylate The title compound was made from 3-(S)-6-Bromo-5-fluoro-3-methyl-3,4-dihydro-1H-isochromen-1-one using a procedure similar to that described for tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate (above), substituting tert-butyl (3R)-3-(hydroxymethyl)piperazine-1-carboxylate as the amino alcohol in Step C. The cis/trans mixture was purified via chiral SFC-HPLC (30% 2:1 MeOH:MeCN/CO$_2$) on OJ column. The faster eluting diastereomer was the trans isomer. LC-MS: (M+1)$^+$ 421.

Intermediate 13H (cis)

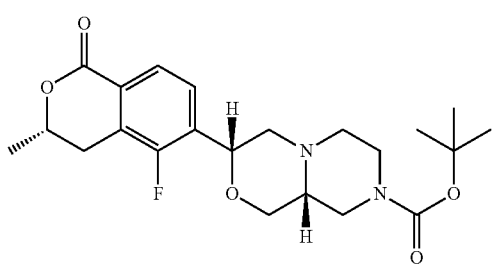 [SMILES: C[C@H]1Cc2c(ccc([C@@H]3CN4CCN(C(=O)OC(C)(C)C)C[C@@H]4CO3)c2F)C(=O)O1]

tert-butyl (3R,9aR)-3-[(3S)-5-fluoro-3-methyl-1-oxo-3,4-dihydro-1H-isochromen-6-yl]hexahydropyrazino[2,1-c][1,4]oxazine-8(1H)-carboxylate The title compound was isolated as the slower eluting peak during SFC-HPLC purification of tert-butyl (3S,9aR)-3-[(3S)-5-fluoro-3-methyl-1-oxo-3,4-dihydro-1H-isochromen-6-yl]hexahydropyrazino[2,1-c][1,4]oxazine-8(1H)-carboxylate (above): LC-MS: (M+1)+ 421.

Intermediate 14B (cis)

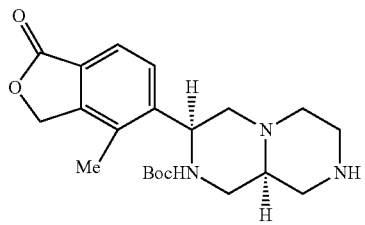

(3S,9aS)-tert-butyl 3-(4-methyl-1-oxo-1,3-dihydroisobenzofuran-5-yl)hexahydro-1H-pyrazino[1,2-a]pyrazine-2(6H)-carboxylate Step A: (S)-tert-butyl 4-((S)-2-hydroxy-2-(4-methyl-1-oxo-1,3-dihydroisobenzofuran-5-yl)ethyl)-3-(hydroxymethyl)piperazine-1-carboxylate (S)-4-Methyl-5-(oxiran-2-yl)isobenzofuran-1(3H)-one (0.75 g, 3.95 mmol) and (S)-tert-butyl 3-(hydroxymethyl)piperazine-1-carboxylate (1.02 g, 4.73 mmol) in ethanol (12 mL) were heated in microwave at 150° C. for 1.5 h. The reaction solution was concentrated and the residue was purified by MPLC on a Biotage system using 40-100% ethyl acetate/hexane to give the title compound. LC/MS: (M+1)+: 407.15.

Step B: (S)-benzyl 4-((S)-2-hydroxy-2-(4-methyl-1-oxo-1,3-dihydroisobenzofuran-5-yl)ethyl)-3-(hydroxymethyl)piperazine-1-carboxylate To a solution of (S)-tert-butyl 4-((S)-2-hydroxy-2-(4-methyl-1-oxo-1,3-dihydroisobenzofuran-5-yl)ethyl)-3-(hydroxymethyl)piperazine-1-carboxylate (2.57 g, 6.32 mmol) in methylene chloride (3 mL) was added trifluoroacetic acid (10 mL, 130 mmol) at rt for 1 h. After removing the volatiles under reduced pressure the residue was dissolved in methylene chloride (100 mL). To the above solution was added triethylamine (4.40 mL, 31.6 mmol) and benzyl chloroformate (0.95 mL, 6.64 mmol) at 0° C. for 0.5 h. The reaction was quenched by water followed by addition of saturated sodium carbonate. The mixture was extracted with methylene chloride, dried over sodium sulfate, concentrated and the residue was purified by MPLC on a Biotage system using 40-100% EtOAc/hexane to give the title compound. LC/MS: (M+1)+: 441.11.

Step C: (9aR)-benzyl 8-allyl-7-(4-methyl-1-oxo-1,3-dihydroisobenzofuran-5-yl)hexahydro-1H-pyrazino[1,2-a]pyrazine-2(6H)-carboxylate A solution of (S)-benzyl 4-((S)-2-hydroxy-2-(4-methyl-1-oxo-1,3-dihydroisobenzofuran-5-yl)ethyl)-3-(hydroxymethyl)piperazine-1-carboxylate (1.4 g, 3.2 mmol) in thionyl chloride (20 mL, 274 mmol) was heated at reflux for 1 h. After removing the volatiles, the residue was dissolved in N,N-dimethylformamide (20 mL) and treated with allylamine (1.31 mL, 17.48 mmol) at 0° C. The resulting solution was treated with sodium iodide (0.088 g, 0.318 mmol) and heated at 90° C. for 1 h. The solution was diluted in ethyl acetate (300 mL) and was washed with saturated sodium bicarbonate three times, dried over sodium sulfate, concentrated and the residue was purified by MPLC on a Biotage system using 40-100% ethyl acetate/hexane to give the title compound. LC/MS: (M+1)+: 462.12.

Step D: (3S,9aS)-8-benzyl 2-tert-butyl 3-(4-methyl-1-oxo-1,3-dihydroisobenzofuran-5-yl)tetrahydro-1H-pyrazino[1,2-a]pyrazine-2,8(9H,9aH)-dicarboxylate A mixture of (9aR)-benzyl 8-allyl-7-(4-methyl-1-oxo-1,3-dihydroisobenzofuran-5-yl)hexahydro-1H-pyrazino[1,2-a]pyrazine-2(6H)-carboxylate (0.98 g, 2.12 mmol), 1,3-dimethylpyrimidine-2,4,6(1H,3H,5H)-trione (0.995 g, 6.37 mmol) and tetrakis(triphenylphosphine)palladium (0) (123 mg, 0.106 mmol) in methylene chloride (10 mL) was heated at 35° C. for 4 h. After cooling to rt, di-tert-butyl dicarbonate (556 mg, 2.55 mmol) and triethylamine (1194 μl, 8.49 mmol) was added and the resulting solution was stirred at rt overnight. After concentration, the residue was purified and resolved by MPLC on a Biotage system using 20-100% EtOAc/hexane to give the title compound (less polar). LC/MS: (M+1)+: 522.12; and the corresponding (3R,9aS) isomer of the title compound (more polar). LC/MS: (M+1)+: 522.12.

Step E: (3S,9aS)-tert-butyl 3-(4-methyl-1-oxo-1,3-dihydroisobenzofuran-5-yl)hexahydro-1H-pyrazino[1,2-a]pyrazine-2(6H)-carboxylate To a solution of the title compound of Step D ((0.46 g, 0.88 mmol) in methanol (30 mL) was added palladium on carbon (10%, 0.094 g, 0.088 mmol) and the mixture was subjected to hydrogenation at rt overnight. After filtration the filtrate was concentrated to give the title compound. LC/MS: (M+1)+: 388.10.

Intermediate 15

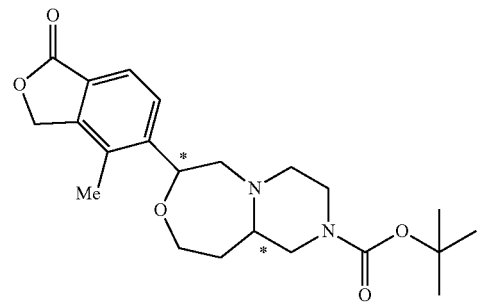 [SMILES: Cc1c(C2CN3CCN(C(=O)OC(C)(C)C)CC3CCO2)ccc2c1COC2=O]

tert-butyl 7-(4-methyl-1-oxo-1,3-dihydro-2-benzofuran-5-yl)octahydro-2H-pyrazino[1,2-d][1,4]oxazepine-2-carboxylate, and four separated isomers Step A: tert-butyl 3-(2-hydroxyethyl)piperazine-1-carboxylate tert-Butyl 3-(2-methoxy-2-oxoethyl)piperazine-1-carboxylate (7.28 g, 28.2 mmol) was dissolved in THF (100 mL) at 0° C. then added LAH (21.14 mL, 21.14 mmol). The reaction was monitored by TLC. After 30 mins, the reaction was first quenched with 0.8 mL water, then added 1.6 mL 2N NaOH followed by 4 mL water. The above slurry was diluted with ethyl acetate and MgSO₄ was added. The mixture was stirred at RT for ½ h, then filtered and concentrated to yield the title compound: LC-MS (IE, m/z): 231 [M+1]⁺.

Step B: tert-butyl 3-(2-hydroxyethyl)-4-(2-(4-methyl-1-oxo-1,3-dihydroisobenzofuran-5-yl)-2-oxoethyl)piperazine-1-carboxylate tert-Butyl 3-(2-hydroxyethyl)piperazine-1-carboxylate (6.91 g, 30.0 mmol) and 5-(2-bromoacetyl)-4-methylisobenzofuran-1(3H)-one (6.73 g, 25 mmol) were dissolved in tetrahydrofuran (100 mL) then added Hunig's base (8.73 mL, 50.0 mmol) and stirred at RT overnight. The reaction was poured into brine and extracted with EtOAc (2×). The combined organic layer was dried over Na₂SO₄, filtered and evaporated to dryness. The crude product was chromatographed through an ISCO Redi-Sep 330 g column and eluted with 5% MeOH/DCM solvent system to the title compound. LC-MS (IE, m/z): 419 [M+1]⁺.

Step C: tert-butyl 4-(2-hydroxy-2-(4-methyl-1-oxo-1,3-dihydroisobenzofuran-5-yl)ethyl)-3-(2-hydroxyethyl)piperazine-1-carboxylate tert-Butyl 3-(2-hydroxyethyl)-4-(2-(4-methyl-1-oxo-1,3-dihydroisobenzofuran-5-yl)-2-oxoethyl)piperazine-1-carboxylate (6.16 g, 14.7 mmol) was dissolved in methanol (100 mL) at 0° C. and then NaBH₄ (1.67 g, 44.2 mmol) was added. The reaction mixture was warmed up to RT. After ten minutes, TLC showed no SM left. The methanol was evaporated and the residue was taken up with brine and extracted with ethyl acetate twice. The combined organic layers were dried with MgSO₄, filtered and concentrated. The crude product was chromatographed through an ISCO 330 g Redi-sep column and eluted with 5% MeOH/DCM to yield the title compound: LC-MS (IE, m/z): 421 [M+1]⁺.

Step D: tert-butyl 7-(4-methyl-1-oxo-1,3-dihydro-2-benzofuran-5-yl)octahydro-2H-pyrazino[1,2-c][1,4]oxazepine-2-carboxylate tert-Butyl 4-(2-hydroxy-2-(4-methyl-1-oxo-1,3-dihydroisobenzofuran-5-yl)ethyl)-3-(2-hydroxyethyl)piperazine-1-carboxylate (2.22 g, 5.30 mmol) was dissolved in benzene (30 mL) and then cyanomethylene tributyl phosphorane (2.31 g, 9.55 mmol) was added, which was then heated to 100° C. overnight. The benzene was removed by rotary evaporation, and the residue was chromatographed through an ISCO redi-sep 330 g column and eluted with 15% acetone: 85% DCM. This separated the cis-diastereomers from the trans-diastereomers of the title compound. The cis-diastereomers were further separated to S,S and R,R diastereomers using the following conditions: Chiralpak AD column: 30×250 mm, 30% (2:1 MeOH:CH₃CN)/CO₂, 70 mL/min, 100 bar, 41 mg/mL in MeOH/MeCN/DCM, 35° C., 254 nm: cis-diastereomer A (retention time 3.2 mins): ¹H-NMR (500 MHz, CDCl₃) δ ppm 7.83 (d, J=8 HZ, 1H), 7.78 (d, J=8 Hz, 1H), 5.27 (s, 2H), 4.97 (dd, J=4.75, 2.8 Hz, 1H), 4.13 (t, J=3.45 Hz, 0.5H), 4.10 (t, J=3.45 Hz, 0.5H), 3.91 (t, J=12 Hz, 1H), 3.82 (b, 2H), 3.17 (d, J=5.3 Hz, 0.5H), 3.13 (d, J=5.1 Hz, 0.5H), 2.93 (d, J=2.9 Hz, 0.5H), 2.90 (d, J=2.9 Hz, 0.5H), 2.88 (b, 1H), 2.69 (b, 4H), 2.31 (s, 3H), 1.89-1.92 (m, 2H), 1.49 (s, 9H): cis-diastereomer B (retention time 4.21 min): ¹H-NMR (500 MHz, CDCl₃) δ ppm 7.83 (d, J=8 HZ, 1H), 7.78 (d, J=8 Hz, 1H), 5.27 (s, 2H), 4.97 (dd, J=4.75, 2.75 Hz, 1H), 4.13 (t, J=3.45 Hz, 0.5H), 4.10 (t, J=3.45 Hz, 0.5H), 3.91 (t, J=10.12 Hz, 1H), 3.82 (b, 2H), 3.17 (d, J=5.1 Hz, 0.5H), 3.14 (d, J=5.1 Hz, 0.5H), 2.93 (d, J=2.9 Hz, 0.5H), 2.90 (d, J=2.9 Hz, 0.5H), 2.88 (b, 1H), 2.69 (b, 4H), 2.31 (s, 3H), 1.89-1.92 (m, 2H), 1.49 (s, 9H): The trans-diastereomers were further separated to the S,R and R,S diastereomers using the following condition: Chiralpak AD column: 30×250 mm, 20% (2:1 MeOH:CH₃CN)/CO₂, 70 ml/min, 100 bar, 33 mg/mL in MeOH/MeCN/DCM, 35° C., 254 nm. The retention times of trans-diastereomer A and trans-diastereomer B were 6.68 mins and 8.08 mins on the analytical column Chiralpak AD: 4.6×250 mm, 15% (2:1 MeOH: CH₃CN)/CO₂, 2.1 ml/min, 100 bar, 35° C. 254 nm: trans-diastereomer A: ¹H-NMR (500 MHz, CDCl₃) δ ppm 7.78 (d, J=8 HZ, 1H), 7.69 (d, J=8 Hz, 1H), 5.27 (s, 2H), 5.13 (d, J=8.8 Hz, 1H), 3.99-4.12 (m, 2H), 3.78-3.95 (b, 2H), 3.02 (b, 1H), 2.87 (d, J=9.1 Hz, 0.5H), 2.84 (d, J=9.0 Hz, 0.5H), 2.77 (b, 2H), 2.65 (d, J=14.5 Hz, 1H), 2.40-2.44 (m, 2H), 2.34 (s, 3H), 2.02-2.08 (m, 1H), 1.92-1.98 (m, 1H), 1.50 (s, 9H): trans-diastereomer B: ¹H-NMR (500 MHz, CDCl₃) δ ppm 7.78 (d, J=8 HZ, 1H), 7.68 (d, J=8 Hz, 1H), 5.27 (s, 2H), 5.13 (d, J=8.8 Hz, 1H), 4.00-4.12 (m, 2H), 3.98 (b, 2H), 3.01 (b, 1H), 2.86 (d, J=9.1 Hz, 0.5H), 2.83 (d, J=9.0 Hz, 0.5H), 2.76 (b, 2H), 2.65 (d, J=13 Hz, 1H), 2.40-2.44 (m, 2H), 2.34 (s, 3H), 2.03-2.08 (m, 1H), 1.94-1.97 (m, 1H), 1.50 (s, 9H).

Intermediates 16 (Isomer Mixture), 16A and 16B

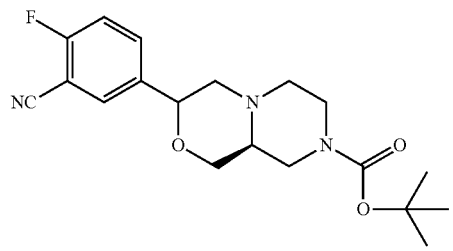

isomeric Mixture (Step F)

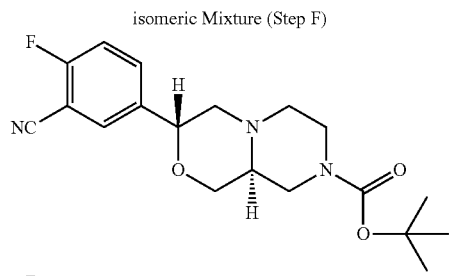

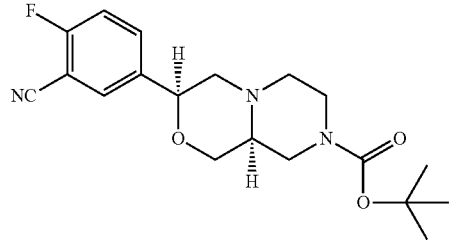

separated isomers (Step G)

tert-butyl (3R,9aS)-3-(3-cyano-4-fluorophenyl)
hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8 (1H)-carboxylate Step A: 2-fluoro-5-(1-hydroxyethyl)benzonitrile 3-Cyano-4-fluorobenzaldehyde (2.17 g, 14.7 mmol) was dissolved in THF (50 mL) then cooled to −70° C. To this mixture was added methyl magnesiumbromide (5.34 mL, 16.0 mmol). The mixture was stirred for 1 h, then was quenched with brine and extracted with ether. The ethereal layer was separated, dried over $Na_2SO_4$, filtered, and evaporated to dryness. The residue was purified by MPLC chromatography through a 120 g Redi-sep column using 0-50% EtOAc/hexane eluent to yield 2-fluoro-5-(1-hydroxyethyl) benzonitrile: LC-MS: M+1=166.

Step B: 5-acetyl-2-fluorobenzonitrile

2-Fluoro-5-(1-hydroxyethyl)benzonitrile (0.80 g, 4.8 mmol) was dissolved in DCM (50 mL). To this mixture was added pyridinium dichromate (2.73 g, 7.27 mmol) and the mixture was stirred at RT overnight. Florisil (26 g) was added to the reaction mixture which was then diluted with 50 mL of ether and filtered through a pad of Celite. The filtrate was evaporated to dryness and the residue was purified by MPLC through a 120 g Redi-sep column, eluting with 0-100% EtOAc/hexane to yield 5-acetyl-2-fluorobenzonitrile.

Step C: 5-(bromoacetyl)-2-fluorobenzonitrile

5-Acetyl-2-fluorobenzonitrile (400 mg, 2.45 mmol) was dissolved in THF (20 mL) then copper (II) bromide (1.10 g, 4.90 mmol) was added and the mixture was stirred at RT for 48 h. The reaction mixture was diluted with 20 mL of ether then washed with water, followed by brine. The organic layer was separated, dried over $Na_2SO_4$, and filtered. The filtrate was evaporated to dryness then purified by MPLC chromatography through an 80 g Redi-sep column with 0-50% ethyl acetate/hexane eluent to yield 5-(bromoacetyl)-2-fluorobenzonitrile: LC-MS: M+1=244.

Step D: tert-butyl (3S)-4-[2-(3-cyano-4-fluorophenyl)-2-oxoethyl]-3-(hydroxymethyl)piperazine-1-carboxylate 5-(Bromoacetyl)-2-fluorobenzonitrile (590 mg, 2.44 mmol) and (S)-4-N-BOC-2-hydroxymethyl-piperazine (527 mg, 2.44 mmol) were dissolved in THF (40 mL) at 0° C. then TEA (247 mg, 2.44 mmol) was added. The reaction mixture was stirred at RT for 16 h, then poured into water and extracted with ethyl acetate. The organic layer was dried over $Na_2SO_4$, filtered, and evaporated to dryness. The crude product was purified by MPLC through an 80 g Redi-sep column using 0-100% EtOAc/hexane to yield the title compound.

Step E: tert-butyl (3S)-4-[2-(3-cyano-4-fluorophenyl)-2-hydroxyethyl]-3-(hydroxymethyl)piperazine-1-carboxylate tert-Butyl (3S)-4-[2-(3-cyano-4-fluorophenyl)-2-oxoethyl]-3-(hydroxymethyl)piperazine-1-carboxylate (800 mg, 2.12 mmol) was dissolved in ethanol (50 mL) then sodium borohydride (321 mg, 8.48 mmol) was added and the mixture was stirred at RT for 16 h. LC-MS analysis showed product to be present. The ethanol was removed and the residue was redissolved in EtOAc and stirred with 1N HCl for 5 min. The mixture was then neutralized with saturated aqueous $NaHCO_3$ and extracted twice with EtOAc. The organic layers were washed with brine, dried over $Na_2SO_4$, filtered, and evaporated to dryness to yield the title compound. LC-MS: M+1=280.

Step F: tert-butyl (9aS)-3-(3-cyano-4-fluorophenyl) hexahydropyrazino[2,1-c][1,4]oxazine-8(1-carboxylate tert-Butyl (3S)-4-[2-(3-cyano-4-fluorophenyl)-2-hydroxyethyl]-3-(hydroxymethyl)piperazine-1-carboxylate (358 mg, 0.944 mmol) was dissolved in DCM (25 mL) and cooled to 0° C. To this mixture was added TEA (0.197 mL, 1.42 mmol) followed by methanesulfonyl chloride (0.096 mL, 1.2 mmol). The mixture was warmed to RT and stirred overnight. The reaction mixture was washed twice with brine, dried, and evaporated to dryness. The residue was purified by chromatography through a 40 g Redi-sep column, eluting with EtOAc/Hex 0-100% to yield the intermediate chloride (470 mg, 1.81 mmol). This chloride was then dissolved in THF (25 mL) and tetrabutylammonium chloride (436 mg, 1.18 mmol) was added at 0° C. followed by NaH (47.2 mg, 1.18 mmol) then the mixture was stirred at reflux overnight. The reaction mixture was diluted with EtOAc and washed with brine. The organic layer was dried over $Na_2SO_4$, filtered, and evaporated to dryness. The crude residue was purified by MPLC chromatography through a 40 g Redi-sep column, eluting with 0-100% ethyl acetate to yield the title compound as a mixture of two isomers: $^1$H-NMR (500 MHz, $CDCl_3$): δ ppm 7.86 (d, J=5.5 Hz, 0.5H), 7.75-7.81 (m, 0.5H), 7.65 (d, J=6 Hz, 1H), 7.58-7.61 (m, 0.5H), 7.19-7.24 (q, 1H), 4.79 (s, 0.5H), 4.66 d, J=10.5 Hz, 0.5H), 3.96 (dd, J=3, 11 Hz, 1H), 3.55-4.0 (b, 2H), 3.54 (dd, J=2.5, 11.5 Hz, 0.5H), 3.46 (t, J=10.5 Hz, 0.5H), 3.24 (t, J=8.5 Hz, 0.5H), 3.18 (d, J=2.5 Hz, 0.5H) 3. (b, 2H), 2.89 (dd, J=2.1, 11.5 Hz, 0.5H), 2.7-2.8 (m, 2H), 2.5 (b, 1H), 2.38-2.45 (m, 1H), 2.25 (t, J=8.5 Hz, 1H), 2.17 (t, J=11 Hz, 1H), 1.48 (s, 9H); LC-MS: M+1=362.

Step G: tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate The title compounds were obtained by preparative HPLC separation of the mixture of isomers obtained in the prior step.

Intermediates 16C and 16D

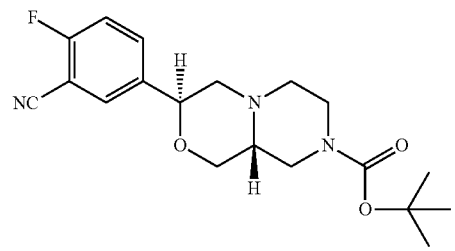

-continued

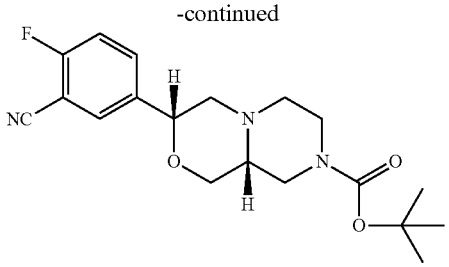

tert-butyl (3S,9aR)-3-(3-cyano-4-fluorophenyl)
hexahydropyrazino[2,1-c][1,4]oxazine-8(1H)-carboxylate and tert-butyl(3R,9aR)-3-(3-cyano-4-fluorophenyl)hexahydropyrazino[2,1-c][1,4]oxazine-8(1H)-carboxylate Step A:
3-bromo-4-fluoro-N-methoxy-N-methylbenzamide A solution of 3-bromo-4-fluorobenzoic acid (100 g, 0.456 mol) and CDI (77.2 g, 0.547 mol) in 1 L of dry DCM was stirred at r.t. for 30 min and then O,N-dimethyl-hydroxylamine (53.4 g, 0.547 mol) was added. The resulted mixture was stirred overnight. The solvents were removed under vacuum and the residue was purified via column chromatograph to afford 3-bromo-4-fluoro-N-methoxy-N-methylbenzamide.

Step B: 1-(3-bromo-4-fluorophenyl)ethanone

A solution of 3-bromo-4-fluoro-N-methoxy-N-methylbenzamide (50 g, 0.19 mol) in 500 mL of THF was cooled to 0° C. in ice bath, and then the mixture was added MeMgCl (27.3 g, 0.21 mol) dropwise. The reaction mixture was stirred under $N_2$ for 1 h. The reaction mixture was quenched with sat. $NH_4Cl$ and extracted with EtOAc. The combined organic layers were washed with brine, dried over $Na_2SO_4$ and concentrated in vacuum. The residue was purified with silica gel column chromatography to give 1-(3-bromo-4-fluorophenyl)ethanone.

Step C: 5-acetyl-2-fluorobenzonitrile

A solution of 1-(3-bromo-4-fluorophenyl)ethanone (81.3 g, 0.344 mol) in 300 mL of DMF was added CuCN (67.4 g, 0.749 mol) and the mixture was heated to reflux and stirred under $N_2$ for 10 h. The reaction mixture was quenched with water and extracted with ether. The organic layer was washed with brine dried over $Na_2SO_4$ and concentrated in vacuum. The residue was purified with silica gel column chromatography to give the product 5-acetyl-2-fluorobenzonitrile.

Step D: 5-(bromoacetyl)-2-fluorobenzonitrile

A solution of 5-acetyl-2-fluorobenzonitrile (20.0 g, 0.123 mol) in 500 mL of DCM was heated to reflux for 2 h, and then a solution of bromine in 300 mL DCM was added dropwise into the boiling mixture. The reaction mixture was heated to reflux and stirred under $N_2$ protection overnight. The reaction mixture was washed with water and extracted with DCM. The organic layer was washed with brine, dried over $Na_2SO_4$ and concentrated in vacuum. The residue was purified via silica gel column chromatography to give 5-(bromoacetyl)-2-fluorobenzonitrile.

Step D: tert-butyl (3R)-4-[2-(3-cyano-4-fluorophenyl)-2-oxoethyl]-3-(hydroxymethyl)piperazine-1-carboxylate To a solution of 5-(bromoacetyl)-2-fluorobenzonitrile (13.1 g, 0.054 mol) in DMF (160 mL) was added tert-butyl (3R)-3-(hydroxymethyl)piperazine-1-carboxylate (13.1 g, 0.065 mol) and $K_2CO_3$ (11.77 g, 0.075 mol), and the mixture was stirred at RT for 3 h. The mixture was washed with water, and extracted with EtOAc. The organic layer was washed with brine, dried over $Na_2SO_4$ and concentrated in vacuum to give the title compound which was used for the next step without further purification.

Step E: tert-butyl (3R)-4-[2-(3-cyano-4-fluorophenyl)-2-hydroxyethyl]-3-(hydroxymethyl)piperazine-1-carboxylate To a solution of tert-butyl (3R)-4-[2-(3-cyano-4-fluorophenyl)-2-oxoethyl]-3-(hydroxymethyl)piperazine-1-carboxylate (20 g, 0.053 mol) in MeOH (400 mL) was added partionwise $NaBH_4$ (15.6 g, 0.424 mol) at 0° C. and the mixture was stirred at r.t overnight. The reaction mixture was added water, extracted with EtOAc. The organic layer was combined, washed with brine, dried over $Na_2SO_4$ and concentrated in vacuum. The residue was purified with silica gel column chromatography to give the title compound.

Step F: tert-butyl (9aR)-3-(3-cyano-4-fluorophenyl) hexahydropyrazino[2,1-c][1,4]oxazine-8(1H)-carboxylate A solution of tert-butyl (3R)-4-[2-(3-cyano-4-fluorophenyl)-2-hydroxyethyl]-3-(hydroxymethyl)piperazine-1-carboxylate (5.0 g, 13.2 mmol) in 100 mL of THF was stirred at 0° C. for 10 min, and then NaH (60%) (1.32 g, 33.0 mmol) was added at 0° C. The resulting white suspension was stirred vigorously at 0° C. for 5 min, then at r.t for 1 h. The reaction suspension was then recooled to 0° C., N-Tosylimidazole was added and the resulting solution was stirred for a further 10 min at 0° C. before being warmed again to r.t and stirred for 1 h. The reaction solution was then cooled once more to 0° C., and excess sodium hydride was carefully quenched by the slow addition of sat. $NH_4Cl$ solution. The resulting biphasic solution was partitioned between sat. $NH_4Cl$ and EtOAc. The organic layer was washed with water and brine, dried over $Na_2SO_4$ and concentrated in vacuum. The residue was purified with silica gel column chromatography to give the title compound: $^1$H-NMR (300 MHz, $CDCl_3$) δ7.76~7.79 (m, 1H), 7.49~7.58 (m, 1H), 7.11~7.15 (m, 1H), 7.16~7.12 (m, 1H), 3.86~4.06 (m, 2H), 3.33~3.48 (m, 1H), 3.08~3.17 (m, 1H), 2.80~2.94 (m, 2H), 2.64~2.74 (m, 2H), 2.29~2.46 (m, 2H), 2.09~2.20 (m, 1H), 1.40 (d, J=3.0 Hz, 9H).

Step G: tert-butyl (3S,9aR)-3-(3-cyano-4-fluorophenyl)hexahydropyrazino[2,1-c][1,4]oxazine-8(1H)-carboxylate and tert-butyl (3R,9aR)-3-(3-cyano-4-fluorophenyl)hexahydropyrazino[2,1-c][1,4]oxazine-8(1H)-carboxylate The single isomers of were obtained by preparative HPLC separation of the mixture of isomers obtained in the prior step.

Intermediates 17A and 17B (Method 1)

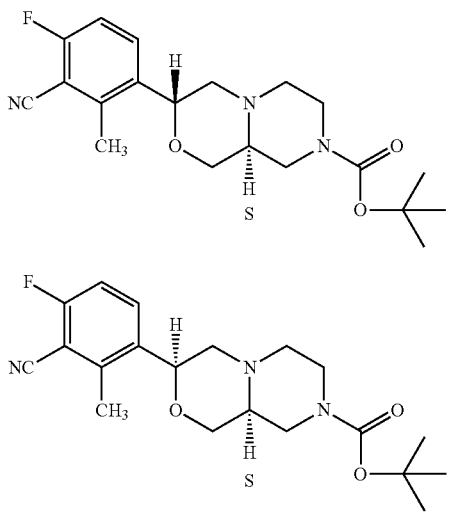

17A: tert-butyl(3R,9aS)-3-(3-cyano-4-fluoro-2-methylphenyl)hexahydropyrazino[2,1-c][1,4]oxazine-8(1H)-carboxylate 17B: tert-butyl(3S,9aS)-3-(3-cyano-4-fluoro-2-methylphenyl)hexahydropyrazino[2,1-c][1,4]oxazine-8(1H)-carboxylate

Step A: 3-bromo-6-fluoro-2-methylbenzonitrile (Method A)

Commercially available 2-fluoro-6-methylbenzonitrile (Apollo Scientific, 15.0 g, 111 mmol) was dissolved in triflic acid (75 mL) at 0° C. then NBS (20.7 g, 117 mmol) was added. The reaction mixture was stirred at RT for 1 h then poured into ice water and extracted twice with DCM. The organic layer was washed with brine, dried over $Na_2SO_4$, then filtered and evaporated to dryness to yield 3-bromo-6-fluoro-2-methylbenzonitrile: LC-MS: M+1=214, 216.

Alternate Step A (Method B)

To a 3 L 3 Neck RB equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By this time, HPLC shows the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over $MgSO_4$, concentrated, then stored in a −10° C. freezer overnight. Precipitate formed over this time, and was filtered and washed with 5% EtOAc/Hexanes. A second crop of precipitate was combined with the first crop to provide 3-bromo-6-fluoro-2-methyl-benzonitrile.

Step B: 3-ethenyl-6-fluoro-2-methylbenzonitrile

3-Bromo-6-fluoro-2-methylbenzonitrile (23.6 g, 110 mmol), potassium vinyl trifluoroborate (29.5 g, 221 mmol), $PdCl_2$(dppf)-$CH_2Cl_2$ Adduct (4.03 g, 5.51 mmol), and TEA (30.7 mL, 221 mmol) were added to 250 mL of ethanol. The reaction mixture was degassed then stirred at reflux for 4 h. LC-MS confirmed the presence of product. The reaction mixture was diluted with ethyl acetate, washed twice with brine, dried, and evaporated to dryness. The crude material was then purified by MPLC chromatography using a 330 g Redi-sep column and eluting with a 10% EtOAc/Hexane solvent system to yield 3-ethenyl-6-fluoro-2-methylbenzonitrile.

Step C: 6-fluoro-2-methyl-3-(oxiran-2-yl)benzonitrile

3-Ethenyl-6-fluoro-2-methylbenzonitrile (14.9 g, 92.0 mmol) was added to DCM (400 mL) at 0° C. then mCPBA (47.85 g, 277.5 mmol) was added and the mixture was stirred at RT for 72 h. The reaction mixture was washed with saturated aqueous $Na_2S_2O_3$, then with 1N NaOH, and brine. The organic layer was separated, dried over $Na_2SO_4$, filtered, and evaporated to dryness. The crude product was purified by chromatography through a 330 g Redi-sep column, eluting with 0-100% hexane/DCM solvent system to afford 6-fluoro-2-methyl-3-(oxiran-2-yl)benzonitrile. LC-MS: M+1=178.

Step D: tert-butyl (3S)-4-[2-(3-cyano-4-fluoro-2-methylphenyl)-2-hydroxyethyl]-3-(hydroxymethyl)piperazine-1-carboxylate 6-Fluoro-2-methyl-3-(oxiran-2-yl)benzonitrile (12.0 g, 67.7 mmol) and (S)-4-N-BOC-2-hydroxymethylpiperazine (22.0 g. 102 mmol) were suspended in ethanol (100 mL) then heated in a microwave apparatus for 30 minutes at 150° C. The reaction mixture was cooled and evaporated dryness. The residue was purified by MPLC chromatography through a 330 g Redi-sep column eluting with 5% MeOH/95% EtOAc solvent system to yield the title compound. LC-MS: M+1=394.

Step E: tert-butyl (9aS)-3-(3-cyano-4-fluoro-2-methylphenyl)hexahydropyrazino[2,1-c][1,4]oxazine-8(1H)-carboxylate tert-Butyl (3S)-4-[2-(3-cyano-4-fluoro-2-methylphenyl)-2-hydroxyethyl]-3-(hydroxymethyl)piperazine-1-carboxylate (18.5 g, 47.0 mmol) and cyanomethylenetri-n-butylphosphorane (20.4 g, 85.0 mmol) were dissolved in 180 mL of benzene. The reaction mixture was degassed and heated to 100° C. for 16 h. LC-MS analysis indicated product peak (M+1=376). The reaction was cooled and evaporated to dryness. The residue was purified by chromatography through a 330 g Redi-sep column, eluting with a 20% acetone/80% hexane mixture to yield a cis-trans mixture of the title compound.

Step F: tert-butyl(3R,9aS)-3-(3-cyano-4-fluoro-2-methylphenyl)hexahydropyrazino[2,1-c][1,4]oxazine-8(1H)-carboxylate and tert-butyl(3S,9aS)-3-(3-cyano-4-fluoro-2-methylphenyl)hexahydropyrazino[2,1-c][1,4]oxazine-8(1H)-carboxylate The cis-trans isomers of the product of Step E were separated using a Chiralpak AD 4.6×250 mm 10μ column with 20% IPA/80% heptane solvent system: 17A (trans-isomer eluted first): $^1$H-NMR (500 MHz, CDCl$_3$): δ ppm 7.74 (dd, J=6, 8.5 Hz, 1H), 7.095 (t, J=8.5 Hz, 1H), 4.838 (d, J=10 Hz, 1H), 3.98 (dd, J=3, 11.5 Hz, 1H), 3.84-4.21 (b, 2H), 3.50 (t, J=11 Hz, 1H), 2.98-3.18 (b, 1H), 2.85 (dd, J=2, 11.5 Hz, 1H), 2.75 (d, J=10 Hz, 1H), 2.6 ppm (s, 3H), 2.45-2.68 (b, 1H), 2.24-2.31 (m, 2H), 2.16 (t, J=11 Hz, 1H), 1.50 ppm (s, 9H); LC-MS: M+1=376; 17B (cis-isomer eluted second): $^1$H-NMR (500 MHz, CDCl$_3$): δ ppm 8.20 (t, J=6.95 Hz, 1H), 7.06 (t, J=8.5 Hz, 1H), 4.91 (t, J=3.5 Hz, 1H), 3.70-4.07 (b, 2H), 3.55 (d, J=11 Hz, 1H), 3.26 (t, J=9 Hz, 1H), 3.15 (dd, J=3, 12 Hz, 1H), 2.98-3.11 (b, 1H), 2.82 (dd, J=4, 12 Hz, 2H), 2.63 (s, 3H), 2.59-2.7 (b, 1H), 2.44-2.49 (m, 2H), 1.50 (s, 9H); LC-MS: M+1=376.

Intermediate 17B (Method 2)

Step A: 2-Fluoro-6-methyl-benzonitrile

A 10 L round bottom flask equipped with adapter, thermocouple and stir bar was charged with DMA (6 L) and degassed under vacuum and purged with N$_2$ three times. To the mixture was added Palladium Tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and Zinc Cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH and extracted three times with 1.5 L EtOAc. The extracts were washed with 2 L brine, dried over Na$_2$SO$_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By that time, HPLC showed the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over MgSO$_4$, concentrated, then stored in a –10° C. freezer overnight. Precipitate formed over this time, and was filtered and washed with 5% EtOAc/Hexanes, providing a first crop of product. A second crop of precipitate provided further 3-Bromo-6-fluoro-2-methyl-benzonitrile.

Step C: 3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-Bromo-6-fluoro-2-methyl-benzonitrile (115 g, 537 mmol) and cis-PdCl$_2$(PPh$_3$)$_2$ (18.9 g, 26.9 mmol) in degassed Dioxane (1149 mL) and the mixture was stirred at 100° C. for 22 hours. By this time HPLC showed complete conversion of starting material (requires at least 12 hours), completion of the reaction can be seen by plating of palladium metal onto the side of the flask. At this time the reaction was cooled to 0° C. and THF (575 mL) and Water (230 mL) were added followed by NBS (110 g, 618 mmol) (added portionwise over 15 min, maintaining internal temperature<5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over MgSO$_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester Diisopropylethylamine (44.0 mL, 252 mmol) was added to a stirred, room temperature mixture of 72 wt % 3-(2-Bromoacetyl)-6-fluoro-2-methyl-benzonitrile (69 g, 194 mmol) and (S)-4-N-Boc-2-hydroxymethyl-piperazine (42.0 g, 194 mmol) in THF (1000 mL) and the mixture was stirred at room temperature for 18 h. The reaction was diluted with 1 L EtOAc, washed 2× with 500 mL 10% w/w NaHCO$_3$ aqueous solution, dried over MgSO$_4$, filtered and concentrated. The residue was purified by column chromatography on silica gel (40-80% EtOAc/Hexanes, linear gradient), to give the title compound.

Step E: (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester Mesyl-Cl (17.2 mL, 221 mmol) was added dropwise to a stirred, <5° C. internal temperature mixture of (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (66.6 g, 170 mmol) and triethylamine (71.1 mL, 510 mmol) in CH$_2$Cl$_2$ (1000 mL) (exotherm occurs, so must keep addition slow), and the reaction was allowed to warm to room temperature for 30 minutes, by which time reaction was complete. The solution was washed with 500 mL 10% w/w NaHCO$_3$ aqueous solution. The organics were dried over MgSO$_4$, filtered and concentrated. The resulting material was taken up in a minimal amount of EtOAc (125 mL) with some heating (solution kept<50° C.) until all solids dissolved. The solution was allowed to cool with stirring, then dropwise overnight 350 mL hexanes was added. By the next morning the solution had clarified and there was considerable powder. The solids were collected by filtration and washed with 20% EtOAc/Hexanes, providing product. The mother liquors were concentrated until precipitate appeared, which was filtered to give additional (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester.

Step F: (3S,9aS)-3-(3-Cyano-4-fluoro-2-methyl-phenyl)-hexahydro-pyrazino[2,1-c][1,4]oxazine-8-carboxylic acid tert-butyl ester To a 1 L 3 neck RB was charged 5% Pd/CaCO$_3$ (10.0 g., 4.02 mmol), MeOH (405 mL), and (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester (15.0 g., 40.2 mmol). The solution was sparged with N$_2$ for 5 min, then put under an atmosphere of hydrogen with balloon pressure and warmed to 40° C. with stirring. After 38 h, HPLC shows full conversion of the olefin, with a 5:1 cis:trans ratio of diastereomers. The suspension was cooled to room temperature, filtered through a pad of Celite and concentrated. The residue was purified via column chromatography (60-100% EtOAc/

Hexanes, linear gradient), to provide the title compound. $^1$H NMR (400 MHz, CDCl$_3$): δ 8.18 (m, 1H), 7.03 (t, J=7.9 Hz, 1H), 4.87 (s, 1H), 4.10-3.60 (m, 2H), 3.56 (d, J=10.5 Hz, 1H), 3.25-2.88 (m, 3H), 2.80-2.35 (m, 8H), 1.50 (s, 9H).

Intermediate 17A (Method 2)

A three-necked, round-bottomed flask equipped with a nitrogen inlet adapter, thermocouple, and a septum was charged with (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (330 g, 840 mmol), TFA (1.65 L, 21 mol), and 3300 mL of DCM. Et$_3$SiH (292 g, 2.52 mol, 3 equiv) was added in one portion and the reaction mixture stirred at room temperature for 24 h. The reaction mixture was concentrated and azeotroped with toluene (100 mL) to remove the TFA. The resulting material was dissolved in DCM (1.7 L) and carefully charged with 2.5 M Na$_2$CO$_3$ (pH should be basic). Boc$_2$O (218 g, 1.2 equiv) was added in one portion and the reaction mixture was stirred at room temperature for 2 h. The organic layer was separated, concentrated, and purified via column chromatography (0-30% acetone-hexanes) to give a mixture of product cis/trans isomers. Chiral SFC purification (Berger MultiGram™ SFC, Mettler Toledo Co, Ltd, AD 250 mm*50 mm, 5 um column, A: supercritical CO$_2$, B: methanol, A:B=85:15 at 150 mL/min) afforded the major trans diastereomer 17A as well as the cis diastereomer 17B.

Intermediates 17C and 17D (Method 1)

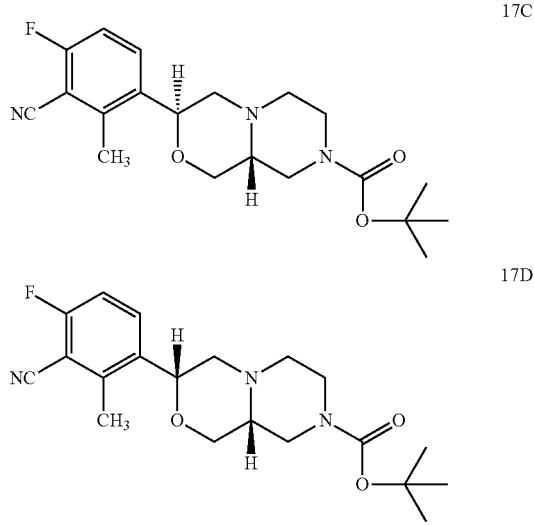

17C: tert-butyl(3S,9aR)-3-(3-cyano-4-fluoro-2-methylphenyl)hexahydropyrazino[2,1-c][1,4]oxazine-8 (1H)-carboxylate 17D: tert-butyl(3R,9aR)-3-(3-cyano-4-fluoro-2-methylphenyl)hexahydropyrazino[2,1-c][1,4]oxazine-8 (1H)-carboxylate Step A: tert-butyl (3R)-4-[2-(3-cyano-4-fluoro-2-methylphenyl)-2-hydroxylethyl]-3-(hydroxymethyl) piperazine-1-carboxylate 6-Fluoro-2-methyl-3-(oxiran-2-yl)benzonitrile (prepared as described above for I-17A and I-17B, Method 1, Steps A-C) (4.80 g, 27.1 mmol) and (R)-4-N-BOC-2-hydroxymethyl-piperazine (commercially available, e.g. from Acesys Pharmatech, catalog #A1612R; and also described in J. Org. Chem., 2007, 72(22), p. 8591-8592) (8.79 g. 40.6 mmol) were suspended in EtOH (30 mL) and heated in a microwave apparatus at 150° C. for 1 h. The reaction mixture was cooled and evaporated to dryness. The residue was purified by chromatography through a 330 g ISCO Redi-sep column eluting with ethyl acetate to 5% MeOH/ethyl acetate gradient to yield the title compound. LC-MS: M+1=394;

Step B: tert-butyl(3S,9aR)-3-(3-cyano-4-fluoro-2-methylphenyl)hexahydropyrazino[2,1-c][1,4]oxazine-8(1H)-carboxylate and tert-butyl(3R,9aR)-3-(3-cyano-4-fluoro-2-methylphenyl) hexahydropyrazino[2,1-c][1,4]oxazine-8(1H)-carboxylate tert-Butyl (3R)-4-[2-(3-cyano-4-fluoro-2-methylphenyl)-2-hydroxylethyl]-3-(hydroxymethyl)piperazine-1-carboxylate (7.14 g, 18.2 mmol) and cyanomethylene tributylphosphorane (7.88 g, 32.7 mmol) were dissolved in benzene (60.0 mL) then heated at 100° C. overnight. The reaction mixture was cooled and evaporated to dryness. The residue was purified by chromatography through a 330 g ISCO Redi-sep column eluting with a 10% acetone/DCM-to 20% acetone/DCM gradient to yield trans-cis mixture. The isomers were resolved by chiral HPLC (70 mL/min of 15% 2:1 MeOH:MeCN:CO$_2$ on a 30×250 mm Chiralpak IC column (Diacel Chemical Industries, LTD.) at 100 bar and 35° C., 230 nM). Isomer 17C (faster eluting): $^1$H-NMR (500 MHz, CDCl$_3$): δ ppm 7.73 (dd, J=9.0, 6.0 Hz, 1H), 7.09 (t, J=8.4 Hz, 1H), 4.83 (d, J=9.3 Hz, 1 Hz, 1H), 4.05 (b, 2H), 3.98 (dd, J=11.25, 2.7, 1H), 3.49 (t, J=10.5 Hz, 1H), 3.031 (b, 1H), 2.84 (d, J=11, 6 Hz, 1H), 2.74 (d, J=11.5 Hz, 1H), 2.59 (s, 3H), 2.54 (b, 1H), 2.22-2.30 (m, 2H), 2.146 (t, J=11.0 Hz, 1H), 1.5 (s, 9H): Isomer 17D (slower eluting): $^1$H-NMR (500 MHz, CDCl$_3$): δ ppm 8.19 (b, 1H), 7.05 (t, J=8.5 Hz, 1H), 4.90 (s, 1H), 3.98 (b, 3H), 3.54 (d, J=12.5 Hz, 1H), 3.24 (b, 1H), 3.14 (dd, J=12, 2.5 Hz, 1H), 3.05 (b, 1H), 2.80 (dd, J=11.25, 2.5 Hz, 2H), 2.68 (b, 1H), 2.63 (s, 3H), 2.46 (b, 1H), 1.5 (s, 9H).

Intermediate 17C and 17D (Method 2)

Step A: 2-Fluoro-6-methyl-benzonitrile

A 10 L round bottom flask equipped with adapter, thermocouple and stir bar was charged with DMA (6 L) and degassed under vacuum and purged with N$_2$ three times. To the mixture was added palladium tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and zinc cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH, which was extracted three times with 1.5 L EtOAc, washed with 2 L brine, dried over Na$_2$SO$_4$, filtered and concentrated. The crude product was treated with mCPBA (~0.2 equivalents) in cooled DCM to oxidize triphenylphosphine and facilitate purification, and was then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. The reaction was poured into 1 L of ice, diluted with 700 mL 30% EtOAc/Hexanes, and agitated. The aqueous layer was cut, and the organics washed twice with 1N NaOH and then with water. The organics were dried over MgSO$_4$, concentrated, then stored in a −10° C. freezer overnight. Precipitate formed over this time, and was filtered and washed with 5% EtOAc/Hexanes, providing a first crop of product. A second crop of precipitate provided additional 3-Bromo-6-fluoro-2-methyl-benzonitrile.

Step C:
3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-bromo-6-fluoro-2-methyl-benzonitrile (115 g, 537 mmol) and cis-PdCl$_2$(PPh$_3$)$_2$ (18.9 g, 26.9 mmol) in degassed dioxane (1149 mL) and the mixture was stirred at 100° C. for 22 hours. Completion of the reaction could be seen by plating of palladium metal onto the side of the flask. The reaction was cooled to 0° C. and THF (575 mL) and Water (230 mL) were added followed by NBS (110 g, 618 mmol) (added portionwise over 15 min, maintaining internal temperature<5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over MgSO$_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: 3S 9aR-3-(3-Cyano-4-fluoro-2-methyl-phenyl)-3-hydroxy-hexahydro-pyrazino[2,1-c][1,4]oxazine-8-carboxylic acid tert-butyl ester Diisopropylethylamine (156 mL, 894 mmol) was added to a stirred, room temperature mixture of 3-(2-Bromo-acetyl)-6-fluoro-2-methyl-benzonitrile (176 g, 688 mmol) and (R)-4-N-Boc-2-hydroxymethyl-piperazine (149 g, 688 mmol) in THF (3500 mL) and the mixture was stirred at room temperature for 18 h. The reaction was diluted with 3 L EtOAc, washed twice with 1500 mL 10% NaHCO$_3$ aqueous solution, dried over MgSO$_4$, filtered and concentrated. The residue was purified by column chromatography on silica gel (40-80% EtOAc/Hexanes, linear gradient), to provide the title compound.

Step E: 17C and 17D

A 5000-mL, three-necked, round-bottomed flask equipped with a nitrogen inlet adapter, thermocouple, and a septum was charged with the product of Step D (273 g, 696.2 mmol), TFA (1340 mL, 17.45 mol, 25 equiv), and 1300 mL of DCM. Et$_3$SiH (333 mL, 2.1 mol, 3 equiv) was added in one portion and the reaction mixture was stirred at room temperature for 12 h. The reaction mixture was concentrated to remove the TFA. The resulting material was dissolved in DCM (600 mL) and carefully charged with 2.5 M Na$_2$CO$_3$ (1400 mL, 3.5 mol, 5 equiv) (pH should be basic). Boc$_2$O (243 mL, 1.05 mol, 1.5 equiv) was added in one portion and the reaction mixture was stirred at room temperature for 2 h. The organic layer was separated, concentrated, and purified via column chromatography (0-30% acetone-hexanes) to give the product (approximately 2:1 trans:cis), which was separated by Chiral SFC to give both single isomers: Chiral SFC HPLC separation conditions: Instrument: Berger MultiGram SFC, Mettler Toledo Co, Ltd.; Column: Chiralpak AD column (Diacel Chemical Industries, LTD.) 250 mm×50 mm, 5 um.; Mobile phase: A: Supercritical CO$_2$, B: MeOH, A:B=85:15 at 150 mL/min.; Column Temp: 38° C.; Nozzle Pressure: 100 Bar; Nozzle Temp: 60° C.; Evaporator Temp: 20° C.; Trimmer Temp: 25° C.; Wavelength: 235 nm. 17C trans isomer $^1$H NMR 400 MHz, CDCl$_3$ δ: 7.720-7.683 (dd, J=9.6 Hz, 1H), 7.056 (t, J=8 Hz, 1H), 4.811-4.787 (d, J=9 Hz, 1H), 3.962-3.928 (dd, J=9.6 Hz, 3H), 3.465 (t, J=10 Hz 1H), 3.002 (s, 1H), 2.826-2.797 (d, J=11 Hz, 1H), 2.719 (s, 1H), 2.638-2.559 (m, 4H), 2.091-2.253 (m, 3H), 1.469 (s, 9H); 17D cis isomer $^1$H NMR 400 MHz, CDCl$_3$ δ: 8.182-8.146 (t, J=7 Hz, 1H), 7.019 (t, J=9 Hz, 1H), 4.873 (s, 1H), 3.952-3.711 (m, 2H), 3.530-3.503 (d, J=11 Hz, 1H), 3.215-3.020 (m, 3H), 2.801-2.761 (d, J=16 Hz, 1H), 2.593 (s, 4H), 2.452-2.430 (m, 3H), 1.463 (s, 9H).

Intermediate 18A

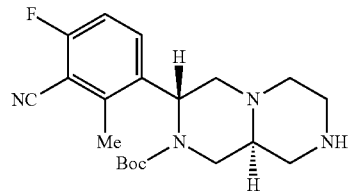 [SMILES: Cc1c([C@@H]2CN3CCNC[C@H]3CN2C(=O)OC(C)(C)C)ccc(F)c1C#N]

(3R,9aS)-tert-butyl 3-(3-cyano-4-fluoro-2-methylphenyl)hexahydro-1H-pyrazino[1,2-a]pyrazine-2(6H)-carboxylate Step A: (3S)-tert-butyl 4-(2-(3-cyano-4-fluoro-2-methylphenyl)-2-hydroxyethyl)-3-(hydroxymethyl)piperazine-1-carboxylate A mixture of 6-fluoro-2-methyl-3-(oxiran-2-yl)benzonitrile (785 mg, 4.43 mmol) and (S)-tert-butyl 3-(hydroxymethyl)piperazine-1-carboxylate (1340 mg, 6.2 mmol) in ethanol (10 mL) was heated in microwave at 150° C. for 3 h. The volatile was evaporated and the residue was purified on Biotage using 40-100% ethyl acetate/hexane to give the title compound: LC/MS: (M+1)$^+$: 394.19.

Step B: (3S)-benzyl 4-(2-(3-cyano-4-fluoro-2-methylphenyl)-2-hydroxyethyl)-3-(hydroxymethyl)piperazine-1-carboxylate To a solution of (3S)-tert-butyl 4-(2-(3-cyano-4-fluoro-2-methylphenyl)-2-hydroxyethyl)-3-(hydroxymethyl)piperazine-1-carboxylate (2.87 g, 7.32 mmol) in methylene chloride (20 mL) was added trifluoroacetic acid (20 mL) at rt, and the resulting solution was stirred at rt for 1 h. After removing the volatile solvents, the residue was dissolved in methylene chloride (50 mL). To the above solution was added triethylamine (6.12 mL, 43.9 mmol) and benzyl chloroformate (1.1 mL, 7.3 mmol) dropwise at 0° C. The reaction solution was stirred at 0° C. for 1 h before quenching with saturated sodium bicarbonate solution (200 mL). The mixture was then extracted with methylene chloride (3×100 mL). The combined organic phase was dried over sodium sulphate and concentrated to give the title compound. LC/MS: (M+1)$^+$: 428.18.

Step C: (7R,9aR)-benzyl 8-allyl-7-(3-cyano-4-fluoro-2-methylphenyl)hexahydro-1H-pyrazino[1,2-a]pyrazine-2(6H)-carboxylate and (7S,9aR)-benzyl 8-allyl-7-(3-cyano-4-fluoro-2-methylphenyl)hexahydro-1H-pyrazino[1,2-a]pyrazine-2(6H)-carboxylate A solution of (3S)-benzyl 4-(2-(3-cyano-4-fluoro-2-methylphenyl)-2-hydroxyethyl)-3-(hydroxymethyl)piperazine-1-carboxylate (1.68 g, 3.93 mmol) in sulfonyl chloride (14.0 g, 118 mmol) was heated at 90° C. for 1 h. After removing the volatile, the residue was dissolved in DMF (16 mL), treated with allylamine (1.726 mL, 23.58 mmol) and sodium iodide (0.059 g, 0.39 mmol) in a sealed tube at 0° C. and the resulting mixture was heated at 90° C. for 1 h. The mixture was diluted in ethyl acetate (300 mL), was washed with saturated sodium bicarbonate (3×200 mL), dried over sodium sulphate, concentrated, and the residue was purified on Biotage using 40-80% ethyl acetate/hexane to give the title compound (more polar on TLC). LC/MS: (M+1)$^+$: 449.24.

Step D: (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate A mixture of (7R,9aR)-benzyl 8-allyl-7-(3-cyano-4-fluoro-2-methylphenyl)hexahydro-1H-pyrazino[1,2-c]pyrazine-2(6H)-carboxylate (1260 mg, 2.81 mmol), 1,3-dimethylpyrimidine-2,4,6(1H,3H,5H)-trione (1316 mg, 8.430 mmol) and tetrakis(triphenylphosphine)palladium(0) (162 mg, 0.140 mmol) in methylene chloride (10 mL) was heated at 35° C. for 4 h. After cooling to rt, di-tert-butyl dicarbonate (736 mg, 3.37 mmol) and triethylamine (1579 µL, 11.24 mmol) were added and the resulting solution was stirred at rt overnight. After concentration, the residue was purified on Biotage using 40% EtOAc/hexane to give the title compound. LC/MS: (M+1)$^+$: 509.32.

Step E: (3R,9aS)-tert-butyl 3-(3-cyano-4-fluoro-2-methylphenyl)hexahydro-1H-pyrazino[1,2-a]pyrazine-2(6H)-carboxylate To a solution of (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate (600 mg, 1.180 mmol) in MeOH (100 mL) was added Palladium on carbon (10%, 126 mg, 0.118 mmol) and the resulting mixture was subjected to hydrogenation at rt overnight. The reaction mixture was filtered through Celite, washed with mixture of methanol and methylene chloride (1:1) and the filtrate was concentrated to give the title compound: LC/MS: (M+1)$^+$: 375.28.

Intermediate 18B

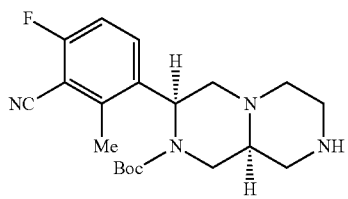 [SMILES: Cc1c([C@H]2CN3CCNC[C@H]3CN2C(=O)OC(C)(C)C)ccc(F)c1C#N]

(3S,9aS)-tert-butyl 3-(3-cyano-4-fluoro-2-methylphenyl)hexahydro-1H-pyrazino[1,2-a]pyrazine-2(6H)-carboxylate

Step A: (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate A mixture of (7S,9aR)-benzyl 8-allyl-7-(3-cyano-4-fluoro-2-methylphenyl)hexahydro-1H-pyrazino[1,2-a]pyrazine-2(6H)-carboxylate (518 mg, 1.155 mmol), 1,3-dimethylpyrimidine-2,4,6(1H,3H,5H)-trione (518 mg, 1.16 mmol) and tetrakis(triphenylphosphine)palladium(0) (66.7 mg, 0.058 mmol) in methylene chloride (10 mL) was heated at 35° C. for 4 h. After cooling to rt, di-tert-butyl dicarbonate (302 mg, 1.39 mmol) and triethylamine (649 µL, 4.62 mmol) was added and the resulting solution was stirred at rt overnight. After concentration, the residue was purified on Biotage using 40% EtOAc/hexane to give the title compound: LC/MS: (M+1)$^+$: 509.26.

Step B: (3S,9aS)-tert-butyl 3-(3-cyano-4-fluoro-2-methylphenyl)hexahydro-1H-pyrazino[1,2-a]pyrazine-2(6H)-carboxylate To a solution of (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate (0.78 g, 1.534 mmol) in MeOH (100 Ml) was added palladium on carbon (10%, 0.163 g, 0.153 mmol) and the resulting mixture was subjected to hydrogenation at rt overnight. The reaction mixture was filtered through Celite, washed with mixture of methanol and methylene chloride (1:1) and the filtrate was concentrated to give the title compound: LC/MS: (M+1)$^+$: 375.28.

Intermediate 18C

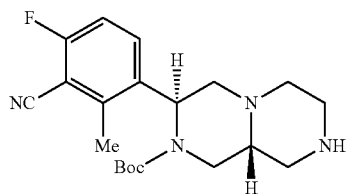 [SMILES: Cc1c([C@H]2CN3CCNC[C@@H]3CN2C(=O)OC(C)(C)C)ccc(F)c1C#N]

(3S,9aR)-tert-butyl 3-(3-cyano-4-fluoro-2-methylphenyl)hexahydro-1H-pyrazino[1,2-a]pyrazine-2(6H)-carboxylate The title compound was prepared in an analogous fashion to that described for the synthesis of (3R,9aS)-tert-butyl 3-(3-cyano-4-fluoro-2-methylphenyl)hexahydro-1H-pyrazino[1,2-a]pyrazine-2(6H)-carboxylate starting from 6-fluoro-2-methyl-3-(oxiran-2-yl)benzonitrile and (R)-tert-butyl 3-(hydroxymethyl)piperazine-1-carboxylate. LC/MS: 375.16 (M+1)+.

Intermediate 18D

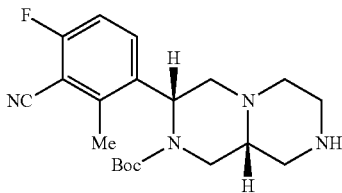 [SMILES: Cc1c([C@@H]2CN3CCNC[C@@H]3CN2C(=O)OC(C)(C)C)ccc(F)c1C#N]

(3R,9aR)-tert-butyl 3-(3-cyano-4-fluoro-2-methylphenyl)hexahydro-1H-pyrazino[1,2-a]pyrazine-2(6H)-carboxylate The title compound was prepared in an analogous fashion to that described for the synthesis of (3S,9aS)-tert-butyl 3-(3-cyano-4-fluoro-2-methylphenyl)hexahydro-1H-pyrazino[1,2-a]pyrazine-2(6H)-carboxylate starting from (7R,9aS)-benzyl 8-allyl-7-(3-cyano-4-fluoro-2-methylphenyl)hexahydro-1H-pyrazino[1,2-a]pyrazine-2(6H)-carboxylate (obtained from the synthesis of (3S,9aR)-tert-butyl 3-(3-cyano-4-fluoro-2-methylphenyl)hexahydro-1H-pyrazino[1,2-a]pyrazine-2(6H)-carboxylate). LC/MS: 375.14 (M+1)$^+$.

Intermediate 19A and 19B

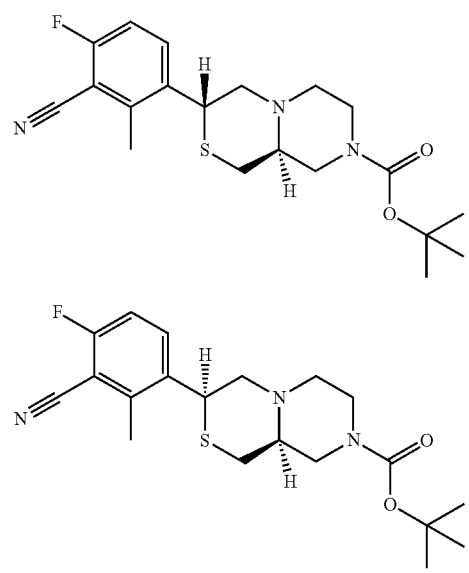

(3S,9aS)-tert-butyl 3-(3-cyano-4-fluoro-2-methylphenyl)hexahydropyrazino[2,1-c][1,4]thiazine-8(1H)-carboxylate and (3R,9aS)-tert-butyl 3-(3-cyano-4-fluoro-2-methylphenyl)hexahydropyrazino[2,1-c][1,4]thiazine-8(1H)-carboxylate Step A: (3S)-tert-butyl 3-(acetylthiomethyl)-4-(2-(3-cyano-4-fluoro-2-methylphenyl)-2-hydroxyethyl)piperazine-1-carboxylate (3S)-tert-butyl 4-(2-(3-cyano-4-fluoro-2-methylphenyl)-2-hydroxyethyl)-3-(hydroxymethyl)piperazine-1-carboxylate (synthesis described above, 0.090 g, 0.23 mmol) was dissolved in THF (2.3 mL) and cooled to 0° C. Triethylamine (0.038 mL, 0.274 mmol) was added followed by addition of Ms-Cl (0.020 mL, 0.252 mmol), and DMAP (2.79 mg, 0.023 mmol). The ice bath was removed and stirring was continued for 2 hours. The reaction mixture was then concentrated under reduced pressure. The resulting material was re-dissolved in DMSO (2 mL) and treated with potassium thioacetate (0.035 g, 0.306 mmol). The reaction mixture was stirred at room temperature under nitrogen overnight and then heated at 45° C. for 2 h. The mixture was diluted with ethyl acetate and washed with water (3 times) and brine, dried (Na$_2$SO$_4$), filtered and concentrated. The crude product was purified by column chromatography (100% hexane to 80% EtOAc/Hexane) to give the desired product LC/MS: M+1=452.3.

Step B: (3S)-tert-butyl 3-(acetylthiomethyl)-4-(2-chloro-2-(3-cyano-4-fluoro-2-methylphenyl)ethyl)piperazine-1-carboxylate To a solution of (3S)-tert-butyl 3-(acetylthiomethyl)-4-(2-(3-cyano-4-fluoro-2-methylphenyl)-2-hydroxyethyl)piperazine-1-carboxylate (30.8 mg, 0.0680 mmol) in toluene (0.62 mL) was added thionyl chloride (14.9 μL, 0.205 mmol). The mixture was cooled with an ice bath and then pyridine (22.1 μL, 0.273 mmol) was added dropwise. The reaction mixture was stirred at 0° C. for 20 min, and then allowed to warm to room temperature over an hour and finally heated at 70° C. for 30 min. The reaction mixture was concentrated and the residue was diluted with ethyl acetate, washed with a minimum amount of saturated sodium bicarbonate aqueous solution, and then brine. The organic layer was separated, filtered through a pad of anhydrous sodium sulfate and concentrated. Used directly in the next step.

Step C: (3S,9aS)-tert-butyl 3-(3-cyano-4-fluoro-2-methylphenyl)hexahydropyrazino[2,1-c][1,4]thiazine-8(1H)-carboxylate and (3R,9aS)-tert-butyl 3-(3-cyano-4-fluoro-2-methylphenyl)hexahydropyrazino[2,1-c][1,4]thiazine-8(1H)-carboxylate (3S)-tert-Butyl 3-(acetylthiomethyl)-4-(2-chloro-2-(3-cyano-4-fluoro-2-methylphenyl)ethyl)piperazine-1-carboxylate (320 mg, 0.681 mmol) in THF (34 mL) was treated with sodium methoxide (441 mg, 2.04 mmol). The mixture was stirred at room temperature under N$_2$ for 3 h. LC-MS showed the formation of the desired product as a pair of diastereomers. The reaction mixture was concentrated and partitioned between ethyl acetate and water. The organic layer was separated and washed with brine, dried and evaporated to dryness. The crude product was purified by column chromatography (100% hexane for 2 CV, 100% hexane to 35% EtOAc/Hexane for 4 CV, then kept at 35% for 4 CV, then increased to 80% EtOAc/hexane through 4 CV. (CV=column volume) to give the title compound. $^1$H-NMR for 19B (500 MHz, CD$_3$OD) δ ppm 8.76 (q, J=6.5 Hz, 9.0 Hz, 1H), 7.13 (t, J=8.5 Hz, 1H), 4.05 (bs, 1H), 3.90-4.00 (q, 2H), 3.35 (q, J=2.5 Hz, 13.0 Hz, 1H), 3.06 (m, 1H), 2.95 (m, 1H), 2.64-2.77 (m, 2H), 2.54 (s, 3H), 2.43 (m, 1H), 2.31 (m, 2H), 2.20 (m, 1H), 1.47 (s, 9H). LC-MS: M+1=392.4; $^1$H-NMR for 19A (500 MHz, CD$_3$OD) δ ppm 7.72 (q, J=6.0 Hz, 9.0 Hz, 1H), 7.23 (t, J=9.0 Hz, 1H), 4.49 (broad doublet, J=10.5 Hz, 1H), 4.14 (m, 2H), 3.46 (m, 1H), 3.14-3.23 (m, 3H), 2.83-2.98 (m, 5H), 2.66 (s, 3H), 1.48 (s, 9H); LC-MS: M+1=392.4.

Intermediates 20A and 20B

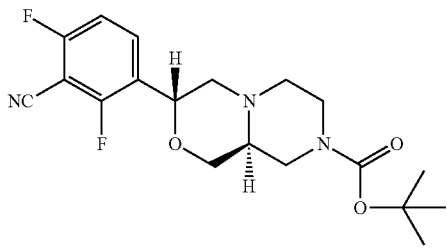

20A

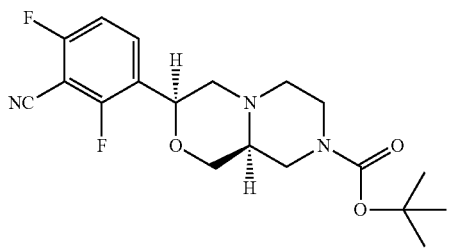

20B

20A: tert-butyl (3R,9aS)-3-(3-cyano-2,4-difluorophenyl)hexahydropyrazino[2,1-c][1,4]oxazine-8(1H)-carboxylate 20B: tert-butyl (3S,9aS)-3-(3-cyano-2,4-difluorophenyl)hexahydropyrazino[2,1-c][1,4]oxazine-8(1H)-carboxylate

Step A: 2,6-difluoro-3-hydroxybenzonitrile 2,6-difluoro-3-methoxybenzonitrile (4.42 g, 26.1 mmol) was dissolved in DCM (10 mL) at 0° C. then 1 M BBr3 (52.2 mL, 52.2 mmol) was added. The reaction mixture was then warmed up to RT and stirred overnight. The reaction mixture was poured into ice water and extracted with more DCM. The organic layer was separated, dried over $Na_2SO_4$, filtered, and evaporated to dryness to yield 2,6-difluoro-3-hydroxybenzonitrile: LC-MS: M+1=156.

Step B: 3-cyano-2,4-difluorophenyl trifluoromethanesulfonate 2,6-Difluoro-3-hydroxybenzonitrile (3.50 g, 22.6 mmol) was dissolved in DCM (50 mL), cooled to 0° C., and TEA was added (7.87 mL, 56.4 mmol) followed by triflic anhydride (7.63 mL, 45.1 mmol). The reaction mixture was stirred for 1 hour, then was poured into ice water and extracted with more DCM. The organic layer was separated and washed with sat'd aqueous $NaHCO_3$, then brine, then was dried over $MgSO_4$, filtered, and evaporated to dryness. The crude material was purified by MPLC chromatography through a 330 g Redi-sep column eluting with 0-80% EtOAc/hexane to yield 3-cyano-2,4-difluorophenyl trifluoromethanesulfonate.

Step C: 3-ethenyl-2,6-difluorobenzonitrile

3-Cyano-2,4-difluorophenyl trifluoromethanesulfonate (5.20 g, 18.1 mmol), potassium vinyl trifluoroborate (4.85 g, 36.2 mmol), $PdCl_2$(dppf)-$CH_2Cl_2$ Adduct (0.662 g, 0.905 mmol), and TEA (5.05 mL, 36.2 mmol) were added to 75 mL of ethanol. The reaction mixture was degassed then heated at reflux for 4 h. LC-MS analysis confirmed product peak. The reaction mixture was diluted with ethyl acetate, washed twice with brine, dried, and evaporated to dryness. The crude material was then purified by MPLC chromatography through a 330 g Redi-sep column eluting with 10% EtOAc/Hexane solvent system to yield 3-ethenyl-2,6-difluorobenzonitrile.

Step D: 2,6-difluoro-3-(oxiran-2-yl)benzonitrile

3-Ethenyl-2,6-difluorobenzonitrile (1.70 g, 10.3 mmol) was added to DCM (10 mL) at 0° C. Then mCPBA (5.33 g, 30.9 mmol) was added and the mixture was stirred at RT for 48 h. The reaction mixture was washed with saturated aqueous $Na_2S_2O_3$, then with 1N NaOH, and brine. The organic layer was separated and dried over $Na_2SO_4$, filtered, and evaporated to dryness. The crude product was purified by MPLC chromatography through a 120 g Redi-sep column, eluting with a 0-100% EtOAc/hexane solvent system. 2,6-Difluoro-3-(oxiran-2-yl)benzonitrile was isolated.

Step E: tert-butyl (3S)-4-[2-(3-cyano-2,4-difluorophenyl)-2-hydroxyethyl]-3-(hydroxymethyl)piperazine-1-carboxylate 2,6-Difluoro-3-(oxiran-2-yl)benzonitrile (1.50 g, 8.28 mmol) and (S)-4-N-BOC-2-hydroxymethylpiperazine (2.40 g, 11.1 mmol) were suspended in ethanol (15 mL) then heated in a microwave apparatus for 30 min at 150° C. The reaction mixture was cooled and evaporated dryness. The residue was purified by chromatography through a 120 g Redi-sep column eluting with 5% MeOH/95% EtOAc to yield the title compound LC-MS: M+1=398.

Step F: tert-butyl(9aS)-3-(3-cyano-2,4-difluorophenyl)hexahydropyrazino[2,1-c][1,4]oxazine-8(1H)-carboxylate tert-Butyl (3S)-4-[2-(3-cyano-2,4-difluorophenyl)-2-hydroxyethyl]-3-(hydroxymethyl)piperazine-1-carboxylate (1.2 g, 3.0 mmol) and cyanomethylenetri-n-butylphosphorane (1.31 g, 5.44 mmol) were dissolved in 5 mL of benzene. The reaction mixture was degassed and heated to 100° C. for 16 h. LC-MS analysis showed product peak at 2.07 min (M+1=380). The reaction was cooled and evaporated to dryness. The residue was purified by MPLC chromatography through an 80 g Redi-sep column eluting with a 40% EtOAc/60% hexane mixture to yield a cis-trans mixture of the title compound.

Step G: Isomers 20A and 20B

The isomers of the product of Step F were separated by chiral HPLC using a Chirapak AD 4.6×250 mm 10μ column and eluting with 25% IPA/75% heptane. The (3R,9aS) trans-isomer 20A eluted first and the (3S,9aS) cis-isomer 20B eluted second: 31A: $^1$H-NMR (500 MHz, CDCl$_3$): δ ppm 7.79-7.84 (q, 1H), 7.08 (t, J=8 Hz, 1H), 4.94 (d, J=10.5 Hz, 1H), 4.0 (b, 2H), 3.96 (d, J=11 Hz, 1H), 3.48 (t, J=10.5 Hz, 1H), 3.02 (b, 1H), 2.97 (d, J=11 Hz, 1H), 2.75 (d, J=10.5 Hz, 1H), 2.53 (b, 1H), 2.25-2.29 (q, 2H), 2.13 (t, J=11 Hz, 1H), 1.51 (s, 9H): LC-MS: M+1=380. 31B: $^1$H-NMR (500 MHz, CDCl$_3$): δ ppm 8.29 (d, J=5.5 Hz, 1H), 7.08 (t, J=8.5 Hz, 1H), 5.0 (s, 1H), 3.70-4.10 ppm (b, 2H), 3.61 (d, J=11 Hz, 1H), 3.34 (b, 1H), 3.12 (d, J=12.5 Hz, 1H), 3.03 (b, 1H), 2.84 (d, J=12 Hz, 1H), 2.79 (d, J=11.5 Hz, 1H) 2.68 (b, 1H), 2.44-2.5 (m, 2H), 1.50 (s, 9H): LC-MS: M+1=380.

Intermediates 20C and 20D

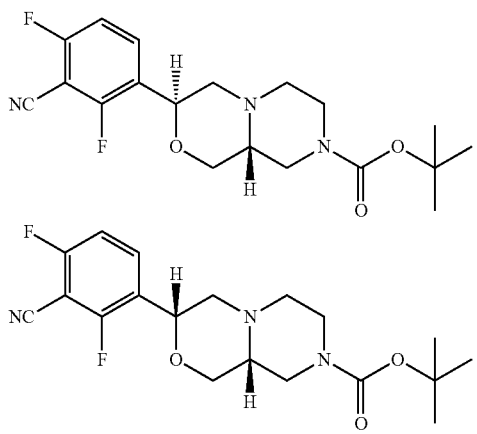

20C: (3S,9aR)-tert-butyl 3-(3-cyano-2,4-difluorophenyl)hexahydropyrazino[2,1-c][1,4]oxazine-8 (1H)-carboxylate and 20D: (3R,9aR)-tert-butyl 3-(3-cyano-2,4-difluorophenyl)hexahydropyrazino[2,1-c][1,4]oxazine-8 (1H)-carboxylate Step A: (3R)-tert-butyl 4-(2-(3-cyano-2,4-difluorophenyl)-2-hydroxyethyl)-3-(hydroxymethyl)piperazine-1-carboxylate 2,6-difluoro-3-(oxiran-2-yl)benzonitrile (3.70 g, 20.4 mmol) and (R)-tert-butyl 3-(hydroxymethyl)piperazine-1-carboxylate (6.63 g, 30.6 mmol) were dissolved in ethanol (36.0 mL) then placed in 3-20 mL sealed tubes and microwaved at 140° C. for 1 h. The solvents were evaporated and the combined residue was purified by chromatography through a 120 g ISCO Redi-sep column with 50% to 100% ethyl acetate/hexane solvent system to yield the title compound LC-MS (IE, m/z): 398 [M+1]$^+$.

Step B: (9aR)-tert-butyl 3-(3-cyano-2,4-difluorophenyl)hexahydropyrazino[2,1-][1,4]oxazine-8(1H)-carboxylate and (3S,9aR)-tert-butyl 3-(3-cyano-2,4-difluorophenyl)hexahydropyrazino[2,1-c][1,4]oxazine-8(1H)-carboxylate (3R)-tert-Butyl 4-(2-(3-cyano-2,4-difluorophenyl)-2-hydroxyethyl)-3-(hydroxymethyl)piperazine-1-carboxylate (7.30 g, 18.4 mmol) was dissolved in benzene (90 mL) and added cyanomethylene tributyl phosphorane (7.98 g, 33.1 mmol). The mixture was placed into five separate 20 mL microwave tubes, degassed and heated at 100° C. overnight. LC-MS showed product peak. Combined all reaction mixtures and concentrated. The crude product was purified by chromatography using a 330 g ISCO Redi-Sep column with 10% acetone/hexane solvent system to yield the title compound. The diastereomers were resolved by prep SFC using the following condition: 15% MeOH with 0.2% DEA)/CO$_2$ on Chiral OJ 21×250 mm column, 50 ml/min, 191 mg/mL in hot MeOH/MeCN, 35° C., 220 nm. 20C: $^1$H-NMR (600 MHz, CDCl$_3$) δ ppm 7.788 (t, J=7.9 Hz, 0.5H), 7.777 (t, J=7.9 Hz, 0.5H), 7.066 (t, J=8.35 Hz, 1H), 4.93 (d, J=9.1 Hz, 1H), 3.943 (dd, J=9.25, 3.15 Hz, 1H), 4.097-3.80 (b, 2H), 3.469 (t, J=10.7 Hz, 1H), 3.01 (b, 1H)), 2.94 (dd, J=10, 1.7 Hz, 1H), 2.733 (d, J=9.9 Hz, 1H), 2.51-2.52 (b, 1H), 2.202-2.264 (m, 2H)), 2.115 (t, J=10.9 Hz, 1H), 1.476 (s, 9H). 20D: $^1$H-NMR (600 MHz, CDCl$_3$) δ ppm 8.259 (d, J=6.1 Hz, 1H), 7.045 (t, J=8.3 Hz, 1H), 5.031 (s, 1H), 3.64-4.04 (b, 2H), 3.589 (dd, J=11.4, 2.8 Hz, 1H), 3.30 (b, 1H), 3.085 (dd, J=12, 3.1 Hz, 1H), 3.001 (b, 1H)), 2.802 (dd, J=12, 4.15 Hz, 1H), 2.757 (d, J=10.7 Hz, 1H), 2.638 (b, 1H), 2.401-2.46 (m, 2H), 1.476 (s, 9H).

Intermediates 21A and 21B

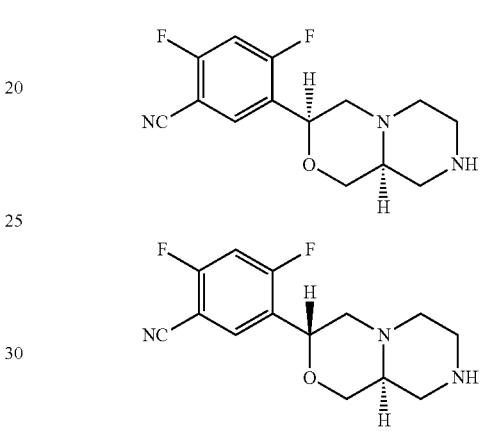

21A: 2,4-difluoro-5-[(3S,9aS)-octahydropyrazino[2,1-c][1,4]oxazin-3-yl]benzonitrile and 21B: 2,4-difluoro-5-[(3R,9aS)-octahydropyrazino[2,1-c][1,4]oxazin-3-yl]benzonitrile Step A: 5-cyano-2,4-difluorobenzoic acid To a solution of 5-bromo-2,4-difluorobenzonitrile (6.00 g, 27.5 mmol) in 80 mL of THF and 20 mL of water was added TEA (3.00 g, 29.7 mmol) and Pd(dppf)Cl$_2$ (0.8 g). The reaction was heated to 100° C. at 2 MPa of CO for 18 hours. After cooling to room temperature, the reaction was poured into 500 mL of water. The brown solid precipitated out was filtered. The filtrate cake was washed with water and then purified by silica gel column to give 5-cyano-2,4-difluorobenzoic acid.

Step B: 5-(bromoacetyl)-2,4-difluorobenzonitrile

Oxalyl chloride (5 mL) was added dropwise at 0° C. to a suspension of 5-cyano-2,4-difluorobenzoic acid (2.00 g, 10.9 mmol) in 30 mL of DCM with 0.5 mL of DMF. The mixture was stirred at 25° C. for 45 minutes and the clear solution was concentrated to dryness under reduced pressure. This acid chloride was taken up in 70 mL of THF and cooled to 0° C. with ice/water. CH$_2$N$_2$ solution (70 mmol in ~150 mL of ether) was added dropwise and stirred at 0° C. for 2 hours before 15 mL of concentrated (47%) HBr was added. The mixture was stirred at 0° C. for 20 minutes then diluted with 600 mL of EtOAc. Then the mixture was washed subsequently with water (30 mL), saturated NaHCO$_3$ (30 mL) and brine (30 mL). The EtOAc layer was dried over anhydrous Na₂SO₄ and concentrated to give 5-(bromoacetyl)-2,4-difluorobenzonitrile.

Step C: tert-butyl(3S)-4-[2-(5-cyano-2,4-difluorophenyl)-2-oxoethyl]-3-(hydroxymethyl)piperazine-1-carboxylate A suspension of 5-(bromoacetyl)-2,4-difluorobenzonitrile (2.5 g, 9.6 mmol), tert-butyl (3S)-3-(hydroxymethyl)piperazine-1-carboxylate (2.1 g, 9.6 mmol) and DIEA (1.90 g, 14.4 mmol) in 50 mL of THF was stirred at 20° C. for 10 hours. The reaction mixture was poured into ice water and extracted with EtOAc (3×200 mL). The combined organic layers were washed with water and brine, dried and concentrated. The residue was purified by column chromatography eluting with 5% MeOH in DCM to afford the title compound.

Step D: 21B: 2,4-difluoro-5-[(3R,9aS)-octahydropyrazino[2,1-c][1,4]oxazin-3-yl]benzonitrile and 21A: 2,4-difluoro-5-[(3S,9aS)-octahydropyrazino[2,1-c][1,4]oxazin-3-yl]benzonitrile To a solution of tert-butyl (3S)-4-[2-(5-cyano-2,4-difluorophenyl)-2-oxoethyl]-3-(hydroxymethyl)piperazine-1-carboxylate (3.1 g, 7.8 mmol) in 50 mL of TFA was added Et₃SiH (10.4 g, 89.0 mmol). The mixture was stirred at 50° C. for 90 minutes and concentrated to dryness under reduced pressure. The residue was washed with ether and the resulting oil was purified and the isomers separated by SFC (Column: Chiralpak AD-H 100×4.6 mm I.D., 5 um; Mobile phase: methanol (0.05% DEA) in CO₂ from 5% to 40%; Flow rate: 4.5 mL/min; Wavelength: 220 nm; Temp: 40. Gradient: 0 min 5%, 0.5 min 5%, 2.25 min 40%, 3.65 min 40%, 4.0 min 5%, 5.0 min 5%) to give the title compounds: Isomer A ¹H-NMR (MeOD, 400 MHz) δ 8.24-8.28 (m, 1H), 7.27-7.32 (m, 1H), 5.03 (brs, 1H), 3.66-3.68 (m, 1H), 3.48-3.50 (m, 3H), 3.34-3.37 (m, 1H), 3.14-3.17 (m, 3H), 2.84-2.88 (m, 3H); MS m/z 280 (M+1)⁺; Isomer B ¹H-NMR (MeOD, 400 MHz) δ 7.87-7.91 (m, 1H), 7.26-7.31 (m, 1H), 4.91 (s, 1H), 4.02-4.04 (m, 1H), 3.49-3.51 (m, 1H), 3.37-3.42 (m, 1H), 3.14-3.28 (m, 5H), 3.00-3.07 (m, 2H), 2.78-2.82 (m, 1H), 2.61-2.67 (m, 1H), 2.49-2.56 (m, 1H), 2.24-2.51 (m, 1H); MS m/z 280 (M+1)⁺.

Intermediate 22

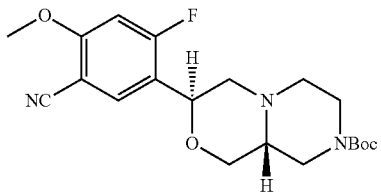 [SMILES: COc1cc(F)c([C@H]2CN3CCN(C(=O)OC(C)(C)C)C[C@@H]3CO2)cc1C#N]

tert-Butyl (3S,9aR)-3-(5-cyano-2-fluoro-4-methoxyphenyl)hexahydropyrazino[2,1-c][1,4]oxazine-8(1H)-carboxylate Step A: 1-bromo-4-fluoro-2-methoxybenzene To a solution of 2-bromo-5-fluorophenol (50 g, 0.26 mol) in 300 mL of DMF was added K₂CO₃ (72.8 g, 0.520 mol) at one portion and MeI (44.6 g, 0.310 mol) was added dropwise at 0° C. After the mixture was stirred at r.t. for 3 hours, the reaction was poured into 1 L of water and extracted with EtOAc (300 mL×3). The combined organic layers were washed with water, brine, dried and concentrated to afford 1-bromo-4-fluoro-2-methoxybenzene.

Step B: 4-fluoro-2-methoxybenzonitrile

To a solution of 1-bromo-4-fluoro-2-methoxybenzene (25 g, 0.12 mol) in 250 mL of DMF was added Zn(CN)₂ (28.6 g, 0.240 mol) and Pd(PPh₃)₄ (7.05 g, 6.10 mmol) at one portion and the reaction was charged with Ar and heated to 100° C. for 10 hours. Then the reaction was poured into 1 L of EtOAc and filtered through a kieselguhr pad. The filtrate was washed with water, brine, dried and concentrated to solid, which was purified by silica gel column to give 4-fluoro-2-methoxybenzonitrile.

Step C: 5-bromo-4-fluoro-2-methoxybenzonitrile

To a solution of 4-fluoro-2-methoxybenzonitrile (35 g, 0.23 mol) in 300 mL of concentrated H₂SO₄ was added NBS (42 g, 0.23 mol) portionwise at −10° C. and the reaction was stirred at r.t. for 2 hours. Then the reaction was poured into 2 L of ice portionwise, and the solid precipitated out was filtered. The filter cake was washed with water, then the solid was dried in vacuo to give 5-bromo-4-fluoro-2-methoxybenzonitrile.

Step D: 5-(bromoacetyl)-4-fluoro-2-methoxybenzonitrile

To a 500 mL flask was added 5-bromo-4-fluoro-2-methoxybenzonitrile (4.00 g, 17.4 mmol), Bis(Triphenylphosphine)Palladium(II)Chloride (0.61 g, 0.87 mmol), tributyl(1-ethoxy-vinyl)tin (9.42 mL, 26.1 mmol) followed by addition of 1,4 dioxane (40 mL). The resulting mixture was stirred at 95° C. for 3 h; the flask was taken out of the oil bath and cooled to rt followed by treatment with a mixture of THF/H2O (50/25 mL) and placed in an ice bath. To the flask was added NBS (6.19 g, 34.8 mmol) in small portions; after stirred for 0.5 h at 0° C., LC indicated formation of the desired product. The reaction mixture was taken out of the ice bath and slowly warmed up to rt. The reaction mixture was extracted with EtOAc (3×100 mL), washed with brine and water, it was then dried (Na₂SO₄), filtered and concentrated to dryness followed by separation over silica gel with the solvent systems of hexanes/EtOAc (1/0.5) to give the desired product. LC/MS: [(M+2)]⁺=274.

Step E: tert-butyl (3R)-4-[5-cyano-2-fluoro-4-methoxyphenyl)-2-oxoethyl]-3-(hydroxymethyl)piperazine-1-carboxylate To a 250 mL flask was added 5-(bromoacetyl)-4-fluoro-2-methoxybenzonitrile (2.00 g, 7.35 mmol), (R)—N-Boc-2-hydroxymethyl-piperazine (3.18 g, 14.7 mmol), DIEA (2.57 mL, 14.7 mmol) and THF (50 mL) and stirred at rt for 1 h; LC analysis of the reaction mixture indicated completion of the reaction. The solution was treated with EtOAc (100 mL), washed with brine, dried (Na₂SO₄), filtered and concentrated to dryness. The residue was then purified over silica gel with the solvent systems of 5% MeOH in DCM to furnish the desired product. LC/MS: [(M+1)]⁺=408.

Step F: tert-Butyl (3S,9aR)-3-(5-cyano-2-fluoro-4-methoxyphenyl)hexahydropyrazino[2,1-c][1,4]oxazine-8(1H)-carboxylate To a 500 mL flask were added tert-butyl (3R)-4-[5-cyano-2-fluoro-4-methoxyphenyl)-2-oxoethyl]-3-(hydroxymethyl) piperazine-1-carboxylate (2.20 g, 5.40 mmol), triethylsilane (4.31 mL, 27.0 mmol), and a mixture of DCM/TFA (50/20 mL). The resulting mixture was then stirred for overnight at rt. LC analysis of the reaction mixture indicated completion of the reduction. The reaction mixture was concentrated to dryness and the resulting residue was dissolved in DCM (20 mL) and aq. NaHCO$_3$ and BOC$_2$O (1.2 g, 5.4 mmol), and stirred at rt for 2 h. Analysis of the reaction mixture by LC indicated complete reaction. The reaction mixture was further diluted with DCM (50 mL) and the mixture transferred into a separatory funnel and the layers separated. The organic layer was washed with brine, water, dried (Na$_2$SO$_4$), filtered, and purified over silica gel with the solvent systems of 5% MeOH in DCM to furnish the title compound. Note: The trans isomer was formed exclusively. LC/MS: [(M+1)]$^+$=392; $^1$H-NMR (500 MHz, CDCl$_3$) δ ppm 7.75 (d, J=7.5 Hz, 1H), 6.67 (d, J=11.5 Hz, 1H), 4.88 (d, J=9.5 Hz, 1H), 3.94 (s, 3H), 3.51-3.45 (m, 2H), 2.94-2.91 (m, 2H), 2.78-2.25 (m, 1H), 2.28-2.13 (m, 4H), 2.17-2.13 (m, 2H), 1.5 (s, 9H).

Intermediates 23A and 23B

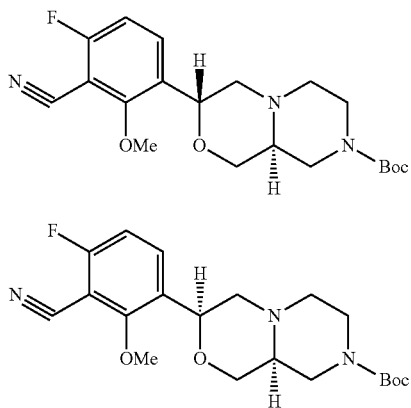

23A: tert-butyl (3R,9aS)-3-(3-cyano-4-fluoro-2-methoxyphenyl)hexahydropyrazino[2,1-c][1,4]oxazine-8(1H)-carboxylate and 23B: tert-butyl (3S,9aS)-3-(3-cyano-4-fluoro-2-methoxyphenyl) hexahydropyrazino[2,1-c][1,4]oxazine-8(1H)-carboxylate

Step A: 3-bromo-6-fluoro-2-methoxybenzonitrile (Method 1)

2-Fluoro-6-methoxybenzonitrile (8.30 g, 54.9 mmol) was dissolved in triflic acid (75 mL) at 0° C. then NBS (10.3 g, 57.7 mmol) was added. The reaction mixture was stirred at RT for 1 h. LC-MS showed no starting material peak. The reaction mixture was poured into ice and extracted twice with DCM. The combined organic layers were washed with brine, dried over Na$_2$SO$_4$, filtered, and evaporated to dryness. The residue was purified by chromatography through a 330 g Redi-Sep column and eluted with 10% to 50% EtOAc/hexane solvent system to yield the title compound.

Step B: 3-ethenyl-6-fluoro-2-methoxybenzonitrile 3-bromo-6-fluoro-2-methoxybenzonitrile (4.40 g, 19.1 mmol), potassium vinyl trifluoroborate (5.12 g, 38.3 mmol), PdCl$_2$(dppf)-CH$_2$Cl$_2$ Adduct (0.7 g, 1 mmol) and TEA (5.33 mL, 38.3 mmol) were added to 80 mL ethanol in a 200 mL flask. The reaction mixture was degassed and heated to reflux for 4 h. The reaction mixture was cooled and then most of the EtOH was removed. The residue was diluted with ethyl acetate. The mixture was washed with brine twice. The organic layer was separated and dried over Na$_2$SO$_4$, filtered, and evaporated to dryness. The residue was purified through a 330 g RediSep column and eluted with 10% EtOAc/hexane solvent system to yield the title compound.

Step C: 6-fluoro-2-methoxy-3-(oxiran-2-yl)benzonitrile

3-Ethenyl-6-fluoro-2-methoxybenzonitrile (1.67 g, 9.43 mmol) was added to DCM (50 mL) at 0° C. then mCPBA (4.88 g, 28.3 mmol) was added and the reaction mixture was stirred at RT for 16 h. The reaction mixture was washed with saturated aqueous Na$_2$S$_2$O$_3$, then with 1N NaOH followed by brine. The organic layer was separated and dried over Na$_2$SO$_4$, filtered, and evaporated to dryness. The crude product was purified by chromatography through a 120 g Redi-sep column and eluting with a 0-100% EtOAc/hexane solvent system. Isolated 6-fluoro-2-methoxy-3-(oxiran-2-yl)benzonitrile.

Step D: tert-butyl (3S)-4-[2-(3-cyano-4-fluoro-2-methoxyphenyl)-2-hydroxyethyl]-3-(hydroxymethyl) piperazine-1-carboxylate 6-Fluoro-2-methoxy-3-(oxiran-2-yl)benzonitrile (1.4 g, 7.3 mmol) and (S)-4-N-BOC-2-hydroxymethylpiperazine (3.13 g, 14.5 mmol) were suspended in ethanol (15 mL) then heated in a microwave apparatus for 60 min at 150° C. The reaction mixture was cooled and evaporated to dryness. The residue was purified by chromatography through a 40 g Redi-sep column and eluting with 5% MeOH/95% EtOAc to yield the title compound: LC-MS: M+1=410;

Step E: tert-butyl (9aS)-3-(3-cyano-4-fluoro-2-methoxyphenyl)hexahydropyrazino[2,1-c][1,4]oxazine-8 (1H)-carboxylate tert-Butyl (3S)-4-[2-(3-cyano-4-fluoro-2-methoxyphenyl)-2-hydroxyethyl]-3-(hydroxymethyl)piperazine-1-carboxylate (2 g, 4.88 mmol) and cyanomethylenetri-n-butylphosphorane (2.122 g, 8.79 mmol) were dissolved in 15 mL benzene. The reaction mixture was degassed and heated to 100° C. for 16 hrs. LC-MS showed product peak at 2.07 (M+1=380). The reaction was cooled and evaporated to dryness. The residue was chromatographed through a 80 g Redi-sep column and eluted with 40% EtOAc/60% hexane mixture to yield cis-trans mixture of the title compound.

Step F: Trans Isomer (3R,9aS) 23A and Cis Isomer (3S,9aS) 23B

The isomers were separated by Chirapak AD-H 250 mm×30 mm I.D. with 85% SFC CO$_2$ and 15% EtOH. The trans-isomer eluted first, then the cis-isomer. 23A: $^1$H-NMR (500 MHz, CDCl$_3$): δ ppm 7.72 ppm (t, J=8 Hz, 1H), 6.96 (t, J=8 Hz, 1H), 4.92 (d, J=9.5 Hz, 1H), 4.17 (s, 3H), 4.03 (b, 2H), 3.96 (d, J=11 Hz, 1H), 3.49 (t, J=10.5 Hz, 1H), 3.05 (b, 1H), 2.95 (d, J=10.5 Hz, 1H), 2.74 (s, 1H), 2.54 (b, 1H), 2.24 (d, J=10.5 Hz, 2H), 2.07 (t, J=10.5 Hz, 1H), 1.50 (s, 9H); LC-MS: M+1=392; 23B: $^1$H-NMR (500 MHz, CDCl$_3$): δ ppm 8.28 (b, 1H), 6.96 (t, J=8.5 Hz, 1H), 5.06 (s, 1H), 4.16 (s, 3H), 3.80-4.05 ppm (b, 2H), 3.80 (s, 1H), 3.74 (s, 1H), 3.423 (b, 1H), 3.04 (d, J=10.5 Hz, 1H), 2.81 (b, 3H), 2.56 (b, 2H) 2.68, 1.50 (s, 9H); LC-MS: M+1=392.

Method 2 for making
3-bromo-6-fluoro-2-methoxybenzonitrile

Step A: 1-bromo-4-fluoro-2-methoxybenzene

A solution of 2-bromo-5-fluorophenol (15 g, 79 mmol) in 125 mL of anhydrous DMF was added K$_2$CO$_3$ (17.0 g, 138 mmol) and MeI (14.0 g, 102 mmol) under cooling, then the reaction was stirred at room temperature for 3 hours. The mixture was poured to water, extracted with diethyl ether, washed with water and brine, dried over anhydrous Na$_2$SO$_4$ and concentrated to give 1-bromo-4-fluoro-2-methoxybenzene.

Step B: 3-bromo-6-fluoro-2-methoxybenzoic acid

A solution of dry diisopropylamine (10 g, 99 mmol) in dry THF under nitrogen was cooled with a −78° C. bath, n-butyl lithium (2.50 M in hexane, 40 mL, 99 mmol) was added and the solution was stirred at −78° C. for 20 minutes. 1-Bromo-4-fluoro-2-methoxybenzene (17.0 g, 82.5 mmol) was added. After stirring at −78° C. for 2 hours, the solution was bubbled with CO$_2$ and then warmed to 0° C. Then 1 N HCl was added until pH=3-4 and the mixture was extracted with AcOEt. The combined organic layers were washed with brine, dried over anhydrous sodium sulphate and concentrated to afford 3-bromo-6-fluoro-2-methoxybenzoic acid.

Step C: 3-bromo-6-fluoro-2-methoxybenzamide

Oxalyl chloride (15 mL) was added dropwise at 0° C. to a suspension of 3-bromo-6-fluoro-2-methoxybenzoic acid (15 g, 60 mmol) in 100 mL of DCM with 0.5 mL of DMF. The mixture was stirred at 25° C. for 2 hours and the clear solution was concentrated to dryness under reduced pressure. The residue dissolved in 60 mL of anhydrous acetonitrile was added to 600 mL of aqueous NH$_3$.H$_2$O at 0° C. and stirred for 2 hours, then filtered to give 3-bromo-6-fluoro-2-methoxybenzamide.

Step D: 3-bromo-6-fluoro-2-methoxybenzonitrile

A solution of 3-bromo-6-fluoro-2-methoxybenzamide (14 g, 61 mmol) in 100 mL of DMF was added 2,4,6-trichloro-[1,3,5]triazine (12.3 g, 67.0 mmol) portionwise at 0° C. and stirred for 2 hours before poured to ice/water. The white solid was collected by filtration and was washed with water, dissolved in DCM, dried over anhydrous Na$_2$SO$_4$ and concentrated to afford 3-bromo-6-fluoro-2-methoxybenzonitrile. $^1$H-NMR (400 MHz, CDCl$_3$) δ ppm 7.71~7.74 (m, 1H), 6.84~6.88 (m, 1H), 4.09 (s, 3H);

Intermediates 24A and 24B

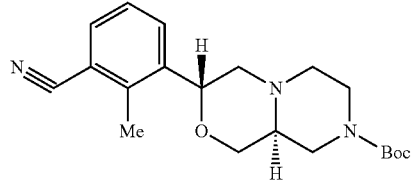

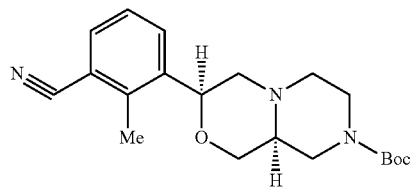

tert-butyl (3R,9aS)-3-(3-cyano-2-methylphenyl)hexahydropyrazino[2,1-c]oxazine-8(1H)-carboxylate
and tert-butyl (3S,9aS)-3-(3-cyano-2-methylphenyl)hexahydropyrazino[2,1-c][1,4]oxazine-8(1H)-carboxylate Part A
3-bromo-2-methylbenzonitrile was prepared starting from commercially available 3-bromo-2-methylbenzoic acid using an analogous sequence to that described in Method 2, Steps C and D, for making 3-bromo-6-fluoro-2-methoxybenzonitrile.

Part B
The preparation of the title compounds was accomplished in an analogous fashion as that described for making Intermediates 17A and 17B (Method 1) starting with 3-bromo-2-methylbenzonitrile in place of 3-bromo-6-fluoro-2-methylbenzonitrile. The trans and cis were separated with AD-H column, 30×250 mm, 25% IPA (0.2% DEA)/CO$_2$, 70 mL/min, 100 bar, 50 in MeOH, 35C, 220 nm. S-trans isomer (eluted first)-$^1$H-NMR (500 MHz, CDCl$_3$): δ ppm 7.74 (d, J=7.5 Hz, 1H), 7.57 (d, J=7.5 Hz, 1H), 7.34-7.32 (m, 1H), 4.87 (d, J=10 Hz, 1H), 4.07-4.02 (m, 2H), 3.98-3.96 (m, 2H), 3.52-3.48 (m, 1H), 2.86 (d, J=10 Hz, 1H), 2.75-2.73 (m, 1H), 2.59 (s, 3H), 2.29-2.24 (m, 2H), 2.19-2.15 (m, 2H), 1.49-1.48 (m, 9H); LC/MS: [(M+1)]$^+$=358: S-cis isomer (eluted second)-$^1$H-NMR (500 MHz, CDCl$_3$): δ ppm 8.14 (d, J=7 Hz, 1H), 7.59 (d, J=8 Hz, 1H), 7.32-7.31 (m, 1H), 4.93 (s, 1H), 4.08-4.03 (m, 2H), 3.59-3.56 (m, 2H), 3.31 (s, 1H), 3.18-3.15 (m, 2H), 2.82-2.87 (m, 2H), 2.65 (s, 3H), 2.53-2.49 (m, 2H), 1.49 (s, 9H); LC/MS: [(M+1)]$^+$=358

Intermediates 24C and 24D

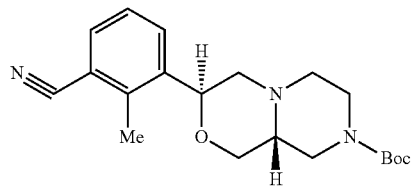

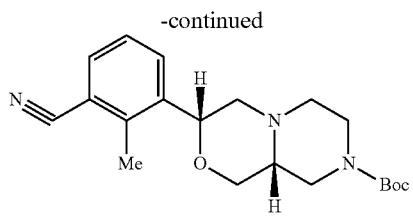

tert-butyl (3S,9aR)-3-(3-cyano-2-methylphenyl)
hexahydropyrazino[2,1-c][1,4]oxazine-8(1H)-carboxylate and tert-butyl(3R,9aR)-3-(3-cyano-2-methylphenyl)hexahydropyrazino[2,1-c][1,4]oxazine-8
(1H)-carboxylate Step A: 3-(2-Chloroacetyl)-2-methylbenzonitrile To a solution of 3-iodo-2-methylbenzonitrile (7.71 g, 31.7 mmol) and 2-chloro-N-methoxy-N-methylacetamide (6.55 g, 47.6 mmol) in THF (100 mL) at −78° C. was added n-butyllithium (2.5 M in hexanes, 14.0 mL, 34.9 mmol) dropwise. After complete addition, the mixture was stirred 15 min. at −78° C., then quenched with the dropwise addition of 1 N HCl. The mixture was partitioned between EtOAc/water and the layers separated. The aqueous was extracted with EtOAc (2×) and the combined organic layers were washed with brine, dried (magnesium sulfate), filtered and concentrated. Recrystallization of the resulting residue from hexanes provided 3-(2-chloroacetyl)-2-methylbenzonitrile: $^1$H NMR (500 MHz, CDCl$_3$), δ 7.76 (m, 2H), 7.41 (m, 1H), 4.55 (s, 2H), 2.68 (s, 3H).

Step B: tert-butyl (3R)-4-[2-(3-cyano-2-methylphenyl)-2-oxoethyl]-3-(hydroxymethyl)piperazine-1-carboxylate To a solution of 3-(chloroacetyl)-2-methylbenzonitrile (1.7 g, 8.8 mmol) in THF (17.6 mL) was added (R)-4-N-boc-2-hydroxymethyl-piperazine (2.279 g, 10.54 mmol) and DIPEA (3.07 mL, 17.56 mmol) at rt. The reaction mixture was stirred at rt over the weekend. After concentration, the residue was partitioned between EtOAc and aqueous NaHCO$_3$ (saturated). The aqueous layer was extracted with EtOAc (2×). The combined organic phase was washed with brine, dried over anhydrous MgSO$_4$, and filtered. Concentration was followed by purification by prep TLC (silica gel; 10% MeOH/DCM) to give the title compound: LC/MS (M+1)$^+$=374.14

Step C: 2-methyl-3-[(3S,9aR)-octahydropyrazino[2,1-c][1,4]oxazin-3-yl]benzonitrile and 2-methyl-3-[(3R,9aR)-octahydropyrazino[2,1-c][1,4]oxazin-3-yl]benzonitrile To a solution of tert-butyl (3R)-4-[2-(3-cyano-2-methylphenyl)-2-oxoethyl]-3-(hydroxymethyl)piperazine-1-carboxylate (2.38 g, 6.37 mmol) in DCM (21.24 mL) and TRIETHYLSILANE (5.09 mL, 31.9 mmol) was added TFA (10.62 mL) drop-wise at room temperature. The reaction mixture was stirred at rt for 5 h. After concentration, the residue was partitioned between DCM and aqueous NaHCO$_3$ saturated. The aqueous layer was extracted with DCM (2×). The combined organic phase was washed with brine, dried over anhydrous MgSO$_4$, and filtered. After concentration, the residue was redissolved in 20 mL of DCM, and BOC$_2$O (3.70 mL, 15.9 mmol) was added at rt. The mixture was left to stir at rt for 2 h. After concentration, the residue was partitioned between EtOAc and aqueous NaHCO$_3$ saturated. The aqueous layer was extracted with EtOAc (2×). The combined organic phase was washed with brine, dried over anhydrous MgSO$_4$, and filtered. After concentration, the mixture was purified by prep TLC (silica gel; 10% MeOH/DCM) to give a mixture of cis and trans products. The mixture was resolved by prep SFC with 15% MeOH:MeCN at 35° C. on OD-H column to give two single diastereomers.

Intermediates 25A and 25B

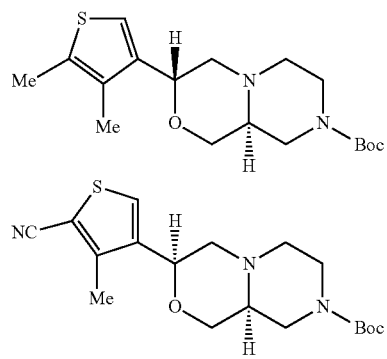

tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate Step A: 2,4-dibromo-3-methylthiophene To a solution of 2,3,5-tribromo-4-methylthiophene (46.2 g, 138 mmol) in 500 mL of THF was added dropwise n-BuLi (55.2 mL, 138.0 mmol) at −70° C. The mixture was stirred at −70° C. for 15 minutes and 50 mL of water was added slowly. The resulting mixture was allowed to warm to room temperature and stirred for 10 minutes and extracted with EtOAc. The organic layers were washed with water and brine, dried over anhydrous Na$_2$SO$_4$ and concentrated to give crude 2,4-dibromo-3-methylthiophene.

Step B: 4-bromo-3-methylthiophene-2-carbonitrile

A mixture of 2,4-dibromo-3-methylthiophene (20.0 g, 78.1 mmol) and CuCN (6.30 g, 70.3 mmol) in 150 mL of DMF was stirred at reflux for 4 hours before cooling down. The reaction mixture was poured into 1 L of ether with stirring and the precipitate was removed by filtration. The filtrate was washed with water (3×100 mL), brine (100 mL), dried over anhydrous Na$_2$SO$_4$ and concentrated. The residue was purified by silica column chromatography (petrol ether: EtOAc=50:1) to afford 4-bromo-3-methylthiophene-2-carbonitrile.

Step C: 4-ethenyl-3-methylthiophene-2-carbonitrile

A mixture of 4-bromo-3-methylthiophene-2-carbonitrile (3.00 g, 14.8 mmol), potassium vinyltrifluoroborate (2.40 g, 17.8 mmol) and Pd(dppf)Cl$_2$ (0.5 g) in 30 mL of EtOH and 30 mL of TEA was refluxed under Ar for 4 hours. The reaction mixture was concentrated, and the residue was purified by column chromatography (petrol ether: EtOAc=50:1) to afford 4-ethenyl-3-methylthiophene-2-carbonitrile.

Step D: 3-methyl-4-(oxiran-2-yl)thiophene-2-carbonitrile

A suspension of 4-ethenyl-3-methylthiophene-2-carbonitrile (1.70 g, 11.4 mmol) in 30 mL of t-Bu-OH and 60 mL of water was added NBS (2.40 g, 13.7 mmol) portionwise. The mixture was stirred at 90° C. for 1 hour then cooled down to 10° C. Then a solution of NaOH (0.7 g in 10 mL of water, 17.5 mmol) was added dropwise and stirred for 15 minutes. The reaction mixture was extracted with EtOAc twice and concentrated. The residue was purified by silica column chromatography (petrol ether:EtOAc=20:1) to afford 3-methyl-4-(oxiran-2-yl)thiophene-2-carbonitrile.

Step E: tert-butyl(3S)-4-[2-(5-cyano-4-methylthiophen-3-yl)-2-hydroxyethyl]-3-(hydroxymethyl)piperazine-1-carboxylate A mixture of 3-methyl-4-(oxiran-2-yl)thiophene-2-carbonitrile (1.3 g, 7.9 mmol) and tert-butyl (3S)-3-(hydroxymethyl)piperazine-1-carboxylate (2.0 g, 9.5 mmol) in 5 mL of EtOH was heated in a microwave apparatus at 140° C. for 90 minutes and then cooled down. The reaction mixture was concentrated, and the residue was purified by column chromatography (DCM:MeOH=10:1) to afford the title compound.

Step F: tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate tert-Butyl (3S)-4-[2-(5-cyano-4-methylthiophen-3-yl)-2-hydroxyethyl]-3-(hydroxymethyl)piperazine-1-carboxylate (1.40 g, 3.67 mmol) and cyanomethylene tributylphosphorane (1.59 g, 6.61 mmol) were dissolved in benzene (15 mL) in a microwave tube then sealed, degassed and heated to 100° C. overnight. The reaction mixture was cooled and the benzene was evaporated off. The residue was then purified by chromatography through a 80 g Redi-sep column eluting with acetone:DCM (5:95). The cis-isomer tert-butyl (3S,9aS) eluted first; the trans-isomer (3R,9aS) eluted second: Isomer 1: $^1$H-NMR (500 MHz, CDCl$_3$): δ ppm 8.06 (s, 1H), 4.76 (s, 1H), 4.00 (b, 1H), 3.79 (d, J=11 Hz, 0.5H), 3.70 (d, J=10 Hz, 0.5H), 3.42 (d, J=11.5 Hz, 1H), 3.15 (t, J=10.5 Hz, 1H), 3.10 (s, 0.5H), 3.08 (s, 0.5H), 2.99 (b, 1H), 2.75 (t, J=13.0 Hz, 2H), 2.46 (b, 1H), 2.41 (s, 3H), 2.24-2.40 (m, 2H), 1.45 (s, 9H); LC-MS: M+1=264; Isomer 2: $^1$H-NMR (500 MHz, CDCl$_3$): δ ppm 7.50 (s, 1H), 4.66 (d, J=10 Hz, 1H), 3.80-4.15 (m, 3H), 3.45 (t, J=10 Hz, 1H), 3.02 (b, 1H), 2.89 (d, J=11.5 Hz, 1H), 2.75 (d, J=9.5 Hz, 1H), 2.53 (b, 1H), 2.43 (s, 3H), 2.27 (t, J=10.5 Hz, 3H), 1.49 (s, 9H); LC-MS: M+1=264.

Intermediate 26A

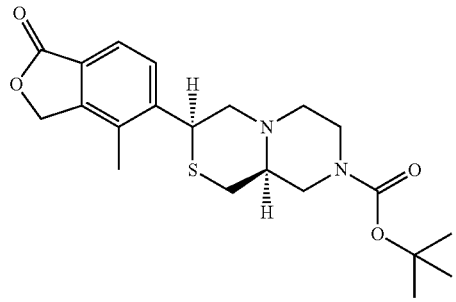 [SMILES: Cc1c([C@H]2CN3CCN(C(=O)OC(C)(C)C)C[C@H]3CS2)ccc2c1COC2=O]

(3S,9aS)-tert-butyl 3-(4-methyl-1-oxo-1,3-dihydroisobenzofuran-5-yl)hexahydropyrazino[2,1-c][1,4]thiazine-8(1H)-carboxylate

Step A: (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate (S)-tert-Butyl 4-((R)-2-hydroxy-2-(4-methyl-1-oxo-1,3-dihydroisobenzofuran-5-yl)ethyl)-3-(hydroxymethyl)piperazine-1-carboxylate was prepared starting from 4-methyl-5-[(2R)-oxiran-2-yl]-2-benzofuran-1(3H)-one in an analogous fashion to that described above for the synthesis of (S)-tert-butyl 4-(2-hydroxy-2-(4-methyl-1-oxo-1,3-dihydroisobenzofuran-5-yl)ethyl)-3-(hydroxymethyl)piperazine-1-carboxylate.

Step B: (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate To the solution of (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate (817 mg, 2.01 mmol) in anhydrous THF (20 mL) under nitrogen atmosphere at 0° C. was added anhydrous triethylamine (0.560 mL, 4.02 mmol), followed by addition of methanesulfonyl chloride (0.234 mL, 3.01 mmol) and 4-dimethylaminopyridine (24.6 mg, 0.201 mmol). The ice bath removed and reaction mixture was stirred for 2 hours. Resulting mixture was then concentrated under reduced pressure. Resulting oil was redissolved in anhydrous DMSO (13 mL) and treated with potassium thioacetate (1235 mg, 10.81 mmol). The reaction mixture was stirred at room temperature under nitrogen for 2 hours. The mixture was diluted with ethyl acetate, washed with water (3 times), brine, and dried (MgSO$_4$), filtered and concentrated. The crude product was purified on Biotage SP1 (40+M equilibrated), eluting with 20-80% ethyl acetate/hexanes, 20 CV. LC/MS: [(M+1)]$^+$=465.2.

Step C: (3S)-tert-butyl 3-(acetylthiomethyl)-4-(2-chloro-2-(4-methyl-1-oxo-1,3-dihydroisobenzofuran-5-yl)ethyl)piperazine-1-carboxylate To a cooled with an ice bath solution of (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate (573 mg, 1.233 mmol) in anhydrous toluene (12.3 mL) was added thionyl chloride (0.268 mL, 3.70 mmol). Then, anhydrous pyridine (0.399 mL, 4.93 mmol) was added dropwise. The reaction mixture was kept at 0° C. for 20 min, then warmed to room temperature and stirred for 3 hours. TLC showed the consumption of the starting material. The reaction was concentrated under reduced pressure and dried on high vacuum overnight. Used directly in the next step.

Step D: (3S,9aS)-tert-butyl 3-(4-methyl-1-oxo-1,3-dihydroisobenzofuran-5-yl)hexahydropyrazino[2,1-c][1,4]thiazine-8(1H)-carboxylate A solution of (3S)-tert-butyl 3-(acetylthiomethyl)-4-(2-chloro-2-(4-methyl-1-oxo-1,3-dihydroisobenzofuran-5-yl)ethyl)piperazine-1-carboxylate (596 mg, 1.234 mmol) in anhydrous THF (20 mL) was treated dropwise with sodium methoxide, 25% solution in methanol (0.846 mL, 3.70 mmol). The reaction mixture was stirred for 2 hours under nitrogen at room temperature. LCMS showed formation of the desired product. Solvent was removed under reduced pressure. Residue was redissolved in dichloromethane and washed with brine. Organic layer was dried over MgSO$_4$, filtered and concentrated. Residue was purified on Biotage SP1, eluting with 20-80% ethyl acetate/hexanes, 16 CV: ¹H NMR (500 MHz, CDCl₃) δ 8.64 (d, J=8.0 Hz, 1H), 7.77 (d, J=8.0 Hz, 1H), 5.29 (s, 2H), 3.81-4.20 (m, 3H), 3.38 (dd, J=2.3, 12.6 Hz), 3.00-3.22 (m, 2H), 2.57-2.82 (m, 2H), 2.24-2.56 (m, 7H), 1.51 (s, 9H).

Intermediates 27A and 27B

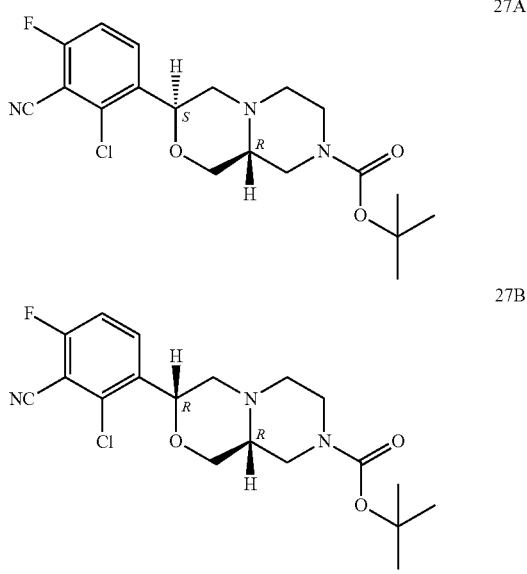

27A: tert-butyl (3S,9aR)-3-(2-chloro-3-cyano-4-fluorophenyl)hexahydropyrazino[2,1-c][1,4]oxazine-8(1H)-carboxylate and 27B: tert-butyl (3R,9aR)-3-(2-chloro-3-cyano-4-fluorophenyl)hexahydropyrazino[2,1-c][1,4]oxazine-8(1H)-carboxylate Step A: 3-bromo-2-chloro-6-fluorobenzonitrile 2-Chloro-6-fluorobenzonitrile (15.6 g, 100 mmol) was dissolved in trific acid (75 mL) at 0° C., then NBS (17.8 g, 100 mmol) was added. The reaction was warmed up to room temperature and stirred overnight. The reaction mixture was poured into ice and extracted with DCM (2×). DCM layers were washed with NaHCO₃ and brine. The DCM was dried over Na₂SO₄ then filtered and concentrated. The product was purified by chromatography through a 330 g ISCO Redi-Sep column with 10-20% ethyl acetate/hexane solvent system to yield 3-bromo-2-chloro-6-fluorobenzonitrile.

Step B: 2-chloro-6-fluoro-3-vinylbenzonitrile

3-Bromo-2-chloro-6-fluorobenzonitrile (15.4 g, 65.6 mmol), potassium vinyl trifluoroborate (17.6 g, 131 mmol), triethylamine (18.3 mL, 131 mmol) and PdCl₂(dppf)-CH₂Cl₂ adduct (2.68 g, 3.28 mmol) were added to ethanol (75 mL) then degassed and heated at reflux for 3 h. The reaction was diluted with ethyl acetate and washed with brine, dried and evaporated to dryness. The product was purified by chromatography through a 330 g ISCO Redi-Sep column with 10% ethyl acetate/hexane solvent system to yield 2-chloro-6-fluoro-3-vinylbenzonitrile.

Step C: 2-chloro-6-fluoro-3-(oxiran-2-yl)benzonitrile 2-chloro-6-fluoro-3-vinylbenzonitrile dissolved in CHCl₃ (300 mL) then added mCPBA (29.4 g, 171 mmol) and stirred at RT for 16 h. When TLC showed starting materials were consumed, the mixture was washed with Na₂S₂O₃ (1×), 1N NaOH (1×), brine (2×), then dried over Na₂SO₄. Filtered and concentrated then purified by MPLC chromatography using 330 g ISCO Redi-sep column and eluted with 20% ethyl acetate/hexane solvent system to yield 2-chloro-6-fluoro-3-(oxiran-2-yl)benzonitrile.

Step D: (3R)-tert-butyl 4-(2-(2-chloro-3-cyano-4-fluorophenyl)-2-hydroxyethyl)-3-(hydroxymethyl)piperazine-1-carboxylate 2-Chloro-6-fluoro-3-(oxiran-2-yl)benzonitrile (9.1 g, 46 mmol) and (R)-tert-butyl 3-(hydroxymethyl)piperazine-1-carboxylate (14.9 g, 69.1 mmol) were dissolved in ethanol (105 mL) and dispensed into 9 sealed tubes then microwaved at 140° C. for 1 h. The combined reaction mixture was concentrated and purified through a 330 g ISCO Redi-sep column with 50%-100 ethyl acetate/hexane solvent system to yield the title compound.

Step E: (9aR)-tert-butyl 3-(2-chloro-3-cyano-4-fluorophenyl)hexahydropyrazino[2,1-c][1,4]oxazine-8(1H)-carboxylate (3R)-tert-butyl 4-(2-(2-chloro-3-cyano-4-fluorophenyl)-2-hydroxyethyl)-3-(hydroxymethyl)piperazine-1-carboxylate (15.6 g, 37.3 mmol) and cyanomethylene tri-n-butyl phosphorane (16.4 g, 67.8 mmol) were dissolved in benzene (90 mL), degassed and heated at 100° C. for 16 h. The reaction mixture was concentrated and chromatographed through a 330 g ISCO Redi-sep column and eluted with 35% EtOAc/hexane to yield the title compound (cis-trans diastereomers mixture). LC-MS (IE, m/z): 396 [M+1]⁺;

The cis-trans diastereomers were separated by SFC-HPLC using the following condition: Chiralpak AD 21×250 mm, 20% IPA, 50 ml/min, ~85 mg/mL in 1:1 MeOH/MeCN, 100 bar, 220 nm, 35° C. 27A: ¹H-NMR (600 MHz, CDCl₃) δ ppm 7.826 (dd, J=8.7, 6.5 Hz, 1H), 7.184 (t, J=8.4 Hz, 1H), 4.975 (dd, J=9.6, 1.9 Hz, 1H), 3.989 (b, 2H), 3.953 (dd, J=5.7, 3.2 Hz, 1H) 3.484 (t, J=10.85 Hz, 1H), 3.015 (dd, J=11.4, 2.2 Hz, 2H), 2.733 (d, J=10.3 Hz, 1H), 2.52 (b, 1H), 2.18-2.26 (m, 2H), 1.981 (t, J=10.85 Hz, 1H), 1.474 (s, 9H). 27B: ¹H-NMR (600 MHz, CDCl₃) δ ppm 8.331 (s, 1H), 7.163 (t, J=8.35 Hz, 1H), 5.038 (t, J=3.7 Hz, 1H), 3.738-3.947 (b, 2H), 3.649 (d, J=10.9 Hz, 1H) 3.371 (s, 1H), 3.02 (dd, J=12, 4.1 Hz, 2H), 2.843 (dd, J=12, 3.8 Hz, 1H), 2.784 (d, J=9.4 Hz, 2H), 2.556 (b, 2H), 1.471 (s, 9H).

Intermediates 27C and 27D

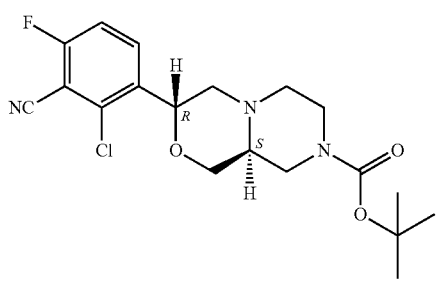

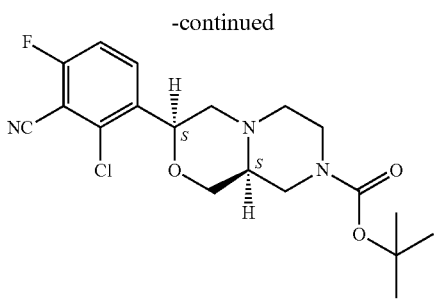

tert-butyl (3R,9aS)-3-(2-chloro-3-cyano-4-fluorophenyl)hexahydropyrazino[2,1-c][1,4]oxazine-8(1H)-carboxylate and tert-butyl (3S,9aS)-3-(2-chloro-3-cyano-4-fluorophenyl)hexahydro-pyrazino[2,1-c][1,4]oxazine-8(1H)-carboxylate The title compounds were prepared in an analogous fashion to that described for the 27A and 27B except using (S)-tert-butyl 3-(hydroxymethyl)piperazine-1-carboxylate in Step D and with a minor change in the last step as described as follows:

tert-Butyl (3S)-4-[2-(2-chloro-3-cyano-4-fluorophenyl)-2-hydroxyethyl]-3-(hydroxymethyl)piperazine-1-carboxylate (4.00 g, 9.66 mmol) and cyanomethylene tri-n-butylphosphorane (4.20 g, 517 mmol) were dissolved in 60 mL benzene. The reaction mixture was degassed and heated to 100° C. for 3 h. The reaction was cooled and evaporated to dryness. The residue was purified by chromatography through a 330 g Redi-sep column, eluting with 33% EtOAc/67% hexane. 27C-trans (eluted first): $^1$H-NMR (500 MHz, CDCl$_3$): δ ppm. 7.86 (t, J=6.5 Hz, 1H), 7.21 (t, J=7.5 Hz, 1H), 5.01 (d, J=10.5 Hz, 1H), 4.04 (b, 2H), 3.99 (d, J=11.5 Hz, 2H) 3.52 (t, J=10 Hz, 1H), 3.05 (d, J=11.5 Hz, 2H), 2.77 (d, J=10.5 Hz, 1H), 2.57 (b, 1H), 2.21-2.29 (m, 2H), 2.02 (t, J=11.5 Hz, 1H), 1.51 (s, 9H); LC-MS: M+1=396: 27D-cis: $^1$H-NMR (500 MHz, CDCl$_3$): δ ppm 8.36 (s, 1H), 7.19 ppm (t, J=8.5 Hz, 1H), 5.07 ppm (s, 1H), 3.91 (b, 2H), 3.68 (d, J=11.5 Hz, 1H), 3.40 (s, 1H), 3.06 (d, J=12 Hz, 2H), 2.87 (s, 1H), 2.86 (s, 1H), 2.815 (d, J=10.5 Hz, 1H) 2.60 (d, J=10 Hz, 2H); 1.50 (s, 9H); LC-MS: M+1=396.

Intermediate 28

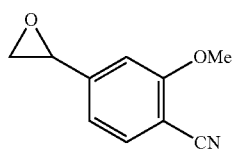 [SMILES: COc1cc(C2CO2)ccc1C#N]

2-Methoxy-4-(oxiran-2-yl)benzonitrile

Step A: 4-Formyl-2-methoxyphenyl trifluoromethanesulfonate

To a solution of vanillin (20 g, 131 mmol) in DMF (200 mL) at room temperature was added potassium carbonate (36.30 g, 263 mmol) and 4-nitrophenyl trifluoromethanesulfonate (53.5 g, 197 mmol) and the reaction mixture was stirred for 8 hr. EtOAc (600 mL) was added to the reaction mixture and the organic layer was washed three times with water, dried, filtered, and concentrated. The crude compound was then purified by flash chromatography (ethylacetate/hexanes 1:9→3:7) to provide sulfonate.

Step B: 4-Formyl-2-methoxybenzonitrile

A mixture of the sulfonate (37.0 g, 130 mmol), zinc cyanide (61.1 g, 521 mmol) and tetrakis triphenylphosphine palladium (0) (22.57 g, 19.53 mmol) in DMF (300 mL) were stirred at 110° C. for 8 hr. EtOAc was added to the reaction mixture and the organic layer was washed two times with water, dried, filtered and concentrated. The crude product was then purified by column chromatography (silica gel, ethylacetate/hexanes 3:7) which afforded the title compound: LC/MS: (IE, m/z) [M+1]$^+$=162.34.

Step C: 2-Methoxy-4-(oxiran-2-yl)benzonitrile

To a cool solution of NaH (0.16 g, 3.9 mmol) in THF (40 mL) was added dropwise a solution of trimethylsulfonium iodide (0.91 g, 4.5 mmol) in DMSO (20 mL). The resulting mixture was stirred at 0° C. under N2 for 20 min. A solution of 4-formyl-2-methoxybenzonitrile (0.60 g, 3.72 mmol) in THF (20 mL) was added. The resulting reaction mixture was stirred at 0° C. under N$_2$ for 1 hr, and then it was warmed gradually to room temperature and stirred at that temperature for 12 hr. The starting material was consumed as indicated by TLC (25% ethyl acetate/hexanes). The reaction mixture was cooled to 0° C. and quenched with dropwise addition of water. The mixture was extracted with ethyl acetate (2×70 mL). The combined organic layers were washed with water, brine, then dried (MgSO$_4$) and filtered. The filtrate was concentrated in vacuo. The residue was purified via column chromatography (silica gel, 10-30% EtOAc-hexanes) to afford 2-methoxy-4-(oxiran-2-yl)benzonitrile: $^1$H NMR (CDCl$_3$, 500 MHz) δ 7.57 (d, J=8 Hz, 1H), 6.99 (dd, J=1.1 Hz, J=1.2 Hz, 1H), 6.89 (s, 1H), 3.97 (s, 3H), 3.94-3.92 (m, 1H), 3.22 (dd, J=5.2, Hz, J=4.1 Hz, 1H), 2.77 (d, J=2.5 Hz, 1H); LC/MS: (IE, m/z) [M+1]$^+$=176.33.

Intermediates 29A and 29B

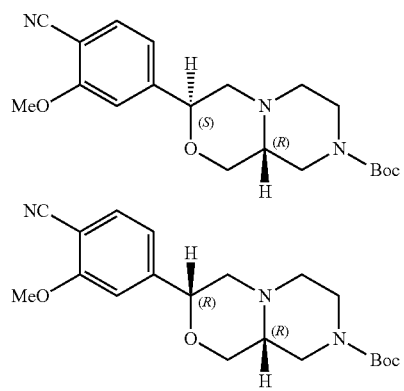

29A: tert-Butyl (3S,9aR)-3-(4-cyano-3-methoxyphenyl)hexahydropyrazino[2,1-c][1,4]oxazine-8(1H)-carboxylate and 29B: tert-Butyl (3R,9aR)-3-(4-cyano-3-methoxyphenyl)hexahydropyrazino[2,1-c][1,4]oxazine-8(1H)-carboxylate Step A: tert-Butyl (3R)-4-[2-(4-cyano-3-methoxyphenyl)-2-hydroxyethyl]-3 (hydroxymethyl)piperazine1-carboxylate A Pyrex vessel was charged with magnetic stirring bar, (2.0 g, 11.42 mmol) of 2-methoxy-4-(oxiran-2-yl)benzonitrile, (3.70 g, 17.12 mmol) of tert-butyl (3R)-3-(hydroxymethyl) piperazine-1-carboxylate, and 6 mL of EtOH. Then it was introduced in the microwave reactor and irradiated at 150° C. for 3 h. The mixture was cooled to room temperature and the solvent was evaporated and the resulting residue was purified by column chromatography (silica gel, 1-20% dichloromethane/MeOH) which afforded the product as a mixture of two diastereomers (1:1) LC/MS: (IE, m/z) [(M+1)-t-Bu]$^+$= 336.41

Step B: tert-Butyl (9aR)-3-(4-cyano-3-methoxyphenyl)hexahydropyrazino[2,1-c][1,4]oxazine-8(1H)-carboxylate The isomeric mixture of the prior step (3.48 g, 8.89 mmol, 1:1) in benzene was treated with (tributyl-$\lambda^5$-phosphanylidene)acetonitrile (3.22 g, 13.3 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1→3:7, as eluent) to give an isomeric mixture of the bicyclic title compound.

Step C: tert-Butyl(3S,9aR)-3-(4-cyano-3-methoxyphenyl)hexahydropyrazino[2,1-c][1,4]oxazine-8 (1H)-carboxylate and tert-Butyl(3R,9aR)-3-(4-cyano-3-methoxyphenyl)hexahydropyrazino[2,1-c][1, 4]oxazine-8(1H)-carboxylate The isomeric mixture was further separated into its enantiomers using a 21×250 mm ChiralCel OJ-H, column, eluting with 15% MeOH/CO$_2$ with a flow rate of 50 mL/min, 100 bar, 59 mg/mL in MeOH, 35C, 220 nm, Thr=200: trans-$^1$H NMR (CDCl$_3$, (trans) isomer, 500 MHz) δ 7.54 (d, J=7.9 Hz, 1H), 7.05 (s, 1H), 6.97 (d, J=7.9 Hz, 1H), 4.72 (d, J=8.9 Hz, 1H), 4.12-4.0 (m, 2H), 3.98 (s, 3H), 3.49 (t, J=9.4 Hz, J=9.0 Hz, 1H), 3.03 (bs, 1H), 2.94 (d, J=11.2 Hz, 1H), 2.76 (d, J=9 Hz, 1H), 2.56 (bs, 1H), 2.29-2.192 (m, 3H), 1.69 (bs, 1H), 1.50 (s, 9H); LC/MS: (IE, m/z) [(M+1)-t-Bu]$^+$=318.40; cis-$^1$H NMR (CDCl$_3$, (cis) isomer, 500 MHz) δ 7.58 (d, J=7.9 Hz, 1H), 7.21 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (d, J=11.6 Hz, 1H), 3.05 (bs, 1H), 2.81 (bs, 2H), 2.72-2.42 (m, 3H), 1.50 (s, 9H); LC/MS: (IE, m/z) [(M+1)-t-Bu]$^+$=318.35.

Intermediates 30 and 31

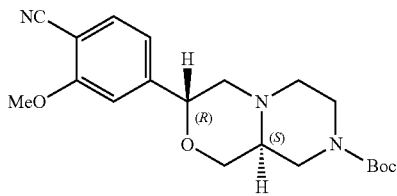

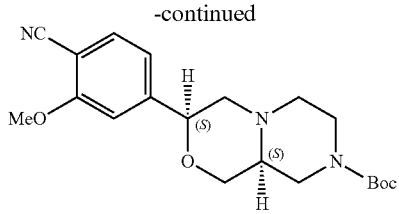

30: tert-Butyl (3R,9aS)-3-(4-cyano-3-methoxyphenyl)hexahydropyrazino[2,1-c][1,4]oxazine-8(1H)-carboxylate and 31: tert-Butyl (3S,9aS)-3-(4-cyano-3-methoxyphenyl)hexahydropyrazino[2,1-c][1,4]oxazine-8(1H)-carboxylate Step A: tert-Butyl (3S)-4-[2-(4-cyano-3-methoxyphenyl)-2-hydroxyethyl]-3-(hydroxymethyl)piperazine-1-carboxylate A Pyrex vessel was charged with magnetic stirring bar, (0.350 g, 2.00 mmol) of 2-methoxy-4-(oxiran-2-yl)benzonitrile, (0.457 g, 2.20 mmol) of tert-butyl (3S)-3-(hydroxymethyl)piperazine-1-carboxylate, and 6 mL of EtOH. Then it was introduced in the microwave reactor and irradiated at 150° C. for 3 hr. Then the mixture was cooled to room temperature and the solvent was evaporated and the resulting residue was purified by column chromatography (silica gel, 1-20% dichloromethane/MeOH) which afforded the title compound as a mixture of two diastereomers (1:1). LC/MS: (IE, m/z) [(M+1)-t-Bu]$^+$=336.1.

Step B: tert-Butyl (9aS)-3-(4-cyano-3-methoxyphenyl)hexahydropyrazino[2,1-c][1,4]oxazine-8(1H)-carboxylate The isomeric mixture of the prior step (0.55 g, 1.40 mmol, 1:1) in benzene was treated with (tributyl-$\lambda^5$-phosphanylidene)acetonitrile (0.678 g, 2.81 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1→3:7, as eluent) to give an isomeric mixture of the bicyclic title compound LC/MS: (IE, m/z) [(M+1)-t-Bu]$^+$=318.06.

Step C: 29C: and 29D tert-Butyl (9aS)-3-(4-cyano-3-methoxyphenyl)hexahydropyrazino[2,1-c][1,4]oxazine-8(1H)-carboxylate was further separated into its enantiomers using a 21×250 mm ChiralCel OJ-H, column, eluting with 15% MeOH/CO$_2$ with a flow rate of 50 mL/min, 100 bar, 59 mg/mL in MeOH, 35C, 220 nm, Thr=200: trans-$^1$H NMR (CDCl$_3$, (trans) isomer, 500 MHz) δ 7.55 (d, J=8.0 Hz, 1H), 7.06 (s, 1H), 6.97 (d, J=8.0 Hz, 1H), 4.71 (d, J=9.4 Hz, 1H), 4.12-4.0 (m, 2H), 3.98 (s, 3H), 3.48 (t, J=9.4 Hz, J=10.3 Hz, 1H), 3.03 (bs, 1H), 2.94 (d, J=11.0 Hz, 1H), 2.76 (d, J=7.8 Hz, 1H), 2.54 (bs, 1H), 2.29-2.192 (m, 3H), 1.51 (s, 9H); LC/MS: (IE, m/z) [(M+1)-t-Bu]$^+$=318.17; cis-$^1$H NMR (CDCl$_3$, (cis) isomer, 500 MHz) δ 7.58 (d, J=8.0 Hz, 1H), 7.22 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (dd, J=3.6 Hz, J=3.7 Hz, 1H), 3.01 (bs, 1H), 2.80 (bs, 2H), 2.72-2.42 (m, 3H), 1.50 (s, 9H); LC/MS: (IE, m/z) [(M+1)-t-Bu]+=318.35.

Intermediate 32

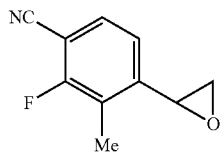

2-fluoro-3-methyl-4-(oxiran-2-yl)benzonitrile

Step A: 4-ethenyl-2-fluoro-3-methylbenzonitrile

A mixture of 4-bromo-2-fluoro-3-methylbenzonitrile (7.00 g, 32.7 mmol), potassium vinyltrifluoroborate (5.3 g, 39 mmol) and Pd(dppf)Cl$_2$ (0.5 g, 0.7 mmol) in 70 mL of EtOH and 30 mL of TEA was refluxed under Ar for 4 hours. Concentrated, the residue was purified by column chromatography (petrol ether:EtOAc=10:1) to afford 4-ethenyl-2-fluoro-3-methylbenzonitrile.

Step B: 2-fluoro-3-methyl-4-(oxiran-2-yl)benzonitrile

A mixture of 4-ethenyl-2-fluoro-3-methylbenzonitrile (4.60 g, 28.5 mmol) and mCPBA (85%, 12.3 g, 71.4 mmol) in 300 mL of DCM was stirred at room temperature for 120 hours. The reaction mixture was cooled to 0° C. and was washed subsequently with saturated NaHCO$_3$ (50 mL), saturated Na$_2$SO$_3$ (50 mL), 5% NaOH (2×50 mL) and brine (50 mL), dried over anhydrous Na$_2$SO$_4$ and concentrated. The residue was purified by column chromatography (petrol ether:EtOAc=20:1) to afford the title compound: $^1$H-NMR (400 MHz, CDCl$_3$) δ ppm 7.36-7.39 (m, 1H), 7.04-7.06 (m, 1H), 3.92-3.94 (m, 1H), 3.15-3.17 (m, 1H), 2.57-2.59 (m, 1H), 2.30 (d, J=2.0 Hz, 3H).

Intermediate 33

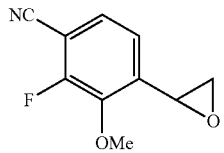

2-fluoro-3-methoxy-4-(oxiran-2-1 benzonitrile

Step A: 2-fluoro-6-nitrophenol

Concentrated HNO$_3$ (95%, 44 g, 0.62 mol) was added dropwise at 0-5° C. to the solution of 2-fluorophenol (64.6 g, 0.58 mol) in 1 L of DCM. The mixture was stirred at 0° C. for 1 hour before filtration. The filtrate was washed with water and brine, dried over anhydrous Na$_2$SO$_4$ and concentrated. The residue was purified by column chromatography (DCM:PE=1:2) to afford 2-fluoro-6-nitrophenol.

Step B: 1-fluoro-2-methoxy-3-nitrobenzene

MeI (27.1 g, 191 mmol) was added dropwise to the suspension of 2-fluoro-6-nitrophenol (25.0 g, 159 mmol) and K$_2$CO$_3$ (44.0 g, 318 mmol) in 200 mL of DMF. The mixture was stirred overnight at 25° C. then warmed to 60° C. and stirred for 3 hours. The mixture was diluted with 1 L of EtOAc and washed with water (3×100 mL) and brine (100 mL), dried over anhydrous Na$_2$SO$_4$ and concentrated to afford the title compound.

Step C: 3-fluoro-2-methoxyaniline

A mixture of 1-fluoro-2-methoxy-3-nitrobenzene (25.0 g, 146 mmol) and Pd/C (10%, 7.5 g) in 500 mL of MeOH was stirred at room temperature under 55 psi of H$_2$ for 4 hours before filtration. The filtrate was concentrated to give the title compound.

Step D: 1-bromo-3-fluoro-2-methoxybenzene

NaNO$_2$ (12.0 g, 173 mmol, in 40 mL of water) solution was added dropwise to the mixture of 3-fluoro-2-methoxyaniline (20.0 g, 158 mmol) in 200 mL of hydrobromic acid (47%) and 100 mL of water at −5~0° C. and stirred for 1 hour. This solution was then added slowly to the suspension of CuBr (45.2 g, 315 mmol) in 50 mL of hydrobromic acid (47%) at 0° C. The resulting mixture was stirred at 0° C. for 1 hour then warmed to 50° C. and stirred for 1 hour. The reaction mixture was poured into ice water and extracted with ether (2×500 mL). The combined organic layer was washed with brine, dried over anhydrous Na$_2$SO$_4$ and concentrated to give 1-bromo-3-fluoro-2-methoxybenzene.

Step E: 4-bromo-2-fluoro-3-methoxybenzoic acid n-BuLi (17.0 mL, 42.5 mmol) was added dropwise to the solution of NH(i-Pr)$_2$ (4.50 g, 44.5 mmol) in 70 mL of THF at −70° C. The mixture was stirred at 0° C. for 15 minutes and then cooled to −70° C. again. The solution of 1-bromo-3-fluoro-2-methoxybenzene (8.30 g, 40.5 mmol, in 30 mL of THF) was added dropwise. The resulting mixture was stirred at −70° C. for 1 hour then poured into fresh dry ice and stirred overnight. The mixture was diluted with 1 L of ether and washed with water twice. The combined water layer was washed with ether then acidified to pH=2 with hydrochloric acid and extracted with EtOAc twice. The combined EtOAc layer was washed with brine, dried over anhydrous Na$_2$SO$_4$ and concentrated to give 4-bromo-2-fluoro-3-methoxybenzoic acid.

Step F: 4-bromo-2-fluoro-3-methoxybenzonitrile

Oxalyl chloride (20 mL) was added dropwise at 0° C. to a suspension of 4-bromo-2-fluoro-3-methoxybenzoic acid (8.30 g, 33.3 mmol) in 100 mL of DCM with 0.5 mL of DMF. The mixture was stirred at 25° C. for 2 hours and the clear solution was concentrated to dryness under reduced pressure. The residue dissolved in 60 mL of anhydrous acetonitrile was added to 600 mL of aqueous NH$_3$.H$_2$O at 0° C. and stirred for 2 hours then extracted with EtOAc twice. The combined EtOAc layer was washed with water and brine, dried over anhydrous Na$_2$SO$_4$ and concentrated. The residue (6.9 g) was dissolved in 60 mL of DMF and cooled to 0° C. with ice/water bath. Cyanuric chloride (7.70 g, 41.7 mmol) was added and stirred for 2 hours at 0° C. before poured to ice/water. The solid was collected by filtration and was washed with water, dissolved in DCM, dried over anhydrous Na₂SO₄ and concentrated to afford 4-bromo-2-fluoro-3-methoxybenzonitrile.

Step G: 2-fluoro-3-methoxy-4-vinylbenzonitrile

A mixture of 4-bromo-2-fluoro-3-methoxybenzonitrile (6.0 g, 26 mmol), potassium vinyltrifluoroborate (4.20 g, 31.3 mmol) and Pd(dppf)Cl₂ (0.8 g) in 60 mL of EtOH and 60 mL of TEA was refluxed under Ar for 4 hours. The resulting mixture was concentrated and the residue was purified by column chromatography (PE:EtOAc=20:1) to afford 2-fluoro-3-methoxy-4-vinylbenzonitrile.

Step H:
2-fluoro-3-methoxy-4-(oxiran-2-yl)benzonitrile mCPBA (85%, 9.9 g, 48.9 mmol) was added to the solution of 2-fluoro-3-methoxy-4-vinylbenzonitrile (3.4 g, 19.2 mmol) in 160 mL of DCM at 0° C. The mixture was stirred at room temperature for 60 hours before being diluted with 300 mL of DCM and cooled to 0° C. The mixture was washed subsequently with saturated NaHCO₃ (50 mL), aqueous Na₂SO₃ (2×50 mL), 5% NaOH (50 mL) and brine. The organic layer was concentrated, and the residue was purified by column chromatography (PE:EtOAc=5:1) to afford 2-fluoro-3-methoxy-4-(oxiran-2-yl)benzonitrile: ¹H NMR (400 MHz, CDCl₃) δ 7.24 (d, J=7.6 Hz, 1H), 6.98 (d, J=7.6 Hz, 1H), 4.14-4.18 (m, 1H), 4.03 (s, 3H), 3.17-3.19 (m, 1H), 2.63-2.66 (m, 1H); MS m/z 194 (M+1)⁺.

Intermediate 34

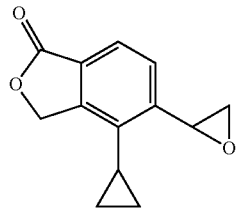 [SMILES: O=C1OCc2c1ccc(C1CO1)c2C1CC1]

4-cyclopropyl-5-oxiran-2-yl-2-benzofuran-1(3H)-one

Step A: 5-bromo-4-iodo-2-benzofuran-1(3H)-one

To a cooled (0° C.) solution of 5-bromo-2-benzofuran-1(3H)-one (50 g, 0.235 mol) in trifluoromethanesulfonic acid (400 mL) was added N-iodosuccinimide (55.5 g, 0.247 mol). The resulting mixture was stirred at room temperature overnight, then poured slowly into ice water (2 L), filtered and the filtrate extracted with EtOAc. The combined organic layers were washed with water and brine, dried and concentrated to give 5-bromo-4-iodo-2-benzofuran-1(3H)-one.

Step B: 5-bromo-4-vinyl-2-benzofuran-1(3H)-one

A mixture of 5-bromo-4-iodo-2-benzofuran-1(3H)-one (1 g, 2.95 mmol), potassium vinyltrifluoroborate (474 mg, 3.54 mmol) and Pd(dppf)Cl₂ (200 mg) in 20 mL of TEA and 20 mL of EtOH was heated to reflux under N₂ for 2 hours. Most of the solvent was removed, and the residue was dissolved in EtOAc (100 mL). The solution was washed with 0.1 N HCl, sodium bicarbonate, and brine, dried over sodium sulfate, filtered and concentrated to provide the title compound.

Step C:
5-bromo-4-cyclopropyl-2-benzofuran-1(3H)-one

To a cooled (0° C.) mixture of 5-bromo-4-vinyl-2-benzofuran-1(3H)-one (2.2 g, 9.21 mol) and Pd(OAc)₂ (100 mg) in EtOAc (50 mL) was added a solution of CH₂N₂ in ether (100 mL) slowly. The resulting mixture was stirred at room temperature overnight, then quenched with acetic acid, filtered and the filtrate washed with water and brine, dried and concentrated to provide the title compound.

Step D:
4-cyclopropyl-5-vinyl-2-benzofuran-1(3H)-one

A mixture of 5-bromo-4-cyclopropyl-2-benzofuran-1(3H)-one (760 mg, 3.004 mmol), potassium vinyltrifluoroborate (805 mg, 6.008 mmol) and Pd(dppf)Cl₂ (100 mg) in 20 mL of TEA and 20 mL of EtOH was heated to reflux under N₂ for 8 hours. When TLC showed complete reaction most of the solvent was removed, and the residue was dissolved in EtOAc (100 mL). The solution was washed with 0.1 N HCl, sodium bicarbonate, and brine, dried over sodium sulfate, filtered and concentrated. The resulting oil was purified by column chromatography to give 4-cyclopropyl-5-vinyl-2-benzofuran-1(3H)-one.

Step E: 4-cyclopropyl-5-oxiran-2-yl-2-benzofuran-1(3H)-one

To a solution of 4-cyclopropyl-5-vinyl-2-benzofuran-1(3H)-one (440 mg, 2.2 mmol) in 50 mL of DCM was slowly added mCPBA (1.14 g, 6.6 mmol) in 50 mL of DCM at 0° C. After warming to room temperature, the mixture was stirred for 12 hours. The mixture was washed with aqueous Na₂SO₃ until potassium iodide (KI) indicator paper did not change color. The organic layers were combined, washed with brine and then concentrated. The residue was purified via prep-TLC to give the title compound: ¹H-NMR (400 MHz, CDCl₃) δ ppm 7.77 (d, J=8.6 Hz, 1H), 7.39 (d, J=7.8 Hz, 1H), 5.39 (s, 2H), 4.43-4.45 (m, 1H), 3.26-3.28 (m, 1H), 2.68-2.70 (m, 1H), 1.94-2.01 (m, 1H), 1.08-1.12 (m, 2H), 0.65-0.75 (m, 2H).

Intermediate 35

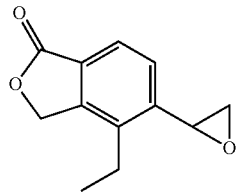

4-ethyl-5-oxiran-2-yl-2-benzofuran-1(3H)-one

Step A: 5-bromo-4-ethyl-2-benzofuran-1(3H)-one

A mixture of 5-bromo-4-vinyl-2-benzofuran-1(3H)-one (2.0 g, 8.37 mmol) and Pd/C (400 mg) in 50 mL of MeOH was stirred at rt under H₂ (1 atm) overnight, and then filtered. The filtrate was concentrated. The resulting material was purified by column chromatography to give 5-bromo-4-ethyl-2-benzofuran-1(3H)-one.

Step B: 4-ethyl-5-vinyl-2-benzofuran-1(3H)-one

A mixture of 5-bromo-4-ethyl-2-benzofuran-1(3H)-one (1.81 g, 7.51 mmol), potassium vinyltrifluoroborate (1.21 g, 9.01 mmol) and Pd(dppf)Cl$_2$ (200 mg) in 20 mL of TEA and 20 mL of EtOH was heated to reflux under N$_2$ overnight and then concentrated. The resulting material was purified by column chromatography to give 4-ethyl-5-vinyl-2-benzofuran-1(3H)-one.

Step C: 4-ethyl-5-oxiran-2-yl-2-benzofuran-1(3H)-one

A solution of 4-ethyl-5-vinyl-2-benzofuran-1(3H)-one (1.1 g, 5.85 mmol) in 50 mL of DCM was slowly added mCPBA (3.60 g, 85% purity, 17.6 mmol) in 50 mL of DCM at 0° C. Warmed to room temperature, the mixture was stirred for 3 days. The mixture was washed with aqueous Na$_2$SO$_3$ until KI paper didn't change color. The organic layers were combined, washed with brine and concentrated. The residue was purified by column chromatography to give the title compound: $^1$H-NMR (400 MHz, CDCl$_3$) δ ppm 7.75 (d, J=8.6 Hz, 1H), 7.41 (d, J=7.8 Hz, 1H), 5.30 (s, 2H), 4.11-4.13 (m, 1H), 3.23-3.25 (m, 1H), 2.75-2.82 (m, 2H), 2.70-2.72 (m, 1H), 1.27 (t, J=7.4 Hz, 3H).

The Boc-piperazine intermediates described in the following Table 1 were prepared from the indicated epoxides (prepared as described above) and (S)-4-N-BOC-2-hydroxymethylpiperazine or (R)-4-N-BOC-2-hydroxymethylpiperazine in an analagous fashion to that described for tert-butyl (3S,9aR)-3-(4-cyano-3-methoxyphenyl)hexahydropyrazino[2,1-c][1,4]oxazine-8(1H)-carboxylate.

TABLE 1

| INTERMEDIATE | Epoxide starting intermediate | INTERMEDIATE structure |
|---|---|---|

36B — Prep SFC with 10% IPA/CO$_2$ on OD column; LC/MS: (IE, m/z) [(M + 1) − t-Bu]$^+$ = 320.04.

37C — Trans and cis isomers were separated by prep SFC with 15% (2:1 MeOH:MeCN)/CO$_2$ on OD column. Trans isomer eluted first; $^1$H NMR (500 MHz, CDCl$_3$) δ 7.29-7.16 (m, 2H), 4.83 (dd, J = 10.1, 1.7 Hz, 1H), 3.92-3.82 (m, 6H), 3.33 (t, J = 10.7 Hz, 1H), 2.90-2.80 (m, 2H), 2.60 (d, J = 10.6 Hz, 1H), 2.40 (br s, 1H), 2.16-2.04 (m, 2H), 1.90 (t, J = 10.8 Hz, 1H), 1.32 (s, 9H).

38B — Trans and cis were resolved chiraly by OJ column, 21 × 250 mm, 15% 2:1 MeOH:MeCN/CO$_2$, 60 ml/min, 100 bar, 40 mg/mL in MeCN/MeOH, 35 C., 220 nm. LC/MS: [(M + 1)]$^+$ = 415

39A — Trans and cis were resolved by AD column, 21 × 250 mm, and 30% 2:1 MeOH:MeCN/ CO$_2$, 50 ml/min, 100 bar, 80 mg/mL in MeCN/MeOH, 35 C., 220 nm. LC/MS: [(M + 1)]$^+$ = 403

Intermediate 40A

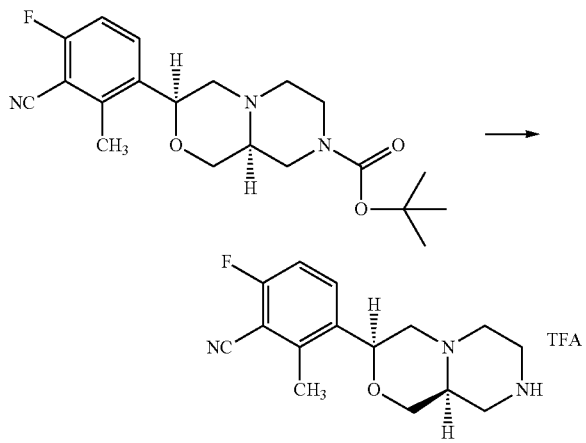

6-fluoro-2-methyl-3-[(3S,9aS)-octahydropyrazino[2,1-c][1,4]oxazin-3-yl]benzonitrile 2,2,2-trifluoroacetate tert-Butyl (3S,9aS)-3-(3-cyano-4-fluoro-2-methylphenyl)hexahydropyrazino[2,1-c][1,4]oxazine-8(1H)-carboxylate (1.88 g, 5.01 mmol) was treated with 10 mL TFA at RT for 1 h. The TFA was then removed under reduced pressure to yield the title compound. LC-MS: M+1=276: $^1$H-NMR (600 MHz, DMSO) δ ppm 7.954 (dd, J=8.7, 6.25 Hz, 1H), 7.412 (t, J=8.85 Hz, 1H), 4.939 (dd, J=8.4, 2.75 Hz, 1H), 3.848 (d, J=11.8 Hz, 1H), 3.762 (b, 1H), 3.189-3.536 (m, 8H), 3.072 (d, J=12 Hz, 1H), 2.485 (s, 3H).

Intermediate 40B

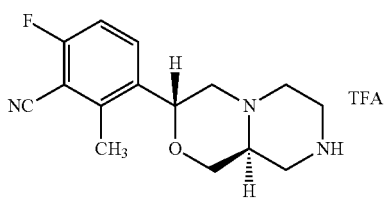 [SMILES: Cc1c([C@@H]2CN3CCNC[C@H]3CO2)ccc(F)c1C#N]

6-fluoro-2-methyl-3-[(3R,9aS)-octahydropyrazino[2,1-c][1,4]oxazin-3-yl]benzonitrile 2,2,2-trifluoroacetate tert-Butyl (3R,9aS)-3-(3-cyano-4-fluoro-2-methylphenyl)hexahydropyrazino[2,1-c][1,4]oxazine-8(1H)-carboxylate (1.73 g, 4.61 mmol) was treated with 10 mL TFA at RT for 1 h. The trifluoroacetic acid was then removed under reduced pressure to yield the title compound. LC-MS: M+1=276: $^1$H-NMR (600 MHz, DMSO) δ ppm 7.724 (dd, J=9.0, 6.2 Hz, 1H), 7.353 (t, J=8.85 Hz, 1H), 4.738 (d, J=10.3 Hz, 1H), 3.924 (d, J=11.10 Hz, 1H), 3.386 (t, J=11.65 Hz, 1H), 3.285 (d, J=12.3 Hz, 1H), 3.20 (d, J=11.8 Hz, 1H), 3.01 (b, 1H), 2.934 (d, J=11.6 Hz, 1H), 2.884 (d, J=11.0 Hz, 1H), 2.642 (b, 1H), 2.476 (s, 3H), 2.47 (b, 1H), 2.329-2.367 (m, 1H), 2.054-2.089 (m, 1H).

Intermediate 40C-1 (Method 1)

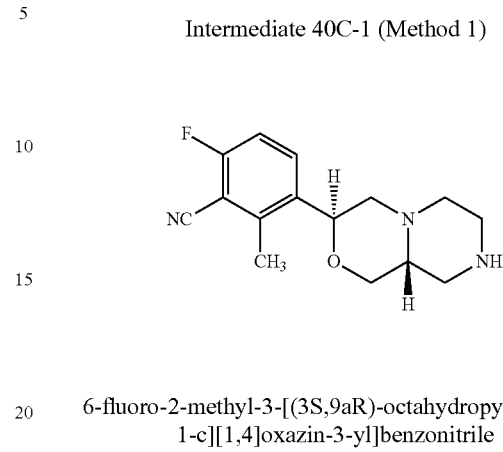

6-fluoro-2-methyl-3-[(3S,9aR)-octahydropyrazino[2,1-c][1,4]oxazin-3-yl]benzonitrile tert-butyl(3S,9aR)-3-(3-cyano-4-fluoro-2-methylphenyl)hexahydropyrazino[2,1-c][1,4]oxazine-8(1H)-carboxylate (1-17C) (3.00 g, 7.99 mmol) was dissolved in TFA (10 mL) and stirred for 1 hr. The trifluoroacetic acid was removed under reduced pressure and azeotroped with dichloroethane (3×) then was dried over high vacuum to yield the title compound: LC-MS (IE, m/z): 276 [M+1]$^+$; $^1$H-NMR (500 MHz, DMSO) δ ppm 7.755 (dd, J=8.75, 6.2 Hz, 1H), 7.38 (t, J=8.85 Hz, 1H), 4.80 (d, J=10.1 Hz, 1H), 3.98 (dd, J=11.25, 2.5 Hz, 1H), 3.456 (t, J=10.7 Hz, 1H), 3.354 (d, J=12.6 Hz, 1H), 3.273 (d, J=11.8 Hz, 1H), 2.984-3.089 (m, 3H), 2.715 (t, J=11.37 Hz, 1H), 2.639 (t, J=10 Hz, 1H), 2.50 (s, 3H), 2.46 (b, 1H), 2.337 (t. J=10.9 Hz, 1H).

Intermediate 40C-2 (Method 2)

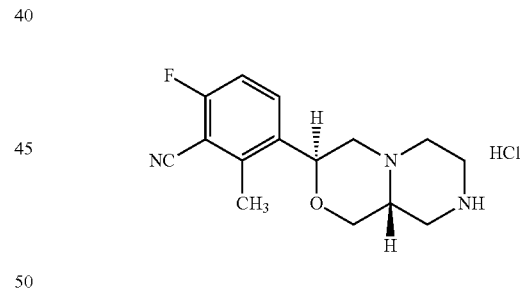

6-fluoro-2-methyl-3-[(3S,9aR)-octahydropyrazino[2,1-c][1,4]oxazin-3-yl]benzonitrile hydrochloride tert-butyl(3S,9aR)-3-(3-cyano-4-fluoro-2-methylphenyl)hexahydropyrazino[2,1-c][1,4]oxazine-8(1H)-carboxylate (1-17C) (158.8 g, 423.0 mmol) was suspended with 318 mL of 2-propanol. The resulting slurry was treated with HCl solution in 2-propanol (5.5 M, 1000 mL, 5499 mmol), and the mixture was heated to 50° C. for 2 hours. The mixture was concentrated to remove approximately 400 mL of 2-propanol, then was cooled to rt and agitated overnight. The mixture was filtered to collect the solid product and the wet cake was washed with 50 mL of 2-propanol. The filter cake was dried under vacuum for two days at 40° C. with nitrogen bleed to afford the title compound.

Intermediate 40D

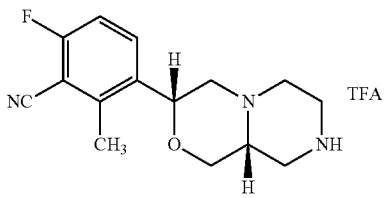 [SMILES: Cc1c([C@@H]2CN3CCNC[C@@H]3CO2)ccc(F)c1C#N]

6-fluoro-2-methyl-3-[(3R,9aR)-octahydropyrazino[2,1-c][1,4]oxazin-3-yl]benzonitrile 2,2,2-trifluoroacetate (3R,9aR)-tert-Butyl 3-(3-cyano-4-fluoro-2-methylphenyl)hexahydropyrazino[2,1-c][1,4]oxazine-8(1H)-carboxylate (1.09 g, 2.90 mmol) was stirred in trifluoroacetic acid (10 mL) for 1 h then concentrated and azeotroped with dichloroethane (3×) to yield the title compound. LC-MS (IE, m/z): 276 [M+1]+; $^1$H-NMR (500 MHz, DMSO) δ ppm 7.989 (t, J=6.4 Hz, 1H), 7.416 (t, J=8.85 Hz, 1H), 4.959 (dd, J=7.75, 2.35 Hz, 1H), 3.855 (d, J=11.9 Hz, 1H), 3.755 (b, 1H), 3.236-3.54 (m, 8H), 3.066 (d, J=11.5 Hz, 1H), 2.50 (s, 3H).

Intermediate 41B

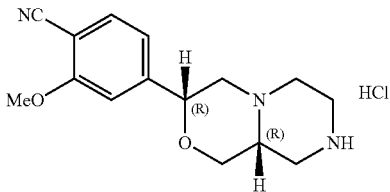

2-Methoxy-4-[(3R,9aR)-octahydropyrazino[2,1-c][1,4]oxazin-3-yl]benzonitrile hydrochloride tert-Butyl (3R,9aR)-3-(4-cyano-3-methoxyphenyl)hexahydropyrazino[2,1-c][1,4]oxazine-8(1H)-carboxylate (120 mg, 0.321 mmol) was dissolved in 10 mL of 4 M HCl in dioxane and stirred at room temperature for 8 h. The mixture was concentrated to ¼ the original volume and diluted with 10 mL of diethyl ether. The precipitate was filtered and dried under high vacuum to afford the title compound: NMR (DMSO-d$_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]+=274.

Intermediate 41D

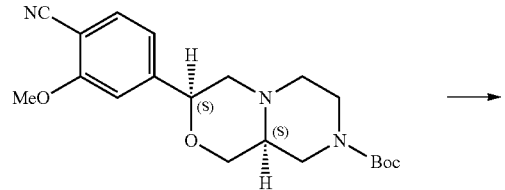

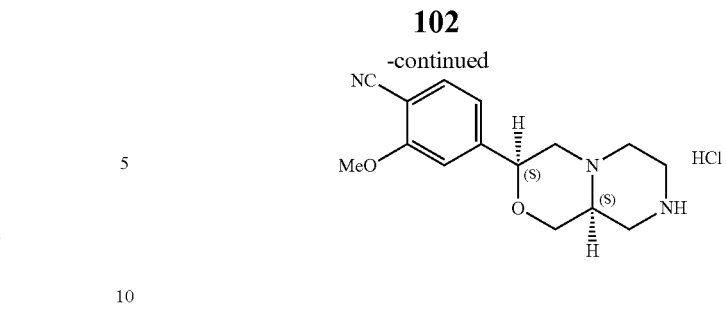

2-Methoxy-4-[(3S,9aS)-octahydropyrazino[2,1-c][1,4]oxazin-3-yl]benzonitrile hydrochloride tert-Butyl (3S,9aS)-3-(4-cyano-3-methoxyphenyl)hexahydropyrazino[2,1-c][1,4]oxazine-8(1H)-carboxylate (38.0 mg, 0.102 mmol) was dissolved in 10 mL of 4 M HCl in dioxane and stirred at room temperature for 8 h. The mixture was concentrated to ¼ the original volume and diluted with 5 mL of diethyl ether. The precipitate was filtered and dried under high vacuum to afford the title compound: $^1$H NMR (DMSO-d$_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]+=274.

The intermediates shown in Table 2 below were prepared in an analagous fashion to that described for the syntheses of Intermediates 40A: 6-fluoro-2-methyl-3-[(3S,9aS)-octahydropyrazino[2,1-c][1,4]oxazin-3-yl]benzonitrile 2,2,2-trifluoroacetate, and 41D: 2-methoxy-4-[(3S,9aS)-octahydropyrazino[2,1-c][1,4]oxazin-3-yl]benzonitrile hydrochloride, using either HCl or TFA to remove the Boc protective group present in the corresponding Boc-piperazine precursor (the acid used in the reaction and the mass spec data are provided below each structure in Table 2). It is understood that the resulting intermediates may be TFA or HCl salts, or they may be obtained as free base amines by routine partitioning of the product with an organic solvent and a basic aqueous solution such as saturated sodium bicarbonate solution and concentration of the resulting organic solution.

TABLE 2

| Intermediate # | |
|---|---|
| 42A | ![structure] <br> TFA; MS (M + H)+ 275 |
| 42B | ![structure] <br> TFA; MS (M + H)+ 275 |

TABLE 2-continued
| Intermediate # | | |
|---|---|---|
| 43A | 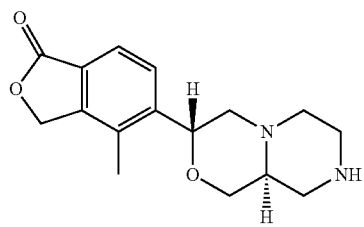 TFA; MS (M + H)+ 289 | |
| 43B | 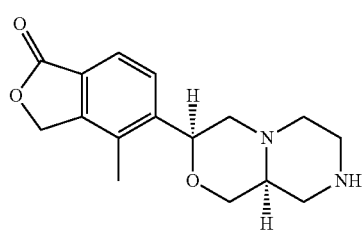 TFA; MS (M + H)+ 289 | |
| 43D | 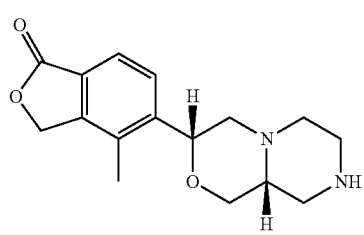 TFA; MS (M + H)+ 289 | |
| 44A | 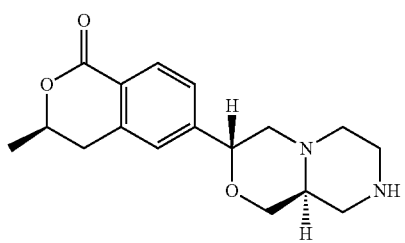 HCl; MS (M + H)+ 303 | |
| 44B | 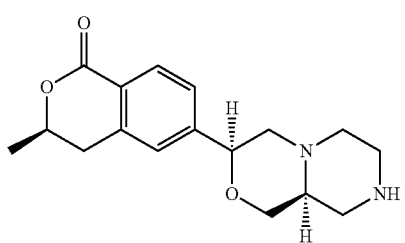 HCl | |
| 44C | 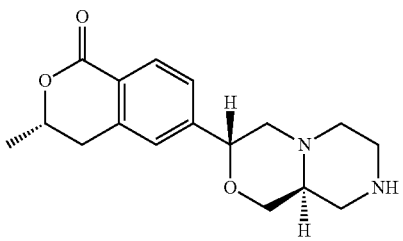 HCl | |
| 44E | 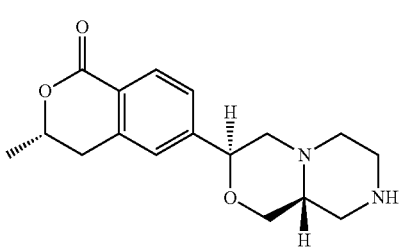 HCl | |
| 44F | 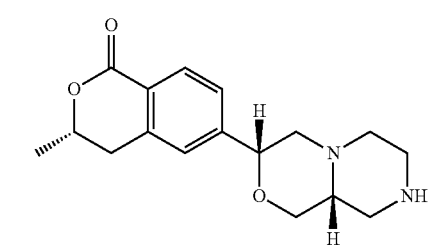 HCl; | |
| 44G | 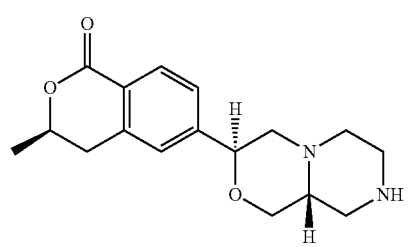 HCl; MS (M + H)+ 303 | |
| 45B | 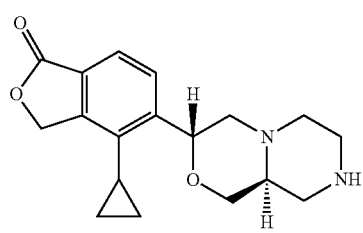 TFA; MS (M + H)+ 315 | |

TABLE 2-continued
| Intermediate # | | |
|---|---|---|
| 46A | 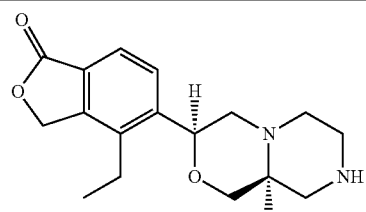 | |
| | TFA; MS (M + H)+ 303 | |
| 47A | 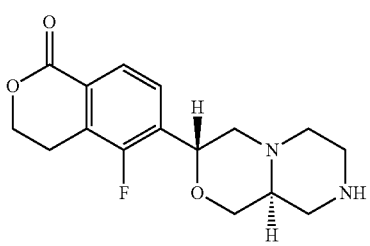 | |
| | HCl; MS (M + H)+ 307 | |
| 48A | 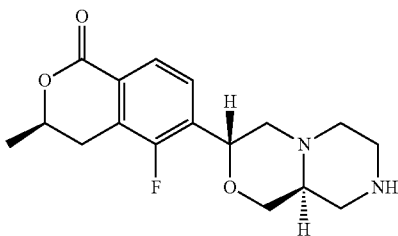 | |
| | HCl; MS (M + H)+ 321 | |
| 48C | 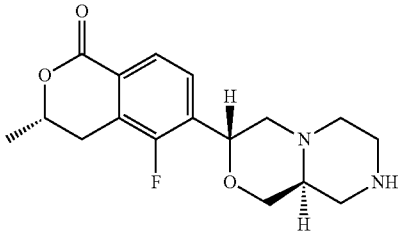 | |
| | HCl; MS (M + H)+ 321 | |
| 48D | 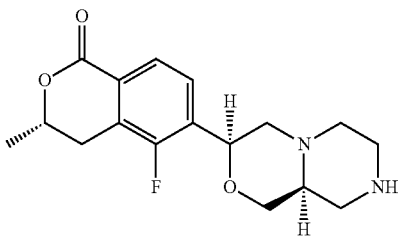 | |
| | HCl; MS (M + H)+ 321 | |
| 48F | 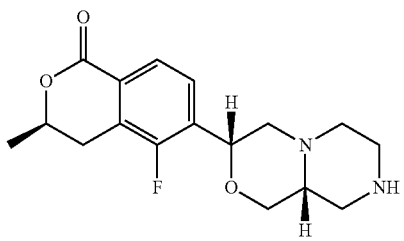 | |
| | HCl; MS (M + H)+ 321 | |
| 48G | 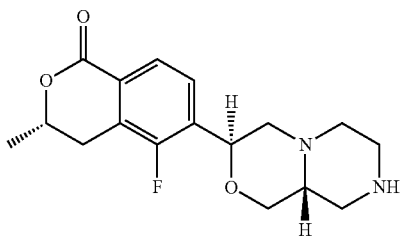 | |
| | HCl; MS (M + H)+ 321 | |
| 48H | 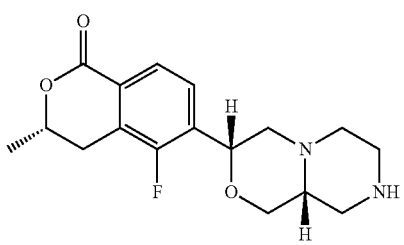 | |
| | HCl; MS (M + H)+ 321 | |
| 49A | 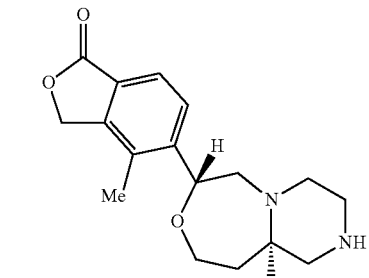 | |
| | TFA; MS (M + H)+ 303 | |
| 49B | 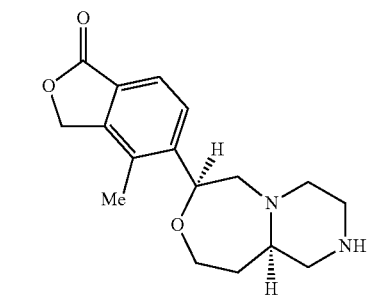 | |
| | TFA; MS (M + H)+ 303 | |

TABLE 2-continued

| Intermediate # | Structure |
|---|---|
| 49C | (structure shown) Me-substituted isobenzofuranone fused to oxazepine-piperazine bicyclic system. TFA; MS (M + H)⁺ 303 |
| 49D | (structure shown) Me-substituted isobenzofuranone fused to oxazepine-piperazine bicyclic system (diastereomer). TFA; MS (M + H)⁺ 303 |
| 50A | (structure shown) 4-Fluoro-3-cyanophenyl substituted octahydropyrazino[2,1-c][1,4]oxazine. TFA; MS (M + H)⁺ 262 |
| 50D | (structure shown) 4-Fluoro-3-cyanophenyl substituted octahydropyrazino[2,1-c][1,4]oxazine. HCl; |
| 51A | (structure shown) 6-Fluoro-2-methyl-3-cyanophenyl substituted thiazine-piperazine bicycle. TFA; LC/MS: [(M + 1)]⁺ = 292 |
| 52A | (structure shown) 4-Fluoro-2-fluoro-3-cyanophenyl substituted octahydropyrazino[2,1-c][1,4]oxazine. TFA; LC/MS: [(M + 1)]⁺ = 280 |
| 52B | (structure shown) 4-Fluoro-2-fluoro-3-cyanophenyl substituted octahydropyrazino[2,1-c][1,4]oxazine. TFA; LC/MS: [(M + 1)]⁺ = 280 |
| 52C | (structure shown) 4-Fluoro-2-fluoro-3-cyanophenyl substituted octahydropyrazino[2,1-c][1,4]oxazine. TFA; LC/MS: [(M + 1)]⁺ = 280 |
| 52D | (structure shown) 4-Fluoro-2-fluoro-3-cyanophenyl substituted octahydropyrazino[2,1-c][1,4]oxazine. TFA; LC/MS: [(M + 1)]⁺ = 280 |
| 53C | (structure shown) 4-Fluoro-5-methoxy-3-cyanophenyl substituted octahydropyrazino[2,1-c][1,4]oxazine. TFA; LC/MS: [(M + 1)]⁺ = 292 |
| 54A | (structure shown) 4-Fluoro-3-cyano-2-methoxyphenyl substituted octahydropyrazino[2,1-c][1,4]oxazine. TFA; LC/MS: [(M + 1)]⁺ = 292 |

TABLE 2-continued

| Intermediate # | | |
|---|---|---|
| 55A | 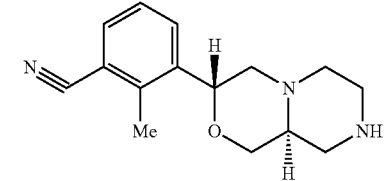 | |
| | TFA; LC/MS: [(M + 1)]⁺ = 258 | |
| 55D | 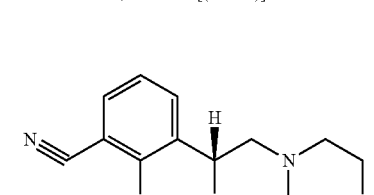 | |
| | HCl; LC/MS: [(M + 1)]⁺ = 258 | |
| 56A | 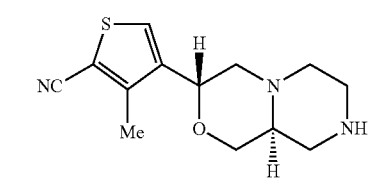 | |
| | TFA; LC/MS: [(M + 1)]⁺ = 264 | |
| 57A | 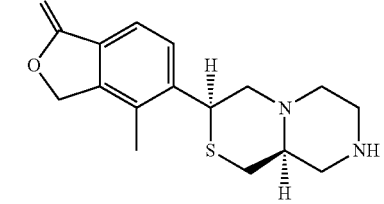 | |
| | TFA; LC/MS: [(M + 1)]⁺ = 305 | |
| 58A | 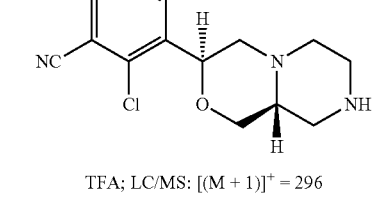 | |
| | TFA; LC/MS: [(M + 1)]⁺ = 296 | |
| 58B | 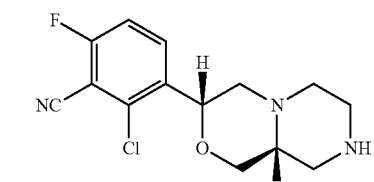 | |
| | TFA; LC/MS: [(M + 1)]⁺ = 296 | |
| 58C | | |
| | TFA; LC/MS: [(M + 1)]⁺ = 296 | |
| 58D | | |
| | TFA; LC/MS: [(M + 1)]⁺ = 296 | |
| 59B | | |
| | HCl; LC/MS: (IE, m/z) [M + 1]⁺ = 276 | |
| 60C | | |
| | TFA; LC/MS: [(M + 1)]⁺ = 292 | |

I-50D: $^{1}$H-NMR (400 MHz, MeOD) δ: 7.84~7.86 (m, 1H), 7.77~7.81 (m, 1H), 7.40 (t, J=8.0 Hz, 1H), 5.02~5.07 (m, 1H), 4.20~4.23 (m, 1H), 3.89~3.93 (m, 1H), 3.55~3.63 (m, 6H), 3.33~3.34 (m, 1H), 3.19~3.24 (m, 1H), 3.01~3.12 (m, 1H).

Intermediate 61

6-methoxy-2-methyl-3-[(3S,9aR)-octahydropyrazino[2,1-c][1,4]oxazin-3-yl]benzonitrile A microwave vial was charged with 6-fluoro-2-methyl-3-[(3S,9aR)-octahydropyrazino[2,1-c][1,4]oxazin-3-yl]benzonitrile trifluoroacetate (110 mg, 0.290 mmol), sodium carbonate (30 mg, 0.290 mmol), and methanol (2 mL). The Intermediate 62

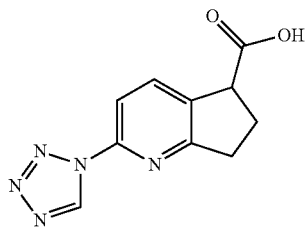 [SMILES: O=C(O)C1CCc2nc(-n3cnnn3)ccc21]

2-(1H-tetrazol-1-yl)-6,7-dihydro-5H-cyclopenta[b]
pyridine-5-carboxylic acid

Step A: 6,7-Dihydro-5H-cyclopenta[b]pyridin-5-ol

To a solution of 6,7-dihydro-5H-cyclopenta[b]pyridine (5.0 g, 42 mmol) and MgSO$_4$ (10 g, 84 mmol) in acetone (250 mL) was added a solution of KMnO$_4$ (13 g, 84 mmol) in water (500 mL) at 60 degrees. The mixture was allowed to stir for 30 minutes at 60° C. IPA was slowly added to quench excess KMnO$_4$. The reaction was filtered through a pad of Celite. The filtrate was concentrated under reduced pressure and pumped on a high vacuum pump to ensure complete removal of water. The residue was dissolved in ethanol (200 mL), and cooled with an ice bath. To this solution was slowly added NaBH$_4$ (3.2 g, 84 mmol). When TLC showed complete reduction, water was added to quench excess NaBH$_4$. Ethanol was removed on a rotavapor. The crude material was dissolved in EtOAc, washed with aq. NaHCO$_3$, dried over sodium sulfate, and purified by MPLC (MeOH-DCM: 0-7%). The title compound was collected. LC-MS (IE, m/z): 136 [M+1]$^+$.

Step B: 6,7-dihydro-5H-cyclopenta[b]pyridine-5-carbonitrile

To a solution of 6,7-Dihydro-5H-cyclopenta[b]pyridin-5-ol (2.7 g, 20 mmol) in CHCl$_3$ (30 mL) was dropped thionyl chloride (4.4 mL, 60 mmol) slowly at 0° C. The mixture was allowed to stir at 0° C. for an additional 3 hours when the addition was done. The solvent was removed under reduced pressure, and the residue was pumped under high vacuum for 15 more minutes. The crude material was dissolved in CHCl$_3$ (300 mL), and washed with pH=7 buffer (200 mL). The buffer was extracted once with IPA-CHCl$_3$ (1:3, 100 mL). The organic extractions were combined, dried over sodium sulfate, and concentrated. To the flask was added tetrabutylammonium cynanide (6.4 g, 24 mmol) and acetonitrile (40 mL). The mixture was heated to 50° C. for 16 hours. After removing acetonitrile on a rotary evaporator, the residue was dissolved in water, extracted three times with IPA-CHCl$_3$ (1:3, 100 mL each). The extractions were combined and purified by MPLC (DCM-MeOH). The title compound was collected after removal of solvent. LC-MS (IE, m/z): 154 [M+1]$^+$.

Step C: Methyl 6,7-dihydro-5H-cyclopenta[b]pyridine-5-carboxylate 1-oxide

To a flask charged with 6,7-dihydro-5H-cyclopenta[b]pyridine-5-carbonitrile (2.6 g, 18 mmol) and a stir bar was added concentrated HCl (5 mL). The mixture was heated to 70° C. for 15 minutes. The volatiles were removed under reduced pressure, and the residue was pumped under high vacuum for 15 minutes. To the flask was added MeOH (20 mL) and toluene (40 mL). The solution was cooled to 0° C. with an ice bath, which was followed by addition of TMS-diazomethane (36 mL, 72 mmol). When LC showed complete reaction, excess TMS-diazomethane was decomposed with HOAc, and the crude product was purified by MPLC. LC-MS (IE, m/z): 179 [M+1]$^+$. The adduct obtained was dissolved in CHCl$_3$ (50 mL) and cooled to 0° C. To the solution was added mCPBA (3.1 g, 18 mmol). The mixture was allowed to stir for 3 hours. Sodium thiosulfate solution was added to consume excess mCPBA, and the crude product was extracted with IPA-CHCl$_3$ (1:3, 100 mL) three times. The extractions were combined, dried over sodium sulfate, adsorbed onto silica gel, and purified by MPLC (DCM:MeOH with 10% aq NH$_4$OH). After removal of solvent, methyl 6,7-dihydro-5H-cyclopenta[b]pyridine-5-carboxylate 1-oxide was collected: LC-MS (IE, m/z): 194 [M+1]$^+$.

Step D: methyl 2-amino-6,7-dihydro-5H-cyclopenta[b]pyridine-5-carboxylate

To a solution of methyl 6,7-dihydro-5H-cyclopenta[b]pyridine-5-carboxylate 1-oxide (700 mg, 3.6 mmol) in CF$_3$-toluene (20 mL) and CHCl$_3$ (20 mL) was added tert-butylamine (3.8 mL, 36 mmol). The solution was cooled to 0° C. in an ice bath. To the solution was added p-toluenesulfonic anhydride (3.5 g, 10.9 mmol) in small portions until all SM was consumed according to LC-MS. The volatiles were removed under reduced pressure, and the residue was redissolved in TFA (20 mL). The solution was heated to 70° C. for 2 hours. The reaction was stopped at that point. TFA was removed on a rotavapor, and the residue was taken up in saturated sodium carbonate, and extracted three times with IPA-CHCl$_3$ (1:3, 50 mL each). The extractions were combined, dried over sodium sulfate, adsorbed onto silica gel, and purified by MPLC (DCM:MeOH with 10% aq NH$_4$OH). After removal of solvent the title compound was collected: LC-MS (IE, m/z): 193 [M+1]$^+$.

Step E: methyl 2-(1H-tetrazol-1-yl)-6,7-dihydro-5H-cyclopenta[b]pyridine-5-carboxylate To a flask charged with methyl 2-amino-6,7-dihydro-5H-cyclopenta[b]pyridine-5-carboxylate (500 mg, 2.6 mmol) and a stir bar was added sodium azide (340 mg, 5.2 mmol), triethyl orthoformate (2.2 mL, 13 mmol), and HOAc (10 mL). The mixture was heated to 100° C. for 2 hours. The solvent was removed on a rotavapor, and the residue was taken into aq. sodium carbonate, extracted with EtOAc (50 mL×3), dried over sodium sulfate, and purified by MPLC (DCM-MeOH). After removal of solvent, the title compound was collected. LC-MS (IE, m/z): 248 [M+1]$^+$.

Step F: 2-(1H-tetrazol-1-yl)-6,7-dihydro-5H-cyclopenta[b]pyridine-5-carboxylic acid To a solution of methyl 2-(1H-tetrazol-1-yl)-6,7-dihydro-5H-cyclopenta[b]pyridine-5-carboxylate (460 mg, 1.9 mmol) in THF (6 mL) was added lithium hydroxide (1.0 N aq. 3.8 mL, 3.8 mmol). The mixture was allowed to stir at 0° C. for 2 hours. The reaction was diluted with water (10 mL). The pH was carefully adjusted to about 5 with 1N HCl. The solution was then extracted with EtOAc (30 mL×3). The extractions were combined, dried over sodium sulfate, and concentrated to furnish the title compound: LC-MS (IE, m/z): 231 [M+1]⁺; ¹H-NMR (500 MHz, CD₃OD) δ ppm 9.87 (s, 1H), 8.09 (d, J=8.0 Hz, 1H), 7.90 (d, J=8.0 Hz, 1H), 4.20 (t, J=8.0 Hz, 1H), 3.15 (m, 1H), 3.08 (m, 1H), 2.51 (m, 2H).

Intermediate 63

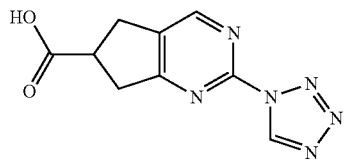 [SMILES: O=C(O)C1Cc2cnc(-n3cnnn3)nc2C1]

2-1H-tetrazol-1-yl)-6,7-dihydro-5H-cyclopenta[d]pyrimidine-6-carboxylic acid

Step A: Methyl 3-oxocyclopentanecarboxylate

3-Oxocyclopentanecarboxylic acid (342 mg, 2.67 mmol) and the catalyst Amberlyst-15 (30 mg, 2.67 mmol) were combined in a sealed tube and heated to 100° C. overnight. The reaction was filtered and washed well with methanol. The filtrate was concentrated in vacuo to give the title compound.

Step B: Methyl 2-[(dimethylamino)methylidene]-3-oxocyclopentanecarboxylate and methyl 3-[(dimethylamino)methylidene]-4-oxocyclopentanecarboxylate Methyl 3-oxocyclopentanecarboxylate (364 mg, 2.56 mmol) and 1-tert-butoxy-N,N,N',N'-tetramethylmethanediamine (447 mg, 2.56 mmol) were combined and heated at 110° C. for 1.5 h. The reaction was purified by Isco Combiflash (12 g silica gel, 30 mL/min, 254 nM, 0% to 100% (10% methanol in dichloromethane)/dichloromethane. The title compound eluted at 53% (10% methanol in dichloromethane)/dichloromethane as a mixture of two regioisomers. The mixture was separated by prep SFC with 40% methanol/carbon dioxide on IA column (30×250 mm), 70 mL/min., 35° C., 220 nM, 140 mg/mL in methanol to afford the title compound.

Step C: Methyl 2-amino-6,7-dihydro-5H-cyclopenta[d]pyrimidine-6-carboxylate

To a solution of methyl 3-[(dimethylamino)methylidene]-4-oxocyclopentanecarboxylate (71.7 mg, 0.36 mmol) in anhydrous methanol (2.5 mL) was added guanidine hydrochloride (124.7 mg, 1.3 mmol) followed by sodium methoxide in methanol (0.24 mL, 1.27 mmol). The mixture was heated to 90° C. in a sealed tube overnight. The crude reaction was quenched with 2 N HCl and concentrated in vacuo. The aqueous residue was purified by HPLC (30×100 mm Waters Sunfire column; 5 micron; 35 mL/min.; 210 nM; 0% to 40% CH₃CN+0.05% TFA/water+0.05% TFA over 15 min.; the compound eluted at 10% CH₃CN+0.05% TFA/water+0.05% TFA) to afford the title compound after lyophilization.

Step D: Methyl 2-(1H-tetrazol-1-yl)-6,7-dihydro-5H-cyclopenta[d]pyrimidine-6-carboxylate To a mixture of Methyl 2-amino-6,7-dihydro-5H-cyclopenta[d]pyrimidine-6-carboxylate (65.2 mg, 0.364 mmol) in ethyl acetate (5 mL) was added trimethylsilyl trifluoroacetate (0.107 mL, 0.619 mmol) at room temperature. The mixture was stirred at room temperature then triethyl orthoformate (0.103 mL, 0.619 mmol) was added. The mixture was stirred for another 5 minutes then azidotrimethylsilane (0.081 mL, 0.619 mmol) was added. The reaction was stirred at room temperature overnight then concentrated in vacuo and the residue was triturated twice with dichloromethane. The resulting solid was collected by centrifugation and dried in vacuo to afford the title compound: LC/MS: [(M+1)]+=233.

Step E: 2-(1H-tetrazol-1-yl)-6,7-dihydro-5H-cyclopenta[d]pyrimidine-6-carboxylic acid The title compound was prepared from methyl 2-(1H-tetrazol-1-yl)-6,7-dihydro-5H-cyclopenta[d]pyrimidine-6-carboxylate in an analogous fashion to that described in Step F of the synthesis of 2-(1H-tetrazol-1-yl)-6,7-dihydro-5H-cyclopenta[b]pyridine-5-carboxylic acid.

Intermediate 64

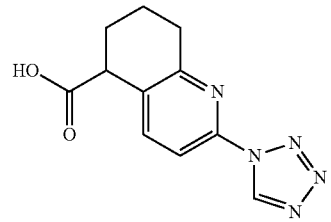 [SMILES: O=C(O)C1CCCc2nc(-n3cnnn3)ccc21]

2-1H-tetrazol-1-yl)-5,6,7,8-tetrahydroquinoline-5-carboxylic acid

Step A: methyl 5,6,7,8-tetrahydroquinoline-5-carboxylate

Methyl quinoline-5-carboxylate (3.67 g, 19.61 mmol) was dissolved in TFA (60 mL) and added platinum oxide (0.49 g, 2.16 mmol) then hydrogenated at room temperature overnight. The catalyst was filtered off and the filtrate was evaporated to dryness. The residue was chromatographed through a 120 g ISCO Redi-sep column and eluted with 5% of (10% NH₄OH in MeOH) in DCM to yield methyl 5,6,7,8-tetrahydroquinoline-5-carboxylate: LC-MS: M+1=192.

Step B: methyl 5,6,7,8-tetrahydroquinoline-5-carboxylate-1-oxide 5,6,7,8-tetrahydroquinoline-5-carboxylate (2.05 g, 10.72 mmol) was dissolved in chloroform (100 ml) and added m-chloroperbenzoic acid (2.77 g, 16.08 mmol). The reaction was stirred at room temperature for 1½ hr. The reaction was washed 2× with NaHCO₃, 1× with brine, dried over Na₂SO₄ then filtered and evaporated to dryness. The residue chromatographed through 120 g ISCO Redi-sep column and eluted with gradient solvent system of 100% ethyl acetate to 10% MeOH/90% EtOAc to yield the title compound: LC-MS: M+1=208

Step C: methyl 2-amino-5,6,7,8-tetrahydroquinoline-5-carboxylate

Methyl 5,6,7,8-tetrahydroquinoline-5-carboxylate-1-oxide (2.05 g, 9.89 mmol) and t-butyl amine (5.22 mL, 49.5 mmol) were dissolved in benzotrifluoride (50 ml) and cooled with an ice bath. The p-toluenesulfonic anhydride (6.46 g, 19.79 mmol) was added portionwise keeping the reaction's internal temperature below 5° C. The reaction was monitored and after 10 mins when the LC-MS showed M+1=263 and 207 (M-56) at 1.20 indicating formation of intermediate methyl 2-(tert-butylamino)-5,6,7,8-tetrahydroquinoline-5-carboxylate. TFA (10 mL) was then added to the reaction mixture and heated at 70° C. for 5 hrs. The reaction was cooled and evaporated to dryness. The residue was taken up with water and the pH was adjusted to ~8 with 5N NaOH. The reaction was extracted 2× with DCM. The combined DCM layers were washed with brine and dried over $Na_2SO_4$, filtered and evaporated to dryness. The residue was chromatographed through an 80 g ISCO Redi-sep column and eluted with solvent system of 5% (10% $NH_4OH$ in MeOH)/DCM to yield the title compound: LC-MS: M+1=207.

Step D: methyl 2-(1H-tetrazol-1-yl)-5,6,7,8-tetrahydroquinoline-5-carboxylate

Methyl 2-amino-5,6,7,8-tetrahydroquinoline-5-carboxylate (850 mg, 4.12 mmol) was stirred in acetic acid (15 mL) and tri-ethyl orthoformate (1.373 mL, 8.24 mmol) followed by sodium azide (482 mg, 7.42 mmol) then heated to 80° C. for 3 hrs. The reaction was cooled and evaporated to dryness. The mixture was taken up in DCM and washed with saturated $NaHCO_3$ solution, then with brine. The organic layer was dried over $Na_2SO_4$, filtered and evaporated to dryness. The residue was chromatographed through a 40 g ISCO Redi-sep column and eluted with ethyl acetate:hexane (2:3) to yield methyl 2-(1H-tetrazol-1-yl)-5,6,7,8-tetrahydroquinoline-5-carboxylate.

Step E: 2-(1H-tetrazol-1-yl)-5,6,7,8-tetrahydroquinoline-5-carboxylic acid

Methyl 2-(1H-tetrazol-1-yl)-5,6,7,8-tetrahydroquinoline-5-carboxylate (1.04 g, 4.01 mmol) and lithium hydroxide (0.202 g, 4.81 mmol) were stirred in a mixture of tetrahydrofuran (10 mL)/water (10.00 mL) for 75 mins. The TLC showed some 20% starting material so more LiOH (50 mg, 1.19 mmol) was added and stirred for another 1 hr. The reaction was adjusted with 2N HCl (3 mL, 6 mmol) to pH 4-5 then extracted with ethyl acetate 2×. The ethyl acetate layers were combined and dried over $Na_2SO_4$, filtered and evaporated to dryness to yield the title compound: LC-MS: (M+1)-28=218.

Intermediate 65

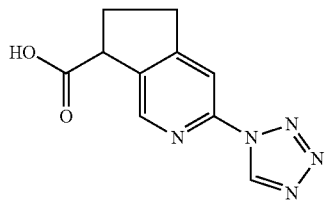 [SMILES: O=C(O)C1CCc2cc(-n3cnnn3)ncc21]

3-(1H-tetrazol-1-yl)-6,7-dihydro-5H-cyclopenta[c]pyridine-7-carboxylic acid

Step A: N-5-bromo-4-methylpyridin-2-yl)-2,2-dimethylpropanamide

To a solution of 5-bromo-4-methylpyridin-2-amine (20.6 g, 110 mmol) in 80 mL of pyridine was added trimethylacetyl chloride (19.9 g, 165 mmol) dropwise. The reaction mixture was allowed to stir at room temperature for 12 hours. The mixture was diluted with water and extracted with dichloromethane (3×). The organic layers were washed with water (2×), and brine, dried over $Na_2SO_4$ and concentrated then purified by chromatography. On elution with 2->20% EtOAc/hexanes, the title compound was obtained: LC/MS (M+1)$^+$= 270.9.

Step B: N-[5-bromo-4-(2-hydroxyethyl)pyridin-2-yl]-2,2-dimethylpropanamide

A solution of N-(5-bromo-4-methylpyridin-2-yl)-2,2-dimethylpropanamide (30.0 g, 111 mmol) in THF (80 mL) was cooled in an ice bath and treated dropwise with a solution of lithium diisopropylamine in heptane/THF/ethylbenzene (2.0 M, 138 mL). After stirring 1 h, the solution was treated with paraformaldehyde (24.9 g, 277 mmol) and allowed to warm gradually to room temperature while stirring 12 h. The mixture was diluted with saturated sodium bicarbonate solution and extracted with ethyl acetate (3×). The combined organic layers were washed with brine, dried ($Na_2SO_4$), filtered and concentrated. Purification by MPLC (eluent 6-50% ethyl acetate/hexanes) afforded the title compound: LC/MS (M+1)$^+$=300.87.

Step C: tert-butyl {6-[(2,2-dimethylpropanoyl)amino]-4-(2-hydroxyethyl)pyridin-3-yl}acetate A 250 mL round bottomed flask was charged with N-[5-bromo-4-(2-hydroxyethyl)pyridin-2-yl]-2,2-dimethylpropanamide (1.9 g, 6.31 mmol), tris(dibenzylideneacetone)dipalladium(0) (0.173 g, 0.189 mmol), and 2-(dicyclohexylphosphino)-2',4',6'-triisopropylbiphenyl (0.180 g, 0.379) and the mixture was flushed with nitrogen for 30 min. tetrahydrofuran was added, followed by a solution of 2-tert-butoxy-2-oxoethylzinc chloride in diethyl ether (0.5 M, 47.9 mL) and the mixture was placed in an oil bath maintained at 45° C. After 12 h, the reaction was recharged with tris(dibenzylideneacetone)dipalladium(0) (0.173 g, 0.189 mmol) and 2-(dicyclohexylphosphino)-2',4',6'-triisopropylbiphenyl (0.180 g, 0.379) and an additional quantity of 2-tert-butoxy-2-oxoethylzinc chloride in diethyl ether (0.5 M, 12.6 mL) was added. After stirring an additional 2 h in the 45° C. bath, the reaction mixture was diluted with ethyl acetate and 10% ammonium hydroxide solution, filtered to remove solids, and the layers separated. The organic layer was washed with water and brine, dried ($Na_2SO_4$), filtered and concentrated. Purification by MPLC (eluent 9-90% ethyl acetate/hexanes) afforded tert-butyl{6-[(2,2-dimethylpropanoyl)amino]-4-(2-hydroxyethyl)pyridin-3-yl}acetate: LC/MS (M+1)$^+$=337.0.

Step D: tert-butyl{4-(2-bromoethyl)-6-[(2,2-dimethylpropanoyl)amino]pyridin-3-yl}acetate A mixture of tert-butyl {6-[(2,2-dimethylpropanoyl)amino]-4-(2-hydroxyethyl)pyridin-3-yl}acetate (2.30 g, 6.84 mmol) with imidazole (0.558 g, 8.20 mmol) in dichloromethane (50 mL) was treated with triphenylphosphine (1.79 g, 6.84 mmol) and carbon tetrabromide (2.72 g, 8.20 mmol). The reaction mixture was allowed to stir at room temperature for 2 h, then was diluted with water and the layers separated. The organic layer was washed successively with 5% hydrochloric acid, saturated sodium bicarbonate solution, and brine, then dried ($Na_2SO_4$), filtered and concentrated. The residue was filtered through a short silica plug (20%

EtOAc:hexanes eluent) to afford the title compound which was used immediately in the next step: LC/MS (M+1)$^+$=398.9.

Step E: tert-butyl 3-[(2,2-dimethylpropanoyl)amino]-6,7-dihydro-5H-cyclopenta[c]pyridine-7-carboxylate A solution of tert-butyl {4-(2-bromoethyl)-6-[(2,2-dimethylpropanoyl)amino]pyridin-3-yl}acetate (6.5 g, 16.3 mmol) in tetrahydrofuran (50 mL) cooled in a dry ice-acetone bath was treated with a solution of lithium diisopropylamide in tetrahydrofuran (50 mL) (prepared from diisopropylamine (3.79 g, 34.7 mmol) and n-butyllithium (2.5 M, 13.7 mL) dropwise via addition funnel over 1 h. After complete addition, the reaction stirred an additional 1 h, then was quenched with saturated sodium bicarbonate solution and allowed to warm to room temperature. The resulting mixture was diluted with ethyl acetate and water and transferred to a separatory funnel. The layers were separated and the aqueous extracted with ethyl acetate (2×). The combined organics were washed with brine, dried (Na$_2$SO$_4$), filtered and concentrated. Purification of the resulting residue (2->25% EtOAc/hexanes eluent) provided the title compound. LC/MS (M+1)$^+$=319.0.

Step F: 3-amino-6,7-dihydro-5H-cyclopenta[c]pyridine-7-carboxylic acid

A solution of 3-[(2,2-dimethylpropanoyl)amino]-6,7-dihydro-5H-cyclopenta[c]pyridine-7-carboxylate (0.624 mg, 1.96 mmol) in 6N hydrochloric acid (25 mL) was heated to reflux for 24 h. The solution was cooled and concentrated to provide the title compound which was used without further purification in the next step: LC/MS (M+1)$^+$=179.0.

Step G: methyl 3-amino-6,7-dihydro-5H-cyclopenta[c]pyridine-7-carboxylate

A solution of 3-amino-6,7-dihydro-5H-cyclopenta[c]pyridine-7-carboxylic acid from Step F in methanol (10 mL) was treated dropwise with a solution of trimethylsilyl diazomethane in diethyl ether (2.0 M, 1.96 mL) at 0° C. After complete addition, the reaction warmed to room temperature and stirred 30 min, then was concentrated. The resulting residue was dried under high vacuum to afford the title compound LC/MS (M+1)$^+$=193.0;

Step H: methyl 3-(1H-tetrazol-1-yl)-6,7-dihydro-5H-cyclopenta[c]pyridine-7-carboxylate A mixture of methyl 3-amino-6,7-dihydro-5H-cyclopenta[c]pyridine-7-carboxylate (365 mg, 1.90 mmol), triethyl orthoformate (451 mg, 3.04 mmol), and sodium azide (185 mg, 2.85 mmol) in acetic acid (8 mL) was maintained in an oil bath heated at 80° C. for 3 h. After cooling to room temperature, the mixture was diluted with water and ethyl acetate and the layers separated. The aqueous was extracted with ethyl acetate (2×) and the combined organic layers were washed with brine, dried (Na$_2$SO$_4$), filtered and concentrated. Purification of the resulting residue (8->80% EtOAc/hexanes eluent) provided the title compound. LC/MS (M+1)$^+$=193.0.

Step I: 3-(1H-tetrazol-1-yl)-6,7-dihydro-5H-cyclopenta[c]pyridine-7-carboxylic acid A solution of 3-(1H-tetrazol-1-yl)-6,7-dihydro-5H-cyclopenta[c]pyridine-7-carboxylate (235 mg, 0.958 mmol) in tetrahydrofuran (5 mL) and water (1.5 mL) at room temperature was treated with lithium hydroxide solution (1 M, 1.44 mL). After 30 min. the solution was concentrated to remove tetrahydrofuran and the remaining aqueous acidified with 1 N hydrochloric acid solution (to pH~4) and extracted with ethyl acetate (3×). The combined organics were washed with brine, dried (Na$_2$SO$_4$), filtered and concentrated to provide the title compound: $^1$H NMR (500 MHz, CD$_3$OD), δ 9.89 (s, 1H), 8.58 (s, 1H), 8.01 (s, 1H), 4.25 (dd, J=5.0, 5.0 Hz, 1H), 3.27-3.05 (m, 2H), 2.47-2.57 (m, 2H); LC/MS (M+1)$^+$=232.2.

Intermediate 66

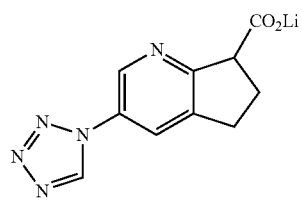

lithium 3-(1H-tetrazol-1-yl)-6,7-dihydro-5H-cyclopenta[b]pyridine-7-carboxylate

Step A: but-3-yn-1-yl methanesulfonate

A solution of but-3-yn-1-ol (45.0 g, 0.64 mol) and methanesulfonyl chloride (81.0 g, 0.71 mol) in 600 mL of DCM was added TEA (78.0 g, 0.77 mol) dropwise at 0° C. The resulting mixture was stirred at room temperature for 2 hours then concentrated to dryness. The residue was dissolved in 1 L of EtOAc then washed with 1N HCl (2×200 mL), brine (200 mL), dried over anhydrous Na$_2$SO$_4$ and concentrated to afford but-3-yn-1-yl methanesulfonate.

Step B: 4-iodobut-1-yne

A suspension of but-3-yn-1-yl methanesulfonate (90.0 g, 0.608 mol) and NaI (137 g, 0.912 mol) in 450 mL of acetone was refluxed under N$_2$ for 4 hours then cooled down. To this reaction mixture was added 450 mL of ether and filtrated. The solid was washed with another 300 mL of ether and the filtrate was distilled. The fraction of 70° C./20 mmHg was collected.

Step C: tert-butyl ethyl but-3-yn-1-ylpropanedioate

A suspension of NaH (60%, 8.50 g, 213 mmol) in 200 mL of DMF was added tert-butyl ethyl malonate (36.3 g, 193 mmol) drop-wise at 25° C. The mixture was stirred for 1 hour and 4-iodobut-1-yne (38.2 g, 212.2 g) was added drop-wise. The resulting suspension was stirred overnight and diluted with 1 L of ether, and washed with water (3×200 mL), brine, dried over anhydrous Na$_2$SO$_4$ and concentrated to afford tert-butyl ethyl but-3-yn-1-ylpropanedioate, which was used directly in the next step.

Step D: tert-butyl ethyl but-3-yn-1-yl(5-nitropyrimidin-2-yl)propanedioate

A suspension of NaH (60%, 2.5 g, 62.4 mmol) in 100 mL of DMF was added tert-butyl ethyl but-3-yn-1-ylpropanedioate (15 g, 62.4 mmol) drop-wise at 25° C. The mixture was stirred at 40° C. for 30 minutes and 2-chloro-5-nitropyrimidine (10.0 g, 62.4 mmol) in 50 mL of DMF was added dropwise. The resulting suspension was stirred at 50° C. for 2 hours and diluted with 500 mL of EtOAc. The mixture was washed with water (3×100 mL), brine, dried over anhydrous Na$_2$SO$_4$ and concentrated. The residue was purified by column chromatography (Petroleum ether:EtOAc=10:1) to afford the title compound; MS m/z 364 (M+1)$^+$.

Step E: 7-tert-butyl 7-ethyl 3-nitro-5,6-dihydro-7H-cyclopenta[b]pyridine-7,7-dicarboxylate A solution of tert-butyl ethyl but-3-yn-1-yl(5-nitropyrimidin-2-yl)propanedioate (10.2 g, 28.1 mmol) in 100 mL of nitrobenzene was heated to 150° C. for 4 hours. Nitrobenzene was removed by vacuum and the residue was purified by column chromatography (Petroleum ether:EtOAc=10:1) to afford the title compound; MS m/z 337 (M+1)$^+$.

Step F: ethyl 3-nitro-6,7-dihydro-5H-cyclopenta[b]pyridine-7-carboxylate

A mixture of 7-tert-butyl 7-ethyl 3-nitro-5,6-dihydro-7H-cyclopenta[b]pyridine-7,7-dicarboxylate (6.2 g, 18.4 mmol) in 30 mL of TFA and 30 mL DCM was stirred at 35° C. for 3 hours then concentrated to dryness. The residue was dissolved in 200 mL of EtOAc and washed with saturated NaHCO$_3$ (2×25 mL) and brine (25 mL), dried over anhydrous Na$_2$SO$_4$ and concentrated to afford the title compound.

Step G: ethyl 3-amino-6,7-dihydro-5H-cyclopenta[b]pyridine-7-carboxylate

A mixture of ethyl 3-nitro-6,7-dihydro-5H-cyclopenta[b]pyridine-7-carboxylate (4.2 g, 17.8 mmol) and Pd/C (0.5 g, 10%) in 80 mL of ethanol was stirred at room temperature under 50 psi of hydrogen for 2 hours then filtered. The filtrate was concentrated to afford the title compound.

Step H: ethyl 3-(1H-tetrazol-1-yl)-6,7-dihydro-5H-cyclopenta[b]pyridine-7-carboxylate To a solution of ethyl 3-amino-6,7-dihydro-5H-cyclopenta[b]pyridine-7-carboxylate (3.0 g, 14.6 mmol) and triethyl orthoformate (6.5 g, 43.6 mmol) in 50 mL of acetic acid was added sodium azide (1.0 g, 16.0 mmol). The mixture was heated to 100° C. for 3 hours. The reaction was complete by TLC. The reaction mixture was cooled to room temperature. The solvent was removed under vacuum. The residue was dissolved in EtOAc, washed with water, dried over anhydrous sodium sulfate, and concentrated. The residue was purified by column chromatography to afford the title compound Step I: lithium 3-(1H-tetrazol-1-yl)-6,7-dihydro-5H-cyclopenta[b]pyridine-7-carboxylate To a mixture of ethyl 3-(1H-tetrazol-1-yl)-6,7-dihydro-5H-cyclopenta[b]pyridine-7-carboxylate (1.5 g, 5.8 mmol) in 50 mL of THF/MeOH/H$_2$O (2:2:1) was added LiOH.H$_2$O (242.8 mg, 5.8 mmol) portionwise. The resulting mixture was stirred for 30 minutes then diluted with 200 mL of water and washed with ether (3×30 mL). The water layer was freeze-dried to afford the title compound: $^1$H-NMR (400 MHz, D$_2$O) δ ppm 8.68 (s, 1H), 8.07 (s, 1H), 3.97 (t, J=7.6 Hz, 1H), 3.00-3.14 (m, 2H), 2.53-2.59 (m, 1H), 2.17-2.32 (m, 1H).

Intermediate 67

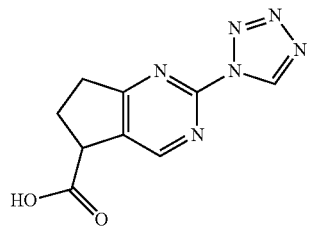 [SMILES: O=C(O)C1CCc2nc(-n3cnnn3)ncc21]

2-(1H-tetrazol-1-yl)-6,7-dihydro-5H-cyclopenta[d]pyrimidine-5-carboxylic acid

Step A: trimethyl butane-1,2,4-tricarboxylate

Sulfuric acid (0.620 mL, 11.6 mmol) was added to a mixture of 1,2,4-butanetricarboxylic acid (30.0 g, 158 mmol) in Methanol (50 mL)/1,2-Dichloroethane (140 mL). The mixture was heated at reflux for 6.5 hours, then was allowed to stand at RT overnight. The solvent was evaporated. Then 200 mL benzene was added to the residue followed by slow addition of cold saturated NaHCO$_3$ solution with vigorous stirring. The phases were separated. The aqueous phase was extracted with benzene (1×100 mL). The organic extracts were combined, washed with brine, dried (MgSO$_4$), filtered, and the solvent was evaporated to afford the title compound.

Step B: dimethyl 2-oxocyclopentane-1,3-dicarboxylate and dimethyl 3-oxocyclopentane-1,2-dicarboxylate Sodium hydride (6.19 g, 155 mmol) was added to Toluene (94 mL) and cooled to 5° C. (reaction temperature). A solution of trimethyl butane-1,2,4-tricarboxylate (29.9 g, 129 mmol) in Toluene (26 mL)/Methanol (0.22 mL) was added drop-wise over a 1¾ hours while keeping the temperature at 5-10° C. The resulting mixture was stirred at 5-10° C. for 2 hours. Then 40 mL of water was added. The layers were separated. The organic phase was extracted with water. The aqueous extracts were combined, acidified by addition to 1.7 M citric acid, and extracted with EtOAc (200 mL, 100 mL×2). The combined EtOAc extracts were washed with brine, dried (MgSO$_4$), filtered, and the solvent was evaporated to afford the product. The crude product was purified by Isco Combiflash (330 g silica gel, 100 mL/min., 254 nM, 0% to 100% EtOAc/Hexanes over 12 column volumes; the desired product elutes at 50% EtOAc; (regioisomer elutes at 65% EtOAc) to afford the title compound.

Step C: methyl 2-amino-4-hydroxy-6,7-dihydro-5H-cyclopenta[d]pyridine-5-carboxylate A resealable tube was charged with dimethyl 3-oxocyclopentane-1,2-dicarboxylate (6.04 g, 30.2 mmol). Dioxane (86 mL) was added followed by guanidine hydrochloride (3.83 g, 40.1 mmol) and potassium tert-butoxide (40 mL, 40 mmol). The tube was sealed and heated at 130° C. for 18 hours. The solvent was evaporated. Methanol (86 mL) was added to the residue followed by slow addition of thionyl chloride (2.2 mL, 30 mmol). The mixture was stirred at RT overnight. The solvent was evaporated. The residue was purified by chromatography on silica gel eluting with DCM:methanol gradient from 0 to 20% over 14 minutes to afford the title compound. This material was used without further purification in the next step: LC/MS (M+H)+=210.

Step D: methyl 2-amino-4-chloro-6,7-dihydro-5H-cyclopenta[d]pyrimidine-5-carboxylate Phosphorus oxychloride (16.0 mL, 172 mmol) was added to methyl 2-amino-4-hydroxy-6,7-dihydro-5H-cyclopenta[d]pyrimidine-5-carboxylate (5.84 g, 27.9 mmol). The resulting mixture was heated in a sealed tube at 100° C. in the microwave for 3 hours. The solvent was evaporated. The residue was dissolved in 6 mL acetonitrile and 6 mL ice/water was added. The resulting mixture was stirred at RT for 15 minutes and purified by reverse phase preparative HPLC on a SunFire column using a gradient from 0 to 100% acetonitrile over 10 minutes (11 injections) to afford the title compound. Additional product was obtained by re-purification of mixed fractions: LC/MS (M+H)=228, 230.

Step E: methyl 2-amino-6,7-dihydro-5H-cyclopenta[d]pyrimidine-5-carboxylate

Triethylamine (3.20 mL, 23.0 mmol) was added to a solution of methyl 2-amino-4-chloro-6,7-dihydro-5H-cyclopenta[d]pyrimidine-5-carboxylate (2.11 g, 9.27 mmol) in dioxane (42 mL) followed by formic acid (0.89 mL, 22.28 mmol) and [1,1'-bis(diphenylphosphino)ferrocene]-dichloropalladium (II) (660 mg, 0.902 mmol). The reaction mixture was heated at 100° C. in a sealed tube overnight. The solvent was evaporated. The residue was purified by chromatography on silica (220 g+125 g cartridges) using $CH_2Cl_2$: MeOH 95:5 to afford the title compound which was used without further purification in the next step.

Step F: 2-amino-6,7-dihydro-5H-cyclopenta[d]pyrimidine-5-carboxylic acid

Sodium hydroxide (13.0 mL, 13.0 mmol) was added to a solution of methyl 2-amino-6,7-dihydro-5H-cyclopenta[d]pyrimidine-5-carboxylate (1.10 g, 5.69 mmol) in methanol (21 mL). The resulting mixture was stirred at RT for 1.5 hours. Hydrochloric acid (13 mL, 13.00 mmol) was added. The solvent was evaporated. The residue was purified by chromatography on silica (24 g cartridge) eluting with $CH_2Cl_2$:MeOH 95:5 (150 mL) and $CH_2Cl_2$:MeOH:AcOH 90:10:1 to afford the title compound.

Step G: 2-(1H-tetrazol-1-yl)-6,7-dihydro-5H-cyclopenta[d]pyrimidine-5-carboxylic acid Trimethylsilyl trifluoroacetate (1.5 mL, 8.7 mmol) was added to a suspension of 2-amino-6,7-dihydro-5H-cyclopenta[d]pyrimidine-5-carboxylic acid (845 mg, 4.72 mmol) in ethyl acetate (10 mL). A solution was obtained but a precipitate formed within 5 minutes. The reaction mixture was stirred at RT for 5 minutes and triethyl orthoformate (1.4 mL, 8.4 mmol) was added. The mixture was stirred at RT for 5 minutes and azidotrimethylsilane (1.1 mL, 8.4 mmol) was added. The resulting suspension was stirred at RT overnight. The solvent was evaporated. The residue was purified by chromatography on silica gel (80 g cartridge) using $CH_2Cl_2$ (A) and $CH_2Cl_2$:MeOH:AcOH 90:10:1 (B) with gradient elution (100% A to 100% B over 16 column volumes) to afford crude product which was further purified by preparative HPLC to afford the title compound: NMR 500 MHz (CD$_3$OD) 10.00 (s, 1H); 8.88 (s, 1H); 4.32 (t, 1H); 3.11-3.15 (m, 2H); 2.47-2.63 (m, 2H); LC/MS (M+Na)+ at 255, (M+1)+ at 233, (M+1-N2)+ at 205.

Intermediates described above may be referred to by their number preceded by "I-". For example, Intermediate 44A is shortened to I-44A. Absolute stereochemistry at the aza-indane chiral center was determined only for Examples 2A and 2B.

Example 1AB

Isomeric Mixture, 1A and 1B

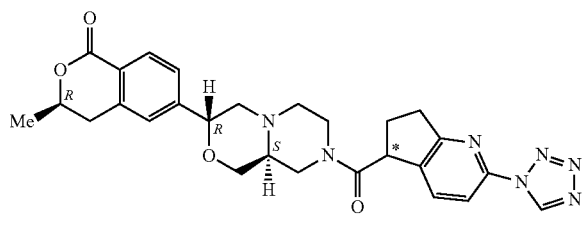

(3R)-3-methyl-6-[(3R,9aS)-8-{[2-(1H-tetrazol-1-yl)-6,7-dihydro-5H-cyclopenta[b]pyridin-5-yl]carbonyl}octahydropyrazino 2,1-c][1,4]oxazin-3-yl]-3,4-dihydro-1H-isochromen-1-one A solution of 2-(1H-tetrazol-1-yl)-6,7-dihydro-5H-cyclopenta[b]pyridine-5-carboxylic acid [I-62] (200 mg, 0.86 mmol) in 2 mL of dry DMF was treated with HATU (362 mg, 0.95 mmol) at room temp. After 5 minutes a solution of (R)-3-methyl-6-((3R,9aS)-octahydropyrazino[2,1-c][1,4]oxazin-3-yl)isochroman-1-one dihydrochloride [I-44A] (325 mg, 0.86 mmol) and DIEA (0.23 mL, 1.3 mmol) in 2 mL of dry DMF was added and the reaction allowed to stir overnight at room temp. The reaction was quenched with 10 mL of water, extracted with EtOAc and the organic layer concentrated. The crude material was purified via MPLC [10-60% (80:10:8:2 mixture of EtOAc:Acetonitrile-IPA:MeOH)/Hexanes] to give the title compound as a mixture of diastereomers: LC-MS: (M+1)$^+$ 516. Chiral resolution of the two aza-indane diastereomers was achieved by chiral preparative SFC with 45% 2:1 MeOH:MeCN on an OD column. The faster eluting isomer was a more potent ROMK inhibitor: 1A: Faster Eluting aza-indane Diastereomer: LC-MS: (M+1)$^+$ 516: $^1$H NMR (500 MHz; DMSO-d$_6$): 10.12 (d, J=7 Hz, 1H), 7.96 (d, J=8.5 Hz, 1H), 7.91-7.84 (m, 2H), 7.44 (m, 1H), 7.39 (m, 1H), 4.98 (m, 1H), 4.69 (m, 2H), 4.65 (m, 1H), 4.54 (m, 1H), 4.38, (m 1H), 4.25 (m, 1H), 3.76 (m, 1H), 3.70 (m, 1H), 3.48 (m, 1H), 3.08 (m, 4H), 2.92 (m, 2H), 2.55 (m, 2H), 2.22 (m, 1H), 2.14 (m, 1H), 1.41 (d, J=6.1 Hz, 3H). 1B: Slower Eluting aza-indane Diastereomer (IC$_{50}$ greater than 1 μM in Thallium Flux and Electrophysiology assays): LC-MS: (M+1)$^+$ 516.

Example 1CD

Isomeric Mixture, 1C and 1D

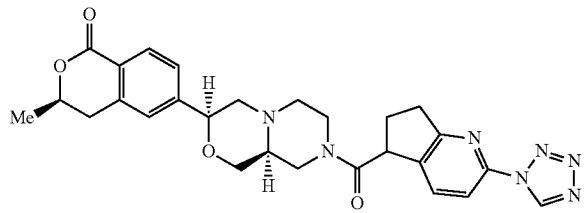 [SMILES: C[C@@H]1Cc2cc([C@H]3CN4CCN(C(=O)C5CCc6nc(-n7cnnn7)ccc65)C[C@H]4CO3)ccc2C(=O)O1]

(3R)-3-methyl-6-[(3S,9aS)-8-{[2-(1H-tetrazol-1-yl)-
6,7-dihydro-5H-cyclopenta[b]pyridin-5-yl]
carbonyl}octahydropyrazino[2,1-c][1,4]oxazin-3-yl]-
3,4-dihydro-1H-isochromen-1-one The title compound (as a mixture of two isomers) was prepared in an analogous fashion to that described above for the synthesis of the mixture of isomers in Example 1A and 1B, but starting from (R)-3-methyl-6-((3S,9aS)-octahydropyrazino[2,1-c][1,4]oxazin-3-yl)isochroman-1-one dihydrochloride [I-44B]. Chiral resolution of the two aza-indane diastereomers of the title compound was achieved by chiral preparative SFC using 40% 2:1 MeOH:MeCN on a Chiralcel OD column. The faster eluting isomer was the more potent ROMK inhibitor. 1C: Faster Eluting aza-indane Diastereomer: LC-MS: (M+1)+ 516: 1D: Slower Eluting aza-indane Diastereomer (IC$_{50}$ greater than 1 µM in Thallium Flux and Electrophysiology assays): LC-MS: (M+1)+ 516.

Example 1EF

Isomeric Mixture, 1E and 1F

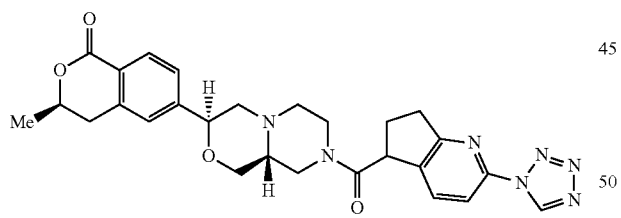

(3R)-3-methyl-6-[(3S,9aR)-8-{[2-(1H-tetrazol-1-yl)-
6,7-dihydro-5H-cyclopenta[b]pyridin-5-yl]
carbonyl}octahydropyrazino[2,1-c][1,4]oxazin-3-yl]-
3,4-dihydro-1H-isochromen-1-one The title compound (as a mixture of two isomers) was prepared in an analogous fashion to that described above for the synthesis of the mixture of isomers in Example 1A and 1B, but starting from (R)-3-methyl-6-(3S,9aR)-octahydropyrazino[2,1-c][1,4]oxazin-3-yl)isochroman-1-one dihydrochloride [I-44G]. Chiral resolution of the two aza-indane diastereomers of the title compound was achieved by chiral preparative SFC using 50% 2:1 MeOH:MeCN on a Chiralpak AS column. 1E: Faster Eluting aza-indane Diastereomer: LC-MS: (M+1)+ 516. 1F: Slower Eluting aza-indane Diastereomer: LC-MS: (M+1)+ 516.

Example 1GH

Isomeric Mixture, 1G and 1H

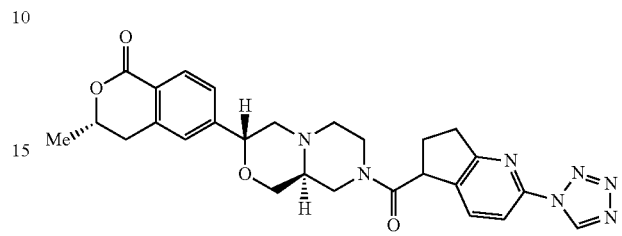

(3S)-3-methyl-6-[(3R,9aS)-8-{[2-(1H-tetrazol-1-yl)-
6,7-dihydro-5H-cyclopenta[b]pyridin-5-yl]
carbonyl}octahydropyrazino[2,1-c][1,4]oxazin-3-yl]-
3,4-dihydro-1H-isochromen-1-one The title compound (as a mixture of two isomers) was prepared in an analogous fashion to that described above for the synthesis of the mixture of isomers in Example 1A and 1B, but starting from (S)-3-methyl-6-((3R,9aS)-octahydropyrazino[2,1-c][1,4]oxazin-3-yl)isochroman-1-one dihydrochloride [I-44C]. Chiral resolution of the two aza-indane diastereomers of the title compound was achieved by chiral preparative SFC using 70% 2:1 MeOH:MeCN on a ChiralpakAD column. The faster eluting isomer was a more potent ROMK inhibitor. 1G: Faster Eluting aza-indane Diastereomer: LC-MS: (M+1)+ 516; $^1$H NMR (500 MHz; CDCl$_3$): 9.54 (s, 1H), 8.10 (m, 1H), 7.94 (m, 1H), 7.78 (m, 1H), 7.37 (m, 1H), 7.31 (m, 1H), 4.76-4.68 (m, 2H), 4.57 (d, J=13.2 Hz, 1H), 4.43-4.37 (m, 1H), 4.08-4.03 (m, 2H), 3.60-3.52 (m, 2H), 3.29-3.23-(m, 1H), 3.17-3.11 (m, 2H), 3.05-2.91 (m, 4H), 2.64-2.54 (m, 1H), 2.5-2.3 (m, 4H), 1.55 (d, J=6.2 Hz, 3H. 1H: Slower Eluting aza-indane Diastereomer (IC$_{50}$ greater than 1 µM in Thallium Flux and Electrophysiology assays): LC-MS: (M+1)+ 516.

Example 1IJ

Isomeric Mixture 1I and 1J

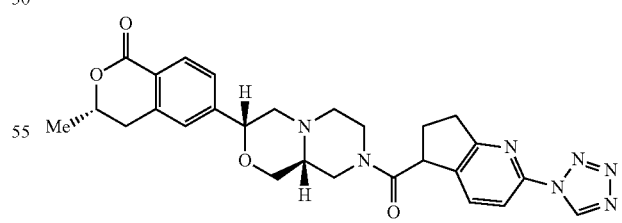

(3S)-3-methyl-6-[(3R,9aR)-8-{[2-(1H-tetrazol-1-yl)-
6,7-dihydro-5H-cyclopenta[b]pyridin-5-yl]
carbonyl}octahydropyrazino[2,1-c][1,4]oxazin-3-yl]-
3,4-dihydro-1H-isochromen-1-one The title compound (as a mixture of two isomers) was prepared in an analogous fashion to that described above for the synthesis of the mixture of isomers in Example 1A and 1B, but starting from (S)-3-methyl-6-((3R,9aR)-octahydropyrazino[2,1-c][1,4]oxazin-3-yl)isochroman-1-one dihydrochloride [I-44F]. Chiral resolution of the two aza-indane diastereomers of the title compound was achieved by chiral preparative SFC using 50% MeOH (0.2% DEA) on a Chiralpak AS-H column. 1I: Faster Eluting aza-indane Diastereomer: LC-MS: (M+1)⁺ 516. 1J: Slower Eluting aza-indane Diastereomer: LC-MS: (M+1)⁺ 516.

Example 1KL

Isomeric Mixture, 1K and 1L

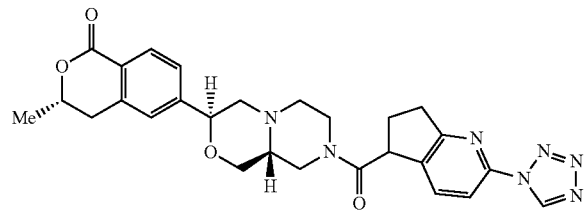 [SMILES: C[C@H]1Cc2cc([C@H]3CN4CCN(C(=O)C5CCc6nc(-n7cnnn7)ccc65)C[C@H]4CO3)ccc2C(=O)O1]

(3S)-3-methyl-6-[(3S,9aR)-8-{[2-(1H-tetrazol-1-yl)-6,7-dihydro-5H-cyclopenta[b]pyridin-5-yl]carbonyl}octahydropyraziazin[2,1-c][1,4]oxazin-3-yl]-3,4-dihydro-1H-isochromen-1-one The title compound (as a mixture of two isomers) was prepared in an analagous fashion to that described above for the synthesis of the mixture of isomers in Example 1A and 1B, but starting from (S)-3-methyl-6-((3S,9aR)-octahydropyrazino[2,1-c][1,4]oxazin-3-yl)isochroman-1-one dihydrochloride [I-44E]. Chiral resolution of the two aza-indane diastereomers of the title compound was achieved by chiral preparative SFC using 40% MeOH (0.2% DEA) on a Chiralcel OD-H column. The faster eluting isomer was a more potent ROMK inhibitor: 1K: Faster Eluting aza-indane Diastereomer: ¹H-NMR (500 MHz, CDCl₃) δ ppm 9.523 (s, 1H), 8.08 (d, J=7.5 Hz, 1H), 7.906 (d, J=8 Hz, 1H), 7.79-7.74 (m, 2H), 7.37-7.28 (m, 1H), 4.75-4.65 (m, 2H), 4.54 (d, J=12.5 Hz, 1H), 4.43-4.37 (m, 1H). 4.07-4.02 (m, 2H), 3.91 (d, J=12.5 Hz, 1H), 3.60-3.49 (m, 2H), 3.25-3.20 (m, 1H), 3.16-3.09 (m, 2H), 3.00-2.95 (m, 5H), 2.91 (d, J=11.5 Hz, 1H), 2.61-2.2.59 (m, 1H), 2.51-2.27 (m, 3H); LC/MS: [(M+1)]⁺= 516. 1L: Slower Eluting aza-indane Diastereomer (IC₅₀ greater than 1 μM in Thallium Flux and Electrophysiology assays): LC-MS: (M+1)⁺ 516.

Example 2AB

Isomeric Mixture, 2A and 2B (Method 1)

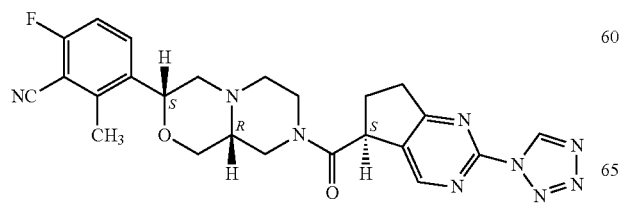

A

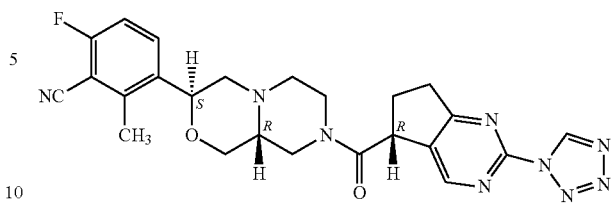

B

2A: 6-Fluoro-2-methyl-3-[(3S,9aR)-8-{[(5S)-2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile and 2B: 6-fluoro-2-methyl-3-[(3S,9aR)-8-{[(5R)-2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile EDC (2.24 g, 11.68 mmol) was added to a suspension of 2-(1H-tetrazol-1-yl)-6,7-dihydro-5H-cyclopenta[d]pyrimidine-5-carboxylic acid [I-67] (2.51 g, 9.73 mmol) and 6-fluoro-2-methyl-3-[(3S,9aR)-octahydropyrazino[2,1-c][1,4]oxazin-3-yl]benzonitrile [I-40C-1] (2.81 g, 10.21 mmol) in dichloromethane (25 mL). The reaction mixture was stirred at RT for 1.5 hours. Most of the solvent was evaporated. The residue was dissolved in EtOAc and washed with water, NaHCO₃ solution and brine, dried (Na₂SO₄), filtered, and the solvent evaporated to afford a crude mixture of the two diastereomers. The crude product was purified on silica (220 g cartridge) with gradient elution from CH₂Cl₂ (solvent A) to 50% CH₂Cl₂:MeOH 90:10 (solvent B) to afford a mixture of the title diastereomers which were separated by chiral preparative SFC HPLC (SFC on Chiralpak IC column, Diacel Chemical Industries, LTD., 30×250 mm, 60% 2:1 MeOH:MeCN/CO₂, 70 mL/min., 100 bar, sample in DCM/MeCN, 35C, 254 nm) to afford the separated aza-indane diastereomers: Isomer 2A, faster eluting, and Isomer 2B, slower eluting. Stereochemical assignment at the aza-indane chiral center was made by X-ray crystallography of the slower eluting isomer. Isomer A was dissolved in 1 mL acetonitrile and 1 eq. 1 M HCl in ether was added, and. the solid was filtered to yield the hydrochloride salt. Isomer 2A HCl salt: NMR 500 MHz (CD₃OD+D₂O) (mixture amide rotamers) 10.04 (s, 1H); 8.72 (s, 0.4H); 8.68 (s, 0.6H); 7.81-7.88 (m, 1H); 7.25-7.31 (m, 1H); 5.12 (t, 1H); 4.63-4.75 (m, 1.5H); 4.40-4.46 (m, 1H); 4.33-4.38 (dd, 0.5H); 4.23-4.28 (dd, 0.5H); 3.72-3.90 (m, 2H); 3.42-3.52 (m, 3H); 3.14-3.28 (m, 3H); 2.84-3.1 (m, 2H); 2.86-2.97 (m, 1H); 2.73-2.82 (m, 1H); 2.60 (s, 3H); 2.50-2.35 (m, 1H); LC/MS 512 (M+Na), 490 (M+H), 462 (M+H–N2): The HCl salt of Isomer 2B was made in a similar fashion. Isomer 2B HCl salt: NMR 500 MHz (CD₃OD+D₂O) (mixture amide rotamers) 10.0 (s, 1H); 8.7 (s, 1H); 7.82-7.86 (dd, 1H); 7.29 (t, 1H); 5.26 d, 1H); 4.66-4.76 (m, 1H); 4.49-4.54 (m, 1H); 4.45-4.59 (m, 1H); 4.35 (d, 0.5H); 3.90-4.03 (m, 1H); 3.76-3.88 (m, 0.5H); 3.11-3.43 (m, 5.5H); 2.88-3.00 (m, 0.5H); 2.70-2.82 (m, 1H); 2.63 (s, 3H); 2.21-2.40 (m, 1H); LC/MS 512 (M+Na), 490 (M+H), 42 (M+H–N2).

Example 2A

Method 2

A 5 L three-necked round bottomed flask was equipped with overhead stirring, N₂ inlet, and thermocouple. To the flask was charged 6-fluoro-2-methyl-3-[(3S,9aR)-octahydropyrazino[2,1-c][1,4]oxazin-3-yl]benzonitrile [I-40C-2] (147.15 g, 423 mmol, based on di-hydrochloride salt), 2-(1H-tetrazol-1-yl)-6,7-dihydro-5H-cyclopenta[d]pyrimidine-5-carboxylic acid [I-67] (95.7% purity, 110 g, 452 mmol), EDCI.HCl (122 g, 634 mmol), and HOBt.H$_2$O (6.47 g, 42.3 mmol), followed by premixed Tetrahydrofuran (1472 mL) and Water (73.6 mL). Addition of THF:water, was accompanied by a temperature increase from 23° C. to 31° C. Four equivalents of DIPEA (300 mL) were added via addition funnel while maintaining the temperature<35° C. The reaction mixture was stirred at ambient temperature over night. The reaction was quenched with ammonium chloride (90 g, 1690 mmol) in 500 mL water. The product was extracted from the aqueous phase with 500 mL of EtOAc followed by 200 mL of EtOAc, and the organic layers were combined. The combined organic layers were washed with ammonium chloridesolution until pH of the aqueous phase was 6-7. Solid was observed to have precipitated, and was filtered from aqueous and organic phase interface. The organic phase was concentrated to remove THF and EtOAc. About 200 mL of acetonitrile was added and the mixture was subjected to rotary evaporation to remove water. More solid precipitated. The solid was filtered and the filtrate was diluted to 1500 mL for SFC chiral HPLC separation input stream. Separation was achieved via the following method: Chiracel AD-H column (Diacel Chemical Industries, LTD., 250×50 mm, 5 um), flow rate 250 mL/min, 35° C., 220 nm, 100 bar, 50% MeOH:MeCN (2:1)/CO$_2$, 260 sec cycle time, 130 g in 1500 mL MeCN, 87 mg/mL, 15 mL/inj. The peak 1 (faster eluting) fraction was concentrated, dissolved in 750 mL ACN, and treated with activated carbon, (Norit SA3, 100 mesh), agitated for about 15 min, filtered on solka flok, and concentrated. The foam residue was dissolved with 350 mL DME with heating at 40-50° C. Precipitation was observed after about 2-3 min at about 35-37° C., and the mixture was allowed to cool to ambient conditions. When the temperature reached about 25° C., 250 mL cyclohexane was added over about 15 min and the batch was agitated about 1 h. The solid product was filtered, and the reactor and cake were washed with 100 mL of cyclohexane, and the solids were pulled to a mostly dry state under N$_2$. The wet cake was dried under vacuum at 60° C. for about 18 h to yield 6-Fluoro-2-methyl-3-[(3S,9aR)-8-{[(5S)-2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile.

Example 2CD

Isomeric Mixture, 2C and 2D

6-Fluoro-2-methyl-3-[(3R,9aR)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile (isomer mixture)

1-Hydroxybenzotriazole (173 mg, 1.280 mmol) was added to a suspension of 2-(1H-tetrazol-1-yl)-6,7-dihydro-5H-cyclopenta[d]pyrimidine-5-carboxylic acid [I-67] (200 mg, 0.861 mmol) in dichloromethane (2 mL) followed by EDC (331 mg, 1.73 mmol), 6-fluoro-2-methyl-3-[(3R,9aR)-octahydropyrazino[2,1-c][1,4]oxazin-3-yl]benzonitrile [I-40D] (551 mg, 1.095 mmol) and triethylamine (0.70 mL, 5.0 mmol). The reaction mixture was stirred at RT overnight. The reaction mixture was diluted with EtOAc and washed with saturated NaHCO$_3$ solution, water and brine, dried (MgSO$_4$), filtered, and the solvent evaporated to afford the title compound as a mixture of two diastereomers. The crude product was purified by MPLC on silica (24 g cartridge) using CH$_2$Cl$_2$ (A) and CH$_2$Cl$_2$:MeOH 90:10 (B) with gradient elution from 100% A to 100% B over 12 CV's to afford the title compound as a mixture of 2 diastereomers. LC/MS 490 (M+H). The mixture of diastereomers was purified by preparative chiral HPLC (SFC) on a Chiralcel AS column, 100 bar, 40% MeOH (0.2% DEA)/CO$_2$, 35° C. to afford the two separated aza-indane diastereomers of the title compound: Isomer 2C (faster eluting) and Isomer 2D (slower eluting). Each isomer was dissolved separately in 1 mL of dichloromethane and 1 eq. 1 M HCl in ether was added. The solvent was evaporated to yield the hydrochloride salts of each isomer. Isomer 2C HCl salt: NMR 600 MHz (CD$_3$OD) (mixture amide rotamers) 9.988 (s, 0.6H); 9.975 (s, 0.4H); 8.73 (s, 0.6H); 8.67 (s, 0.4H); 7.94 (dd, 1H); 7.31 (app t, 1H); 5.15 (d, 1H); 4.80 (t, 0.5H); 4.75 (d, 0.5H); 4.65-4.70 (m, 1H); 4.47 (d, 0.5H); 4.32-4.38 (m, 1H); 4.19-4.29 (m, 2H); 3.84-3.98 (m, 2H 3.57-3.72 (m, 2H); 3.44-3.54 (m, 2H); 3.31-3.38 (m, 0.5H); 3.23 (t, 2H); 2.69-2.86 (m, 1H); 2.62 (s, 3H); 2.33-2.42 (m, 0.5H); 2.20-2.28 (m, 0.5H). LC/MS 531 (M+H+CH$_3$CN). Isomer 2D HCl salt: NMR 500 MHz (CD$_3$OD) (mixture amide rotamers) 9.98 (s, 1H); 8.72 (s, 0.6H)); 8.69 (s, 0.4H); 7.91-7.96 (m, 1H); 7.30 (q, 1H); 5.14-5.18 (m, 1H); 472-4.78 (m, 1.5H); 4.65 (d, 0.5H); 4.49 (d, 0.5H); 4.35 (d, 1H); 4.21-4.30 (m, 2H); 3.32-3.95 (m, 6.5H); 3.18-3.27 (m, 2H); 2.71-2.79 (m, 1H); 2.62 (s, 3H); 2.35-2.42 (m, 0.5H); 2.18-2.26 (m, 0.5H). LC/MS 531 (M+H+CH$_3$CN).

Example 2EF

Isomeric Mixture, 2E and 2F

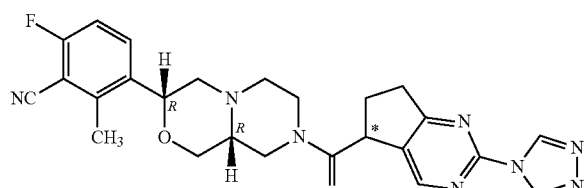

*(2 separated diastereomers)

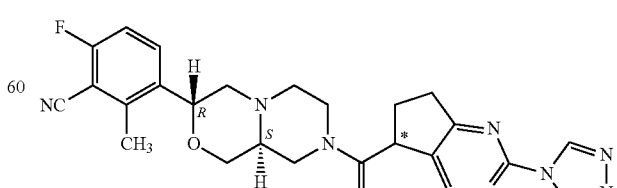

*(2 separated diastereomers)

6-fluoro-2-methyl-3-[(3R,9aS)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile (isomeric mixture)

The title compound (as a mixture of two isomers) was prepared in an analogous fashion to that described above for the synthesis of the mixture of isomers in Example 2C and 2D, but starting with 6-fluoro-2-methyl-3-[(3R,9aS)-octahydropyrazino[2,1-c][1,4]oxazin-3-yl]benzonitrile. [I-40B] The diastereomers were separated by chiral preparative SFC HPLC on a Chiralcel AS-H column, 100 bar, 30% MeOH (0.2% isobutylamine)/$CO_2$, 35° C., followed by further purification by prep TLC on silica gel (eluting with $CH_2Cl_2$:MeOH 95:5) to afford the separated aza-indane diastereomers of the title compound, Isomer 2E (faster eluting) and Isomer 2F (slower eluting). Each isomer was dissolved separately in 1 mL dichloromethane and 1 equivalent of 1 M HCl in ether was added. The solvent was evaporated to yield the hydrochloride salts of the separated diastereomers. Isomer 2E HCl salt: NMR 500 MHz ($CD_3OD$) (mixture amide rotamers) 10.02 (s, 1H); 8.71 (s, 0.5H); 8.67 (s, 0.5H); 7.84 (dd, 1H); 7.27 (t, 1H); 5.08 (d, 1H); 4.62-4.76 (m, 1.5H); 4.30-4.45 (m, 1.5H); 4.19-4.26 (m, 0.5H); 3.8 (q, 1H); 3.65-3.73 (m, 0.5H); 3.33-3.45 (m, 2.5H); 3.20-3.28 (m, 2H); 3.11-3.20 (m, 1.5H); 3.00-3.08 (m, 0.5H); 2.73-2.93 (m, 3.5H); 2.61 (s, 3H); 2.19-2.37 (m, 1H): LC/NIS 531 (M+H+$CH_3CN$), 462 (M+H−N2): Isomer 2F HCl salt: NMR 500 MHz ($CD_3OD$) (mixture amide rotamers) 10.02 (s, 1H); 8.72 (s, 0.4H); 8.68 (s, 0.5H); 7.84 (q, 1H); 7.25-7.30 (m, 1H); 5.11 (t, 1H); 4.63-4.74 (m, 2H); 4.38-4.43 (m, 1H); 4.34 (d, 0.5H); 3.70-3.87 (m, 1.5H); 3.37-3.49 (m, 3.5H); 3.24 (q, 1.5H); 3.10-3.20 (m, 1H); 2.73-3.04 (m, 3.5H); 2.60 (s, 3H); 2.16-2.35 (m, 1H). LC/MS 531 (M+H+$CH_3CN$), 462 (M+H−N2).

Example 2 GH

Isomeric Mixture, 2G and 2H

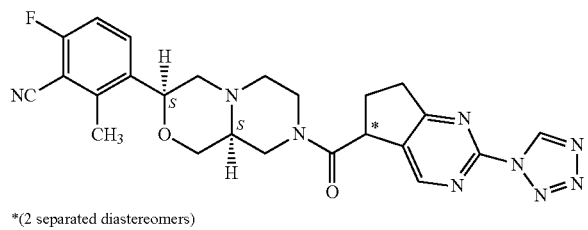

*(2 separated diastereomers)

6-fluoro-2-methyl-3-[(3S,9aS)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile (isomeric mixture)

HATU (266 mg, 0.700 mmol) was added to a solution of 2-(1H-tetrazol-1-yl)-6,7-dihydro-5H-cyclopenta[d]pyrimidine-5-carboxylic acid [I-67] (148 mg, 0.637 mmol) in DMF (1 mL). The mixture was stirred at RT for 5 minutes then a solution of 6-fluoro-2-methyl-3-[(3S,9aS)-octahydropyrazino[2,1-c][1,4]oxazin-3-yl]benzonitrile [I-40A] (411 mg, 0.817 mmol), and Hunig's Base (0.70 mL, 4.0 mmol) in dichloromethane (1 mL) was added. The flask was rinsed twice with dichloromethane (0.3 mL). The reaction mixture was stirred at RT for 2 hours then diluted with EtOAc and washed with saturated $NaHCO_3$ solution, water and brine, dried ($MgSO_4$), filtered and the solvent evaporated to afford crude title compound as a mixture of two diastereomers. This crude material was purified by preparative TLC on silica (2000 μm, eluted twice) using $CH_2Cl_2$:MeOH 95:5 (B) to afford the title compound 2 GH as a mixture of diastereomers: LC/MS 512 (M+Na), 490 (M+H). The diastereomers were separated by chiral preparative SFC HPLC (ChiralCel IC, 21×250 mm, 60% MeOH:MeCN/$CO_2$, 50 mL/min, 100 bar, 114 mg/mL in MeCN/MeOH, 35° C., 220 nm) to afford the separated aza-indane diastereomers Isomer 2G (faster eluting) and Isomer 2H (slower eluting). Each isomer was dissolved separately in 1 mL dichloromethane and 1 equivalent of 1 M HCl in ether was added. The solvent was evaporated to yield the HCL salt of each diastereomer. Isomer 2G HCL salt: NMR 600 MHz ($CD_3OD$)(mixture amide rotamers) 10.012 (s, 0.5H); 10.007 (s, 0.5H); 8.72 (s, 0.5H); 8.68 (s, 0.5H); 8.00 (br app t, 1H); 7.31 (dt, 1H); 5.11 (t, 1H); 4.60-4.72 (m, 2H); 4.41 (d, 0.5H); 4.09-4.31 (m, 3H); 3.91 (t, 0.5H); 3.88 (dd, 1.5H); 3.31-3.62 (m, 4H); 3.20-3.28 (m, 2.5H); 2.72-2.86 (m, 1H); 2.61 (s, 3H); 2.30-2.37 (m, 0.5H); 2.21-2.27 (m, 0.5H); LC/MS 531 (M+H+$CH_3CN$). Isomer 2H HCl salt: NMR 600 MHz ($CD_3OD$) (mixture amide rotamers) 10.02 (s, 1H); 8.72 (s, 0.6H); 8.69 (s, 0.4H); 8.02 (app t, 0.4H); 7.98 (aap t, 0.6H); 7.28-7.33 (m, 1H); 5.09 (d, 1H); 4.72-4.77 (m, 1H); 4.64 (d, 0.5H); 4.57 (d, 3H); 4.34 (d, 0.5H); 4.28 (d, 0.5H); 4.05-4.20 (m, 2.5H); 3.86 (t, 1H); 3.75 (q, 1H); 3.48-3.63 (m, 2H); 3.26 (t, 1H); 3.23 (t, 1H); 2.74-2.81 (m, 1H); 2.61 (s, 3H); 2.30-2.36 (m, 0.5H); 2.20-2.27 (m, 0.5H); LC/MS 531 (M+H+$CH_3CN$).

The following Examples in Table 3 were prepared in an analogous fashion to that described for the synthesis of Examples 1AB through 1L and 2AB through 2H from the appropriate amine and carboxylic acid Intermediates (prepared as described above) using one of the amide coupling agents EDC or HATU. The amide coupling provides two diastereomeric products which are epimers at the chiral center alpha to the amide carbonyl (i.e., the aza-indane chiral center). The two diastereomeric products are typically separated in a similar fashion as described in the above Examples. The chiral HPLC column used for each Example is indicated in Table 3, as well as the order of elution observed. For several of the Examples in Table 3, the two diastereomers were not separated and the mixture of two resulting diastereomers is included.

In Tables 3 and 4, faster eluting and slower eluting refers to the observed elution order of an individual aza-indane diastereomer upon separation from its aza-indane isomer mixture. Absolute stereochemistry of the other stereocenters in each compound are known based on their corresponding intermediate synthesis and are as drawn.

TABLE 3

| EXAMPLE Number | |
|---|---|
| 3 | 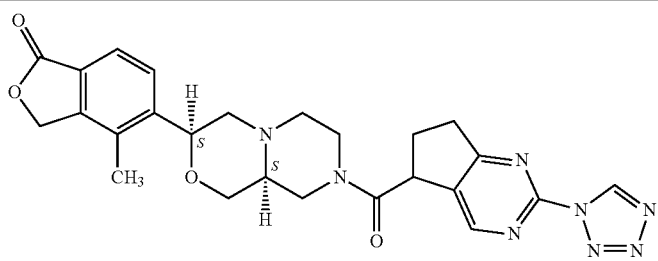
faster eluting isomer from chiral HPLC
SFC: Chiralcel AS-H column (faster eluting). LC/MS 544 (M + H + CH$_3$CN). NMR 500 MHz (CD$_3$OD + D$_2$O) (mixture amide rotamers) 10.01 (s, 1H); 8.73 (br s, 0.75H); 8.70 (br s, 0.25H); 7.87 (dd, 1H); 7.80 (dd, 1H); 5.42 (ab q, 2H); 5.25 (br dt, 1H); 4.74 (dd, 1H); 4.60 (br dt, 0.5H); 4.40 (d, 0.5H); 4.20-4.34 (m, 3H); 3.80-3.95 (m, 1.5H); 3.33-3.76 (m, 5.5H); 3.21-3.28 (m, 2H); 2.73-2.84 (m, 1H); 2.41 (s, 3H); 2.20-2.39 (m, 1H).
4-methyl-5-[(3S,9aS)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]-2-benzofuran-1(3H)-one |
| 4 | 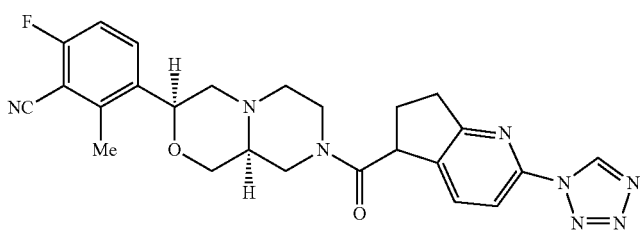
faster eluting isomer from chiral HPLC
SFC on Chiralpak AS column, faster eluting; LC/MS 489 (M + H)$^+$
6-fluoro-2-methyl-3-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 5 | 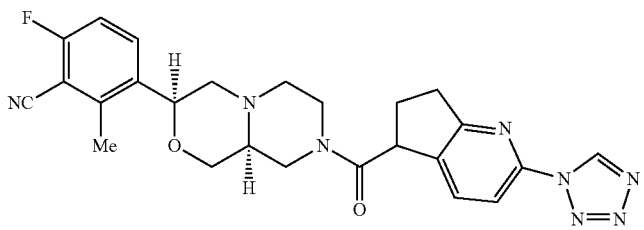
slower eluting isomer from chiral HPLC
SFC on Chiralpak AS column, slower eluting; LC/MS 489 (M + H)$^+$
6-fluoro-2-methyl-3-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 6 | 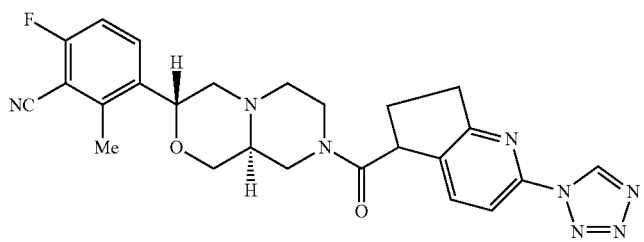
faster eluting isomer from chiral HPLC
SFC on OJ-H column, faster eluting; LC/MS 489 (M + H)$^+$. 6-fluoro-2-methyl-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |

TABLE 3-continued

| EXAMPLE Number | |
|---|---|
| 7 | 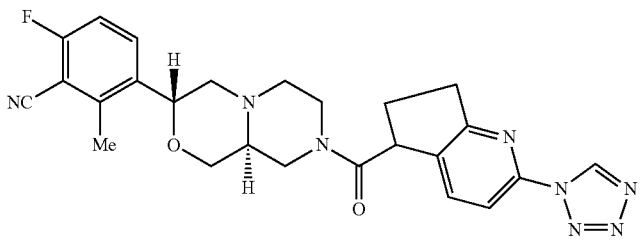<br>slower eluting isomer from chiral HPLC<br>SFC on OJ-H column, slower eluting; LC/MS 489 (M + H)$^+$. 6-fluoro-2-methyl-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 8 | 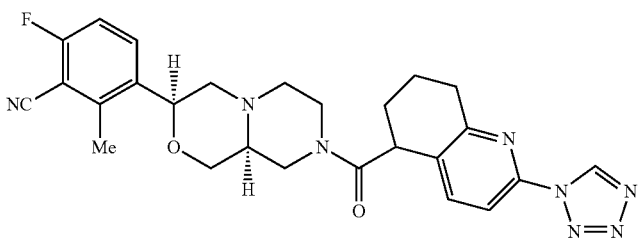<br>faster eluting isomer from chiral HPLC<br>SFC on Chiralpak AS column, faster eluting; LC/MS 503 (M + H)$^+$<br>6-fluoro-2-methyl-3-[(3S,9aS)-8-{[2-(1H-tetrazol-1-yl)-5,6,7,8-tetrahydroquinolin-5-yl]carbonyl}octahydropyrazino[2,1-c][1,4]oxazin-3-yl]benzonitrile |
| 9 | 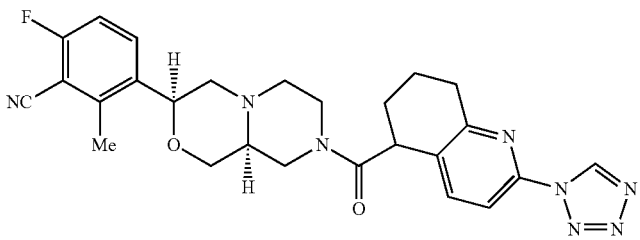<br>slower eluting isomer from chiral HPLC<br>SFC on Chiralpak AS column, slower eluting; LC/MS 503 (M + H)$^+$<br>6-fluoro-2-methyl-3-[(3S,9aS)-8-{[2-(1H-tetrazol-1-yl)-5,6,7,8-tetrahydroquinolin-5-yl]carbonyl}octahydropyrazino[2,1-c][1,4]oxazin-3-yl]benzonitrile |
| 10 | 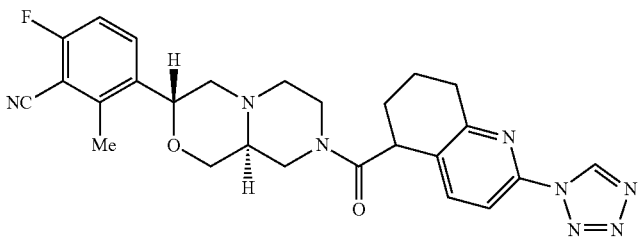<br>faster eluting isomer from chiral HPLC<br>SFC on Chiralpak AS column, faster eluting; LC/MS 503 (M + H)$^+$<br>6-fluoro-2-methyl-3-[(3R,9aS)-8-{[2-(1H-tetrazol-1-yl)-5,6,7,8-tetrahydroquinolin-5-yl]carbonyl}octahydropyrazino[2,1-c][1,4]oxazin-3-yl]benzonitrile |

TABLE 3-continued

EXAMPLE Number

11 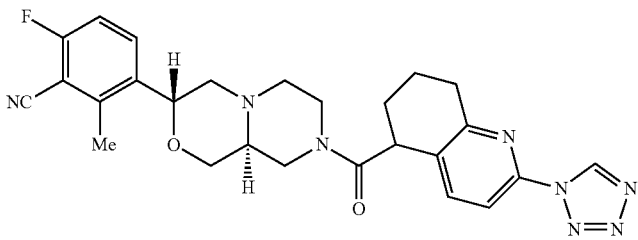

slower eluting isomer from chiral HPLC
SFC on Chiralpak AS column, slower eluting; LC/MS 503 (M + H)$^+$
6-fluoro-2-methyl-3-[(3R,9aS)-8-{[2-(1H-tetrazol-1-yl)-5,6,7,8-tetrahydroquinolin-5-yl]carbonyl}octahydropyrazino[2,1-c][1,4]oxazin-3-yl]benzonitrile 12 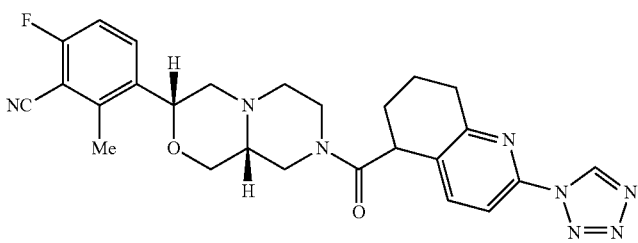

faster eluting isomer from chiral HPLC
SFC on Chiralpak AS column, faster eluting; LC/MS 503 (M + H)$^+$
6-fluoro-2-methyl-3-[(3R,9aR)-8-{[2-(1H-tetrazol-1-yl)-5,6,7,8-tetrahydroquinolin-5-yl]carbonyl}octahydropyrazino[2,1-c][1,4]oxazin-3-yl]benzonitrile 13 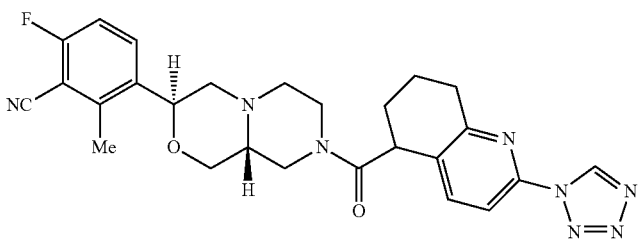

faster eluting isomer from chiral HPLC
SFC on Chiralpak AS column, faster eluting; LC/MS 503 (M + H)$^+$
6-fluoro-2-methyl-3-[(3S,9aR)-8-{[2-(1H-tetrazol-1-yl)-5,6,7,8-tetrahydroquinolin-5-yl]carbonyl}octahydropyrazino[2,1-c][1,4]oxazin-3-yl]benzonitrile 14 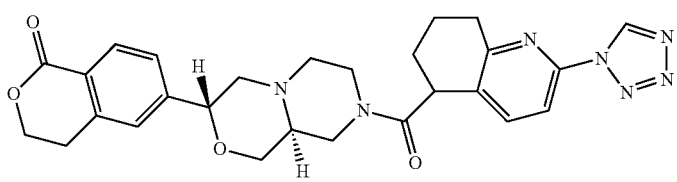

faster eluting isomer from chiral HPLC
SFC on Chiralpak AS column, faster eluting; LC/MS 516 (M + H)$^+$
6-[(3R,9aS)-8-{[2-(1H-tetrazol-1-yl)-5,6,7,8-tetrahydroquinolin-5-yl]carbonyl}octahydropyrazino[2,1-c][1,4]oxazin-3-yl]-3,4-dihydro-1H-isochromen-1-one

TABLE 3-continued

EXAMPLE Number

15

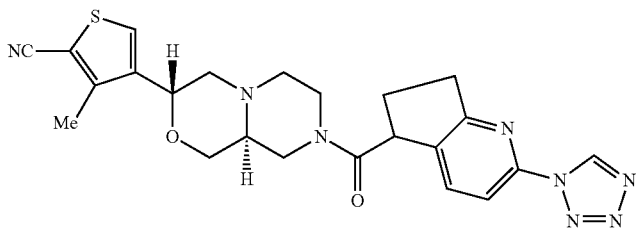

faster eluting isomer from chiral HPLC
SFC on Chiralpak AD column, faster eluting; LC/MS 477 (M + H)⁺
3-methyl-4-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]thiophene-2-carbonitrile

16

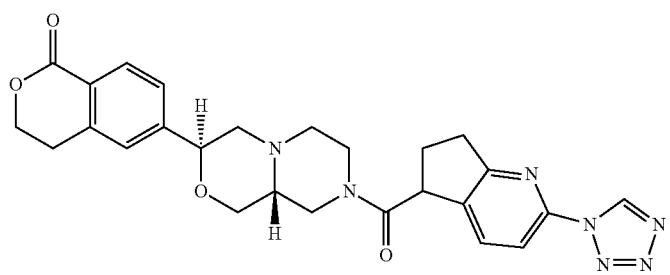

faster eluting isomer from chiral HPLC
SFC on IC column, faster eluting; LC/MS 502 (M + H)⁺
6-[(3S,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one

17

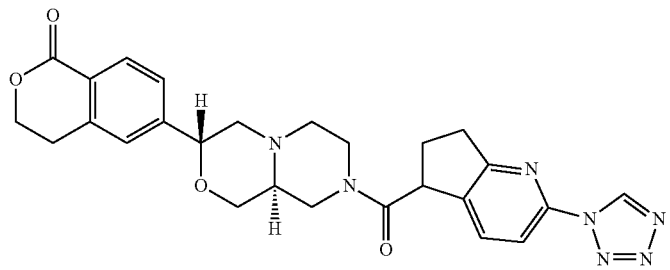

Mixture of two diastereomers at aza-indane center (not separated); LC/MS 502 (M + H)⁺
6-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one

17A

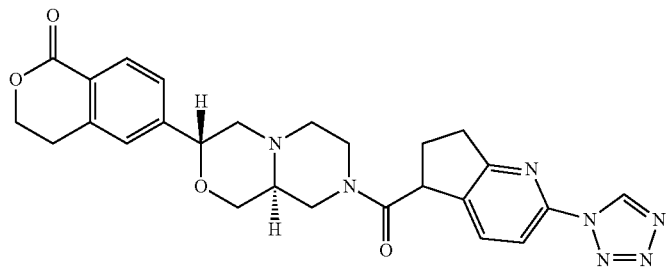

faster eluting isomer from chiral HPLC
SFC on IC column, faster eluting; LC/MS 502 (M + H)⁺
6-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one

TABLE 3-continued

EXAMPLE Number

18
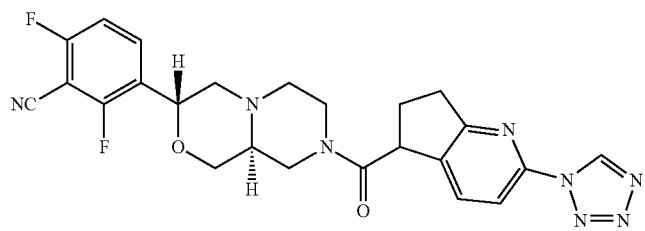

faster eluting isomer from chiral HPLC
SFC on Chiralpak IC column, faster eluting; LC/MS 493 (M + H)⁺
2,6-difluoro-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile 19
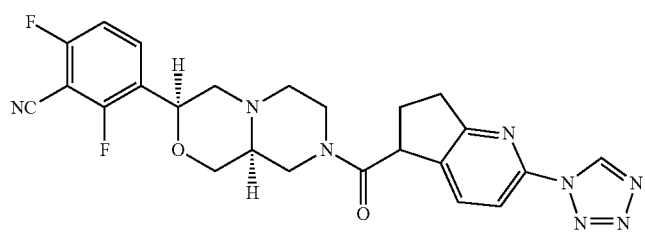

faster eluting isomer from chiral HPLC
SFC on Chiralpak IC column, faster eluting. LC/MS 493 (M + H)⁺
2,6-difluoro-3-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile 20
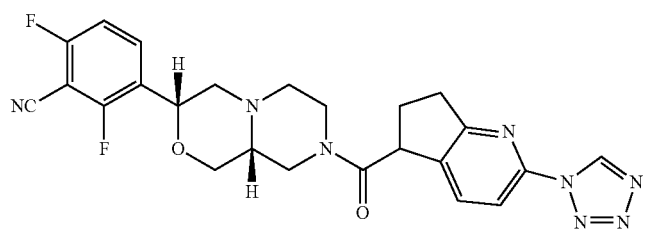

faster eluting isomer from chiral HPLC
SFC on Chiralpak AD column, faster eluting; LC/MS 493 (M + H)⁺
2,6-difluoro-3-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile 21
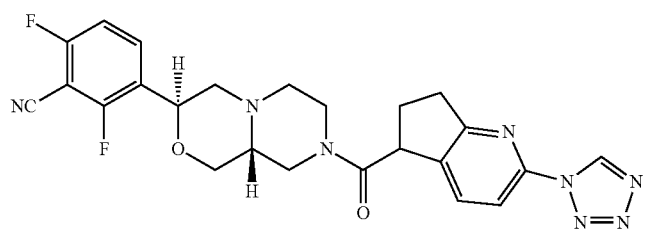

faster eluting isomer from chiral HPLC
SFC on Chiralpak AD column, faster eluting; LC/MS 493 (M + H)⁺
2,6-difluoro-3-[(3S,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile

TABLE 3-continued

EXAMPLE Number

22

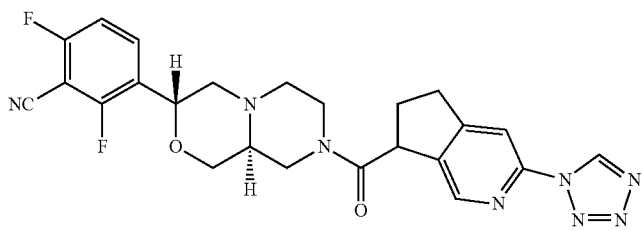

slower eluting isomer from chiral HPLC
SFC on Chiralpak IC column, slower eluting; LC/MS 493 (M + H)+
2,6-difluoro-3-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile

23

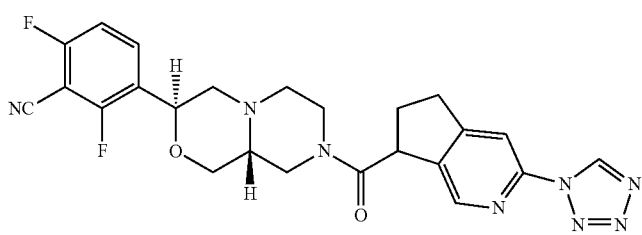

faster eluting isomer from chiral HPLC
SFC on Chiralpak AD column, faster eluting; LC/MS 493 (M + H)+
2,6-difluoro-3-[(3S,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile

24

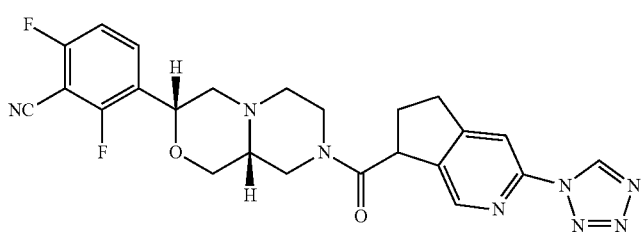

faster eluting isomer from chiral HPLC
SFC on Chiralpak AD column, faster eluting; LC/MS 493 (M + H)+
2,6-difluoro-3-[(3R,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile

25

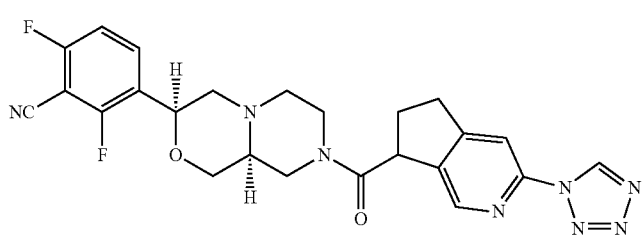

slower eluting isomer from chiral HPLC
SFC on IC column, slower eluting; LC/MS 493 (M + H)+
2,6-difluoro-3-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile TABLE 3-continued

| EXAMPLE Number | |
|---|---|
| 26 | 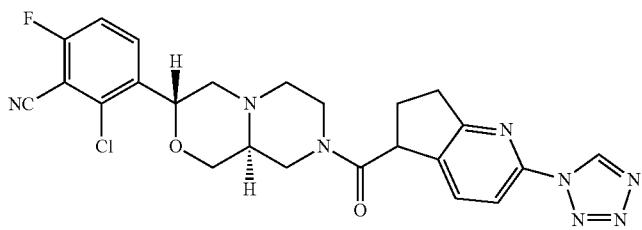
faster eluting isomer from chiral HPLC
SFC on Chiralpak IC column, faster eluting; LC/MS 509 (M + H)⁺. 2-chloro-6-fluoro-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 27 | 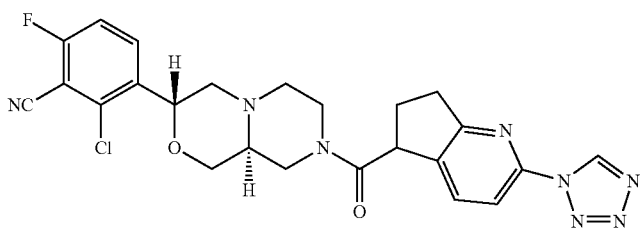
slower eluting isomer from chiral HPLC
SFC on Chiralpak IC column, slower eluting; LC/MS 509 (M + H)⁺. 2-chloro-6-fluoro-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 28 | 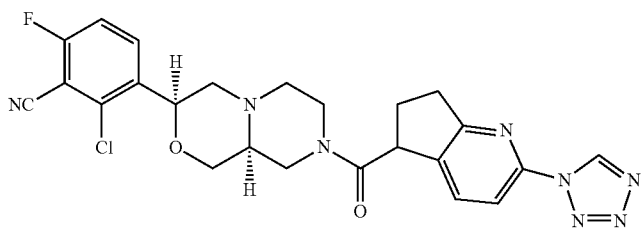
faster eluting isomer from chiral HPLC
SFC on Chiralpak IC column, faster eluting; LC/MS 509 (M + H)⁺. 2-chloro-6-fluoro-3-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 29 | 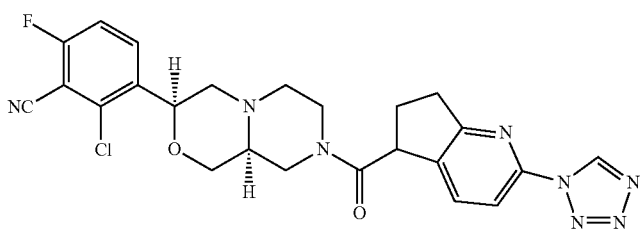
slower eluting isomer from chiral HPLC
SFC on Chiralpak IC column, slower eluting; LC/MS 509 (M + H)⁺. 2-chloro-6-fluoro-3-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |

TABLE 3-continued

| EXAMPLE Number |

30 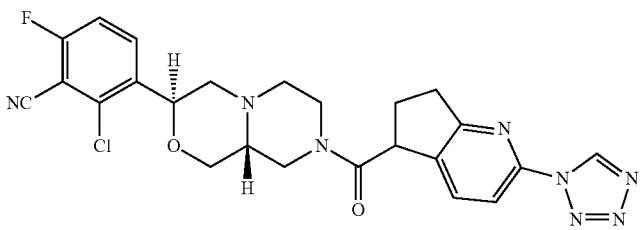

faster eluting isomer from chiral HPLC
SFC on Chiralpak AS column, faster eluting; LC/MS 509 (M + H)+. 2-chloro-6-fluoro-3-
[(3S,9aR)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]benzonitrile 31 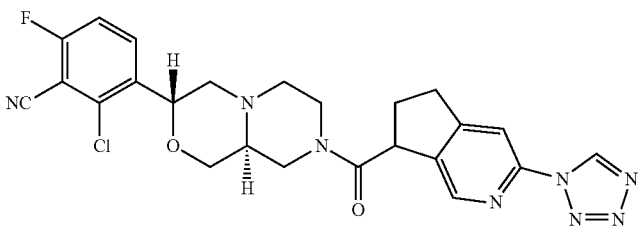

slower eluting isomer from chiral HPLC
SFC on Chiralpak IC column, slower eluting; LC/MS 509 (M + H)+
2-chloro-6-fluoro-3-[(3R,9aS)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile 32 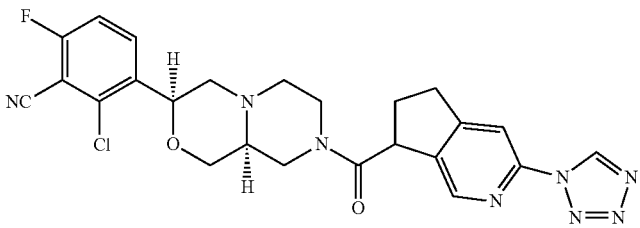

slower eluting isomer from chiral HPLC
SFC on Chiralpak IC column, slower eluting; LC/MS 509 (M + H)+
2-chloro-6-fluoro-3-[(3S,9aS)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile 33 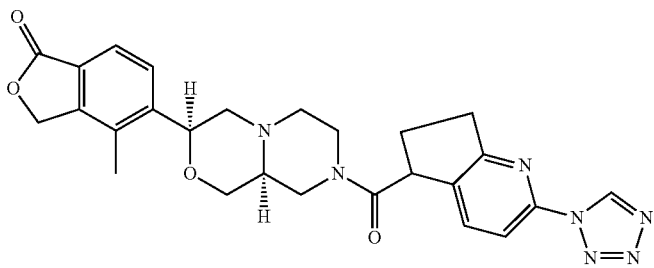

slower eluting isomer from chiral HPLC
SFC on Chiralpak AS column, slower eluting; LC/MS 502 (M + H)+
4-methyl-5-[(3S,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-2-benzofuran-1(3H)-one

TABLE 3-continued

| EXAMPLE Number | |
|---|---|
| 34 | 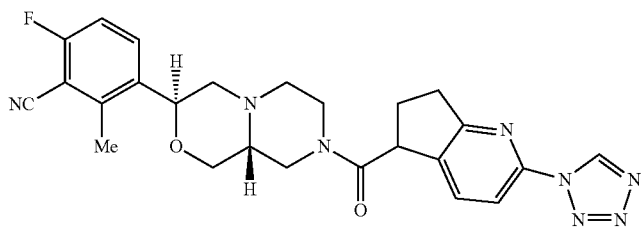
faster eluting isomer from chiral HPLC
SFC on Chiralpak AS column, faster eluting; LC/MS 489 (M + H)⁺. 6-fluoro-2-methyl-3-[(3S,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile |
| 35 | 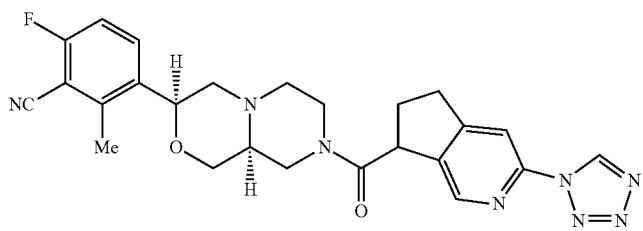
faster eluting isomer from chiral HPLC
SFC on Chiralpak AD-H column, faster eluting; LC/MS 489 (M + H)⁺
6-fluoro-2-methyl-3-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile |
| 36 | 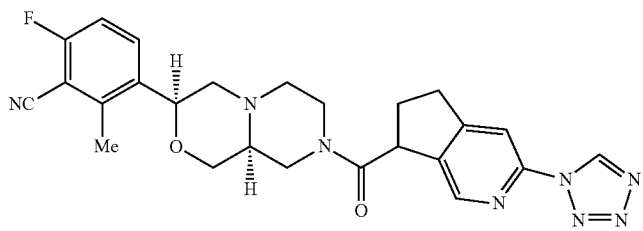
slower eluting isomer from chiral HPLC
SFC on Chiralpak AD-H column, slower eluting; LC/MS 489 (M + H)⁺
6-fluoro-2-methyl-3-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile |
| 37 | 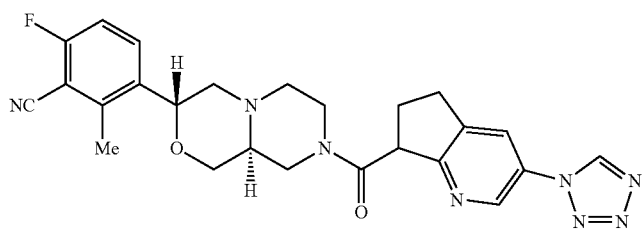
faster eluting isomer from chiral HPLC
SFC on Chiralpak AS-H column, faster eluting; LC/MS 489 (M + H)⁺. 6-fluoro-2-methyl-3-[(3R,9aS)-8-{[3-(1H-tetrazol-1-yl)-6,7-dihydro-5H-cyclopenta[b]pyridin-7-yl]carbonyl}octahydropyrazino[2,1-c][1,4]oxazin-3-yl]benzonitrile |

TABLE 3-continued

| EXAMPLE Number | |
|---|---|
| 38 | 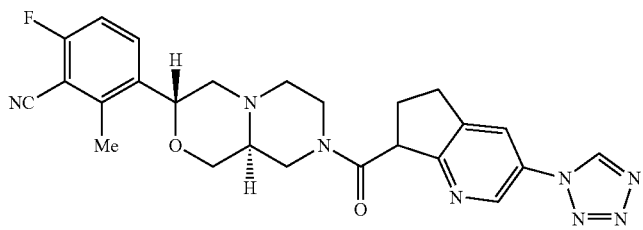 | slower eluting isomer from chiral HPLC
SFC on Chiralpak AS-H column, slower eluting; LC/MS 489 (M + H)$^+$. 6-fluoro-2-methyl-
3-[(3R,9aS)-8-{[3-(1H-tetrazol-1-yl)-6,7-dihydro-5H-cyclopenta[b]pyridin-7-
yl]carbonyl}octahydropyrazino[2,1-c][1,4]oxazin-3-yl]benzonitrile

| | |
|---|---|
| 39 | 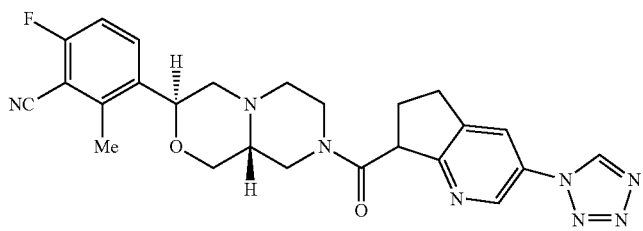 | slower eluting isomer from chiral HPLC
SFC on Chiralpak OJ-H column, slower eluting; LC/MS 489 (M + H)$^+$. 6-fluoro-2-
methyl-3-[(3S,9aR)-8-{[3-(1H-tetrazol-1-yl)-6,7-dihydro-5H-cyclopenta[b]pyridin-7-
yl]carbonyl}octahydropyrazino[2,1-c][1,4]oxazin-3-yl]benzonitrile

| | |
|---|---|
| 40 | 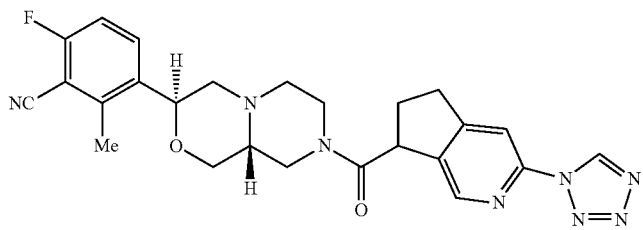 | faster eluting isomer from chiral HPLC
SFC on Chiralpak AD-H column, faster eluting; LC/MS 489 (M + H)$^+$.
6-fluoro-2-methyl-3-[(3S,9aR)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile

| | |
|---|---|
| 41 | 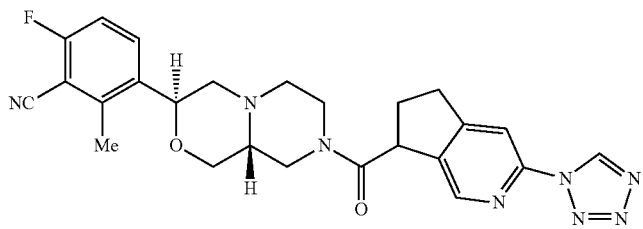 | slower eluting isomer from chiral HPLC
SFC on Chiralpak AD-H column, slower eluting; LC/MS 489 (M + H)$^+$
6-fluoro-2-methyl-3-[(3S,9aR)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile TABLE 3-continued

| EXAMPLE Number |

42 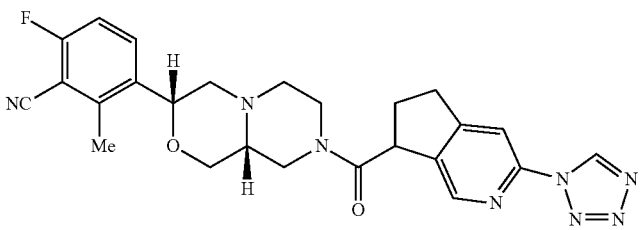

faster eluting isomer from chiral HPLC
SFC on Chiralpak AD-H column, faster eluting; LC/MS 489 (M + H)+
6-fluoro-2-methyl-3-[(3R,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 43 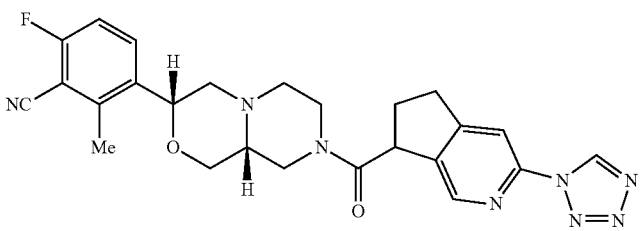

slower eluting isomer from chiral HPLC
SFC on Chiralpak AD-H column, slower eluting; LC/MS 489 (M + H)+
6-fluoro-2-methyl-3-[(3R,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 44 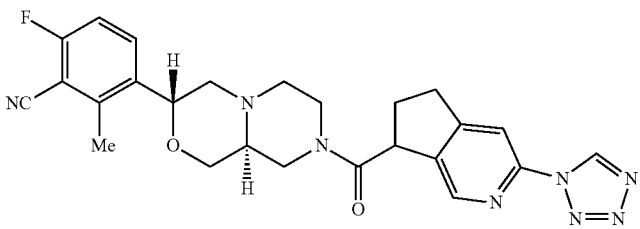

slower eluting isomer from chiral HPLC
SFC on Chiralpak IC-H column, slower eluting; LC/MS 489 (M + H)+
6-fluoro-2-methyl-3-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 45 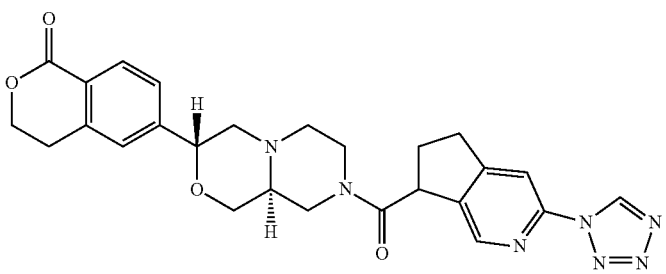

slower eluting isomer from chiral HPLC
SFC on Chiralpak IC-H column, slower eluting; LC/MS 502 (M + H)+
6-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]-3,4-dihydro-1H-isochromen-1-one

TABLE 3-continued

| EXAMPLE Number | |
|---|---|
| 46 | 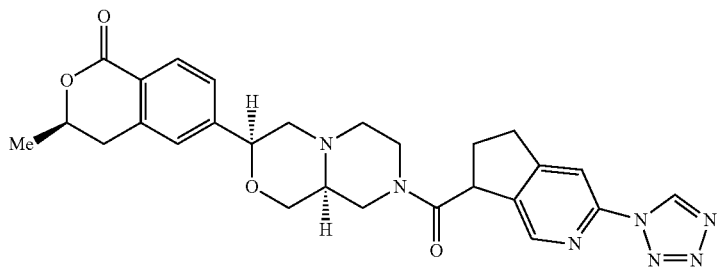 slower eluting isomer from chiral HPLC<br>SFC on Chiralpak IC-H column, slower eluting; LC/MS 516 (M + H)+. (3R)-3-methyl-6-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]-3,4-dihydro-1H-isochromen-1-one |
| 47 | 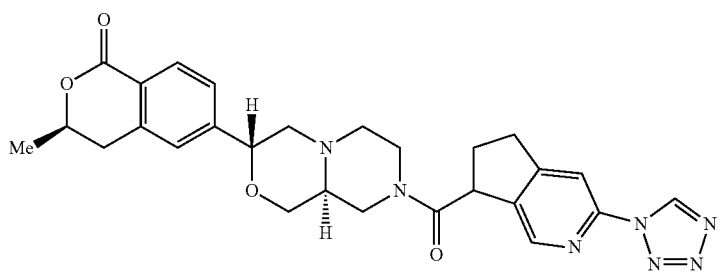 faster eluting isomer from chiral HPLC<br>SFC on Chiralpak IC-H column, faster eluting; LC/MS 516 (M + H)+. (3R)-3-methyl-6-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]-3,4-dihydro-1H-isochromen-1-one |
| 48 | 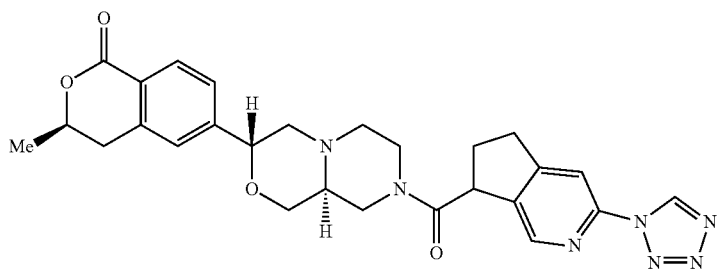 slower eluting isomer from chiral HPLC<br>SFC on Chiralpak IC-H column, slower eluting; LC/MS 516 (M + H)+. (3R)-3-methyl-6-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]-3,4-dihydro-1H-isochromen-1-one |
| 49 | 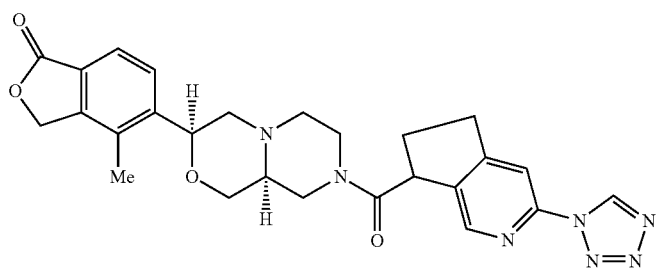 faster eluting isomer from chiral HPLC<br>SFC on Chiralpak AS-H column, faster eluting; LC/MS 502 (M + H)+. 4-methyl-5-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]-2-benzofuran-1(3H)-one |

TABLE 3-continued

EXAMPLE Number

50 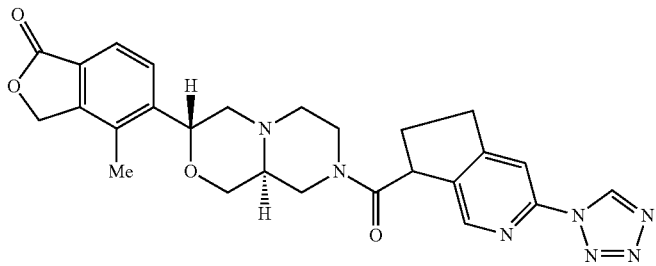

faster eluting isomer from chiral HPLC
SFC on Chiralpak AS-H column, faster eluting; LC/MS 502 (M + H)+
4-methyl-5-[(3R,9aS)-8-{[3-(1H-tetrazol-1-yl)-6,7-dihydro-5H-cyclopenta[c]pyridin-7-
yl]carbonyl}octahydropyrazino[2,1-c][1,4]oxazin-3-yl]-2-benzofuran-1(3H)-one 51 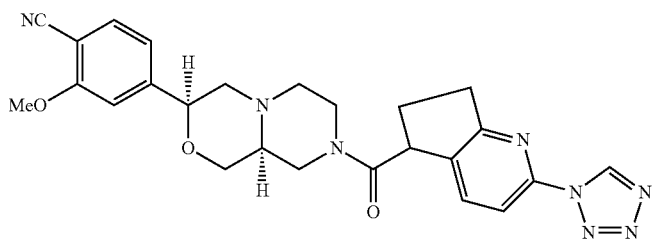

slower eluting isomer from chiral HPLC
SFC on Chiralpak AD column, slower eluting; LC/MS 487 (M + H)+
2-methoxy-4-[(3S,9aS)-8-{[3-(1H-tetrazol-1-yl)-6,7-dihydro-5H-cyclopenta[b]pyridin-5-
yl]carbonyl}octahydropyrazino[2,1-c][1,4]oxazin-3-yl]benzonitrile 52 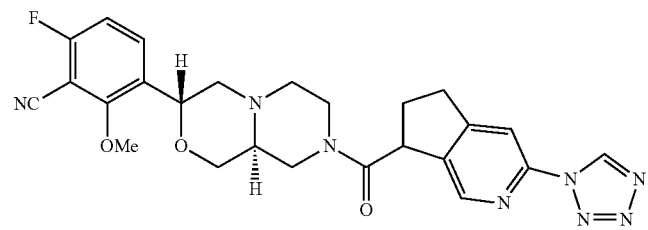

slower eluting isomer from chiral HPLC
SFC on Chiralpak AD-H column, slower eluting; LC/MS 505 (M + H)+
6-fluoro-2-methoxy-3-[(3R,9aS)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile 53 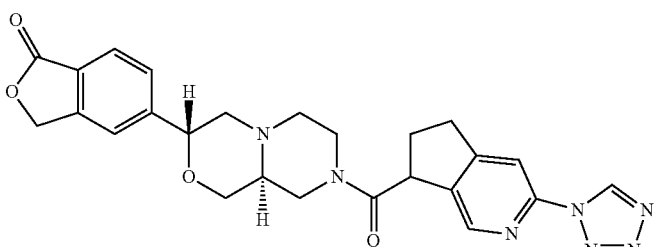

faster eluting isomer from chiral HPLC
SFC on Chiralpak AD-H column, faster eluting; LC/MS 488 (M + H)+
5-[(3R,9aS)-8-{[3-(1H-tetrazol-1-yl)-6,7-dihydro-5H-cyclopenta[c]pyridin-7-
yl]carbonyl}octahydropyrazino[2,1-c][1,4]oxazin-3-yl]-2-benzofuran-1(3H)-one TABLE 3-continued EXAMPLE Number 54
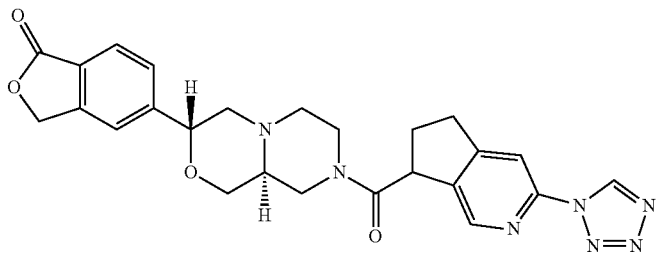

slower eluting isomer from chiral HPLC
SFC on Chiralpak AD-H column, slower eluting; LC/MS 488 (M + H)+
5-[(3R,9aS)-8-{[3-(1H-tetrazol-1-yl)-6,7-dihydro-5H-cyclopenta[c]pyridin-7-
yl]carbonyl}octahydropyrazino[2,1-c][1,4]oxazin-3-yl]-2-benzofuran-1(3H)-one 55
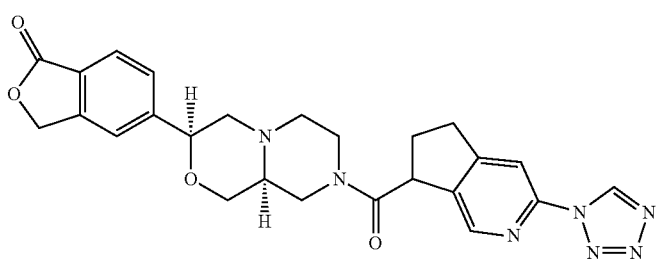

faster eluting isomer from chiral HPLC
SFC on Chiralpak AD-H column, faster eluting; LC/MS 488 (M + H)+
5-[(3S,9aS)-8-{[3-(1H-tetrazol-1-yl)-6,7-dihydro-5H-cyclopenta[c]pyridin-7-
yl]carbonyl}octahydropyrazino[2,1-c][1,4]oxazin-3-yl]-2-benzofuran-1(3H)-one 56
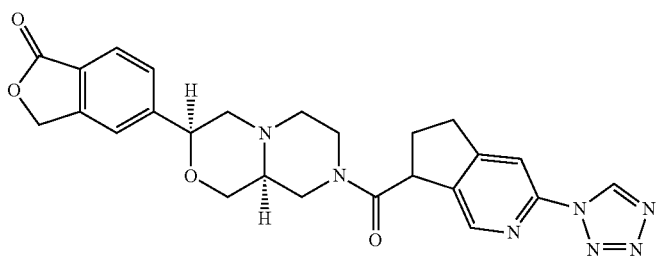

slower eluting isomer from chiral HPLC
SFC on Chiralpak AD-H column, slower eluting; LC/MS 488 (M + H)+
5-[(3S,9aS)-8-{[3-(1H-tetrazol-1-yl)-6,7-dihydro-5H-cyclopenta[c]pyridin-7-
yl]carbonyl}octahydropyrazino[2,1-c][1,4]oxazin-3-yl]-2-benzofuran-1(3H)-one 57
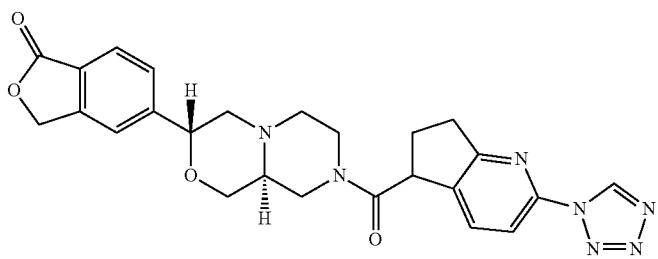

faster eluting isomer from chiral HPLC
SFC on Chiralpak AS column, faster eluting; LC/MS 488 (M + H)+
5-[(3R,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-2-benzofuran-1(3H)-one TABLE 3-continued EXAMPLE Number 58
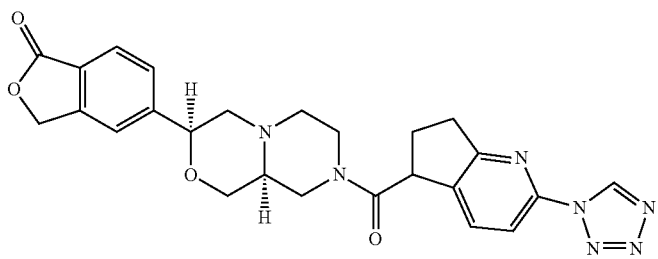

slower eluting isomer from chiral HPLC
SFC on Chiralpak AS column, slower eluting; LC/MS 488 (M + H)⁺
5-[(3S,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-2-benzofuran-1(3H)-one 59
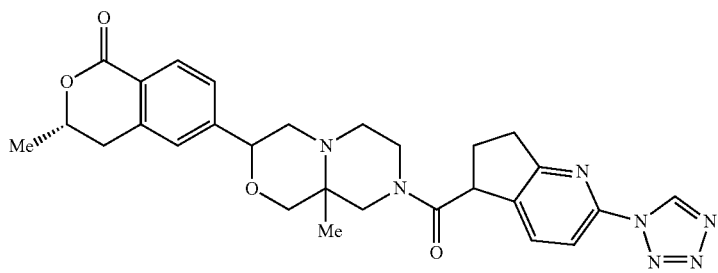

islolated from chiral HPLC on Chiralcel OD-H column, peak 1; LC/MS 530 (M + H)⁺.
(3S)-3-methyl-6-(9a-methyl-8-{[2-(1H-tetrazol-1-yl)-6,7-dihydro-5H-
cyclopenta[b]pyridin-5-yl]carbonyl}octahydropyrazino[2,1-c][1,4]oxazin-3-yl)-3,4-
dihydro-1H-isochromen-1-one 60
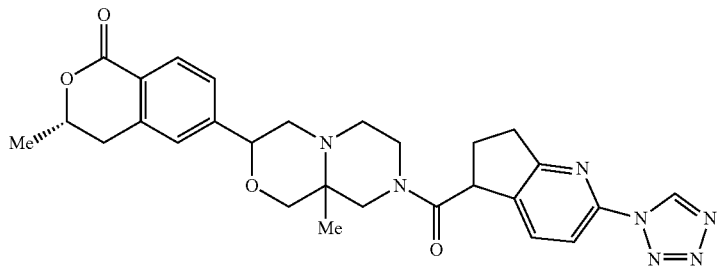

islolated from chiral HPLC on Chiralcel OD column, peak 2; LC/MS 530 (M + H)⁺. (3S)-
3-methyl-6-(9a-methyl-8-{[2-(1H-tetrazol-1-yl)-6,7-dihydro-5H-cyclopenta[b]pyridin-5-
yl]carbonyl}octahydropyrazino[2,1-c][1,4]oxazin-3-yl)-3,4-dihydro-1H-isochromen-1-one 61
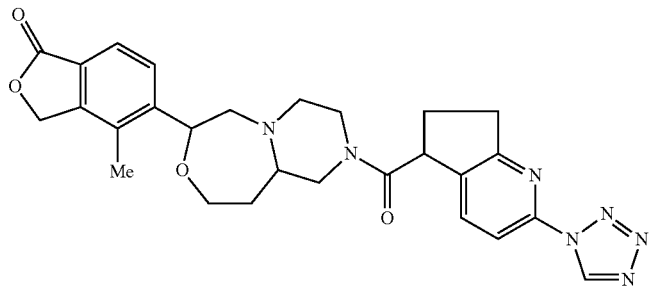

SFC on Chiralpak OJ-H column, slower eluting; cis R,R or S,S at octahydro-2H-
pyrazino[1,2-d][1,4]oxazepine; unknown at aza-indane, single isomer; LC/MS 516
(M + H)⁺; 4-methyl-5-(2-{[2-(1H-tetrazol-1-yl)-6,7-dihydro-5H-cyclopenta[b]pyridin-5-
yl]carbonyl}octahydro-2H-pyrazino[1,2-d][1,4]oxazepin-7-yl)-2-benzofuran-1(3H)-one TABLE 3-continued

| EXAMPLE Number |
|---|

62

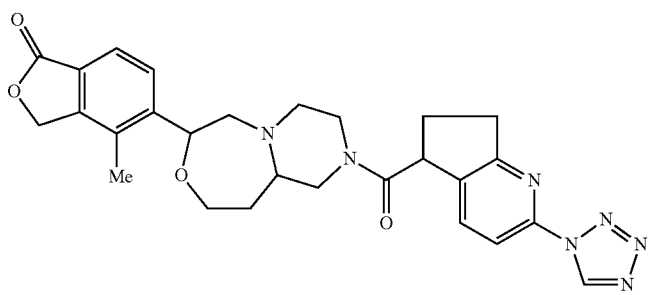

SFC on Chiralpak OJ-H column, slower eluting; cis R,S or S,R at octahydro-2H-pyrazino[1,2-d][1,4]oxazepine; unknown at aza-indane, single isomer; LC/MS 516 (M + H)⁺; 4-methyl-5-(2-{[2-(1H-tetrazol-1-yl)-6,7-dihydro-5H-cyclopenta[b]pyridin-5-yl]carbonyl}octahydro-2H-pyrazino[1,2-d][1,4]oxazepin-7-yl)-2-benzofuran-1(3H)-one

63

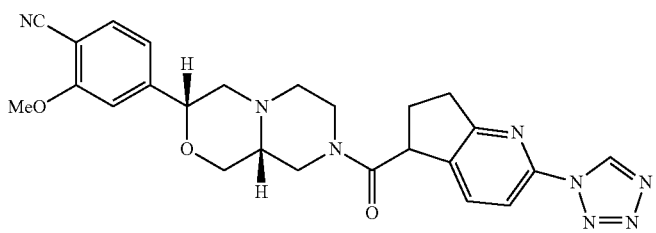

slower eluting isomer from chiral HPLC
SFC on Chiralpak AS column, slower eluting; LC/MS 487 (M + H)⁺
2-methoxy-4-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile

64

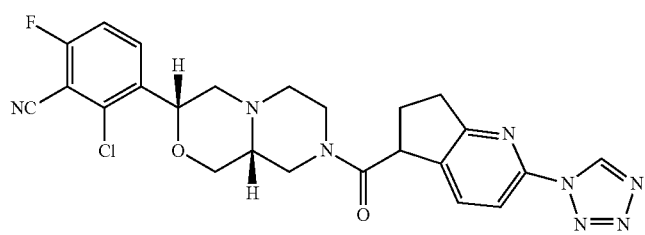

faster eluting isomer from chiral HPLC
SFC on Chiralpak AD-H column, faster eluting; LC/MS 509 (M + H)⁺. 2-chloro-6-fluoro-3-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile

65

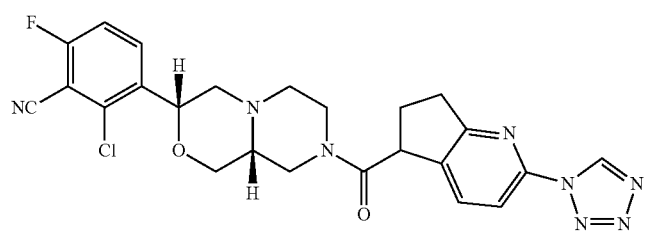

slower eluting isomer from chiral HPLC
SFC on Chiralpak AD-H column, slower eluting; LC/MS 509 (M + H)⁺. 2-chloro-6-fluoro-3-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile TABLE 3-continued

| EXAMPLE Number |
| --- |

66
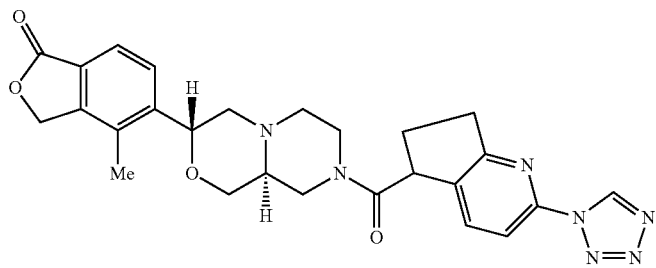

faster eluting isomer from chiral HPLC
SFC on Chiralpak AD-H column, faster eluting; LC/MS 502 (M + H)+
4-methyl-5-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-2-benzofuran-1(3H)-one 67
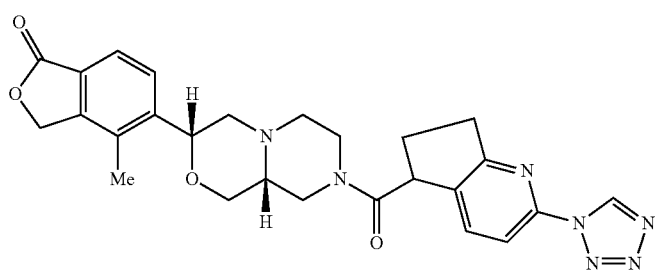

faster eluting isomer from chiral HPLC
SFC on Chiralpak AS column, faster eluting; LC/MS 502 (M + H)+
4-methyl-5-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-2-benzofuran-1(3H)-one 68
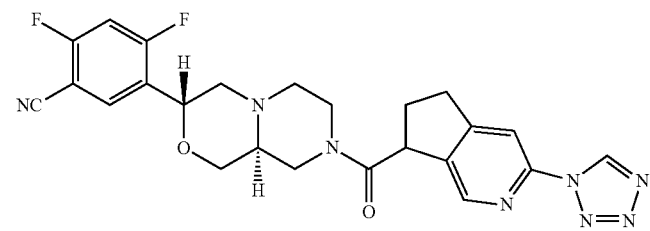

faster eluting isomer from chiral HPLC
SFC on ChiralCel OD-H column, faster eluting; LC/MS 493 (M + H)+
2,4-difluoro-5-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 69
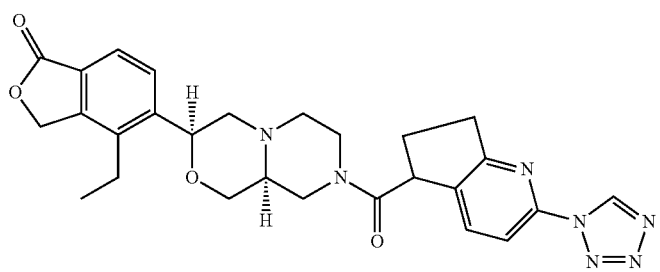

slower eluting isomer from chiral HPLC
SFC on Chiralcel AS column, slower eluting; LC/MS 516 (M + H)+
4-ethyl-5-[(3S,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-2-benzofuran-1(3H)-one TABLE 3-continued EXAMPLE Number 70
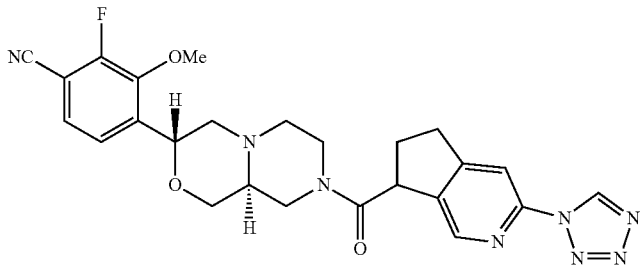
slower eluting isomer from chiral HPLC
SFC on Chiralpak IC column, slower eluting; LC/MS 505 (M + H)+
2-fluoro-3-methoxy-4-[(3R,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 71
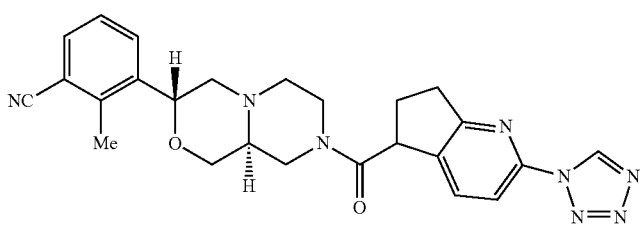
faster eluting isomer from chiral HPLC
SFC on Chiralpak IC column, faster eluting; LC/MS 471 (M + H)+
2-methyl-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]benzonitrile 72
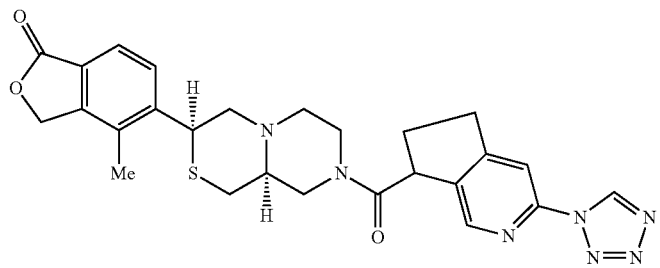
faster eluting isomer from chiral HPLC
SFC on Chiralcel AS column, faster eluting; LC/MS 518 (M + H)+
4-methyl-5-[(3S,9aS)-8-{[3-(1H-tetrazol-1-yl)-6,7-dihydro-5H-cyclopenta[c]pyridin-7-yl]carbonyl}octahydropyrazino[2,1-c][1,4]thiazin-3-yl]-2-benzofuran-1(3H)-one 73
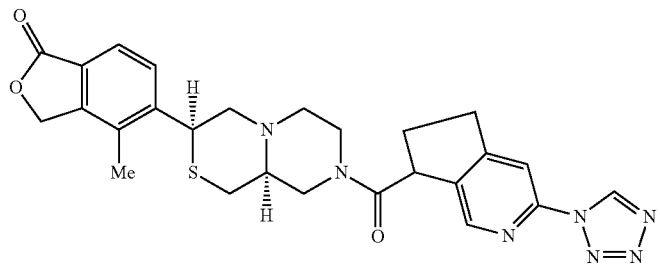
slower eluting isomer from chiral HPLC
SFC on Chiralcel AS column, slower eluting; LC/MS 518 (M + H)+
4-methyl-5-[(3S,9aS)-8-{[3-(1H-tetrazol-1-yl)-6,7-dihydro-5H-cyclopenta[c]pyridin-7-yl]carbonyl}octahydropyrazino[2,1-c][1,4]thiazin-3-yl]-2-benzofuran-1(3H)-one

TABLE 3-continued

| EXAMPLE Number |
| --- |

74 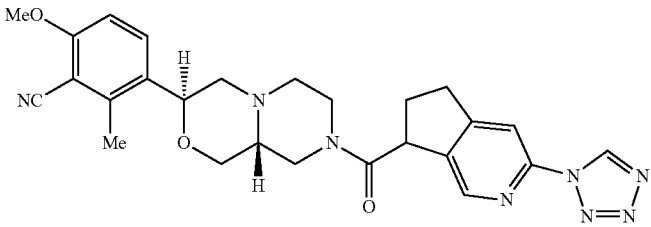

faster eluting isomer from chiral HPLC
SFC on Chiralpak AD-H column, faster eluting; LC/MS 501 (M + H)⁺
6-methoxy-2-methyl-3-[(3S,9aR)-8-{[3-(1H-tetrazol-1-yl)-6,7-dihydro-5H-
cyclopenta[c]pyridin-7-yl]carbonyl}octahydropyrazino[2,1-c][1,4]oxazin-3-yl]benzonitrile 75 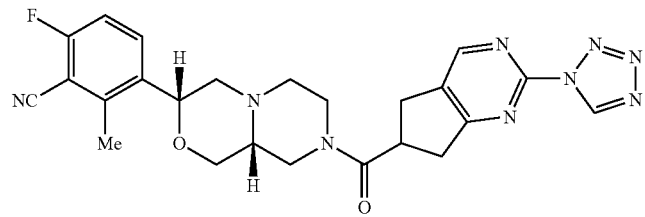

slower eluting isomer from chiral HPLC
SFC on Chiralcel AS column, slower eluting; LC/MS 490 (M + H)⁺. 6-fluoro-2-methyl-3-
[(3R,9aR)-8-{[2-(1H-tetrazol-1-yl)-6,7-dihydro-5H-cyclopenta[d]pyrimidin-6-
yl]carbonyl}octahydropyrazino[2,1-c][1,4]oxazin-3-yl]benzonitrile 76 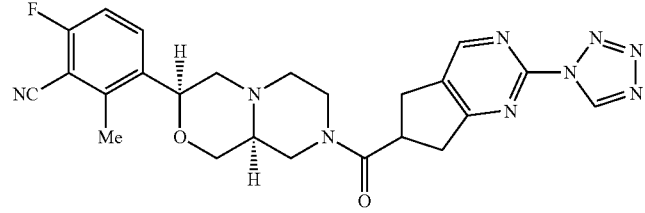

slower eluting isomer from chiral HPLC
SFC on OJ column, slower eluting; LC/MS 490 (M + H)⁺. 6-fluoro-2-methyl-3-[(3S,9aS)-
8-{[2-(1H-tetrazol-1-yl)-6,7-dihydro-5H-cyclopenta[d]pyrimidin-6-
yl]carbonyl}octahydropyrazino[2,1-c][1,4]oxazin-3-yl]benzonitrile 77 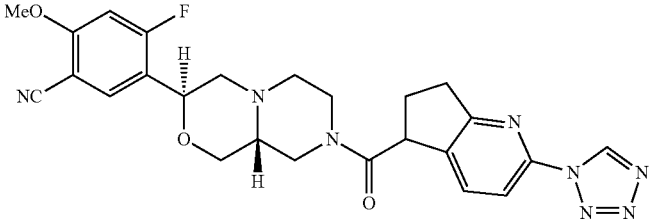

SFC on IA column, faster eluting; LC/MS 505 (M + H)⁺. 4-fluoro-2-methoxy-5-[(3S,9aR)-
8-{[2-(1H-tetrazol-1-yl)-6,7-dihydro-5H-cyclopenta[b]pyridin-5-
yl]carbonyl}octahydropyrazino[2,1-c][1,4]oxazin-3-yl]benzonitrile TABLE 3-continued EXAMPLE Number 78
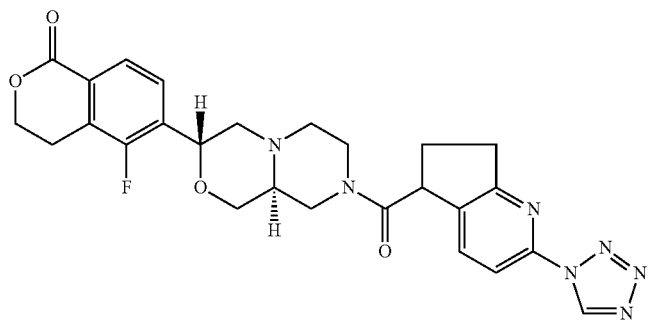

SFC on Chiralcel OJ-H column, slower eluting; LC/MS 520 (M + H)+
5-fluoro-6-[(3R,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one 79
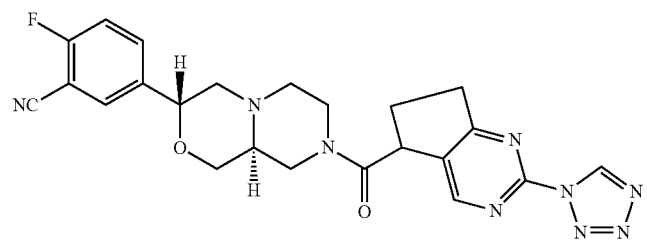

faster eluting isomer from chiral HPLC
SFC on Chiralcel OJ-H column, faster eluting; LC/MS 476 (M + H)+
2-fluoro-5-[(3R,9aS)-8-{[2-(1H-tetrazol-1-yl)-6,7-dihydro-5H-cyclopenta[d]pyrimidin-5-
yl]carbonyl}octahydropyrazino[2,1-c][1,4]oxazin-3-yl]benzonitrile 80
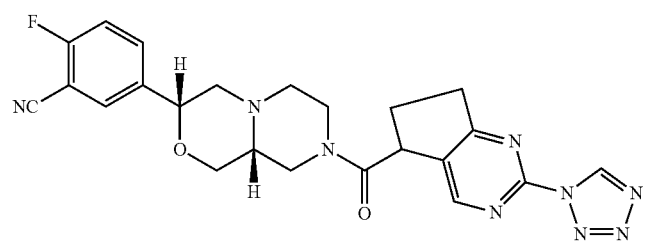

faster eluting isomer from chiral HPLC
SFC on Chiralcel OJ-H column, faster eluting; LC/MS 476 (M + H)+
2-fluoro-5-[(3R,9aR)-8-{[2-(1H-tetrazol-1-yl)-6,7-dihydro-5H-cyclopenta[d]pyrimidin-5-
yl]carbonyl}octahydropyrazino[2,1-c][1,4]oxazin-3-yl]benzonitrile 81
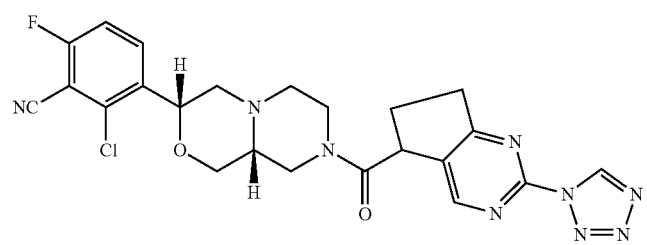

faster eluting isomer from chiral HPLC
SFC on Chiralcel IA column, faster eluting; LC/MS 510 (M + H)+. 2-chloro-6-fluoro-3-
[(3R,9aR)-8-{[2-(1H-tetrazol-1-yl)-6,7-dihydro-5H-cyclopenta[d]pyrimidin-5-
yl]carbonyl}octahydropyrazino[2,1-c][1,4]oxazin-3-yl]benzonitrile

| EXAMPLE Number | |
|---|---|
| 82 | 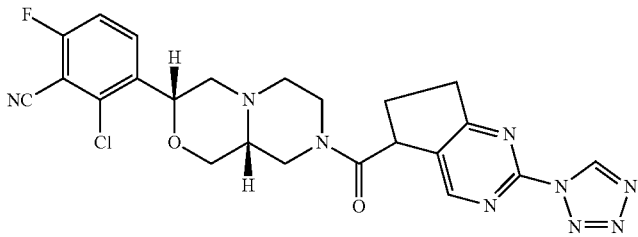<br>slower eluting isomer from chiral HPLC<br>SFC on Chiralcel IA column, slower eluting; LC/MS 510 (M + H)$^+$. 2-chloro-6-fluoro-3-[(3R,9aR)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile |
| 83 | 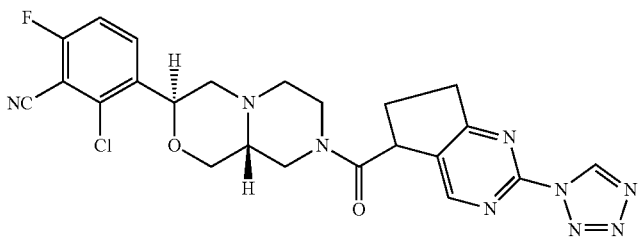<br>slower eluting isomer from chiral HPLC<br>SFC on Chiralcel IA column, slower eluting; LC/MS 510 (M + H)$^+$. 2-chloro-6-fluoro-3-[(3S,9aR)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl]benzonitrile |
| 84 | 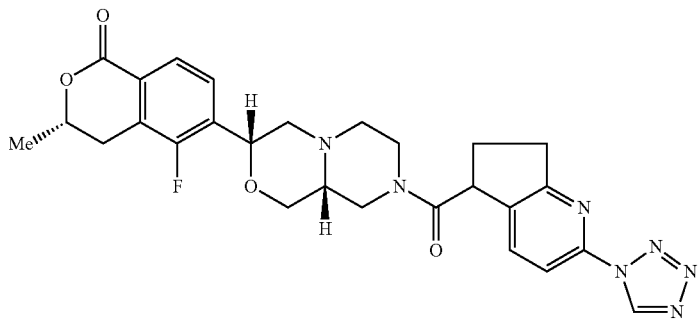<br>faster eluting isomer from chiral HPLC<br>SFC on Chiralcel AS column, faster eluting; LC/MS 534 (M + H)$^+$. (3S)-5-fluoro-3-methyl-6-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one |

TABLE 3-continued

| EXAMPLE Number |

85 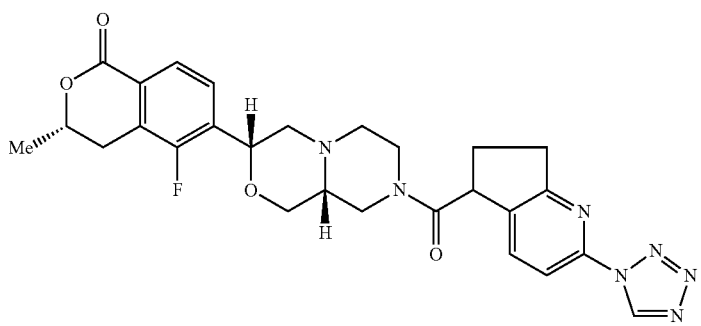

slower eluting isomer from chiral HPLC
SFC on Chiralcel AS column, slower eluting; LC/MS 534 (M + H)+. (3S)-5-fluoro-3-
methyl-6-[(3R,9aR)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one 86 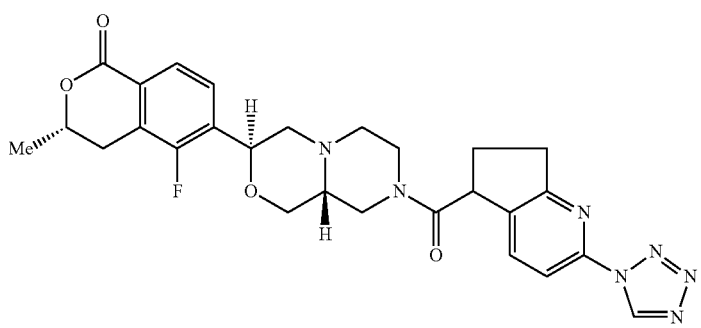

faster eluting isomer from chiral HPLC
SFC on Chiralcel AS column, faster eluting; LC/MS 534 (M + H)+. (3S)-5-fluoro-3-
methyl-6-[(3S,9aR)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one 87 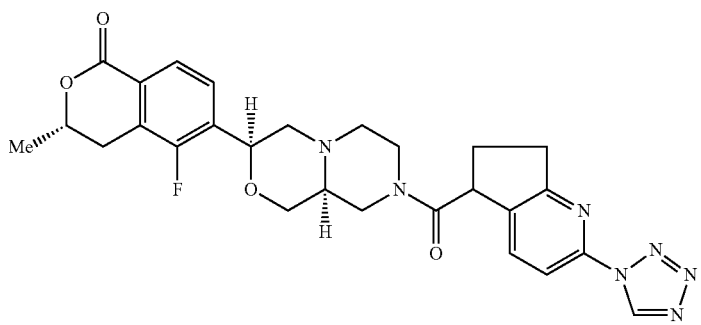

faster eluting isomer from chiral HPLC
SFC on Chiralcel AS column, faster eluting; LC/MS 534 (M + H)+. (3S)-5-fluoro-3-
methyl-6-[(3S,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one TABLE 3-continued

| EXAMPLE Number |
| --- |

88 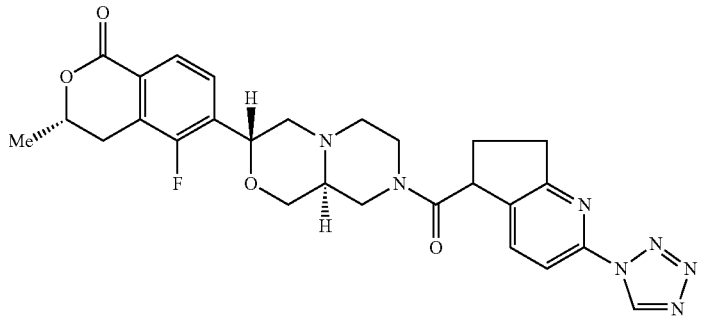

faster eluting isomer from chiral HPLC
SFC on Chiralcel IC column, faster eluting; LC/MS 534 (M + H)+. (3S)-5-fluoro-3-methyl-
6-[(3S,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one 89 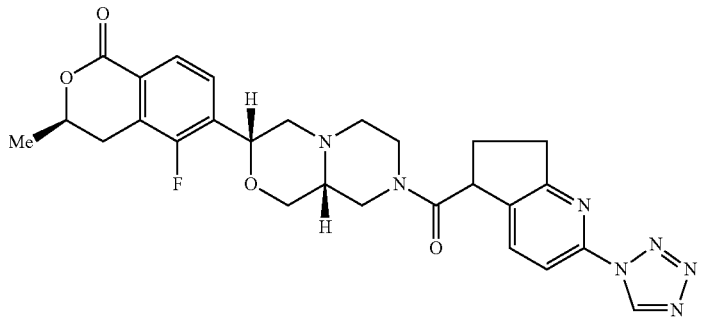

faster eluting isomer from chiral HPLC
SFC on Chiralcel AS column, faster eluting; LC/MS 534 (M + H)+. (3R)-5-fluoro-3-
methyl-6-[(3R,9aR)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one 90 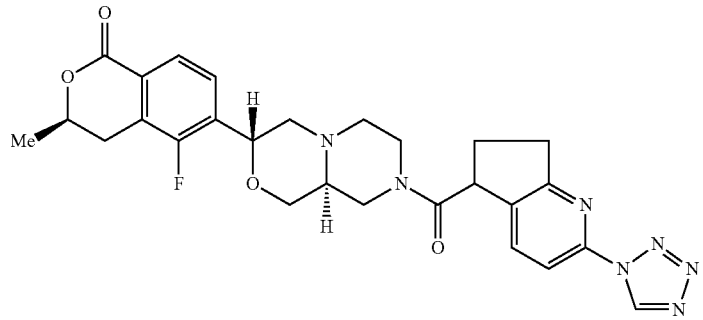

faster eluting isomer from chiral HPLC
SFC on Chiralcel IC column, faster eluting; LC/MS 534 (M + H)+. (3R)-5-fluoro-3-methyl-
6-[(3R,9aS)-8-{[2-(1H-tetrazol-1-yl)-6,7-dihydro-5H-cyclopenta[b]pyridin-5-
yl]carbonyl}octahydropyrazino[2,1-c][1,4]oxazin-3-yl]-3,4-dihydro-1H-isochromen-1-one TABLE 3-continued EXAMPLE Number 91 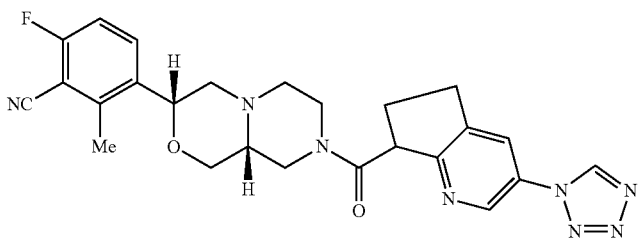

Mixture of two diastereomers at aza-indane center (not separated); LC/MS (M + H) 489. 6-fluoro-2-methyl-3-[(3R,9aR)-8-{[3-(1H-tetrazol-1-yl)-6,7-dihydro-5H-cyclopenta[b]pyridin-7-yl]carbonyl}octahydropyrazino[2,1-c][1,4]oxazin-3-yl]benzonitrile;

92 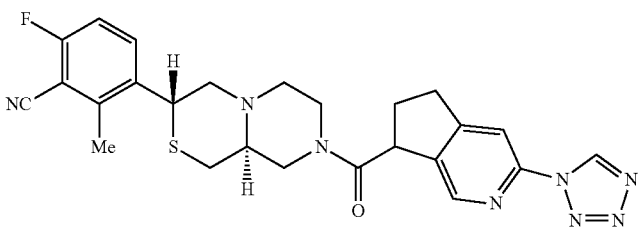

Mixture of two diastereomers at aza-indane center (not separated). 6-fluoro-2-methyl-3-[(3R,9aS)-8-{[3-(1H-tetrazol-1-yl)-6,7-dihydro-5H-cyclopenta[c]pyridin-7-yl]carbonyl}octahydropyrazino[2,1-c][1,4]thiazin-3-yl]benzonitrile; LC/MS (M + H) 505

93 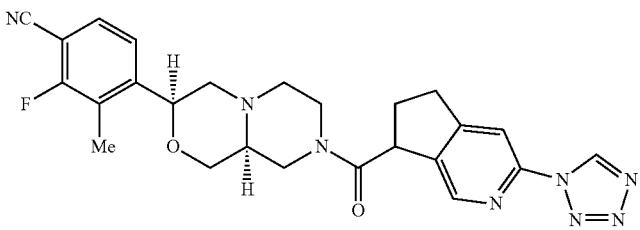

SFC on Chiralcel OD column, faster eluting; LC/MS (M + H) 489.
2-fluoro-3-methyl-4-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile 94 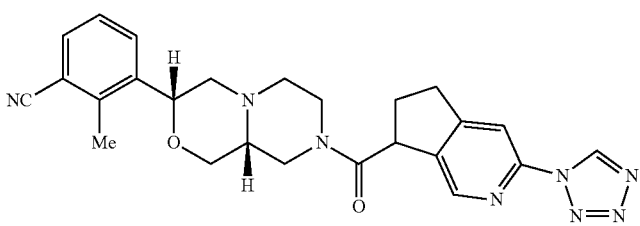

SFC on Chiralcel AS-H column, faster eluting; LC/MS (M + H) 471.
2-methyl-3-[(3R,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl]benzonitrile

TABLE 3-continued

EXAMPLE Number

95

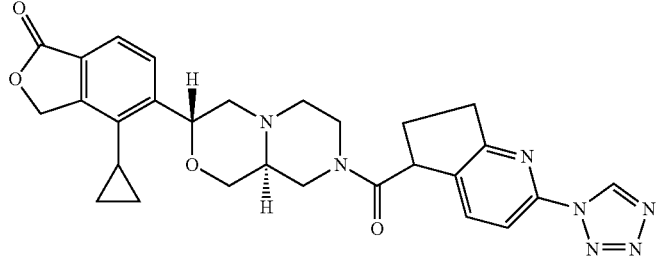

faster eluting isomer from chiral HPLC
SFC on Chiralcel AS column, faster eluting; LC/MS (M + H) 471.
4-cyclopropyl-5-[(3R,9aS)-8-{[2-(1H-tetrazol-1-yl)-6,7-dihydro-5H-cyclopenta[b]pyridin-
5-yl]carbonyl}octahydropyrazino[2,1-c][1,4]oxazin-3-yl]-2-benzofuran-1(3H)-one Example 96AB Isomer Mixture, 96A and 96B 6-fluoro-2-methyl-3-[(3R,9aR)-8-{[3-(1H-tetrazol-1-yl)-6,7-dihydro-5H-cyclopenta[c]pyridin-7-yl]carbonyl}octahydro-2H-pyrazino[1,2-a]pyrazin-3-yl]benzonitrile Step A: (3R,9aS)-tert-butyl 8-(3-(1H-tetrazol-1-yl)-6,7-dihydro-5H-cyclopenta[c]pyridine-7-carbonyl)-3-(3-cyano-4-fluoro-2-methylphenyl)hexahydro-1H-pyrazino[1,2-a]pyrazine-2(6H)-carboxylate To a solution of (3R,9aS)-tert-butyl 3-(3-cyano-4-fluoro-2-methylphenyl)hexahydro-1H-pyrazino[1,2-a]pyrazine-2(6H)-carboxylate [I-18A](250 mg, 0.668 mmol) and 3-(1H-tetrazol-1-yl)-6,7-dihydro-5H-cyclopenta[c]pyridine-7-carboxylic acid [I-65] (201 mg, 0.868 mmol) in DMF (4 mL) was added HATU (381 mg, 1.00 mmol) followed by addition of diisopropylethylamine (350 µL, 2.00 mmol). The resulting solution was stirred at rt for 1 h. Ethyl acetate (100 mL) was added and the mixture was washed with saturated sodium bicarbonate (3×100 mL), dried over sodium sulphate, concentrated and the residue was purified by preparative TLC eluting with 10% methanol/methylene chloride to give the title compound. LC/MS: (M+1)$^+$: 588.2.

Step B: 6-fluoro-2-methyl-3-[(3R,9aR)-8-{[(3-(1H-tetrazol-1-yl)-6,7-dihydro-5H-cyclopenta[c]pyridin-7-yl]carbonyl}octahydro-2H-pyrazino[1,2-a]pyrazin-3-yl]benzonitrile To a solution of the compound of Step A (393 mg, 0.668 mmol) and thioanisole (316 µL, 2.67 mmol) in methylene chloride (3 mL) was added trifluoroacetic acid (3 mL) at 0° C. and the resulting solution was stirred at rt for 1 h. After removing the volatile materials, the residue was partitioned between methylene chloride and 1N sodium hydroxide, the alkaline phase was extracted with methylene chloride, the combined organic phases were dried over sodium sulphate, concentrated and the residue was purified by preparative TLC eluting with 10% methanol/methylene chloride to give the title compound as a mixture of two diasteromers. The two isomers were separated on a Chiralpak AS-H column using 50% methanol (0.2% diethylamine)/CO$_2$. The faster eluting isomer (96A) was the more potent ROMK inhibitor. 96A faster eluting isomer: LC/NIS: (M+1)$^+$: 488.17. $^1$HNMR (500 MHz, CDCl$_3$) δ 9.522 (s, 1H), 8.354-8.529 (d, J=12.3 Hz, 1H), 7.995 (s, 1H), 7.912-7.868 (m, 1H), 7.091-7.054 (t, J=8.4 Hz, 1H), 4.650-4.560 (m, 1H), 4.449-4.418 (m, 1H), 4.249-4.217 (m, 1H), 4.096-3.947 (m, 1H), 3.509 (broad, 1H), 3.294-3.261 ((m, 1H), 3.172-3.126 (m, 2H), 2.976-2.929 (m, 1H), 2.857-2.789 (m, 2H), 2.646 (s, 3H), 2.609-2.539 (m, 2H), 2.467-2.414 (m, 2H), 2.300-2.250 (m, 2H), 2.160-2.120 (m, 1H). The slower eluting isomer (96B) had an IC$_{50}$ greater than 1 µM in Thallium Flux and Electrophysiology assays.

The following Examples in Table 4 were prepared in an analagous fashion to that described for the synthesis of Example 96 from the appropriate amine and carboxylic acid Intermediates (prepared as described above). Data provided includes chiral HPLC conditions (if applicable); and MS and/or HNMR characterization.

TABLE 4

EXAMPLE Number

97 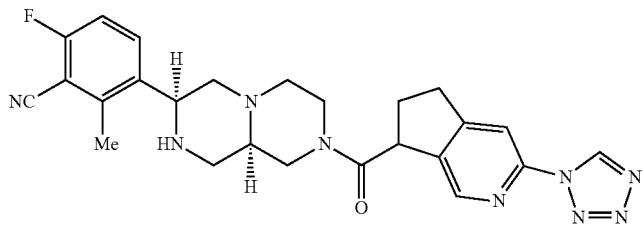

faster eluting isomer from chiral HPLC
SFC on Chiralpak AS-H column, faster eluting; LC/MS 488 (M + H)+. 6-fluoro-2-
methyl-3-[(3S,9aR)-8-{[3-(1H-tetrazol-1-yl)-6,7-dihydro-5H-cyclopenta[c]pyridin-7-
yl]carbonyl}octahydro-2H-pyrazino[1,2-a]pyrazin-3-yl]benzonitrile 98 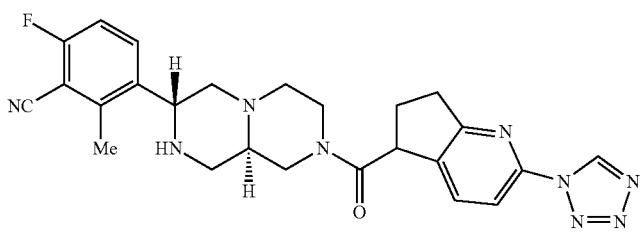

faster eluting isomer from chiral HPLC
SFC on Chiralpak AS column, faster eluting; LC/MS 488 (M + H)+. 6-fluoro-2-methyl-
3-[(3R,9aR)-8-{[2-(1H-tetrazol-1-yl)-6,7-dihydro-5H-cyclopenta[b]pyridin-5-
yl]carbonyl}octahydro-2H-pyrazino[1,2-a]pyrazin-3-yl]benzonitrile 99 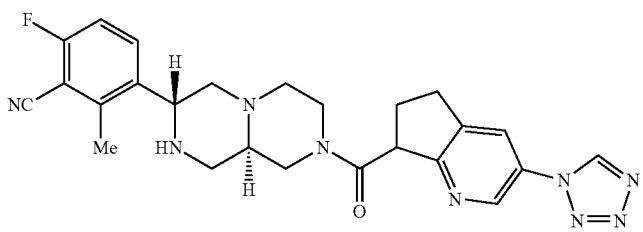

faster eluting isomer from chiral HPLC
SFC on Chiralpak AS column, faster eluting; LC/MS 488 (M + H)+. 6-fluoro-2-methyl-
3-[(3R,9aR)-8-{[3-(1H-tetrazol-1-yl)-6,7-dihydro-5H-cyclopenta[b]pyridin-7-
yl]carbonyl}octahydro-2H-pyrazino[1,2-a]pyrazin-3-yl]benzonitrile 100 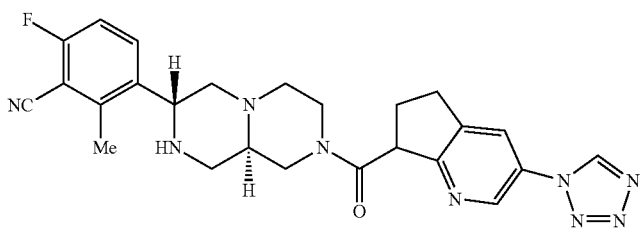

slower eluting isomer from chiral HPLC
SFC on Chiralpak AS column, slower eluting isomer; LC/MS 488 (M + H)+. 6-fluoro-
2-methyl-3-[(3R,9aR)-8-{[3-(1H-tetrazol-1-yl)-6,7-dihydro-5H-cyclopenta[b]pyridin-7-
yl]carbonyl}octahydro-2H-pyrazino[1,2-a]pyrazin-3-yl]benzonitrile TABLE 4-continued EXAMPLE Number 101 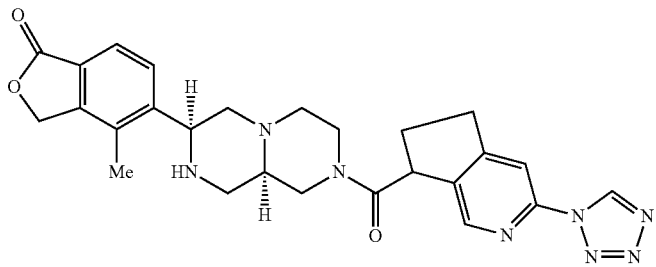

Mixture of two diastereomers at aza-indane center; LC/MS (M + H) 501. 4-methyl-5-
[(3S,9aR)-8-{[3-(1H-tetrazol-1-yl)-6,7-dihydro-5H-cyclopenta[c]pyridin-7-
yl]carbonyl}octahydro-2H-pyrazino[1,2-a]pyrazin-3-yl]-2-benzofuran-1(3H)-one 102 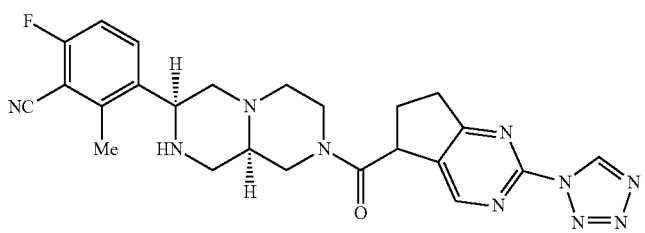

slower eluting isomer from chiral HPLC
SFC on Chiralcel OD-H column, slower eluting; LC/MS 489 (M + H)+. 6-fluoro-2-
methyl-3-[(3S,9aR)-8-{[2-(1H-tetrazol-1-yl)-6,7-dihydro-5H-cyclopenta[d]pyrimidin-
5-yl]carbonyl}octahydro-2H-pyrazino[1,2-a]pyrazin-3-yl]benzonitrile 103 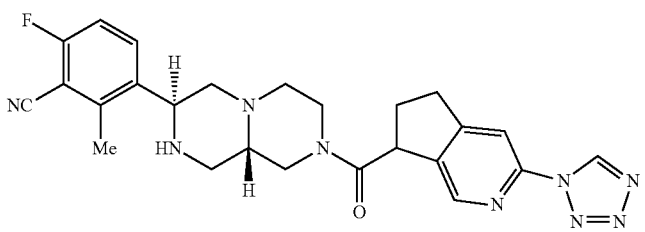

faster eluting isomer from chiral HPLC
SFC on Chiralpak AS-H column, faster eluting; LC/MS 488 (M + H)+. 6-fluoro-2-
methyl-3-[(3S,9aS)-8-{[3-(1H-tetrazol-1-yl)-6,7-dihydro-5H-cyclopenta[c]pyridin-7-
yl]carbonyl}octahydro-2H-pyrazino[1,2-a]pyrazin-3-yl]benzonitrile 104 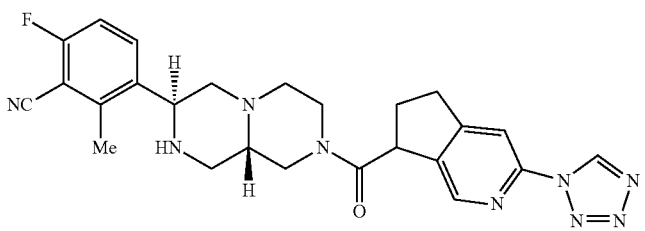

slower eluting isomer from chiral HPLC
SFC on Chiralpak AS-H column, slower eluting; LC/MS 488 (M + H)+. 6-fluoro-2-
methyl-3-[(3S,9aS)-8-{[3-(1H-tetrazol-1-yl)-6,7-dihydro-5H-cyclopenta[c]pyridin-7-
yl]carbonyl}octahydro-2H-pyrazino[1,2-a]pyrazin-3-yl]benzonitrile

TABLE 4-continued

EXAMPLE Number

105

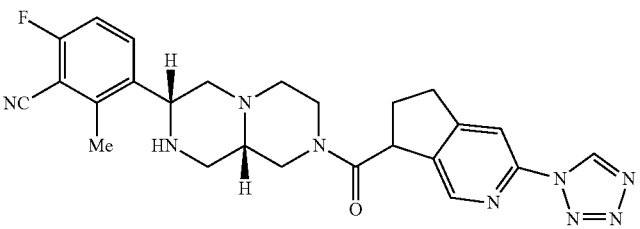

faster eluting isomer from chiral HPLC
SFC on Chiralpak AS-H column, faster eluting; LC/MS 488 (M + H)+. 6-fluoro-2-methyl-3-[(3R,9aS)-8-{[3-(1H-tetrazol-1-yl)-6,7-dihydro-5H-cyclopenta[c]pyridin-7-yl]carbonyl}octahydro-2H-pyrazino[1,2-a]pyrazin-3-yl]benzonitrile

106

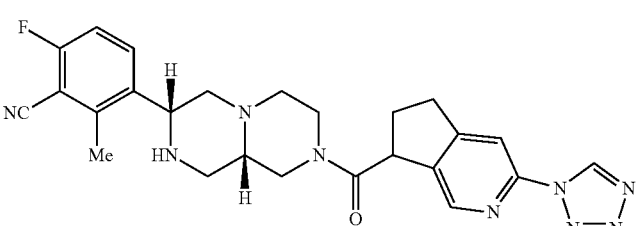

slower eluting isomer from chiral HPLC
SFC on Chiralpak AS-H column, slower eluting; LC/MS 488 (M + H)+. 6-fluoro-2-methyl-3-[(3R,9aS)-8-{[3-(1H-tetrazol-1-yl)-6,7-dihydro-5H-cyclopenta[c]pyridin-7-yl]carbonyl}octahydro-2H-pyrazino[1,2-a]pyrazin-3-yl]benzonitrile The following Thallium Flux Assay and/or the Electrophysiology Assay were performed on each of the final product compounds in the Examples.

Thallium Flux Assay

Cell Culture Conditions—

HEK293 cells stably expressing hROMK (hK$_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain>80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 µl 1000× FluxOR™ Reagent; 100 µl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula Ia of the present invention, preferably with an $IC_{50}$ potency of less than 1 µM in this assay. Alternatively, the control could be another compound (outside the scope of Formula Ia) that has an $IC_{50}$ potency in this assay of less than 1 µM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formula Ia of the present invention, preferably with an $IC_{50}$ potency of less than 1 µM in this assay. Alternatively, the control could be another compound (outside the scope of Formula Ia) that has an $IC_{50}$ potency in this assay of less than 1 µM.

Data collected for compounds in the Examples of the present invention using the Thallium Flux Assay and the Electrophysiology Assay are shown in Table 5 below. All of the final product compounds in the Examples (diastereomeric mixtures and individual diastereomers) had $IC_{50}$ potencies of 1 µM or less in one or both of the Thallium Flux Assay and the Electrophysiology Assay unless otherwise noted in the Examples section.

TABLE 5

| EXAMPLE # | Thallium Flux $IC_{50}$ (µM) | Electrophysiology $IC_{50}$ (µM) |
|---|---|---|
| 1A | 0.34 | 0.19 |
| 1C | 0.31 | 0.18 |
| 1E | 0.57 | 0.2 |
| 1F | 0.76 | 0.28 |
| 1G | 0.35 | 0.18 |
| 1I | 0.38 | 0.12 |
| 1J | 0.45 | 0.10 |
| 1K | 0.35 | 0.18 |
| 2A | 0.22 | 0.10 |
| 2B | 0.35 | 0.10 |
| 2C | 0.12 | 0.15 |
| 2D | 0.13 | 0.10 |
| 2E | 0.13 | |
| 2G | 0.27 | 0.13 |
| 2F | 0.39 | |
| 2H | 0.14 | 0.10 |
| 3 | 0.25 | 0.53 |
| 4 | 0.46 | 0.18 |
| 5 | 0.17 | 0.10 |
| 6 | 0.24 | 0.10 |
| 7 | 0.14 | 0.08 |
| 8 | 0.35 | 0.24 |
| 9 | 0.61 | 0.19 |
| 10 | 0.41 | 0.18 |
| 11 | 0.36 | 0.24 |
| 12 | 0.45 | 0.16 |
| 13 | 0.32 | 0.26 |
| 14 | 0.47 | 0.21 |
| 15 | 0.54 | 0.06 |
| 16 | 0.39 | 0.39 |
| 17 | 0.09 | 0.13 |
| 17A | 0.19 | 0.10 |

TABLE 5-continued

| EXAMPLE # | Thallium Flux IC$_{50}$ (µM) | Electrophysiology IC$_{50}$ (µM) |
|---|---|---|
| 18 | 0.40 | 0.11 |
| 19 | 0.42 | 0.09 |
| 20 | 0.23 | 0.08 |
| 21 | 0.24 | 0.08 |
| 22 | 0.16 | 0.04 |
| 23 | 0.54 | 0.15 |
| 24 | 0.11 | 0.2 |
| 25 | 0.10 | 0.06 |
| 26 | 0.22 | 0.11 |
| 27 | 0.23 | 0.12 |
| 28 | 0.22 | 0.12 |
| 29 | 0.45 | 0.14 |
| 30 | 0.29 | 0.19 |
| 31 | 0.11 | 0.08 |
| 32 | 0.13 | 0.07 |
| 33 | 0.39 | 0.17 |
| 34 | 0.12 | 0.16 |
| 35 | 0.18 | 0.11 |
| 36 | 0.66 | 0.14 |
| 37 | 0.81 | 0.24 |
| 38 | 0.9 | 0.28 |
| 39 | 0.60 | 0.39 |
| 40 | 0.27 | 0.12 |
| 41 | 0.72 | 0.11 |
| 42 | 0.35 | 0.13 |
| 43 | 0.85 | 0.13 |
| 44 | 0.17 | 0.17 |
| 45 | 0.60 | 0.22 |
| 46 | 0.54 | 0.54 |
| 47 | 0.63 | 0.31 |
| 48 | 0.63 | 0.42 |
| 49 | 0.32 | 0.08 |
| 50 | 0.56 | 0.15 |
| 51 | 0.58 | 0.19 |
| 52 | 0.42 | 0.22 |
| 53 | 0.81 | 0.11 |
| 54 | 0.44 | 0.11 |
| 55 | 0.14 | 0.06 |
| 56 | 0.22 | 0.11 |
| 57 | 0.11 | 0.09 |
| 58 | 0.42 | 0.15 |
| 59 | 0.27 | 0.23 |
| 60 | 0.60 | 0.33 |
| 61 | 0.14 | 0.19 |
| 62 | 0.45 | 0.13 |
| 63 | 0.74 | 0.27 |
| 64 | 0.12 | 0.1 |
| 65 | 0.34 | 0.14 |
| 66 | 0.32 | 0.14 |
| 67 | 0.38 | 0.15 |
| 68 | 0.20 | 0.2 |
| 69 | 0.79 | 0.63 |
| 70 | 0.50 | 0.10 |
| 71 | 0.44 | 0.12 |
| 72 | 0.32 | 0.17 |
| 73 | 0.66 | 0.2 |
| 74 | 0.50 | 0.28 |
| 75 | 0.25 | 0.15 |
| 76 | 0.46 | 0.13 |
| 77 | 0.40 | 0.29 |
| 78 | 0.50 | 0.16 |
| 79 | 0.21 | 0.19 |
| 80 | 0.26 | 0.12 |
| 81 | 0.17 | 0.06 |
| 82 | 0.14 | 0.05 |
| 83 | 0.36 | 0.08 |
| 84 | 0.57 | 0.1 |
| 85 | 0.60 | 0.21 |
| 86 | 0.32 | 0.2 |
| 87 | 0.59 | 0.2 |
| 88 | 0.33 | 0.1 |
| 89 | 0.60 | 0.12 |
| 90 | 0.28 | 0.31 |
| 91 | 0.55 | 0.14 |
| 92 | 0.44 | 0.31 |
| 93 | 0.43 | 0.18 |
| 94 | 0.29 | |
| 95 | 0.18 | |
| 96A | 0.20 | 0.10 |
| 97 | 0.16 | 0.09 |
| 98 | 0.39 | 0.17 |
| 99 | 0.43 | 0.35 |
| 100 | 0.75 | 0.28 |
| 101 | 0.55 | 0.23 |
| 102 | 0.45 | 0.10 |
| 103 | 0.18 | 0.11 |
| 104 | 0.36 | 0.12 |
| 105 | 0.14 | 0.08 |
| 106 | 0.4 | 0.12 |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with DSI TA11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers, 1A, 1G, 2A, 2H, 17A, 21, 34, 35, 40, 96A, 97 were evaluated at PO, QD doses of either 3 mg/kg or 10 mg/kg and resulted in typical reductions in daily (24 h) mean systolic blood pressure ranging from 7 mmHg to 21 mmHg by the last day of the studies.

The Spontaneously Hypertensive Rat Assay described is well known and often used in the art as an experimental model simulating human hypertension (see, e.g., Lerman, L. O., et al., *J Lab Clin Med*, 2005; 146:160-173).

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula Ia:

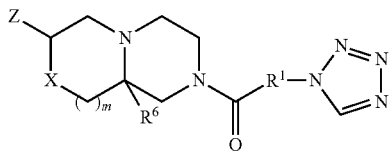

or a pharmaceutically acceptable salt thereof wherein:
Z is

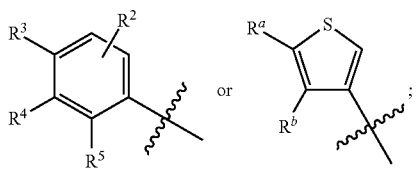

$R^1$ is

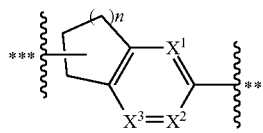

wherein * indicates attachment to the carbonyl carbon and  indicates attachment to the tetrazolyl ring in Formula Ia;
X is O, NH or S;
m is an integer selected from 1 or 2;
n is an integer selected from 1 or 2;
$X^1$, $X^2$ and $X^3$ are each independently selected from $C(R^7)$ or N, provided that at least one of $X^1$, $X^2$ and $X^3$ must be N and at most two of $X^1$, $X^2$ and $X^3$ are N;
$R^a$ is —CN;
$R^b$ is —H or —$C_{1-6}$ alkyl;
$R^2$ is —H, —F, —Cl, —$C_{1-6}$ alkyl, —$C_{3-6}$cycloalkyl or —$OC_{1-6}$ alkyl;
$R^3$ is —H, —F, —Cl, —CN, —$C_{1-6}$alkyl, —$C_{3-6}$cycloalkyl or —$OC_{1-6}$alkyl;
$R^4$ is —F, —Cl, —CN, —$C_{1-6}$ alkyl, —$C_{3-6}$cycloalkyl, —$OC_{1-4}$alkyl or N-tetrazolyl;
or $R^3$ and $R^4$ are joined together with the carbon atoms in the phenyl ring to which they are attached to form:

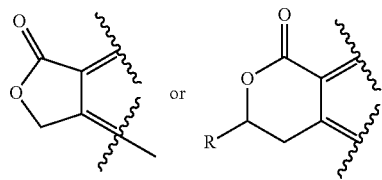

wherein R is —H or —$C_{1-4}$alkyl;
$R^5$ is —H, —Cl, —F, —CN, —$C_{1-4}$alkyl, —$C_{3-6}$cycloalkyl or —$OC_{1-4}$alkyl;
provided that when $R^3$ and $R^4$ are not joined together, then one and only one of $R^3$, $R^4$ or $R^5$ is —CN;
$R^6$ is —H or —$C_{1-4}$alkyl; and
$R^7$ is —H, —F, —Cl or —$C_{1-4}$alkyl.

2. The compound of claim 1 having structural Formula I:

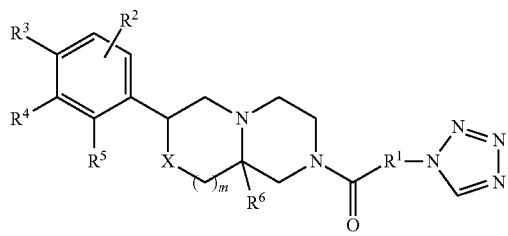

or a pharmaceutically acceptable salt thereof wherein:
X is O, NH or S;
$R^1$ is

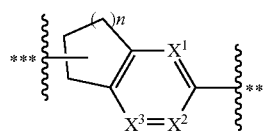

wherein * indicates attachment to the carbonyl carbon and  indicates attachment to the tetrazolyl ring in Formula I;
m is an integer selected from 1 or 2;
n is an integer selected from 1 or 2;
$X^1$, $X^2$ and $X^3$ are each independently selected from $C(R^7)$ or N, provided that at least one of $X^1$, $X^2$ and $X^3$ must be N and at most two of $X^1$, $X^2$ and $X^3$ are N;
$R^2$ is —H, —F, —Cl, —$C_{1-6}$alkyl, —$C_{3-6}$cycloalkyl or —$OC_{1-6}$alkyl;
$R^3$ is —H, —F, —Cl, —CN, —$C_{1-6}$alkyl, —$C_{3-6}$cycloalkyl or —$OC_{1-6}$alkyl;
$R^4$ is —F, —Cl, —CN, —$C_{1-6}$ alkyl, —$C_{3-6}$cycloalkyl, —$OC_{1-4}$alkyl or N-tetrazolyl;
or $R^3$ and $R^4$ are joined together with the carbon atoms in the phenyl ring to which they are attached to form:

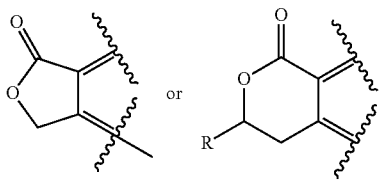

wherein R is —H or —C$_{1-4}$ alkyl;

R$^5$ is —H, —Cl, —F, —CN, —C$_{1-4}$alkyl, —C$_{3-6}$cycloalkyl or —OC$_{1-4}$alkyl;

provided that when R$^3$ and R$^4$ are not joined together, then one and only one of R$^3$, R$^4$ or R$^5$ is —CN;

R$^6$ is —H or —C$_{1-4}$alkyl; and

R$^7$ is —H, —F, —Cl or —C$_{1-4}$alkyl.

3. The compound of claim 1 or a pharmaceutically acceptable salt thereof wherein X is O.

4. The compound of claim 3 or a pharmaceutically acceptable salt thereof wherein m is 1 and R$^6$ is —H.

5. The compound of claim 1 or a pharmaceutically acceptable salt thereof wherein R$^1$ is:

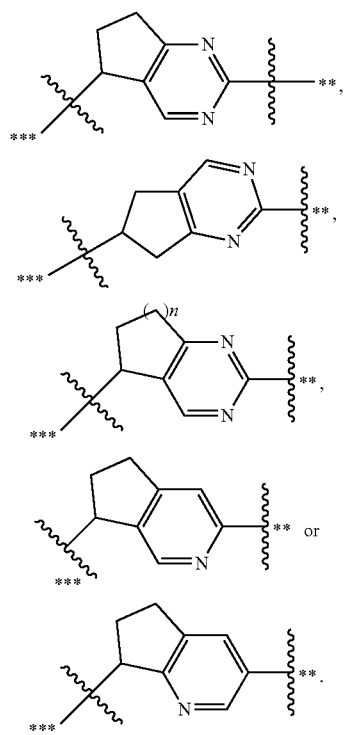

6. The compound of claim 1 or a pharmaceutically acceptable salt thereof wherein R$^2$ is —H or —F; R$^3$ is —H, —F, —CN or —OCH$_3$; R$^4$ is —F, —CN or —OCH$_3$; and R$^5$ is —H, —Cl, —F, —CN, —CH$_3$, —CH$_2$CH$_3$, cyclopropyl or —OCH$_3$; provided that one and only one of R$^3$, R$^4$ or R$^5$ is —CN.

7. The compound of claim 1 or a pharmaceutically acceptable salt thereof wherein R$^3$ and R$^4$ are joined together with the carbon atoms in the phenyl ring to which they are attached to form:

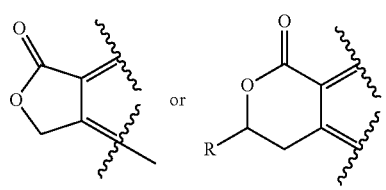

and R is —H or —CH$_3$.

8. The compound of claim 1 or a pharmaceutically acceptable salt thereof wherein:

X is O, NH or S;

R$^1$ is

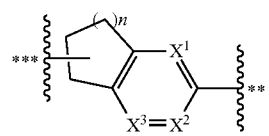

wherein * indicates attachment to the carbonyl carbon and  indicates attachment to the tetrazolyl ring in Formula Ia;

m is an integer selected from 1 or 2;

n is an integer selected from 1 or 2;

X$^1$, X$^2$ and X$^3$ are each independently selected from CH or N, provided that at least one of X$^1$, X$^2$ and X$^3$ must be N and at most two of X$^1$, X$^2$ and X$^3$ are N;

R$^a$ is —CN;

R$^b$ is —H or —C$_{1-3}$alkyl;

R$^2$ is —H or —F;

R$^3$ is —H, —F, —CN or —OCH$_3$;

R$^4$ is —F, —CN or —OCH$_3$;

or R$^3$ and R$^4$ are joined together with the carbon atoms in the phenyl ring to which they are attached to form:

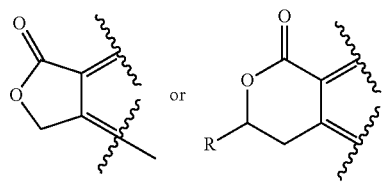

wherein R is —H or —CH$_3$;

R$^5$ is —H, —Cl, —F, —CN, —CH$_3$, —CH$_2$CH$_3$, cyclopropyl or —OCH$_3$;

provided that when R$^3$ and R$^4$ are not joined together, then one and only one of R$^3$, R$^4$ or R$^5$ is —CN; and further provided that when R$^3$ and R$^4$ are joined together, then R$^5$ is —H, —Cl, —F, —CH$_3$ or —CH$_2$CH$_3$;

R$^6$ is —H or —C$_{1-4}$ alkyl; and

R$^7$ is —H, —F, —Cl or —C$_{1-4}$ alkyl.

9. The compound of claim 1 having structural Formula II:

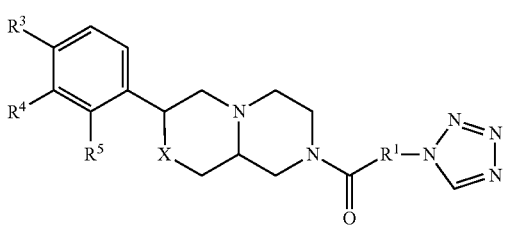

or a pharmaceutically acceptable salt thereof wherein:
X is O or NH;
R¹ is:

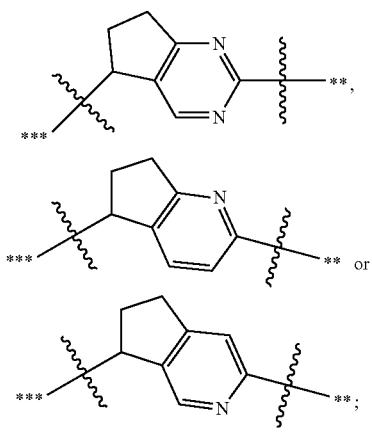

R³ is —F, R⁴ is —CN and R⁵ is —CH₃; or
R³ and R⁴ are joined together with the carbon atoms in the phenyl ring to which they are attached to form:

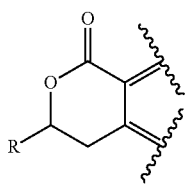

wherein R is —H or —CH₃, and R⁵ is —H.

10. The compound of claim 1 having structural Formula III:

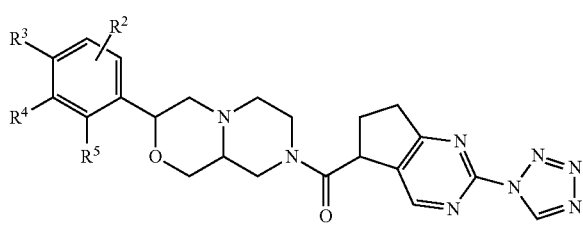

or a pharmaceutically acceptable salt thereof.

11. The compound of claim 1 which is:
6-fluoro-2-methyl-3-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl] benzonitrile;
6-fluoro-2-methyl-3-[(3S,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl] benzonitrile;
6-fluoro-2-methyl-3-[(3S,9aS)-8-{[3-(1H-tetrazol-1-yl)-6,7-dihydro-5H-cyclopenta[c]pyridin-7-yl]carbonyl}octahydropyrazino[2,1-c][1,4]oxazin-3-yl] benzonitrile;
6-fluoro-2-methyl-3-[(3S,9aR)-8-{[3-(1H-tetrazol-1-yl)-6,7-dihydro-5H-cyclopenta[c]pyridin-7-yl]carbonyl}octahydropyrazino[2,1-c][1,4]oxazin-3-yl] benzonitrile;
6-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one;
(3R)-3-methyl-6-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one;
(3S)-3-methyl-6-[(3R,9aS)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one;
6-Fluoro-2-methyl-3-[(3S,9aR)-8-{[(5S)-2-(1H-tetrazol-1-yl)-6,7-dihydro-5H-cyclopenta[d]pyrimidin-5-yl]carbonyl}octahydropyrazino[2,1-c][1,4]oxazin-3-yl] benzonitrile;
6-fluoro-2-methyl-3-[(3R,9aR)-8-{[3-(1H-tetrazol-1-yl)-6,7-dihydro-5H-cyclopenta[c]pyridin-7-yl]carbonyl}octahydro-2H-pyrazino[1,2-a]pyrazin-3-yl] benzonitrile;
6-fluoro-2-methyl-3-[(3S,9aR)-8-{[3-(1H-tetrazol-1-yl)-6,7-dihydro-5H-cyclopenta[c]pyridin-7-yl]carbonyl}octahydro-2H-pyrazino[1,2-a]pyrazin-3-yl] benzonitrile;
6-fluoro-2-methyl-3-[(3S,9aS)-8-{[2-(1H-tetrazol-1-yl)-6,7-dihydro-5H-cyclopenta[d]pyrimidin-5-yl]carbonyl}octahydropyrazino[2,1-c][1,4]oxazin-3-yl] benzonitrile;
(3S)-3-methyl-6-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one;
or (3S)-3-methyl-6-[(3R,9aR)-8-{[2-(1H-tetrazol-1-yl)-6,7-dihydro-5H-cyclopenta[b]pyridin-5-yl]carbonyl}octahydropyrazino[2,1-c][1,4]oxazin-3-yl]-3,4-dihydro-1H-isochromen-1-one;
or a pharmaceutically acceptable salt thereof.

12. A pharmaceutical composition comprised of a compound of claim 1 and a pharmaceutically acceptable carrier.

13. The pharmaceutical composition of claim 12 further comprising an active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pharmaceutically acceptable salt thereof.

14. A method for causing diueresis, natriuresis or both, comprising administering a compound of claim 1 in a therapeutically effective amount to a patient in need thereof.

15. A method for the treatment or prophylaxis of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thrombosis, myocardial infarction, stroke, cardiac insufficiency, pulmonary hypertonia, atherosclerosis, hepatic cirrhosis, ascites, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of claim 1 in a therapeutically or prophylactically effective amount as appropriate, to a patient in need thereof.

\* \* \* \* \*